(12) United States Patent
Wai et al.

(10) Patent No.: US 7,538,112 B2
(45) Date of Patent: May 26, 2009

(54) HIV INTEGRASE INHIBITORS

(75) Inventors: John S. Wai, Harleysville, PA (US);
Joseph P. Vacca, Telford, PA (US);
Linghang Zhuang, Chalfont, PA (US);
Boyoung Kim, Lansdale, PA (US);
Terry A. Lyle, Lederach, PA (US);
Catherine M. Wiscount, Allentown, PA (US); Melissa S. Egbertson, Ambler, PA (US); Lou Anne Neilson, Sellersville, PA (US); Mark Embrey, Harleysville, PA (US); Thorsten E. Fisher, Hatfield, PA (US); Donnette D. Staas, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 414 days.

(21) Appl. No.: 11/579,772

(22) PCT Filed: May 3, 2005

(86) PCT No.: PCT/US2005/015200

§ 371 (c)(1),
(2), (4) Date: Nov. 7, 2006

(87) PCT Pub. No.: WO2005/110414

PCT Pub. Date: Nov. 24, 2005

(65) Prior Publication Data

US 2008/0287394 A1    Nov. 20, 2008

Related U.S. Application Data

(60) Provisional application No. 60/569,150, filed on May 7, 2004.

(51) Int. Cl.
*C07D 487/14* (2006.01)
*A61K 31/5025* (2006.01)
*A61K 31/4985* (2006.01)

(52) U.S. Cl. ..................... 514/250; 544/234
(58) Field of Classification Search ............... 544/234; 514/250
See application file for complete search history.

(56) References Cited

U.S. PATENT DOCUMENTS

| 5,693,640 | A  | 12/1997 | Ladduwahetty et al. |
| 5,756,501 | A  | 5/1998  | Sabb |
| 6,262,055 | B1 | 7/2001  | Young et al. |
| 6,306,891 | B1 | 10/2001 | Selnick et al. |
| 6,380,249 | B1 | 4/2002  | Young et al. |
| 6,841,558 | B2 | 1/2005  | Anthony et al. |
| 6,919,351 | B2 | 7/2005  | Anthony et al. |
| 6,921,759 | B2 | 7/2005  | Anthony et al. |
| 7,169,780 | B2 | 1/2007  | Crescenzi et al. |
| 7,217,713 | B2 | 5/2007  | Crescenzi et al. |
| 7,232,819 | B2 | 6/2007  | Di Francesco et al. |
| 7,253,180 | B2 | 8/2007  | Chen et al. |
| 2004/0157804 | A1 | 8/2004 | Chen et al. |
| 2004/0229909 | A1 | 11/2004 | Kiyama et al. |
| 2005/0165040 | A1 | 7/2005 | Kuki et al. |
| 2006/0217410 | A1 | 9/2006 | Chen et al. |
| 2007/0083045 | A1 | 4/2007 | Di Francesco et al. |
| 2007/0123524 | A1 | 5/2007 | Crescenzi et al. |

FOREIGN PATENT DOCUMENTS

| WO | WO 01/100578 A1 | 1/2001 |
| WO | WO 02/36734 A2 | 5/2002 |
| WO | WO 02/100350 A2 | 12/2002 |
| WO | WO 03/062204 A1 | 7/2003 |
| WO | WO 2004/004657 A2 | 1/2004 |

OTHER PUBLICATIONS

Pearl, L. et al. "A structural model for the retroviral proteases", Nature, 1987, vol. 329, pp. 351-354.
Power, M. et al. "Nucleotide Sequence of SRV-1, a Type D Simian Acquired Immune Deficiency Syndrome Retrovirus", Science, 1986, vol. 231, pp. 1567-1572.
Ratner, L. et al. "Complete nucleotide sequence of the AIDS virus, HTLV-III", Nature, 1985, vol. 313, pp. 277-284.
Toh, H. et al. "Close structural resemblance between putative polymerase of a *Drosophila* transposable genetic element 17.6 and *pol* gene product of Moloney murine leukaemia virus", The EMBO Journal, 1985, vol. 4, pp. 1267-1272.

*Primary Examiner*—Kahsay T Habte
(74) *Attorney, Agent, or Firm*—Kenneth R. Walton; Sheldon O. Heber

(57) ABSTRACT

Hydroxy-substituted pyrazinopyrrolopyridazine dione compounds are inhibitors of HIV integrase and inhibitors of HIV replication. In one embodiment, the dione compounds are of Formula (I) wherein $R^1$, $R^2$, $R^3$, $R^4$, $R^5$, $R^6$ and $R^7$ are defined herein. The compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

13 Claims, No Drawings

HIV INTEGRASE INHIBITORS

This application is the National Stage of International Application No. PCT/US2005/015200, filed on May 3, 2005, which claims the benefit of U.S. Provisional Application No. 60/569,150 (filed May 7, 2004), the disclosure of which is hereby incorporated by reference in its entirety.

FIELD OF THE INVENTION

The present invention is directed to hydroxy-substituted pyrazinopyrrolopyridazine dione compounds and pharmaceutically acceptable salts thereof, their synthesis, and their use as inhibitors of the HIV integrase enzyme. The compounds of the present invention and their pharmaceutically acceptable salts are useful for preventing or treating infection by HIV and for treating, delaying the onset of, or preventing AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, integrase and an HIV protease [Toh et al., *EMBO J.* 1985, 4: 1267; Power et al., *Science* 1986, 231: 1567; Pearl et al., *Nature* 1987, 329: 351]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and of HIV replication in cells is a direct result of inhibiting the strand transfer reaction catalyzed by the recombinant integrase in vitro in HIV infected cells. A particular advantage of the present invention is highly specific inhibition of HIV integrase and HIV replication.

The following references are of interest as background:

U.S. Pat. Nos. 6,380,249, 6,306,891, 6,262,055 disclose 2,4-dioxobutyric acids and acid esters useful as HIV integrase inhibitors.

WO 01/00578 discloses 1-(aromatic- or heteroaromatic-substituted)-3-(heteroaromatic substituted)-1,3-propanediones useful as HIV integrase inhibitors.

US 2003/0055071 (corresponding to WO 02/30930), WO 02/30426, and WO 02/55079 each disclose certain 8-hydroxy-1,6-naphthyridine-7-carboxamides as HIV integrase inhibitors.

WO 02/036734 discloses certain aza- and polyaza-naphthalenyl ketones to be HIV integrase inhibitors.

WO 03/016275 discloses certain compounds having integrase inhibitory activity.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/062204 discloses certain hydroxynaphthyridinone carboxamides that are useful as HIV integrase inhibitors.

WO 2004/004657 discloses certain hydroxypyrrole derivatives that are HIV integrase inhibitors.

WO 2004/035576 and WO 2004/035577 disclose certain tricyclic compounds that are HIV integrase inhibitors.

SUMMARY OF THE INVENTION

The present invention is directed to hydroxy-substituted pyrazinopyrrolopyridazine dione compounds. These compounds and their pharmaceutically acceptable salts are useful in the inhibition of HIV integrase, the prevention of infection by HIV, the treatment of infection by HIV and in the prevention, treatment, and delay in the onset of AIDS, either as compounds or their pharmaceutically acceptable salts, or as pharmaceutical composition ingredients, whether or not in combination with other HIV/AIDS antivirals, anti-infectives, immunomodulators, antibiotics or vaccines. More particularly, the present invention includes compounds of Formula I and pharmaceutically acceptable salts thereof:

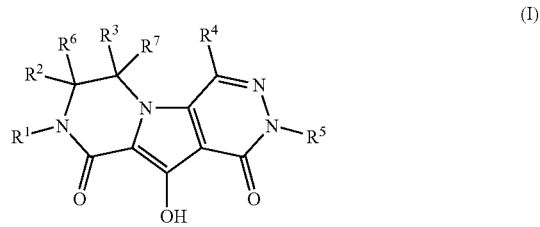

(I)

wherein:
$R^1$ is:
(1) —$C_{1-6}$ alkyl,
(2) —$C_{1-6}$ alkyl substituted with —OH, —O—$C_{1-6}$ alkyl, —O—$C_{1-6}$ haloalkyl, —CN, —$NO_2$, —N($R^A$)$R^B$, —C(O)N($R^A$)$R^B$, —C(O)$R^A$, —$CO_2R^A$, —$SR^A$, —S(O)$R^A$, —$SO_2R^A$, —$SO_2$N($R^A$)$R^B$, —N($R^A$)C(O)$R^B$, —N($R^A$)$CO_2R^B$, —N($R^A$)$SO_2R^B$, —N($R^A$)$SO_2$N($R^A$)$R^B$, —OC(O)N($R^A$)$R^B$, —N($R^A$)C(O)N($R^A$)$R^B$, or —N($R^A$)C(O)C(O)N($R^A$)$R^B$,
(3) —$C_{3-8}$ cycloalkyl, which is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl,
(4) —$C_{1-6}$ alkyl substituted with $C_{3-8}$ cycloalkyl, wherein the $C_{3-8}$ cycloalkyl is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl, (5) heteroaryl, which is optionally substituted with from 1 to 5 substituents each of which is independently any one of substituents (1) to (26) as defined below in part (i) of Part B of the definition of $R^J$,
(6) —$C_{1-6}$ alkyl substituted with $R^J$, wherein $R^J$ is:
 (A) aryl which is:
  (i) optionally substituted with from 1 to 5 substituents each of which is independently:
   (1) —$C_{1-6}$ alkyl, which is optionally substituted with —OH, —O—$C_{1-6}$ alkyl, —O—$C_{1-6}$ haloalkyl, —CN, —NO$_2$, —N(R$^A$)R$^B$, —C(O)N(R$^A$)R$^B$, —C(O)R$^A$, —CO$_2$R$^A$, —SR$^A$, —S(O)R$^A$, —SO$_2$R$^A$, —SO$_2$N(R$^A$)R$^B$, —N(R$^A$)C(O)R$^B$, —N(R$^A$)CO$_2$R$^B$, —N(R$^A$)SO$_2$R$^B$, —N(R$^A$)SO$_2$N(R$^A$)R$^B$, —OC(O)N(R$^A$)R$^B$, —N(R$^A$)C(O)N(R$^A$)R$^B$, or —N(R$^A$)C(O)C(O)N(R$^A$)R$^B$,
   (2) —O—$C_{1-6}$ alkyl,
   (3) —$C_{1-6}$ haloalkyl,
   (4) —O—$C_{1-6}$ haloalkyl,
   (5) —OH,
   (6) halogen,
   (7) —CN,
   (8) —NO$_2$,
   (9) —N(R$^A$)R$^B$,
   (10) —C(O)N(R$^A$)R$^B$,
   (11) —C(O)R$^A$,
   (12) —CO$_2$R$^A$,
   (13) —SR$^A$,
   (14) —S(O)R$^A$,
   (15) —SO$_2$R$^A$,
   (16) —SO$_2$N(R$^A$)R$^B$,
   (17) —N(R$^A$)SO$_2$R$^B$,
   (18) —N(R$^A$)SO$_2$N(R$^A$)R$^B$,
   (19) —N(R$^A$)C(O)R$^B$,
   (20) —N(R$^A$)C(O)—C(O)N(R$^A$)R$^B$, or
   (21) —N(R$^A$)CO$_2$R$^B$, and
  (ii) optionally substituted with 1 or 2 substituents each of which is independently:
   (1) —$C_{3-8}$ cycloalkyl,
   (2) aryl,
   (3) —$C_{1-6}$ alkyl substituted with aryl, —$C_{3-8}$ cycloalkyl, HetA, or HetB,
   (4) -HetA,
   (5) —C(O)-HetA; or
   (6) -HetB;
   wherein:
    each cycloalkyl is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl,
    each aryl is optionally substituted with from 1 to 5 substituents each of which is independently any one of the substituents (1) to (21) as defined above in part (i) of Part A of the definition of $R^J$,
    each HetA is independently (i) a —$C_{4-7}$ azacycloalkyl or oxacycloalkyl or thiacycloalkyl or (ii) a —$C_{3-6}$ diazacycloalkyl or oxazacycloalkyl or thiazacycloalkyl, wherein the S in the thiacycloalkyl or thiazacycloalkyl is optionally oxidized to S(O) or SO$_2$, and wherein any of the rings defined in (i) or (ii) is optionally substituted with from 1 to 4 substituents each of which is independently oxo, —$C_{1-6}$ alkyl, —C(O)R$^A$, —CO$_2$R$^A$, —SR$^A$, —S(O)R$^A$, or —S(O)$_2$R$^A$; and each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently any one of the substituents (1) to (26) as defined below in part (i) of Part B of the definition of $R^J$, or
 (B) heteroaryl which is:
  (i) optionally substituted with from 1 to 6 substituents each of which is independently:
   (1) —$C_{1-6}$ alkyl,
   (2) —$C_{1-6}$ alkyl substituted with —OH, —O—$C_{1-6}$ alkyl, —O—$C_{1-6}$ haloalkyl, —CN, —NO$_2$, —N(R$^A$)R$^B$, —C(O)N(R$^A$)R$^B$, —C(O)R$^A$, —CO$_2$R$^A$, —SR$^A$, —S(O)R$^A$, —S(O)$_2$R$^A$, —S(O)$_2$N(R$^A$)R$^B$, —N(R$^A$)C(O)R$^B$, —N(R$^A$)CO$_2$R$^B$, —N(R$^A$)S(O)$_2$R$^B$, —N(R$^A$)S(O)$_2$N(R$^A$)R$^B$, —OC(O)N(R$^A$)R$^B$, —N(R$^A$)C(O)N(R$^A$)R$^B$, or —N(R$^A$)C(O)C(O)N(R$^A$)R$^B$,
   (3) —O—$C_{1-6}$ alkyl,
   (4) —$C_{1-6}$ haloalkyl,
   (5) —O—$C_{1-6}$ haloalkyl,
   (6) —OH,
   (7) -oxo,
   (8) halogen,
   (9) —CN,
   (10) —NO$_2$,
   (11) —N(R$^A$)R$^B$,
   (12) —C(O)N(R$^A$)R$^B$,
   (13) —C(O)R$^A$,
   (14) —C(O)—$C_{1-6}$ haloalkyl,
   (15) —C(O)OR$^A$,
   (16) —OC(O)N(R$^A$)R$^B$,
   (17) —SR$^A$,
   (18) —S(O)R$^A$,
   (19) —S(O)$_2$R$^A$,
   (20) —S(O)$_2$N(R$^A$)R$^B$,
   (21) —N(R$^A$)S(O)$_2$R$^B$,
   (22) —N(R$^A$)S(O)$_2$N(R$^A$)R$^B$,
   (23) —N(R$^A$)C(O)R$^B$,
   (24) —N(R$^A$)C(O)N(R$^A$)R$^B$,
   (25) —N(R$^A$)C(O)—C(O)N(R$^A$)R$^B$, or
   (26) —N(R$^A$)CO$_2$R$^B$, and
  (ii) optionally substituted with 1 or 2 substituents each of which is independently:
   (1) —$C_{3-8}$ cycloalkyl,
   (2) aryl,
   (3) —$C_{1-6}$ alkyl substituted with aryl, —$C_{3-8}$ cycloalkyl, HetA, or HetB,
   (4) -HetA,
   (5) —C(O)-HetA; or
   (6) -HetB;
   wherein:
    each cycloalkyl is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl,
    each aryl is optionally substituted with from 1 to 5 substituents each of which is independently any one of the substituents (1) to (21) as defined above in part (i) of Part A of the definition of $R^J$,
    each HetA is independently as defined in Part (A)(ii) of the definition of $R^J$, and
    each HetB is independently as defined in Part (A)(ii) of the definition of $R^J$;

(7) aryl, which is optionally substituted with from 1 to 5 substituents each of which is independently any one of the substituents (1) to (21) as defined above in part (i) of Part A of the definition of $R^J$;

$R^2$ is:
(1) —H,
(2) —$C_{1-6}$ alkyl,
(3) —$C_{1-6}$ haloalkyl,
(4) —$C_{1-6}$ alkyl substituted with —OH, —O—$C_{1-6}$ alkyl, —O—$C_{1-6}$ haloalkyl, —CN, —$NO_2$, —N($R^A$)$R^B$, —C(O)N($R^A$)$R^B$, —C(O)$R^A$, —$CO_2R^A$, —$SR^A$, —S(O)$R^A$, —$SO_2R^A$, —$SO_2$N($R^A$)$R^B$, —N($R^A$)C(O)$R^B$, —N($R^A$)$CO_2R^B$, —N($R^A$)$SO_2R^B$, —N($R^A$)$SO_2$N($R^A$)$R^B$, —OC(O)N($R^A$)$R^B$, —N($R^A$)C(O)N($R^A$)$R^B$, or —N($R^A$)C(O)C(O)N($R^A$)$R^B$, or
(5) —$C_{1-6}$ alkyl substituted with HetC, —C(O)-HetC, —$SO_2$-HetC, —N($R^A$)C(O)-HetC, or —N($R^A$)C(O)C(O)-HetC;
  wherein HetC is a 4- to 7-membered, saturated or mono-unsaturated heterocyclic ring containing from 1 to 3 heteroatoms independently selected from 1 to 3 N atoms, zero to 1 O atom, and zero to 1 S atom, where the S is optionally oxidized to S(O) or S(O)$_2$, with the proviso that the ring is attached to the rest of the molecule via a ring N atom, and wherein the saturated or mono-unsaturated heterocyclic ring is optionally substituted with from 1 to 4 substituents each of which is independently halogen, —CN, —$C_{1-6}$ alkyl, —OH, oxo, —C(O)$R^A$, —$CO_2R^A$, —S(O)$R^A$, —$SR^A$, —S(O)$_2R^A$, —$CH_2$—CH=$CH_2$, —O—$C_{1-6}$ alkyl, —$C_{1-6}$ haloalkyl, —$C_{1-6}$ alkylene-CN, —$C_{1-6}$ alkylene-OH, or —$C_{1-6}$ alkylene-O—$C_{1-6}$ alkyl;
or alternatively $R^1$ and $R^2$ together with the ring nitrogen to which $R^1$ is attached and the ring carbon to which $R^2$ is attached form a 5- to 7-membered, saturated heterocyclic ring in which the portion of the ring formed from $R^1$ and $R^2$ is a 3- to 5-membered methylene chain in which one of the methylene moieties is optionally replaced with N(H), wherein the chain is optionally substituted with from 1 to 3 substituents each of which is independently —$C_{1-6}$ alkyl, —OH, or oxo;

$R^3$ is:
(1) —H,
(2) —$C_{1-6}$ alkyl,
(3) —$C_{1-6}$ haloalkyl,
(4) —$C_{1-6}$ alkyl substituted with —OH, —O—$C_{1-6}$ alkyl, —O—$C_{1-6}$ haloalkyl, —CN, —$NO_2$, —N($R^A$)$R^B$, —C(O)N($R^A$)$R^B$, —C(O)$R^A$, —$CO_2R^A$, —$SR^A$, —S(O)$R^A$, —$SO_2R^A$, —$SO_2$N($R^A$)$R^B$, —N($R^A$)C(O)$R^B$, —N($R^A$)$CO_2R^B$, —N($R^A$)$SO_2R^B$, —N($R^A$)$SO_2$N($R^A$)$R^B$, —OC(O)N($R^A$)$R^B$, —N($R^A$)C(O)N($R^A$)$R^B$, or —N($R^A$)C(O)C(O)N($R^A$)$R^B$,
(5) —$C_{1-6}$ alkyl substituted with HetD, —C(O)-HetD, —$SO_2$-HetD, —N($R^A$)C(O)-HetD, or —N($R^A$)C(O)C(O)-HetD,
(6) CycM, AryM, or HetM, or
(7) —$C_{1-6}$ alkyl substituted with CycM, AryM, or HetM;
wherein:
  HetD independently has the same definition as HetC;
  CycM is —$C_{3-8}$ cycloalkyl which is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl;
  AryM is aryl, which is optionally substituted with from 1 to 5 substituents each of which is independently any one of the substituents (1) to (21) as defined above in part (i) of Part A of the definition of $R^J$; and
  HetM is heteroaryl, which is optionally substituted with from 1 to 5 substituents each of which is independently any one of the substituents (1) to (26) as defined above in part (i) of Part B of the definition of $R^J$;
or alternatively $R^2$ and $R^3$ together with the carbon atoms to which they are attached form:
  (i) a 3- to 8-membered saturated carbocyclic ring which is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl,
  (ii) a benzene ring, which is optionally substituted with from 1 to 4 substituents each of which is independently any one of the substituents (1) to (21) as defined above in part (i) of Part A of the definition of $R^J$,
  (iii) a 4- to 7-membered, saturated or mono-unsaturated heterocyclic ring containing from 1 to 3 heteroatoms independently selected from N, O and S, where each S is optionally oxidized to S(O) or S(O)$_2$, and wherein the saturated or mono-unsaturated heterocyclic ring is optionally substituted with from 1 to 4 substituents each of which is independently halogen, —CN, —$C_{1-6}$ alkyl, —OH, oxo, —C(O)$R^A$, —$CO_2R^A$, —S(O)$R^A$, —$SR^A$, —S(O)$_2R^A$, —$CH_2$—CH=$CH_2$, —O—$C_{1-6}$ alkyl, —$C_{1-6}$ haloalkyl, —$C_{1-6}$ alkylene-CN, —$C_{1-6}$ alkylene-OH, or —$C_{1-6}$ alkylene-O—$C_{1-6}$ alkyl, or
  (iv) a 5- or 6-membered heteroaromatic ring, which is optionally substituted with from 1 to 3 substituents each of which is independently any one of the substituents (1) to (26) as defined above in part (i) of Part B of the definition of $R^J$;
  wherein $R^6$ and $R^7$ are absent, when $R^2$ and $R^3$ together with the carbon atoms to which they are attached form a benzene ring or a heteroaromatic ring;

$R^4$ is:
(1) —H,
(2) —$C_{1-6}$ alkyl,
(3) —$C_{1-6}$ haloalkyl,
(4) —$C_{1-6}$ alkyl substituted with —OH, —O—$C_{1-6}$ alkyl, —O—$C_{1-6}$ haloalkyl, —CN, —$NO_2$, —N($R^A$)$R^B$, —C(O)N($R^A$)$R^B$, —C(O)$R^A$, —$CO_2R^A$, —$SR^A$, —S(O)$R^A$, —$SO_2R^A$, —$SO_2$N($R^A$)$R^B$, —N($R^A$)C(O)$R^B$, —N($R^A$)$CO_2R^B$, —N($R^A$)$SO_2R^B$, —N($R^A$)$SO_2$N($R^A$)$R^B$, —OC(O)N($R^A$)$R^B$, —N($R^A$)C(O)N($R^A$)$R^B$, or —N($R^A$)C(O)C(O)N($R^A$)$R^B$,
(5) —OH,
(6) —O—$C_{1-6}$ alkyl,
(7) —O—$C_{1-6}$ haloalkyl,
(8) —CN,
(9) —$NO_2$,
(10) —N($R^C$)$R^D$,
(11) —C(O)N($R^C$)$R^D$,
(12) —C(O)$R^A$,
(13) —$CO_2R^A$,
(14) —$SR^A$,
(15) —S(O)$R^A$,
(16) —$SO_2R^A$,
(17) —$SO_2$N($R^A$)$R^B$,
(18) —N($R^A$)C(O)$R^B$,
(19) —N($R^A$)$CO_2R^B$,
(20) —N($R^A$)$SO_2R^B$,
(21) —N($R^A$)$SO_2$N($R^A$)$R^B$,
(22) —OC(O)N($R^A$)$R^B$,

(23) —N(R$^A$)C(O)N(R$^A$)R$^B$,
(24) —N(R$^A$)C(O)C(O)N(R$^A$)R$^B$,
(25) halogen,
(26) —S—C(O)N(R$^C$)R$^D$,
(27) —N=C(R$^A$)—N(R$^C$)R$^D$,
(28) —C(O)N(R$^A$)—C$_{1-6}$ alkylene-N(R$^C$)R$^D$,
(29) —C(O)—C$_{1-6}$ alkylene-N(R$^C$)R$^D$,
(30) —C(O)N(R$^A$)—C$_{1-6}$ alkylene-C$_{1-6}$ haloalkyl,
(31) —C(O)—C$_{1-6}$ alkylene-C$_{1-6}$ haloalkyl,
(32) —N(SO$_2$R$^A$)—V,
(33) —N[C(O)R$^A$]—V,
(34) —C$_{1-6}$ alkyl substituted HetE, —C(O)-HetE, —SO$_2$-HetE, —N(R$^A$)C(O)-HetE, or —N(R$^A$)C(O)C(O)-HetE,
(35) —C$_{1-6}$ alkyl substituted with CycL, AryL, HetL, or HetS, or
(36) -T-R$^L$,
 wherein:
  T is a single bond, O, C(O), C(O)N(R$^A$), N(R$^A$)C(O), S, S(O), S(O)$_2$, N(R$^A$)S(O)$_2$, S(O)$_2$N(R$^A$), O—C$_{1-6}$ alkylene, C(O)—C$_{1-6}$ alkylene, C(O)N(R$^A$)—C$_{1-6}$ alkylene, N(R$^A$)C(O)—C$_{1-6}$ alkylene, S—C$_{1-6}$ alkylene, S(O)—C$_{1-6}$ alkylene, S(O)$_2$—C$_{1-6}$ alkylene, C$_{1-6}$ alkylene-S, C$_{1-6}$ alkylene-S(O), C$_{1-6}$ alkylene-S(O)$_2$, C$_{1-6}$ alkylene-O, C$_{1-6}$ alkylene-C(O), C$_{1-6}$ alkylene-C(O)N(R$^A$), C$_{1-6}$ alkylene-N(R$^A$)C(O), C$_{1-6}$ alkylene-N(R$^A$)S(O)$_2$, or C$_{1-6}$ alkylene-S(O)$_2$N(R$^A$);
  V is (i) —CH$_2$—C$_{2-6}$ alkenyl or (ii) —C$_{1-6}$ alkyl substituted with C(O)N(R$^C$)R$^D$, CycL, AryL, HetL, or HetS; and
  R$^L$ is CycL, AryL, HetL, or HetS;
CycL is —C$_{3-8}$ cycloalkyl which is optionally substituted with from 1 to 6 substituents each of which is independently halogen, —CN, —C$_{1-6}$ alkyl, —OH, —O—C$_{1-6}$ alkyl, —C$_{1-6}$ haloalkyl, or —O—C$_{1-6}$ haloalkyl;
AryL is aryl, which is optionally substituted with from 1 to 5 substituents each of which is independently any one of the substituents (1) to (21) as defined above in part (i) of Part A of the definition of R$^J$;
HetE independently has the same definition as HetC;
HetL is heteroaryl, which is optionally substituted with from 1 to 5 substituents each of which is independently any one of the substituents (1) to (26) as defined above in part (i) of Part B of the definition of R$^J$;
HetS is a 4- to 7-membered, saturated or mono-unsaturated heterocyclic ring containing at least one carbon atom and from 1 to 4 heteroatoms independently selected from N, O and S, where each S is optionally oxidized to S(O) or S(O)$_2$, with the proviso that HetS is attached to the rest of the molecule via a ring carbon atom; and wherein the saturated or mono-unsaturated heterocyclic ring is optionally substituted with from 1 to 4 substituents each of which is independently halogen, —CN, —C$_{1-6}$ alkyl, —OH, oxo, —C(O)R$^A$, —CO$_2$R$^A$, —S(O)R$^A$, —SR$^A$, —S(O)$_2$R$^A$, —CH$_2$—CH=CH$_2$, —O—C$_{1-6}$ alkyl, —C$_{1-6}$ haloalkyl, —C$_{1-6}$ alkylene-C(O)N(R$^A$)R$^B$, —C$_{1-6}$ alkylene-CN, —C$_{1-6}$ alkylene-OH, or —C$_{1-6}$ alkylene-O—C$_{1-6}$ alkyl;
R$^5$ is:
 (1) —C$_{1-6}$ alkyl,
 (2) —C$_{1-6}$ alkyl substituted with —OH, —O—C$_{1-6}$ alkyl, —O—C$_{1-6}$ haloalkyl, —CN, —NO$_2$, —N(R$^A$)R$^B$, —C(O)N(R$^A$)R$^B$, —C(O)R$^A$, —CO$_2$R$^A$, —SR$^A$, —S(O)R$^A$, —SO$_2$R$^A$, —SO$_2$N(R$^A$)R$^B$, —N(R$^A$)C(O) R$^B$, —N(R$^A$)CO$_2$R$^B$, —N(R$^A$)SO$_2$R$^B$, —N(R$^A$)SO$_2$N (R$^A$)R$^B$, —OC(O)N(R$^A$)R$^B$, —N(R$^A$)C(O)N(R$^A$)R$^B$, or —N(R$^A$)C(O)C(O)N(R$^A$)R$^B$,
 (3) —C$_{3-8}$ cycloalkyl, which is optionally substituted with from 1 to 6 substituents each of which is independently halogen, —CN, —C$_{1-6}$ alkyl, —OH, —O—C$_{1-6}$ alkyl, —C$_{1-6}$ haloalkyl, or —O—C$_{1-6}$ haloalkyl,
 (4) —C$_{1-6}$ alkyl substituted with —C$_{3-8}$ cycloalkyl, wherein the —C$_{3-8}$ cycloalkyl is optionally substituted with from 1 to 6 substituents each of which is independently halogen, —CN, —C$_{1-6}$ alkyl, —OH, —O—C$_{1-6}$ alkyl, —C$_{1-6}$ haloalkyl, or —O—C$_{1-6}$ haloalkyl,
 (5) heteroaryl, which is optionally substituted with from 1 to 5 substituents each of which is independently any one of the substituents (1) to (26) as defined above in part (i) of Part B of the definition of R$^J$,
 (6) —C$_{1-6}$ alkyl substituted with R$^K$, wherein R$^K$ independently has the same definition as R$^J$ as set forth above in the definition of R$^1$, or
 (7) aryl, which is optionally substituted with from 1 to 5 substituents each of which is independently any one of the substituents (1) to (21) as defined above in part (i) of Part A of the definition of R$^J$;
and with the proviso that R$^5$ is —C$_{1-6}$ alkyl substituted with R$^K$, when R$^1$ is other than —C$_{1-6}$ alkyl substituted with R$^J$;
R$^6$ and R$^7$ are each independently —H or —C$_{1-6}$ alkyl;
or alternatively R$^3$ and R$^7$ together with the carbon atom to which they are attached form (i) a 3- to 8-membered saturated carbocyclic ring which is optionally substituted with from 1 to 6 substituents each of which is independently halogen, —CN, —C$_{1-6}$ alkyl, —OH, —O—C$_{1-6}$ alkyl, —C$_{1-6}$ haloalkyl, or —O—C$_{1-6}$ haloalkyl or (ii) a 4- to 7-membered, saturated or mono-unsaturated heterocyclic ring containing from 1 to 3 heteroatoms independently selected from N, O and S, where each S is optionally oxidized to S(O) or S(O)$_2$, and wherein the saturated or mono-unsaturated heterocyclic ring is optionally substituted with from 1 to 4 substituents each of which is independently halogen, —CN, —C$_{1-6}$ alkyl, —OH, oxo, —C(O)R$^A$, —CO$_2$R$^A$, —S(O)R$^A$, —SR$^A$, —S(O)$_2$R$^A$, —CH$_2$—CH=CH$_2$, —O—C$_{1-6}$ alkyl, —C$_{1-6}$ haloalkyl, —C$_{1-6}$ alkylene-CN, —C$_{1-6}$ alkylene-OH, or —C$_{1-6}$ alkylene-O—C$_{1-6}$ alkyl,
each aryl is independently (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic;
each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or S(O)$_2$;
each R$^A$ is independently —H or —C$_{1-6}$ alkyl;
each R$^B$ is independently —H or —C$_{1-6}$ alkyl;
each R$^C$ is independently —H or —C$_{1-6}$ alkyl; and
each R$^D$ is independently —H or —C$_{1-6}$ alkyl;
or alternatively R$^C$ and R$^D$ together with the N to which they are both attached form a 4- to 7-membered, saturated or mono-unsaturated heterocyclic ring containing the N to which they are both attached and optionally containing 1 or 2 additional heteroatoms independently selected from N, O and S, where each S is optionally oxidized to S(O) or S(O)$_2$, and wherein the saturated or mono-unsaturated heterocyclic ring is optionally substituted with from 1 to 4 substituents each of which is independently halogen, —CN, —$C_{1-6}$ alkyl, —OH, oxo, —$C(O)R^A$, —$CO_2R^A$, —$S(O)R^A$, —$SR^A$, —$S(O)_2R^A$, —$CH_2$—$C_{2-6}$ alkenyl, —O—$C_{1-6}$ alkyl, —$C_{1-6}$ haloalkyl, —$C_{1-6}$ alkylene-CN, —$C_{1-6}$ alkylene-OH, or —$C_{1-6}$ alkylene-O—$C_{1-6}$ alkyl.

The present invention also includes pharmaceutical compositions containing a compound of Formula I and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the hydroxy-substituted pyrazinopyrrolopyridazine diones of Formula I above. These compounds and pharmaceutically acceptable salts thereof inhibit HIV integrase and inhibit HIV replication. A first embodiment of the present invention is a compound of Formula II, or a pharmaceutically acceptable salt thereof:

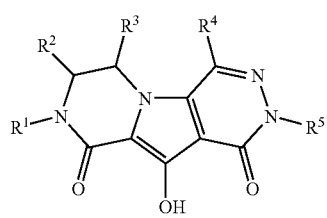

(II)

wherein the variables $R^1$, $R^2$, $R^3$, $R^4$ and $R^5$ are each as originally defined above (i.e., as defined in the Summary of the Invention).

A second embodiment of the present invention is a compound of Formula II, or a pharmaceutically acceptable salt thereof, wherein:

$R^1$ is:
(1) $C_{1-6}$ alkyl,
(2) $C_{1-6}$ alkyl substituted with —OH, —O—$C_{1-6}$ alkyl, —O—$C_{1-6}$ haloalkyl, —CN, —$NO_2$, —$N(R^A)R^B$, —$C(O)N(R^A)R^B$, —$C(O)R^A$, —$CO_2R^A$, —$SR^A$, —$S(O)R^A$, —$SO_2R^A$, —$SO_2N(R^A)R^B$, —$N(R^A)C(O)R^B$, —$N(R^A)CO_2R^B$, —$N(R^A)SO_2R^B$, —$N(R^A)SO_2N(R^A)R^B$, —$OC(O)N(R^A)R^B$, —$N(R^A)C(O)N(R^A)R^B$, or —$N(R^A)C(O)C(O)N(R^A)R^B$,
(3) $C_{3-8}$ cycloalkyl, which is optionally substituted with from 1 to 6 substituents each of which is independently —$C_{1-6}$ alkyl, —OH, —O—$C_{1-6}$ alkyl, or —$C_{1-6}$ haloalkyl,
(4) $C_{1-6}$ alkyl substituted with —$C_{3-8}$ cycloalkyl, wherein the —$C_{3-8}$ cycloalkyl is optionally substituted with from 1 to 6 substituents each of which is independently —$C_{1-6}$ alkyl, —OH, —O—$C_{1-6}$ alkyl, or —$C_{1-6}$ haloalkyl,
(5) heteroaryl, which is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, oxo, or —OH,
(6) $C_{1-6}$ alkyl substituted with $R^J$, wherein $R^J$ is:
 (A) aryl which is:
  (i) optionally substituted with from 1 to 5 substituents each of which is independently any one of the substituents (1) to (21) as originally defined above in part (i) of Part A of the definition of $R^J$, and
  (ii) optionally substituted with 1 or 2 substituents each of which is independently: (1) aryl, (2) —$C_{1-6}$ alkyl substituted with aryl, (3) -HetA, (4) —C(O)-HetA; or (5) -HetB;
   wherein each HetA is independently a —$C_{4-7}$ azacycloalkyl or a —$C_{3-6}$ diazacycloalkyl, either of which is optionally substituted with from 1 to 3 substituents each of which is independently oxo or —$C_{1-6}$ alkyl; and
   wherein each HetB is a 5- or 6-membered heteroaromatic ring containing from 1 to 4 heteroatoms independently selected from N, O and S, wherein the heteroaromatic ring is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or hydroxy; or
 (B) heteroaryl which is:
  (i) optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, oxo, or —OH; and
  (ii) optionally substituted with 1 or 2 substituents each of which is independently aryl or —$C_{1-6}$ alkyl substituted with aryl, or
(7) aryl, which is optionally substituted with from 1 to 5 substituents each of which is independently any one of the substituents (1) to (21) as originally defined above in part (i) of Part A of the definition of $R^J$;

$R^2$ and $R^3$ are each independently: (1) —H, (2) $C_{1-6}$ alkyl, (3) $C_{1-6}$ haloalkyl, or (4) $C_{1-6}$ alkyl substituted with —OH, —O—$C_{1-6}$ alkyl, —O—$C_{1-6}$ haloalkyl, —CN, —$NO_2$, —$N(R^A)R^B$, —$C(O)N(R^A)R^B$, —$C(O)R^A$, —$CO_2R^A$, —$SR^A$, —$S(O)R^A$, —$SO_2R^A$, —$SO_2N(R^A)R^B$, —$N(R^A)C(O)R^B$, —$N(R^A)CO_2R^B$, —$N(R^A)SO_2R^B$, —$N(R^A)SO_2N(R^A)R^B$, —$OC(O)N(R^A)R^B$, —$N(R^A)C(O)N(R^A)R^B$, or —$N(R^A)C(O)C(O)N(R^A)R^B$;

$R^4$ is: (1) —H, (2) $C_{1-6}$ alkyl, (3) $C_{1-6}$ haloalkyl, (4) $C_{1-6}$ alkyl substituted with —OH, —O—$C_{1-6}$ alkyl, —O—$C_{1-6}$ haloalkyl, —CN, —$NO_2$, —$N(R^A)R^B$, —$C(O)N(R^A)R^B$, —$C(O)R^A$, —$CO_2R^A$, —$SR^A$, —$S(O)R^A$, —$SO_2R^A$, —$SO_2N(R^A)R^B$, —$N(R^A)C(O)R^B$, —$N(R^A)CO_2R^B$, —$N(R^A)SO_2R^B$, —$N(R^A)SO_2N(R^A)R^B$, —$OC(O)N(R^A)R^B$, —$N(R^A)C(O)N(R^A)R^B$, or —$N(R^A)C(O)C(O)N(R^A)R^B$, (5) —OH, (6) —O—$C_{1-6}$ alkyl, (7) —O—$C_{1-6}$ haloalkyl, (8) —CN, (9) —$NO_2$, (10) —$N(R^C)R^D$, (11) —$C(O)N(R^C)R^D$, (12) —$C(O)R^A$, (13) —$CO_2R^A$, (14) —$SR^A$, (15) —$S(O)R^A$, (16) —$SO_2R^A$, (17) $SO_2N(R^A)R^B$, (18) —$N(R^A)C(O)R^B$, (19) —$N(R^A)CO_2R^B$, (20) —$N(R^A)SO_2R^B$, (21) —$N(R^A)SO_2N(R^A)R^B$, (22) —$OC(O)N(R^A)R^B$, (23) —$N(R^A)C(O)N(R^A)R^B$, or (24) —$N(R^A)C(O)C(O)N(R^A)R^B$;

$R^5$ is:
(1) $C_{1-6}$ alkyl,
(2) $C_{1-6}$ alkyl substituted with —OH, —O—$C_{1-6}$ alkyl, —O—$C_{1-6}$ haloalkyl, —CN, —$NO_2$, —$N(R^A)R^B$, —$C(O)N(R^A)R^B$, —$C(O)R^A$, —$CO_2R^A$, —$SR^A$, —$S(O)R^A$, —$SO_2R^A$, —$SO_2N(R^A)R^B$, —$N(R^A)C(O)R^B$, —$N(R^A)CO_2R^B$, —$N(R^A)SO_2R^B$, —$N(R^A)SO_2N(R^A)R^B$, —$OC(O)N(R^A)R^B$, —$N(R^A)C(O)N(R^A)R^B$, or —$N(R^A)C(O)C(O)N(R^A)R^B$, (3) $C_{3-8}$ cycloalkyl, which is optionally substituted with from 1 to 6 substituents each of which is independently —$C_{1-6}$ alkyl, —OH, —O—$C_{1-6}$ alkyl, or —$C_{1-6}$ haloalkyl, (4) $C_{1-6}$ alkyl substituted with —$C_{3-8}$ cycloalkyl, wherein the —$C_{3-8}$ cycloalkyl is optionally substituted with from 1 to 6 substituents each of which is independently —$C_{1-6}$ alkyl, —OH, —O—$C_{1-6}$ alkyl, or —$C_{1-6}$ haloalkyl, (5) heteroaryl, which is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or —OH, (6) $C_{1-6}$ alkyl substituted with $R^K$, wherein $R^K$ independently has the same definition as $R^J$ as set forth above in the definition of $R^1$, or (7) aryl, which is optionally substituted with from 1 to 5 substituents each of which is independently any one of the substituents (1) to (21) as originally defined above in part (i) of Part A of the definition of $R^J$;

and with the proviso that $R^5$ is —$C_{1-6}$ alkyl substituted with $R^K$, when $R^1$ is other than —$C_{1-6}$ alkyl substituted with $R^J$;

each aryl is independently (i) phenyl or (ii) a 9- or 10-membered bicyclic, fused carbocyclic ring system in which at least one ring is aromatic;

each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain a heteroatom, at least one ring is aromatic, each N is optionally in the form of an oxide, and each S in a ring which is not aromatic is optionally S(O) or $S(O)_2$;

each $R^A$ is independently —H or —$C_{1-6}$ alkyl; each $R^B$ is independently —H or —$C_{1-6}$ alkyl; each $R^C$ is independently —H or —$C_{1-6}$ alkyl; and each $R^D$ is independently —H or —$C_{1-6}$ alkyl;

or alternatively $R^C$ and $R^D$ together with the N to which they are both attached form a 5- or 6-membered saturated heterocyclic ring containing the N to which they are both attached and optionally containing 1 or 2 additional heteroatoms independently selected from N, O and S.

A third embodiment of the present invention is a compound of Formula I or Formula II, or a pharmaceutically acceptable salt thereof, wherein:

$R^1$ is:
(1) $C_{1-4}$ alkyl, or
(2) $C_{1-4}$ alkyl substituted with $R^J$, wherein $R^J$ is:
  (A) an optionally substituted phenyl of formula:

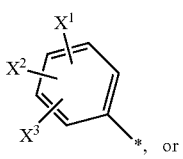

wherein the asterisk * denotes the point of attachment to the rest of the compound, $X^1$ and $X^2$ are each independently selected from the group consisting of —H, halogen, —$C_{1-4}$ alkyl, —O—$C_{1-4}$ alkyl, —$C_{1-4}$ fluoroalkyl, —CN, —$CO_2$H, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, and —N($C_{1-4}$ alkyl)C(O)—$C_{1-4}$ alkyl, and $X^3$ is —H, halogen, —$C_{1-4}$ alkyl, —O—$C_{1-4}$ alkyl, —$C_{1-4}$ fluoroalkyl, —$SO_2$—$C_{1-4}$ alkyl, —C(O)—NH($C_{1-4}$ alkyl), —C(O)—N($C_{1-4}$ alkyl)$_2$, or HetB, or (B) a heteroaryl which is
  (i) 5- or 6-membered heteroaromatic ring containing from 1 to 4 heteroatoms independently selected from N, O and S, wherein the ring is optionally substituted with from 1 to 3 substituents each of which is independently —$C_{1-4}$ alkyl or —OH, or
  (ii) a benzene ring fused to a 5- or 6-membered saturated or unsaturated heterocyclic ring containing from 1 to 3 heteroatoms independently selected from N, O and S, wherein the fused bicyclic ring system is optionally substituted with from 1 to 4 substituents each of which is independently —$C_{1-4}$ alkyl, oxo, or —OH;

and all other variables are as originally defined above; and with the proviso that $R^5$ is —$C_{1-6}$ alkyl substituted with $R^K$, when $R^1$ is —$C_{1-4}$ alkyl.

A fourth embodiment of the present invention is a compound of Formula II, or a pharmaceutically acceptable salt thereof, wherein $R^1$ is as defined in the third embodiment; and all other variables are as defined in the second embodiment; and with the proviso that $R^5$ is —$C_{1-6}$ alkyl substituted with $R^K$, when $R^1$ is —$C_{1-4}$ alkyl.

A fifth embodiment of the present invention is a compound of Formula I or Formula II, or a pharmaceutically acceptable salt thereof, wherein $R^1$ is: (1) —$C_{1-4}$ alkyl or (2) —$CH_2$—$R^J$; $R^J$ is as originally defined or as defined in the third embodiment; and all other variables are as originally defined; and with the proviso that $R^5$ is —$C_{1-6}$ alkyl substituted with $R^K$, when $R^1$ is —$C_{1-4}$ alkyl.

A sixth embodiment of the present invention is a compound of Formula II, or a pharmaceutically acceptable salt thereof, wherein $R^1$ is: (1) —$C_{1-4}$ alkyl or (2) —$CH_2$—$R^J$; $R^J$ is as defined in the second embodiment or as defined in the third embodiment; and all other variables are as defined in the second embodiment; and with the proviso that $R^5$ is —$C_{1-6}$ alkyl substituted with $R^K$, when $R^1$ is —$C_{1-4}$ alkyl.

In an aspect of each of the foregoing embodiments, heteroaryl (B) in the definition of $R^J$ is: (i) a 5- or 6-membered heteroaromatic ring containing from 1 to 4 heteroatoms independently selected from N, O and S, wherein the ring is optionally substituted with from 1 to 3 substituents each of which is independently —$C_{1-4}$ alkyl or —OH, or (ii) a benzene ring fused to a 5- or 6-membered saturated or unsaturated heterocyclic ring containing from 1 to 3 heteroatoms independently selected from N, O and S, wherein the fused bicyclic ring system is unsubstituted.

In another aspect of each of the foregoing embodiments, heteroaryl (B) in the definition of $R^J$ is (i) an optionally substituted 5- or 6-membered heteroaromatic ring as defined in the preceding aspect or (ii) a benzofused ring system selected from the group consisting of 1,3-benzodioxolyl, 2,3-dihydro-1,4-benzodioxinyl, benzo-2,3-dihydrofuranyl, benzoimidazolyl, and benzopiperidinyl.

A seventh embodiment of the present invention is a compound of Formula I or Formula II, or a pharmaceutically acceptable salt thereof, wherein $R^1$ is —$CH_2$—$R^J$; $R^J$ is phenyl, 4-(acetylamino)phenyl, 4-carboxyphenyl, 3-chlorophenyl, 4-chlorophenyl, 2,3-dichlorophenyl, 3,4-dichlorophenyl, 2-chloro-4-fluorophenyl, 3-chloro-4-fluorophenyl, 2-cyanophenyl, 4-fluoro-2-(methylaminocarbonyl)phenyl, 4-fluoro-2-methoxyphenyl, 4-fluoro-2-(methoxycarbonyl)

phenyl, 2-fluorophenyl, 3-fluorophenyl, 4-fluorophenyl, 2,3-difluorophenyl, 2,4-difluorophenyl, 3,4-difluorophenyl, 2,3,4-trifluorophenyl, 2-methoxyphenyl, 3-methoxyphenyl, 4-methoxyphenyl, 3-(methylaminocarbonyl)phenyl, 2-methylphenyl, 3-methylphenyl, 4-methylphenyl, 2,4-dimethylphenyl, 3,4-dimethylphenyl, 3-trifluoromethylphenyl, or 1,3-benzodioxolyl (e.g., 1,3-benzodioxol-4-yl or 1,3-benzodioxol-5-yl); and all other variables are as originally defined. In an aspect of this embodiment, $R^J$ is 4-fluorophenyl or 3-chloro-4-fluorophenyl. In another aspect of this embodiment, $R^J$ is 4-fluorophenyl. In still another aspect of this embodiment, $R^J$ is 3-chloro-4-fluorophenyl.

An eighth embodiment of the present invention is a compound of Formula II, or a pharmaceutically acceptable salt thereof, wherein $R^1$ is —$CH_2$—$R^J$; $R^J$ is as defined in the seventh embodiment; and all other variables are as defined in the second embodiment. In an aspect of this embodiment, $R^J$ is 4-fluorophenyl or 3-chloro-4-fluorophenyl. In another aspect of this embodiment, $R^J$ is 4-fluorophenyl. In still another aspect of this embodiment, $R^J$ is 3-chloro-4-fluorophenyl.

A ninth embodiment of the present invention is a compound of Formula I or Formula II, or a pharmaceutically acceptable salt thereof, wherein $R^1$ is —$C_{1-4}$ alkyl; and all other variables are as originally defined; and with the proviso that $R^5$ is —$C_{1-6}$ alkyl substituted with $R^K$.

A tenth embodiment of the present invention is a compound of Formula II, or a pharmaceutically acceptable salt thereof, wherein $R^1$ is —$C_{1-4}$ alkyl; and all other variables are as defined in the second embodiment; and with the proviso that $R^5$ is —$C_{1-6}$ alkyl substituted with $R^K$.

An eleventh embodiment of the present invention is a compound of Formula I or Formula II, or a pharmaceutically acceptable salt thereof, wherein $R^1$ is methyl or ethyl; and all other variables are as originally defined; and with the proviso that $R^5$ is —$C_{1-6}$ alkyl substituted with $R^K$.

A twelfth embodiment of the present invention is a compound of Formula II, or a pharmaceutically acceptable salt thereof, wherein $R^1$ is methyl or ethyl; and all other variables are as defined in the second embodiment; and with the proviso that $R^5$ is —$C_{1-6}$ alkyl substituted with $R^K$.

A thirteenth embodiment of the present invention is a compound of Formula I or Formula II, or a pharmaceutically acceptable salt thereof, wherein $R^2$ and $R^3$ are each independently —H or —$C_{1-4}$ alkyl; and all other variables are as originally defined or as defined in any one of the preceding embodiments. In an aspect of this embodiment, the compound is a compound of Formula II, and all other variables are as defined in the second embodiment.

A fourteenth embodiment of the present invention is a compound of Formula I or Formula II, or a pharmaceutically acceptable salt thereof, wherein $R^2$ and $R^3$ are each independently —H or —$C_{1-3}$ alkyl (i.e., methyl, ethyl, n-propyl, or isopropyl); and all other variables are as originally defined or as defined in any one of the preceding embodiments (e.g., the second embodiment). In an aspect of this embodiment, $R^2$ is —H; and $R^3$ is —H, methyl, ethyl, n-propyl, or isopropyl. In another aspect of this embodiment, $R^2$ is —H; and $R^3$ is —H, methyl or isopropyl.

A fifteenth embodiment of the present invention is a compound of Formula I or Formula II, or a pharmaceutically acceptable salt thereof, wherein $R^2$ and $R^3$ are both —H; and all other variables are as originally defined or as defined in any one of the preceding embodiments (e.g., the second embodiment).

A sixteenth embodiment of the present invention is a compound of Formula I or Formula II, or a pharmaceutically acceptable salt thereof, wherein $R^4$ is —H, —$C_{1-4}$ alkyl, —OH, —O—$C_{1-4}$ alkyl, —O—$C_{1-4}$ haloalkyl, —CN, —$NO_2$, —$N(R^C)R^D$, —C(O)N($R^C$)$R^D$, —C(O)$R^A$, —$CO_2R^A$, —$SR^A$, —S(O)$R^A$, —$SO_2R^A$, or —$SO_2N(R^A)R^B$; and all other variables are as originally defined or as defined in any one of the preceding embodiments (e.g., the second embodiment).

A seventeenth embodiment of the present invention is a compound of Formula I or Formula II, or a pharmaceutically acceptable salt thereof, wherein $R^4$ is —H, —$C_{1-4}$ alkyl, —OH, —O—$C_{1-4}$ alkyl, —$NH_2$, —NH($C_{1-4}$ alkyl), —N($C_{1-4}$ alkyl)$_2$, 1-piperidinyl, 1-piperazinyl, 4-morpholinyl (i.e.,

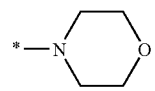

where the asterisk * denotes the point of attachment), or 4-thiomorpholinyl; and all other variables are as originally defined or as defined in any one of the preceding embodiments (e.g., the second embodiment).

An eighteenth embodiment of the present invention is a compound of Formula I or Formula II, or a pharmaceutically acceptable salt thereof, wherein $R^4$ is —$C_{1-4}$ alkyl; and all other variables are as originally defined or as defined in any one of the preceding embodiments (e.g., the second embodiment).

A nineteenth embodiment of the present invention is a compound of Formula I or Formula II, or a pharmaceutically acceptable salt thereof, wherein $R^4$ is —H, methyl, ethyl, $NH_2$, or 4-morpholinyl; and all other variables are as originally defined or as defined in any one of the preceding embodiments.

A twentieth embodiment of the present invention is a compound of Formula I or Formula II, or a pharmaceutically acceptable salt thereof, wherein $R^5$ is:

(1) $C_{1-4}$ alkyl,
(2) $C_{1-4}$ alkyl substituted with —OH, —O—$C_{1-4}$ alkyl, —CN, —$NH_2$, —NH($C_{1-4}$ alkyl), or —N($C_{1-4}$ alkyl)$_2$,
(3) $C_{3-7}$ cycloalkyl, which is optionally substituted with from 1 to 4 substituents each of which is independently —$C_{1-4}$ alkyl, —OH, —O—$C_{1-4}$ alkyl, or —$C_{1-4}$ haloalkyl,
(4) $C_{1-4}$ alkyl substituted with —$C_{3-7}$ cycloalkyl, wherein the —$C_{3-7}$ cycloalkyl is optionally substituted with from 1 to 4 substituents each of which is independently —$C_{1-4}$ alkyl, —OH, —O—$C_{1-4}$ alkyl, or —$C_{1-4}$ haloalkyl,
(5) 5- or 6-membered heteroaromatic ring containing from 1 to 4 heteroatoms independently selected from N, O and S, wherein the ring is optionally substituted with from 1 to 3 substituents each of which is independently —$C_{1-4}$ alkyl or —OH, or
(6) $C_{1-4}$ alkyl substituted with $R^K$, wherein $R^K$ is:
(A) an optionally substituted phenyl of formula:

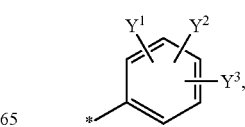

wherein the asterisk * denotes the point of attachment to the rest of the compound, $Y^1$ and $Y^2$ are each independently selected from the group consisting of —H, halogen, —$C_{1-4}$ alkyl, —O—$C_{1-4}$ alkyl, —$C_{1-4}$ fluoroalkyl, —CN, —$CO_2H$, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, and —N($C_{1-4}$ alkyl)C(O)—$C_{1-4}$ alkyl, and $Y^3$ is —H, halogen, —$C_{1-4}$ alkyl, —O—$C_{1-4}$ alkyl, —$C_{1-4}$ fluoroalkyl, —$SO_2$—$C_{1-4}$ alkyl, —C(O)—NH($C_{1-4}$ alkyl), —C(O)—N($C_{1-4}$ alkyl)$_2$, or HetB, or (B) a heteroaryl which is
(i) 5- or 6-membered heteroaromatic ring containing from 1 to 4 heteroatoms independently selected from N, O and S, wherein the ring is optionally substituted with from 1 to 3 substituents each of which is independently —$C_{1-4}$ alkyl or —OH, or
(ii) a benzene ring fused to a 5- or 6-membered saturated or unsaturated heterocyclic ring containing from 1 to 3 heteroatoms independently selected from N, O and S, wherein the fused bicyclic ring system is optionally substituted with from 1 to 4 substituents each of which is independently —$C_{1-4}$ alkyl, oxo, or —OH;

and all other variables are as originally defined or as defined in any one of the preceding embodiments.

A twenty-first embodiment of the present invention is a compound of Formula I or Formula II, or a pharmaceutically acceptable salt thereof, wherein $R^5$ is:

(1) $C_{1-4}$ alkyl,
(2) $(CH_2)_{1-3}$-Q, wherein Q is —OH, —O—$C_{1-4}$ alkyl, —CN, —$NH_2$, —NH($C_{1-4}$ alkyl), or —N($C_{1-4}$ alkyl)$_2$,
(3) $C_{3-7}$ cycloalkyl, which is optionally substituted with from 1 to 4 substituents each of which is independently —$C_{1-4}$ alkyl, —OH, —O—$C_{1-4}$ alkyl, or —$C_{1-4}$ haloalkyl,
(4) $CH_2$—$C_{3-7}$ cycloalkyl, wherein the —$C_{3-7}$ cycloalkyl is optionally substituted with from 1 to 4 substituents each of which is independently —$C_{1-4}$ alkyl, —OH, —O—$C_{1-4}$ alkyl, or —$C_{1-4}$ haloalkyl,
(5) 5- or 6-membered heteroaromatic ring containing from 1 to 4 heteroatoms independently selected from N, O and S, wherein the ring is optionally substituted with from 1 to 3 substituents each of which is independently —$C_{1-4}$ alkyl or —OH, or
(6) $CH_2$—$R^K$;

$R^K$ is as originally defined or as defined in the twentieth embodiment; and all other variables are as originally defined or as defined in any one of the preceding embodiments.

A twenty-second embodiment of the present invention is a compound of Formula I or Formula II, or a pharmaceutically acceptable salt thereof, wherein $R^5$ is:

(1) methyl,
(2) ethyl,
(3) $(CH_2)_{1-2}$—OH,
(4) $(CH_2)_{1-2}$—CN,
(5) $C_{3-6}$ cycloalkyl,
(6) $CH_2$—$R^K$, wherein $R^K$ is phenyl, 4-(acetylamino)phenyl, 4-carboxyphenyl, 3-chlorophenyl, 4-chlorophenyl, 2,3-dichlorophenyl, 3,4-dichlorophenyl, 2-chloro-4-fluorophenyl, 3-chloro-4-fluorophenyl, 2-cyanophenyl, 4-fluoro-2-(methylaminocarbonyl)phenyl, 4-fluoro-2-methoxyphenyl, 4-fluoro-2-(methoxycarbonyl)phenyl, 2-fluorophenyl, 3-fluorophenyl, 4-fluorophenyl, 2,3-difluorophenyl, 2,4-difluorophenyl, 3,4-difluorophenyl, 2,3,4-trifluorophenyl, 2-methoxyphenyl, 3-methoxyphenyl, 4-methoxyphenyl, 3-(methylaminocarbonyl)phenyl, 2-methylphenyl, 3-methylphenyl, 4-methylphenyl, 2,4-dimethylphenyl, 3,4-dimethylphenyl, 3-trifluoromethylphenyl, or 1,3-benzodioxolyl (e.g., 1,3-benzodioxol-4-yl or 1,3-benzodioxol-5-yl);

and all other variables are as originally defined or as defined in any one of the preceding embodiments.

A twenty-third embodiment of the present invention is a compound of Formula I or Formula II, or a pharmaceutically acceptable salt thereof, wherein $R^5$ is —$CH_2$—$R^K$; $R^K$ is as originally defined or as defined in the twentieth embodiment or the twenty-second embodiment; and all other variables are as originally defined or as defined in any one of the preceding embodiments.

It is understood that the definition of $R^5$ in the twentieth, twenty-first, and twenty-second embodiments is subject to the proviso that $R^5$ is an alkyl group substituted with $R^K$ when $R^1$ is other than an alkyl group substituted with $R^J$.

In an aspect of each of the twentieth, twenty-first, and twenty-third embodiments, heteroaryl (B) in the definition of $R^K$ is: (i) 5- or 6-membered heteroaromatic ring containing from 1 to 4 heteroatoms independently selected from N, O and S, wherein the ring is optionally substituted with from 1 to 3 substituents each of which is independently —$C_{1-4}$ alkyl or —OH, or (ii) a benzene ring fused to a 5- or 6-membered saturated or unsaturated heterocyclic ring containing from 1 to 3 heteroatoms independently selected from N, O and S, wherein the fused bicyclic ring system is unsubstituted.

In another aspect of each of the twentieth, twenty-first, and twenty-third embodiments, heteroaryl (B) in the definition of $R^K$ is (i) a 5- or 6-membered heteroaromatic ring as defined in the preceding aspect or (ii) a benzofused ring system selected from the group consisting of 1,3-benzodioxolyl, 2,3-dihydro-1,4-benzodioxinyl, benzo-2,3-dihydrofuranyl, benzoimidazolyl, and benzopiperidinyl.

A twenty-fourth embodiment of the present invention is a compound of Formula I or Formula II, or a pharmaceutically acceptable salt thereof, wherein each $R^A$ and $R^B$ is independently —H or —$C_{1-4}$ alkyl; and all other variables are as originally defined or as defined in any one of the preceding embodiments.

A twenty-fifth embodiment of the present invention is a compound of Formula I or Formula II, or a pharmaceutically acceptable salt thereof, wherein each $R^A$ and $R^B$ is independently —H or methyl; and all other variables are as originally defined or as defined in any one of the preceding embodiments.

A twenty-sixth embodiment of the present invention is a compound of Formula I or Formula II, or a pharmaceutically acceptable salt thereof, wherein each $R^C$ and $R^D$ is independently —H or —$C_{1-4}$ alkyl; or alternatively $R^C$ and $R^D$ together with the N atom to which they are both attached form a 5- or 6-membered saturated heterocyclic ring containing the N to which they are both attached and optionally containing 1 or 2 additional heteroatoms independently selected from 1 or 2 N atoms, zero or 1 O atom, and zero or 1 S atom; and all other variables are as originally defined or as defined in any one of the preceding embodiments. In an aspect of this embodiment, each $R^C$ and $R^D$ is independently —H or —$C_{1-4}$ alkyl; or alternatively $R^C$ and $R^D$ together with the N atom to which they are both attached form 1-piperidinyl, 1-piperazinyl, 4-morphonlinyl, or 4-thiomorpholinyl.

A twenty-seventh embodiment of the present invention is a compound of Formula I or Formula II, or a pharmaceutically acceptable salt thereof, wherein each $R^C$ and $R^D$ is independently —H or —$C_{1-4}$ alkyl; or alternatively $R^C$ and $R^D$ together with the N atom to which they are both attached form a 5- or 6-membered saturated heterocyclic ring containing the N to which they are both attached and optionally containing 1 or 2 additional heteroatoms independently selected from 1 or 2 N atoms, zero or 1 O atom, and zero or 1 S atom, where the S is optionally oxidized to S(O) or S(O)$_2$, and wherein the saturated heterocyclic ring is optionally substituted with from 1 to 4 substituents each of which is independently —C$_{1-4}$ alkyl, oxo, —C(O)R$^A$, —CO$_2$R$^A$, S(O)$_2$R$^A$, or —CH$_2$—CH═CH$_2$; and all other variables are as originally defined or as defined in any one of the preceding embodiments.

A first class of the present invention includes compounds of Formula II, and pharmaceutically acceptable salts thereof, wherein R$^1$ is as defined in the third embodiment; R$^5$ is as defined in the twentieth embodiment; each HetB is independently a 5- or 6-membered heteroaromatic ring containing from 1 to 4 heteroatoms independently selected from N, O and S, wherein the heteroaromatic ring is optionally substituted with 1 or 2 substituents each of which is independently a —C$_{1-3}$ alkyl; and all other variables are as defined in the second embodiment; and with the proviso that R$^5$ is —C$_{1-4}$ alkyl substituted with R$^K$, when R$^1$ is —C$_{1-4}$ alkyl.

A second class of the present invention includes compounds of Formula II, and pharmaceutically acceptable salts thereof, wherein:

R$^1$ is:
(1) C$_{1-4}$ alkyl, or
(2) CH$_2$—R$^J$;

R$^5$ is:
(1) C$_{1-4}$ alkyl,
(2) (CH$_2$)$_{1-3}$-Q, wherein Q is —OH, —O—C$_{1-4}$ alkyl, —CN, —NH$_2$, —NH(C$_{1-4}$ alkyl), or —N(C$_{1-4}$ alkyl)$_2$,
(3) C$_{3-7}$ cycloalkyl, which is optionally substituted with from 1 to 4 substituents each of which is independently —C$_{1-4}$ alkyl, —OH, —O—C$_{1-4}$ alkyl, or —C$_{1-4}$ haloalkyl,
(4) CH$_2$—C$_{3-7}$ cycloalkyl, wherein the —C$_{3-7}$ cycloalkyl is optionally substituted with from 1 to 4 substituents each of which is independently —C$_{1-4}$ alkyl, —OH, —O—C$_{1-4}$ alkyl, or —C$_{1-4}$ haloalkyl,
(5) 5- or 6-membered heteroaromatic ring containing from 1 to 4 heteroatoms independently selected from N, O and S, wherein the ring is optionally substituted with from 1 to 3 substituents each of which is independently —C$_{1-4}$ alkyl or —OH, or
(6) CH$_2$—R$^K$;

and all other variables are as defined in the first class; and with the proviso that R$^5$ is —CH$_2$—R$^K$, when R$^1$ is —C$_{1-4}$ alkyl.

A sub-class of the second class includes compounds of Formula II, and pharmaceutically acceptable salts thereof, wherein R$^1$ is —CH$_2$—R$^J$; and R$^J$ is 4-fluorophenyl; and all other variables are as defined in the second class.

A third class of the present invention includes compounds of Formula II, and pharmaceutically acceptable salts thereof, wherein:
R$^1$ is —CH$_2$—R$^J$, wherein R$^J$ is:
(A) an optionally substituted phenyl of formula:

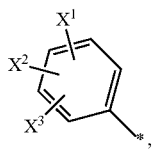

wherein the asterisk * denotes the point of attachment to the rest of the compound,
X$^1$ and X$^2$ are each independently selected from the group consisting of —H, halogen, —C$_{1-4}$ alkyl, —O—C$_{1-4}$ alkyl, —C$_{1-4}$ fluoroalkyl, —CN, —CO$_2$H, —CO$_2$—C$_{1-4}$ alkyl, —SO$_2$—C$_{1-4}$ alkyl, —C(O)—NH(C$_{1-4}$ alkyl), —C(O)—N(C$_{1-4}$ alkyl)$_2$, —NHC(O)—C$_{1-4}$ alkyl, and —N(C$_{1-4}$ alkyl)C(O)—C$_{1-4}$ alkyl, and
X$^3$ is —H, halogen, —C$_{1-4}$ alkyl, —O—C$_{1-4}$ alkyl, —C$_{1-4}$ fluoroalkyl, —SO$_2$—C$_{1-4}$ alkyl, —C(O)—NH (C$_{1-4}$ alkyl), —C(O)—N(C$_{1-4}$ alkyl)$_2$, or HetB, or
(B) a 9- or 10-membered benzofused heterocyclic ring containing 1 or 2 heteroatoms independently selected from N, O and S;

R$^2$ and R$^3$ are each independently —H or —C$_{1-4}$ alkyl;
R$^4$ is —H, —C$_{1-4}$ alkyl, —OH, —O—C$_{1-4}$ alkyl, —O—C$_{1-4}$ haloalkyl, —CN, —NO$_2$, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, or —SO$_2$N(R$^A$)R$^B$;

R$^5$ is:
(1) C$_{1-4}$ alkyl,
(2) (CH$_2$)$_{1-3}$-Q, wherein Q is —OH, —O—C$_{1-4}$ alkyl, —CN, —NH$_2$, —NH(C$_{1-4}$ alkyl), or —N(C$_{1-4}$ alkyl)$_2$,
(3) C$_{3-7}$ cycloalkyl, which is optionally substituted with from 1 to 4 substituents each of which is independently —C$_{1-4}$ alkyl, —OH, —O—C$_{1-4}$ alkyl, or —C$_{1-4}$ haloalkyl,
(4) CH$_2$—C$_{3-7}$ cycloalkyl, wherein the —C$_{3-7}$ cycloalkyl is optionally substituted with from 1 to 4 substituents each of which is independently —C$_{1-4}$ alkyl, —OH, —O—C$_{1-4}$ alkyl, or —C$_{1-4}$ haloalkyl,
(5) 5- or 6-membered heteroaromatic ring containing from 1 to 4 heteroatoms independently selected from N, O and S, wherein the ring is optionally substituted with from 1 to 3 substituents each of which is independently —C$_{1-4}$ alkyl or —OH, or
(6) CH$_2$—R$^K$, wherein R$^K$ is
(A) an optionally substituted phenyl of formula:

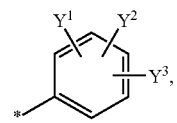

wherein the asterisk * denotes the point of attachment to the rest of the compound,
Y$^1$ and Y$^2$ are each independently selected from the group consisting of —H, halogen, —C$_{1-4}$ alkyl, —O—C$_{1-4}$ alkyl, —C$_{1-4}$ fluoroalkyl, —CN, —CO$_2$H, —CO$_2$—C$_{1-4}$ alkyl, —SO$_2$—C$_{1-4}$ alkyl, —C(O)—NH(C$_{1-4}$ alkyl), —C(O)—N(C$_{1-4}$ alkyl)$_2$, —NHC(O)—C$_{1-4}$ alkyl, and —N(C$_{1-4}$ alkyl)C(O)—C$_{1-4}$ alkyl, and
Y$^3$ is —H, halogen, —C$_{1-4}$ alkyl, —O—C$_{1-4}$ alkyl, —C$_{1-4}$ fluoroalkyl, —SO$_2$—C$_{1-4}$ alkyl, —C(O)—NH(C$_{1-4}$ alkyl), —C(O)—N(C$_{1-4}$ alkyl)$_2$, or HetB, or
(B) a heteroaryl which is
(i) 5- or 6-membered heteroaromatic ring containing from 1 to 4 heteroatoms independently selected from N, O and S, wherein the ring is optionally substituted with from 1 to 3 substituents each of which is independently —C$_{1-4}$ alkyl or —OH, or (ii) a 9- or 10-membered benzofused saturated or unsaturated heterocyclic ring containing from 1 to 3 heteroatoms independently selected from N, O and S;

each HetB is independently a 5- or 6-membered heteroaromatic ring containing from 1 to 4 heteroatoms independently selected from N, O and S, wherein the heteroaromatic ring is optionally substituted with 1 or 2 substituents each of which is independently a —$C_{1-3}$ alkyl;

each $R^A$ is independently —H or —$C_{1-4}$ alkyl;
each $R^B$ is independently —H or —$C_{1-4}$ alkyl;
each $R^C$ is independently —H or —$C_{1-4}$ alkyl; and
each $R^D$ is independently —H or —$C_{1-4}$ alkyl;

or alternatively $R^C$ and $R^D$ together with the N to which they are both attached form a 5- or 6-membered saturated heterocyclic ring containing the N to which they are both attached and optionally containing 1 or 2 additional heteroatoms independently selected from 1 or 2 N atoms, zero or 1 O atom, and zero or 1 S atom.

A sub-class of the third class includes compounds of Formula II, and pharmaceutically acceptable salts thereof, wherein $R^1$ is 4-fluorobenzyl; $R^2$ and $R^3$ are each independently —H, methyl, ethyl, n-propyl, or isopropyl; $R^4$ is —H, methyl, ethyl, OH, methoxy, $NH_2$, or 4-morpholinyl; and $R^5$ is:

(1) methyl,
(2) ethyl,
(3) $(CH_2)_{1-2}$—OH,
(4) $(CH_2)_{1-2}$—CN,
(5) $C_{3-6}$ cycloalkyl, or
(6) $CH_2$—$R^K$, wherein $R^K$ is phenyl, 4-(acetylamino)phenyl, 4-carboxyphenyl, 3-chlorophenyl, 4-chlorophenyl, 2,3-dichlorophenyl, 3,4-dichlorophenyl, 2-chloro-4-fluorophenyl, 3-chloro-4-fluorophenyl, 2-cyanophenyl, 4-fluoro-2-(methylaminocarbonyl)phenyl, 4-fluoro-2-methoxyphenyl, 2-fluorophenyl, 3-fluorophenyl, 4-fluorophenyl, 2,3-difluorophenyl, 2,4-difluorophenyl, 3,4-difluorophenyl, 2,3,4-trifluorophenyl, 2-methoxyphenyl, 3-methoxyphenyl, 4-methoxyphenyl, 3-(methylaminocarbonyl)phenyl, 2-methylphenyl, 3-methylphenyl, 4-methylphenyl, 2,4-dimethylphenyl, 3-trifluoromethylphenyl, or 1,3-benzodioxolyl.

A fourth class of the present invention includes compounds of Formula II, and pharmaceutically acceptable salts thereof, wherein:

$R^1$ is —$C_{1-4}$ alkyl;
$R^2$ and $R^3$ are each independently —H or —$C_{1-4}$ alkyl;
$R^4$ is —H, —$C_{1-4}$ alkyl, —OH, —O—$C_{1-4}$ alkyl, —O—$C_{1-4}$ haloalkyl, —CN, —$NO_2$, —N($R^C$)$R^D$, —C(O)N($R^C$)$R^D$, —C(O)$R^A$, —$CO_2R^A$, —$SR^A$, —S(O)$R^A$, —$SO_2R^A$, or —$SO_2N(R^A)R^B$;
$R^5$ is —$CH_2$—$R^K$, wherein $R^K$ is:
(A) an optionally substituted phenyl of formula:

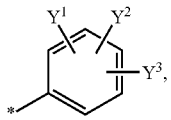

wherein the asterisk * denotes the point of attachment to the rest of the compound,
$Y^1$ and $Y^2$ are each independently selected from the group consisting of —H, halogen, —$C_{1-4}$ alkyl, —O—$C_{1-4}$ alkyl, —$C_{1-4}$ fluoroalkyl, —CN, —$CO_2H$, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, and —N($C_{1-4}$ alkyl)C(O)—$C_{1-4}$ alkyl, and $Y^3$ is —H, halogen, —$C_{1-4}$ alkyl, —O—$C_{1-4}$ alkyl, —$C_{1-4}$ fluoroalkyl, —$SO_2$—$C_{1-4}$ alkyl, —C(O)—NH ($C_{1-4}$ alkyl), —C(O)—N($C_{1-4}$ alkyl)$_2$, or HetB, or (B) a 9- or 10-membered benzofused heterocyclic ring containing 1 or 2 heteroatoms independently selected from N, O and S;

HetB is a 5- or 6-membered heteroaromatic ring containing from 1 to 4 heteroatoms independently selected from N, O and S, wherein the heteroaromatic ring is optionally substituted with 1 or 2 substituents each of which is independently a —$C_{1-3}$ alkyl;

each $R^A$ is independently —H or —$C_{1-4}$ alkyl;
each $R^B$ is independently —H or —$C_{1-4}$ alkyl;
each $R^C$ is independently —H or —$C_{1-4}$ alkyl; and
each $R^D$ is independently —H or —$C_{1-4}$ alkyl;

or alternatively $R^C$ and $R^D$ together with the N to which they are both attached form a 5- or 6-membered saturated heterocyclic ring containing the N to which they are both attached and optionally containing 1 or 2 additional heteroatoms independently selected from 1 or 2 N atoms, zero or 1 O atom, and zero or 1 S atom.

A sub-class of the fourth class includes compounds of Formula II, and pharmaceutically acceptable salts thereof, wherein $R^1$ is methyl or ethyl; $R^2$ and $R^3$ are each independently —H, methyl, ethyl, n-propyl, or isopropyl; $R^4$ is —H, methyl, ethyl, OH, methoxy, $NH_2$, or 4-morpholinyl; and $R^5$ is —$CH_2$—$R^K$, wherein $R^K$ is phenyl, 4-(acetylamino)phenyl, 4-carboxyphenyl, 3-chlorophenyl, 4-chlorophenyl, 2,3-dichlorophenyl, 3,4-dichlorophenyl, 2-chloro-4-fluorophenyl, 3-chloro-4-fluorophenyl, 2-cyanophenyl, 4-fluoro-2-(methylaminocarbonyl)phenyl, 4-fluoro-2-methoxyphenyl, 2-fluorophenyl, 3-fluorophenyl, 4-fluorophenyl, 2,3-difluorophenyl, 2,4-difluorophenyl, 3,4-difluorophenyl, 2,3,4-trifluorophenyl, 2-methoxyphenyl, 3-methoxyphenyl, 4-methoxyphenyl, 3-(methylaminocarbonyl)phenyl, 2-methylphenyl, 3-methylphenyl, 4-methylphenyl, 2,4-dimethylphenyl, 3-trifluoromethylphenyl, or 1,3-benzodioxolyl.

A fifth class of the present invention includes compounds of Formula I, and pharmaceutically acceptable salts thereof, wherein $R^1$ is as defined in the third embodiment; $R^5$ is as defined in the twentieth embodiment; each HetB is independently a 5- or 6-membered heteroaromatic ring containing from 1 to 4 heteroatoms independently selected from N, O and S, wherein the heteroaromatic ring is optionally substituted with 1 or 2 substituents each of which is independently a —$C_{1-3}$ alkyl; and all other variables are as originally defined; and with the proviso that $R^5$ is —$C_{1-4}$ alkyl substituted with $R^K$, when $R^1$ is —$C_{1-4}$ alkyl.

A sixth class of the present invention includes compounds of Formula I, and pharmaceutically acceptable salts thereof, wherein $R^1$ and $R^5$ are each as defined in the second class; and all other variables are as originally defined; and with the proviso that $R^5$ is —$CH_2$—$R^K$, when $R^1$ is —$C_{1-4}$ alkyl.

A seventh class of the present invention includes compounds of Formula I, and pharmaceutically acceptable salts thereof, wherein:

$R^1$ is —$C_{1-4}$ alkyl or —$C_{1-4}$ alkyl substituted with —$C_{3-6}$ cycloalkyl, wherein the cycloalkyl is optionally substituted with from 1 to 3 substituents each of which is independently —$C_{1-4}$ alkyl, —OH, —O—$C_{1-4}$ alkyl, or —$C_{1-4}$ haloalkyl;

$R^2$ is —H or —$C_{1-4}$ alkyl;

or alternatively $R^1$ and $R^2$ together with the ring nitrogen to which $R^1$ is attached and the ring carbon to which $R^2$ is attached form a 5- to 7-membered, saturated heterocyclic ring in which the portion of the ring formed from $R^1$ and $R^2$ is a methylene chain of formula $(CH_2)_{3-5}$, wherein the methylene chain is optionally substituted with —$C_{1-4}$ alkyl, —OH, or oxo;

$R^3$ is:
- (1) —H,
- (2) —$C_{1-4}$ alkyl, or
- (3) —$C_{1-4}$ alkyl substituted with —OH, —O—$C_{1-4}$ alkyl, —C(O)$R^A$, —CO$_2R^A$, —S$R^A$, —S(O)$R^A$, —SO$_2R^A$, or —N($R^A$)SO$_2R^B$;

or alternatively $R^2$ and $R^3$ together with the carbon atoms to which they are attached form:
- (i) a 3- to 6-membered saturated carbocyclic ring which is optionally substituted with from 1 to 2 substituents each of which is independently —$C_{1-4}$ alkyl, —OH, or —O—$C_{1-4}$ alkyl,
- (ii) a benzene ring, which is optionally substituted is optionally substituted with from 1 to 4 substituents each of which is independently halogen, —$C_{1-4}$ alkyl, —O—$C_{1-4}$ alkyl, —$C_{1-4}$ fluoroalkyl, —O—$C_{1-4}$ fluoroalkyl, —CN, —CO$_2$H, —CO$_2$—$C_{1-4}$ alkyl, —SO$_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl, or
- (iii) a 6-membered heteroaromatic ring containing a total of from 1 to 2 N atoms, wherein the heteroaromatic ring is optionally substituted with from 1 to 3 substituents each of which is independently —$C_{1-4}$ alkyl, —O—$C_{1-4}$ alkyl or —OH;

wherein $R^7$ is absent, when $R^2$ and $R^3$ together with the carbon atoms to which they are attached form a benzene ring or a heteroaromatic ring;

$R^4$ is:
- (1) —H,
- (2) —$C_{1-4}$ alkyl,
- (3) —$C_{1-4}$ haloalkyl,
- (4) —$C_{1-4}$ alkyl substituted with —OH, —O—$C_{1-4}$ alkyl, —N($R^A$)$R^B$, —C(O)N($R^A$)$R^B$, —C(O)$R^A$, —CO$_2R^A$, —S$R^A$, —S(O)$R^A$, —SO$_2R^A$, or —SO$_2$N($R^A$)$R^B$,
- (5) —OH,
- (6) —O—$C_{1-4}$ alkyl,
- (7) —O—$C_{1-4}$ haloalkyl,
- (8) —CN,
- (9) —NO$_2$,
- (10) —N($R^C$)$R^D$,
- (11) —C(O)N($R^C$)$R^D$,
- (12) —C(O)$R^A$,
- (13) —CO$_2R^A$,
- (14) —S$R^A$,
- (15) —S(O)$R^A$,
- (16) —SO$_2R^A$,
- (17) —SO$_2$N($R^A$)$R^B$,
- (18) —N($R^A$)C(O)$R^B$,
- (20) —N($R^A$)SO$_2R^B$,
- (21) —N($R^A$)C(O)N($R^A$)$R^B$,
- (22) —N($R^A$)C(O)C(O)N($R^A$)$R^B$,
- (23) halogen,
- (24) —S—C(O)N($R^C$)$R^D$,
- (25) —N=C($R^A$)—N($R^C$)$R^D$,
- (26) —C(O)N($R^A$)—(CH$_2$)$_{1-3}$—N($R^C$)$R^D$,
- (27) —C(O)—(CH$_2$)$_{1-3}$—N($R^C$)$R^D$,
- (28) —C(O)N($R^A$)—(CH$_2$)$_{1-3}$—$C_{1-4}$ fluoroalkyl,
- (29) —N(SO$_2R^A$)—(CH$_2$)$_{1-2}$C(O)N($R^C$)$R^D$,
- (30) —N[C(O)$R^A$]—(CH$_2$)$_{1-2}$C(O)N($R^C$)$R^D$,
- (31) —N(SO$_2R^A$)—CH$_2$—CH=CH$_2$,
- (32) —N(SO$_2R^A$)—(CH$_2$)$_{1-2}$-CycL,
- (33) —$C_{1-4}$ alkyl substituted HetE,
- (34) —$C_{1-4}$ alkyl substituted CycL, AryL, HetL, or HetS,
- (35) HetL or HetS,
- (36) —C(O)N($R^A$)-CycL,
- (37) —C(O)N($R^A$)-AryL, with the proviso that AryL is dihydroindenyl or tetrahydronaphthyl and is attached to the rest of the molecule via a non-aromatic ring carbon,
- (38) —C(O)N($R^A$)—(CH$_2$)$_{1-2}$-AryL,
- (39) —(CH$_2$)$_{1-2}$—S-AryL,
- (40) —(CH$_2$)$_{1-2}$—S(O)$_2$-AryL,
- (41) —N($R^A$)SO$_2$-CycL, or
- (42) —SO$_2$-CycL;

CycL is —$C_{3-6}$ cycloalkyl which is optionally substituted with from 1 to 2 substituents each of which is independently —$C_{1-4}$ alkyl, —OH, or —O—$C_{1-4}$ alkyl;

AryL is dihydroindenyl, tetrahydronaphthyl, naphthyl, or phenyl, wherein the dihydroindenyl, tetrahydronaphthyl, naphthyl, or phenyl is optionally substituted with from 1 to 3 substituents each of which is independently halogen, —$C_{1-4}$ alkyl, —O—$C_{1-4}$ alkyl, —$C_{1-4}$ fluoroalkyl, —O—$C_{1-4}$ fluoroalkyl, —CN, —CO$_2$H, —CO$_2$—$C_{1-4}$ alkyl, —SO$_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl;

HetE is a 5- or 6-membered, saturated heterocyclic ring containing from 1 to 2 heteroatoms independently selected from 1 to 2 N atoms, zero to 1 O atom, and zero to 1 S atom, where the S is optionally oxidized to S(O) or S(O)$_2$, with the proviso that the ring is attached to the rest of the molecule via a ring N atom, and wherein the saturated heterocyclic ring is optionally substituted with from 1 to 4 substituents each of which is independently —$C_{1-4}$ alkyl, oxo, —C(O)$R^A$, or —S(O)$_2R^A$;

HetL is a 5- or 6-membered heteroaromatic ring containing a total of from 1 to 4 heteroatoms independently selected from zero to 4 N atoms, zero to 1 O atom, and zero to 1 S atom, wherein the heteroaromatic ring is optionally substituted with from 1 to 3 substituents each of which is independently —CN, —$C_{1-4}$ alkyl, —O—$C_{1-4}$ alkyl, oxo, —OH, or —(CH$_2$)$_{1-2}$C(O)N($R^A$)$R^B$;

HetS is a saturated or mono-unsaturated 5- or 6-membered heterocyclic ring, wherein the ring contains a total of from 1 to 3 heteroatoms independently selected from 1 to 3 N atoms, zero to 1 O atom, and zero to 1 S atom, where the S is optionally oxidized to S(O) or S(O)$_2$, with the proviso that HetS is attached to the rest of the molecule via a ring carbon atom; and wherein the heterocyclic ring is optionally substituted with from 1 to 4 substituents each of which is independently —$C_{1-4}$ alkyl, oxo, —C(O)$R^A$, —CO$_2R^A$, —S(O)$R^A$, —S$R^A$, —S(O)$_2R^A$, or —(CH$_2$)$_{1-2}$C(O)N($R^A$)$R^B$;

$R^5$ is (CH$_2$)$_{1-2}$—$R^K$ or —CH(CH$_3$)—$R^K$, wherein $R^K$ is:

(A) an optionally substituted phenyl of formula:

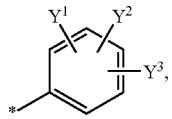

wherein the asterisk * denotes the point of attachment to the rest of the compound, Y$^1$ and Y$^2$ are each independently selected from the group consisting of —H, halogen, —C$_{1-4}$ alkyl, —O—C$_{1-4}$ alkyl, —C$_{1-4}$ fluoroalkyl, —O—C$_{1-4}$ fluoroalkyl, —CN, —CO$_2$H, —CO$_2$—C$_{1-4}$ alkyl, —SO$_2$—C$_{1-4}$ alkyl, —C(O)—NH(C$_{1-4}$ alkyl), —C(O)—N(C$_{1-4}$ alkyl)$_2$, —NHC(O)—C$_{1-4}$ alkyl, and —N(C$_{1-4}$ alkyl)C(O)—C$_{1-4}$ alkyl, and Y$^3$ is —H, halogen, —C$_{1-4}$ alkyl, —O—C$_{1-4}$ alkyl, —C$_{1-4}$ fluoroalkyl, —SO$_2$—C$_{1-4}$ alkyl, —C(O)—NH (C$_{1-4}$ alkyl), —C(O)—N(C$_{1-4}$ alkyl)$_2$, or HetB, or (B) a 9- or 10-membered benzofused heterocyclic ring containing 1 or 2 heteroatoms independently selected from N, O and S;

R$^6$ is —H;

R$^7$ is —H or —C$_{1-4}$ alkyl;

or alternatively R$^3$ and R$^7$ together with the carbon atom to which they are attached form a 3 to 6-membered saturated carbocyclic ring optionally substituted with from 1 to 2 C$_{1-4}$ alkyl;

HetB is a 5- or 6-membered heteroaromatic ring containing from 1 to 4 heteroatoms independently selected from N, O and S, wherein the heteroaromatic ring is optionally substituted with 1 or 2 substituents each of which is independently a —C$_{1-3}$ alkyl;

each R$^A$ is independently —H or —C$_{1-4}$ alkyl;
each R$^B$ is independently —H or —C$_{1-4}$ alkyl;
each R$^C$ is independently —H or —C$_{1-4}$ alkyl; and
each R$^D$ is independently —H or —C$_{1-4}$ alkyl;

or alternatively R$^C$ and R$^D$ together with the N to which they are both attached form a 5- or 6-membered saturated heterocyclic ring containing the N to which they are both attached and optionally containing 1 or 2 additional heteroatoms independently selected from 1 or 2 N atoms, zero or 1 O atom, and zero or 1 S atom, where the S is optionally oxidized to S(O) or S(O)$_2$, and wherein the saturated heterocyclic ring is optionally substituted with from 1 to 4 substituents each of which is independently —C$_{1-4}$ alkyl, oxo, —C(O)R$^A$, —CO$_2$R$^A$, S(O)$_2$R$^A$, or —CH$_2$—CH=CH$_2$.

An eighth class of the present invention includes compounds of Formula I, and pharmaceutically acceptable salts thereof, wherein:

R$^1$ is —C$_{1-4}$ alkyl or —CH$_2$-cyclopropyl;

R$^2$ is —H;

or alternatively R$^1$ and R$^2$ together with the ring nitrogen to which R$^1$ is attached and the ring carbon to which R$^2$ is attached form a 5- or 6-membered, saturated heterocyclic ring in which the portion of the ring formed from R$^1$ and R$^2$ is (CH$_2$)$_3$ or (CH$_2$)$_4$;

R$^3$ is —H, —C$_{1-3}$ alkyl, —(CH$_2$)$_{1-2}$OH, —(CH$_2$)$_{1-2}$SCH$_3$, —(CH$_2$)$_{1-2}$S(O)CH$_3$, —(CH$_2$)$_{1-2}$SO$_2$CH$_3$, —(CH$_2$)$_{1-2}$NHSO$_2$CH$_3$ or —(CH$_2$)$_{1-2}$N(CH$_3$)SO$_2$CH$_3$;

or alternatively R$^2$ and R$^3$ together with the carbon atoms to which they are attached form a 3-membered carbocyclic ring (i.e., a cyclopropyl ring fused to the tricyclic core, wherein R$^2$ and R$^3$ together form methylene);

R$^4$ is:
(1) —H,
(2) —C$_{1-3}$ alkyl,
(3) —(CH$_2$)$_{1-2}$OH, —CH(CH$_3$)OH, —C(CH$_3$)$_2$OH, —(CH$_2$)$_{1-2}$NH$_2$, —(CH$_2$)$_{1-2}$NH—C$_{1-3}$ alkyl, —(CH$_2$)$_{1-2}$N(C$_{1-3}$ alkyl)$_2$, —(CH$_2$)$_{1-2}$OCH$_3$, —(CH$_2$)$_{1-2}$CO$_2$CH$_3$, —(CH$_2$)$_{1-2}$SCH$_3$, —(CH$_2$)$_{1-2}$S(O)CH$_3$, or —(CH$_2$)$_{1-2}$SO$_2$CH$_3$,
(4) —O—C$_{1-3}$ alkyl,
(5) —NH$_2$, —N(H)—C$_{1-3}$ alkyl, or —N(C$_{1-3}$ alkyl)$_2$,
(6)

wherein * denotes the point of attachment to the rest of the molecule, (7) —C(O)NH$_2$, —C(O)N(H)—C$_{1-3}$ alkyl, or —C(O)N(C$_{1-3}$ alkyl)$_2$,
(8)

(9) —C(O)—C$_{1-3}$ alkyl,
(10) —CO$_2$—C$_{1-3}$ alkyl,
(11) —S—C$_{1-3}$ alkyl,
(12) —S(O)—C$_{1-3}$ alkyl,
(13) —SO$_2$—C$_{1-3}$ alkyl,
(14) —SO$_2$N(C$_{1-3}$ alkyl)$_2$,
(15) —NHC(O)—C$_{1-3}$ alkyl or —N(C$_{1-3}$ alkyl)C(O)—C$_{1-3}$ alkyl,

(16) —NHSO$_2$—C$_{1-3}$ alkyl or —N(C$_{1-3}$ alkyl)SO$_2$—C$_{1-3}$ alkyl,
(17) —NHC(O)NH(C$_{1-3}$ alkyl), —NHC(O)N(C$_{1-3}$ alkyl)$_2$, —N(C$_{1-3}$ alkyl)C(O)NH(C$_{1-3}$ alkyl), or —N(C$_{1-3}$ alkyl)C(O)N(C$_{1-3}$ alkyl)$_2$,
(18) —NHC(O)C(O)NH(C$_{1-3}$ alkyl), —NHC(O)C(O)N(C$_{1-3}$ alkyl)$_2$, —N(C$_{1-3}$ alkyl)C(O)C(O)NH(C$_{1-3}$ alkyl), or —N(C$_{1-3}$ alkyl)C(O)C(O)N(C$_{1-3}$ alkyl)$_2$,
(19) —Cl, —Br, or —F,
(20) —S—C(O)N(C$_{1-3}$ alkyl)$_2$,
(21) —N=CH—N(C$_{1-3}$ alkyl)$_2$ or —N=C(C$_{1-3}$ alkyl)-N(C$_{1-3}$ alkyl)$_2$,
(22) —C(O)NH—(CH$_2$)$_{2-3}$—N(C$_{1-3}$ alkyl)$_2$ or —C(O)N(C$_{1-3}$ alkyl)-(CH$_2$)$_{2-3}$—N(C$_{1-3}$ alkyl)$_2$,
(23)

[structures: C(O)CH$_2$-N-pyrrolidinyl, C(O)CH$_2$-N-pyrrolidinonyl, C(O)CH$_2$-N-piperidinyl, C(O)CH$_2$-N-piperidinonyl, C(O)CH$_2$-N-piperazinyl-N-CH$_3$, or C(O)CH$_2$-N-piperazinonyl-N-CH$_3$]

(24) —C(O)NHCH$_2$CH$_2$F, —C(O)NHCH$_2$CHF$_2$, or —C(O)NHCH$_2$CF$_3$,
(25) —N(SO$_2$—C$_{1-3}$ alkyl)-(CH$_2$)$_{1-2}$C(O)N(C$_{1-3}$ alkyl)$_2$,
(26) —N[C(O)—C$_{1-3}$ alkyl]-(CH$_2$)$_{1-2}$C(O)N(C$_{1-3}$ alkyl)$_2$,
(27) —N(SO$_2$—C$_{1-3}$ alkyl)-CH$_2$—CH=CH$_2$,
(28) —N(SO$_2$—C$_{1-3}$ alkyl)-CH$_2$-CycL,
(29)

[structures: CH$_2$-N-pyrrolidinyl, CH$_2$-N-pyrrolidinonyl, CH$_2$-N-isothiazolidine dioxide, CH$_2$-N-piperidinyl, CH$_2$-N-piperidinonyl, CH$_2$-N-thiazinane dioxide, CH$_2$-N-piperazinyl-NH, CH$_2$-N-piperazinyl-N-CH$_3$, CH$_2$-N-piperazinyl-N-CH$_2$CH$_3$, CH$_2$-N-piperazinedionyl-N-CH$_2$CH$_3$, CH$_2$-N-thiomorpholinyl, CH$_2$-N-thiomorpholine dioxide, CH$_2$-N-morpholinyl, CH(CH$_3$)-N-pyrrolidinyl, CH(CH$_3$)-N-pyrrolidinonyl, CH(CH$_3$)-N-piperidinyl, CH(CH$_3$)-N-piperidinonyl, CH(CH$_3$)-N-thiomorpholinyl, CH(CH$_3$)-N-morpholinyl, CH(CH$_3$)-N-thiazinane dioxide, or CH(CH$_3$)-N-thiomorpholine dioxide]

(30) —CH$_2$-HetL,
(31) HetL,
(32)

[structures: 4-pyrrolidinonyl or 1,2,4-triazinone]

(33) —C(O)NH-CycL or —C(O)N(C$_{1-3}$ alkyl)-CycL,
(34)

[structure: C(O)—NH-indanyl]

(35) —C(O)NH—CH$_2$-AryL or —C(O)N(CH$_3$)—CH$_2$-AryL,
(36) —CH$_2$—S-AryL,
(37) —CH$_2$—S(O)$_2$-AryL,
(38) —N(C$_{1-3}$ alkyl)SO$_2$-CycL, or
(39) —SO$_2$-CycL;

CycL is cyclopropyl, cyclobutyl, cyclopentyl, or cyclohexyl;
AryL is phenyl, which is optionally substituted with from 1 to 3 substituents each of which is independently —Cl, —Br, —F, —C$_{1-3}$ alkyl, —O—C$_{1-3}$ alkyl, —CF$_3$, —OCF$_3$, —CO$_2$CH$_3$, —SO$_2$CH$_3$, —C(O)NH(CH$_3$), —C(O)N(CH$_3$)$_2$, —NHC(O)CH$_3$, or —N(CH$_3$)C(O)CH$_3$;
HetL is (i) a 5- or 6-membered heteroaromatic ring selected from the group consisting of pyrrolyl, pyrazolyl, imidazolyl, triazolyl, tetrazolyl, furyl, thienyl, oxazolyl, isoxazolyl, thiazolyl, isothiazolyl, pyridinyl, pyrimidinyl, and pyrazinyl, wherein the heteroaromatic ring is optionally substituted with from 1 to 3 substituents each of which is independently —CN, —$C_{1-4}$ alkyl, —O—$C_{1-4}$ alkyl, —OH, or $(CH_2)_{1-2}C(O)N(C_{1-3}$ alkyl$)_2$, (ii) 2-oxo-pyridin-1(2H)-yl, (iii) 4-cyano-2-oxo-pyridin-1(2H)-yl, (iv) 1-($C_{1-4}$ alkyl)-6-oxo-1,6-dihydropyridin-3-yl, or (v) 1-{[(di-$C_{1-3}$ alkylamino)carbonyl]methyl}-6-oxo-1,6-dihydropyridin-3-yl;

$R^5$ is

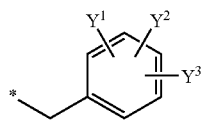

wherein the asterisk * denotes the point of attachment to the rest of the compound;

$Y^1$ and $Y^2$ are each independently selected from the group consisting of —H, —Cl, —Br, —F, —$C_{1-4}$ alkyl, —O—$C_{1-4}$ alkyl, —$CF_3$, —$OCF_3$, —$CO_2CH_3$, —$SO_2CH_3$, —$C(O)NH(CH_3)$, —$C(O)N(CH_3)_2$, —$NHC(O)CH_3$ and —$N(CH_3)C(O)CH_3$; and $Y^3$ is —H, —Cl, —Br, —F, —$C_{1-4}$ alkyl, —O—$C_{1-4}$ alkyl, —$CF_3$, —$SO_2CH_3$, —$C(O)NH(CH_3)$, or —$C(O)N(CH_3)_2$;

$R^6$ is —H; and $R^7$ is —H or —$C_{1-3}$ alkyl.

A sub-class of the eighth class includes compounds of Formula I, and pharmaceutically acceptable salts thereof, wherein $R^5$ is 4-fluorobenzyl or 3-chloro-4-fluorobenzyl; and all other variables are as defined in the eighth class. Another sub-class of the eighth class includes compounds of Formula I, and pharmaceutically acceptable salts thereof, wherein $R^5$ is 4-fluorobenzyl; and all other variables are as defined in the eighth class. Still another sub-class of the eighth class includes compounds of Formula I, and pharmaceutically acceptable salts thereof, wherein $R^5$ is 3-chloro-4-fluorobenzyl; and all other variables are as defined in the eighth class.

A ninth class of the present invention includes compounds of Formula I, and pharmaceutically acceptable salts thereof, wherein: $R^1$ is —$CH_3$, —$CH_2CH_3$, or —$CH(CH_3)_2$; $R^2$ is H; $R^3$ is —$CH_3$ or —$CH_2OH$; $R^4$ is —H, —$CH_3$, —C(O)N(H)CH_3$, —$C(O)N(H)CH_2CH_3$, —$C(O)N(CH_3)_2$, —$N(CH_3)SO_2CH_3$, —$N(CH_2CH_3)SO_2CH_3$, or $SO_2CH_3$; $R^5$ is 4-fluorobenzyl or 3-chloro-4-fluorobenzyl; $R^6$ is H; and $R^7$ is H. A sub-class of the ninth class includes compounds of Formula I, and pharmaceutically acceptable salts thereof, wherein $R^3$ is

and all other variables are as defined in the ninth class.

It is to be understood that additional embodiments of the present invention include, but are not limited to, compounds of Formula I or Formula II, wherein each of two or three or more of $R^1$, $R^2$, $R^3$, $R^4$, $R^5$, $R^6$ and $R^7$ is independently defined in accordance with one of the foregoing embodiments, aspects, classes, or sub-classes as set forth above. Any and all possible combinations of these variables in Formula I and II are within the scope of the present invention.

Another embodiment of the present invention is a compound, or a pharmaceutically acceptable salt thereof, selected from the group consisting of the compounds set forth in Examples 1 to 209. Another embodiment of the present invention is a compound, or a pharmaceutically acceptable salt thereof, selected from the group consisting of the compounds set forth in Examples 1 to 44 and 47 below. Still another embodiment of the present invention is a compound, or a pharmaceutically acceptable salt thereof, selected from the group consisting of the compounds set forth in Examples 37, 50, 56, 62, 69, 86, 87, 88, 151, 153, 159-A, 159-B, 166, 189, 193, and 205.

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), further comprising an effective amount of an HIV infection/AIDS treatment/prophylaxis agent selected from the group consisting of HIV/AIDS antiviral agents, immunomodulators, and anti-infective agents.

(d) The pharmaceutical composition of (c), wherein the HIV infection/AIDS agent is an antiviral selected from the group consisting of HIV protease inhibitors, non-nucleoside HIV reverse transcriptase inhibitors, and nucleoside HIV reverse transcriptase inhibitors.

(e) A pharmaceutical combination which is (i) a compound of Formula I and (ii) an HIV infection/AIDS treatment/prophylaxis agent selected from the group consisting of HIV/AIDS antiviral agents, immunomodulators, and anti-infective agents; wherein the compound of Formula I and the HIV infection/AIDS treatment/prophylaxis agent are each employed in an amount that renders the combination effective for inhibiting HIV integrase, for treating or preventing infection by HIV, or for preventing, treating or delaying the onset of AIDS.

(f) The combination of (e), wherein the HIV infection/AIDS treatment/prophylaxis agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject an effective amount of a compound of Formula I.

(h) A method of preventing or treating infection by HIV in a subject in need thereof which comprises administering to the subject an effective amount of a compound of Formula I.

(i) The method of (h), wherein the compound of Formula (I) is administered in combination with an effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject an effective amount of a compound of Formula I.

(k) The method of (j), wherein the compound is administered in combination with an effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment/prophylaxis agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkylene" refers to any linear or branched chain alkylene group (i.e., a bivalent alkane radical, or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The term "C(O)" refers to carbonyl. The terms "$S(O)_2$" and "$SO_2$" each refer to sulfonyl. The term "S(O)" refers to sulfinyl.

The symbols "*" and "⌇" each refer to the point of attachment of a functional group or other chemical moiety to the rest of the molecule of which it is a part.

The term "cycloalkyl" refers to any cyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "$C_{4-7}$ azacycloalkyl" (or "$C_4$-$C_7$ azacycloalkyl") means a saturated cyclic ring consisting of one nitrogen and from four to seven carbon atoms (i.e., pyrrolidinyl, piperidinyl, azepanyl, or octahydroazocinyl). The term "$C_{4-7}$ oxacycloalkyl" (or "$C_4$-$C_7$ oxacycloalkyl") means a saturated cyclic ring consisting of one oxygen and from four to seven carbon atoms. The term "$C_{4-7}$ thiacycloalkyl" (or "$C_4$-$C_7$ thiacycloalkyl") means a saturated cyclic ring consisting of one sulfur and from four to seven carbon atoms.

The term "$C_{3-6}$ diazacycloalkyl" (or "$C_3$-$C_6$ diazacycloalkyl") means a saturated cyclic ring consisting of two nitrogens and from three to six carbon atoms (e.g., imidazolidinyl, pyrazolidinyl, or piperazinyl). The term "$C_{3-6}$ oxazacycloalkyl" (or "$C_3$-$C_6$ oxazacycloalkyl") means a saturated cyclic ring consisting of one oxygen, one nitrogen and from three to six carbon atoms. The term "$C_{3-6}$ thiazacycloalkyl" (or "$C_3$-$C_6$ thiazacycloalkyl") means a saturated cyclic ring consisting of one sulfur, one nitrogen and from three to six carbon atoms.

The term "aryl" refers to (i) phenyl or (ii) a 9- or 10-membered bicyclic, fused carbocyclic ring system in which at least one ring is aromatic. A class of aryls suitable for use in the present invention is phenyl, naphthyl, and indenyl. Another class of suitable aryls is phenyl and naphthyl. A particularly suitable aryl is phenyl.

The term "heteroaryl" refers to (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain a heteroatom, at least one ring is aromatic, each N is optionally in the form of an oxide, and each S in a ring which is not aromatic is optionally S(O) or $S(O)_2$. Suitable heteroaryls include, for example, pyridinyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, quinolinyl, tetrahydroquinolinyl, isoquinolinyl, tetrahydroisoquinolinyl, indolyl, isoindolyl, benzodioxolyl, benzopiperidinyl, benzisoxazolyl, benzoxazolyl, chromenyl, chromanyl, isochromanyl, cinnolinyl, quinazolinyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, 2,3-dihydrobenzo-1,4-dioxinyl (i.e.,

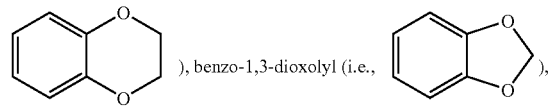

thiazolyl, and isothiazolyl.

A class of heteroaryls suitable for use in the present invention consists of 5- and 6-membered heteroaromatic rings containing from 1 to 4 heteroatoms independently selected from N, O and S, wherein each N is optionally in the form of an oxide. Another class of suitable heteroaryls consists of 5- and 6-membered heteroaromatic ring containing from 1 to 4 heteroatoms independently selected from zero to 4 N atoms, zero or 1 O atom, and zero or 1 S atom, wherein each N atom is optionally in the form of an oxide. Heteroaryls belonging to this class include pyridinyl, pyrrolyl, pyrazinyl, pyrimidinyl, pyridazinyl, triazinyl, furanyl, imidazolyl, pyrazolyl, triazolyl, tetrazolyl, oxazolyl, isooxazolyl, and oxadiazolyl.

Unless expressly stated to the contrary (see, e.g., the definition of HetS), any of the various aryl and heteroaryl groups defined herein are attached to the rest of the compound at any ring atom (i.e., any carbon atom or any heteroatom) provided that a stable compound results.

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms.

When any variable (e.g., $R^A$, $R^B$, and HetB) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "is optionally substituted with from 1 to 5 substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., cycloalkyl, aryl, a heteroaromatic ring, or a saturated heterocyclic ring) provided such ring substitution is chemically allowed and results in a stable compound.

In instances where a hydroxy (—OH) substituent(s) is(are) permitted on a heteroaryl (e.g., a heteroaromatic ring) and keto-enol tautomerism is possible, it is understood that the substituent might in fact be present, in whole or in part, in the keto form, as exemplified here for a hydroxypyridinyl substituent:

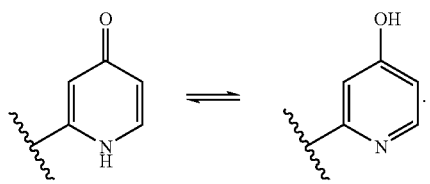

Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

In addition to the presence of oxo substituents due to keto-enol tautomerism as described in the preceding paragraph, oxo substituents are also permitted on saturated ring atoms present in a heteroaryl group (e.g., in the saturated heterocyclic ring of a benzofused bicyclic ring system).

Oxo-substituted heteroaryls also include nitrogen-containing heteroaryls in which the N atom is a tertiary atom (i.e., the N is bound to 3 carbon atoms) and the oxo group is attached to a ring carbon atom, as exemplified by the following oxopyridinyls:

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether individually or in mixtures, are within the scope of the present invention.

As would be recognized by one of ordinary skill in the art, compounds of the present invention can exist as tautomers, such as the following:

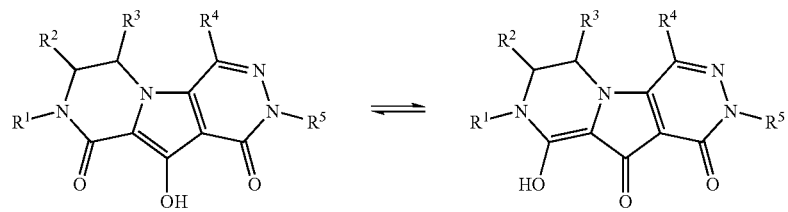

(for hydroxyaminopyridazine analogs:)

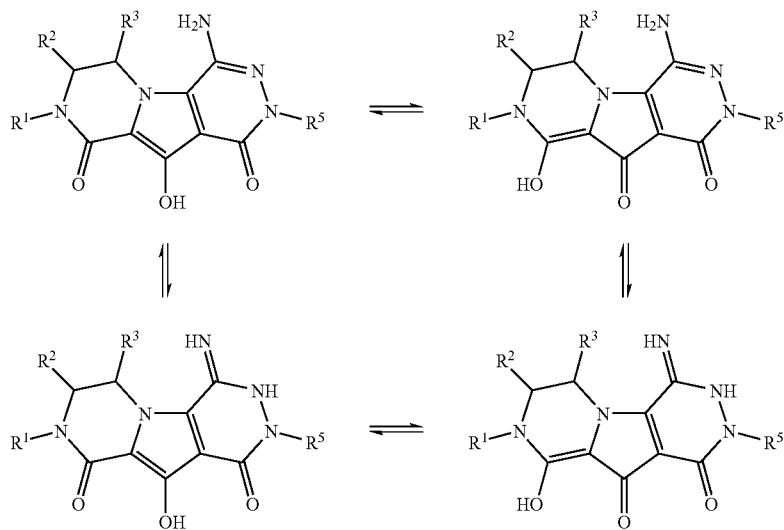

The present invention includes all tautomeric forms, individually and in mixtures.

Certain of the compounds of the present invention can exhibit a chirality resulting from the presence of bulky substituents that hinder the otherwise free rotation about a bond. These rotational enantiomers are named atropisomers, and the interconversion can be sufficiently slow to allow for their separation and characterization. See, e.g., J. March, *Advanced Organic Chemistry*, 4th Edition, John Wiley & Sons, 1992, pp. 101-102; and Ahmed et al., *Tetrahedron* 1998, 13277. For example, certain of the compounds of the present invention in which $R^4$ is (i) —C(=O)N($R^C$)$R^D$, wherein at least one of $R^C$ and $R^D$ is alkyl or $R^C$ and $R^D$ form a ring, or (ii) —N($R^A$)SO$_2$$R^B$, wherein at least one of $R^A$ and $R^B$ is alkyl, can have sufficiently hindered rotation along the bond linking $R^4$ to the tricyclic core of the molecule when $R^3$ is other than H (e.g., $R^3$=alkyl or substituted alkyl) to permit separation of the enantiomers using, e.g., column chromatography on a chiral stationary phase. The present invention includes atropisomers of compounds embraced by Formula I, singly and in mixtures.

The compounds of the present invention are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

Many clinical HIV isolates contain mutations that reduce their susceptibility to the antiretroviral drugs currently approved for clinical use and are therefore known as drug-resistant isolates. Such isolates can be resistant to protease inhibitors, nucleoside analog reverse transcriptase inhibitors, non-nucleoside reverse transcriptase inhibitors, gp41 inhibitors, or any combination thereof. The compounds of the present invention effectively inhibit replication of HIV isolates resistant to antiretroviral drugs currently in clinical use. Accordingly, these compounds provide a therapeutic option for HIV-infected patients harboring drug-resistant virus.

No clinical HIV isolates have been found to be resistant to HIV integrase inhibitors, possibly reflecting the fact that there are presently no HIV integrase inhibitors approved for clinical use. In preclinical laboratory experiments, it has been possible to select viruses resistant to integrase inhibitors in structural classes other than those embraced by the present invention, such as diketo acids, naphthyridine carboxamides, and dihydropyrimidine carboxamides. Mutations in the integrase gene that confer resistance (defined herein as greater than or equal to a 10-fold loss of sensitivity) to such compounds include T66I/S153Y, N155S, and F121Y. Certain compounds of the present invention have less than a 10-fold loss in sensitivity against viruses containing these and other mutations associated with resistance to other integrase inhibitors, and thus can be effective inhibitors of such viruses. Compounds of the present invention which are effective against such viruses include, for example, the compounds of Examples 37, 50, 56, 62, 69, 86, 87, 88, 151, 153, 159-A, 159-B, 166, 189, 193, and 205.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment or prophylaxis. When a compound of the invention or a prodrug thereof is provided in combination with one or more other active agents (e.g., antiviral agents useful for treating or preventing HIV infection or AIDS), "administration" and its variants are each understood to include provision of the compound or prodrug and other agents at the same time or at different times.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HIV integrase, preventing or treating HIV infection or preventing, treating or delaying the onset of AIDS, the compounds of the present invention, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, $18^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to the use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or AIDS, such as those disclosed in Table 1 of WO 01/38332 or in the Table in WO 02/30930. Suitable HIV/AIDS antivirals for use in combination with the compounds of the present invention include, for example, HIV protease inhibitors (e.g., indinavir, atazanavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). It will be understood that the scope of combinations of the compounds of this invention with HIV/AIDS antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of AIDS. The HIV/AIDS antivirals and other agents will typically be employed in these combinations in their conventional dosage ranges and regimens as reported in the art, including, for example, the dosages described in the *Physicians' Desk Reference*, 57th edition, Thomson P D R, 2003. The dosage ranges for a compound of the invention in these combinations are the same as those set forth above. It is understood that pharmaceutically acceptable salts of the compounds of the invention and/or the other agents (e.g., indinavir sulfate) can be used as well.

Abbreviations used in the instant specification, particularly the Schemes and Examples, include the following: AcOH=acetic acid; AIDS=acquired immunodeficiency syndrome; ARC=AIDS related complex; Bn=benzyl; CBZ=carbobenzoxy (alternatively, benzyloxycarbonyl); DME=1,2-dimethoxyethane; DMF=dimethylformamide; DMSO=dimethyl sulfoxide; EDC=1-ethyl-3-(3-dimethylaminopropyl) carbodiimide; EDTA=ethylenediaminetetraacetic acid; ES-MS=electron spray mass spectroscopy; Et=ethyl; EtOH=ethanol; HIV=human immunodeficiency virus; HOBT or HOBt=1-hydroxy benzotriazole hydrate; HPLC=high performance liquid chromatography; i-Bu=isobutyl; i-Pr=isopropyl; Me=methyl; MTBE=methyl tert-butyl ether; NMR=nuclear magnetic resonance; Ph=phenyl; t-Bu=tert-butyl; TFA=trifluoroacetic acid; THF=tetrahydrofuran.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Compounds of Formula I of the present invention can be prepared as shown in Schemes 1 to 5. Scheme 1 presents a general method for the preparation of compounds of the present invention embraced by Formula (I), wherein piperazin-2-one 1-1 is treated with dialkylalkoxymethylenemalonate 1-2 and then with a deprotonating agent (e.g., Li or Na bis(trimethylsilyl)amide or Na hydride) at a temperature in a range of from about 0 to 80° C. in an anhydrous non-protic solvent (e.g., DMF or THF) to give alkyl 8-hydroxy-1-oxo-1,2,3,4-tetrahydropyrrolopyrazine-7-carboxylate 1-4. The phenolic hydroxyl group on intermediate 1-4 is capped with appropriate protecting group (e.g., benzyl, methyl, or toluenesulfonyl), and is halogenated with a brominating agent (e.g., bromine or N-bromosuccinimide) in an appropriate solvent (e.g., a halogenated hydrocarbon such as dichloromethane or chloroform) to give the bromide 1-6. Conversion of bromide 1-6 to the corresponding carbonyl derivative 1-7 or 1-9 is achieved via a palladium catalyzed coupling reaction with vinyl alkylethers (Littke et al *J. Am. Chem. Soc.* 2001, 6989; Cabri et al *Tetrahedron Lett.* 1991, 1753) or appropriately substituted trialkyl(vinyl)tin 1-8 followed by an oxidation of the vinyl group (Littke et al *J. Am. Chem. Soc.* 2002, 6343; Ley et al *Org. Lett.* 2003, 185). Further elaboration of 1-7 or 1-9 to a compound of Formula I can be achieved through the formation of the third pyridazine ring by reaction with an appropriately substituted hydrazine. Alternatively, 1-10 can also be obtained by reaction of 1-7 or 1-9 with hydrazine, followed by alkylation with a suitable alkylating reagent. The protecting group on the phenolic hydroxy group can be removed before or after the formation of the tricyclic system. A description of protecting groups suitable for use herein and of methods for their attachment to and cleavage from the hydroxy group are described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3rd edition, 1999, and 2nd edition, 1991.

Certain of the dialkylalkoxymethylenemalonates suitable for use as 1-2 (e.g., diethylethoxymethylenemalonate or dimethylmethoxy-methylenemalonate) are available from commercial sources. Others can be obtained by preparative methods known in the art. For example, heterocyclylalkyloxymethylene malonates can be prepared by the method described in Boger et al., *J. Org. Chem* 1988, 3408, or routine variations thereof.

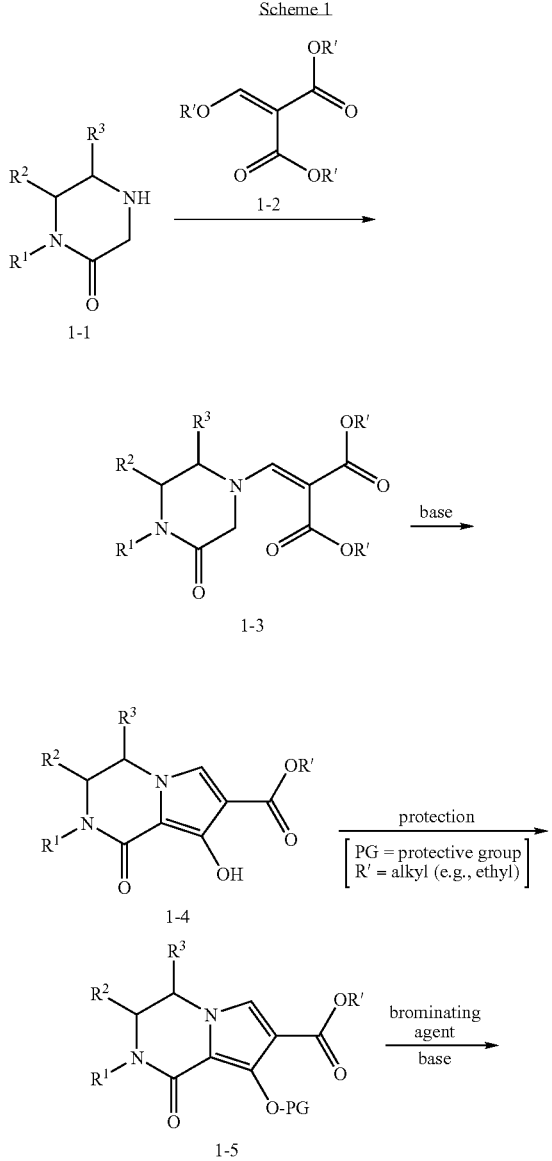

Scheme 1

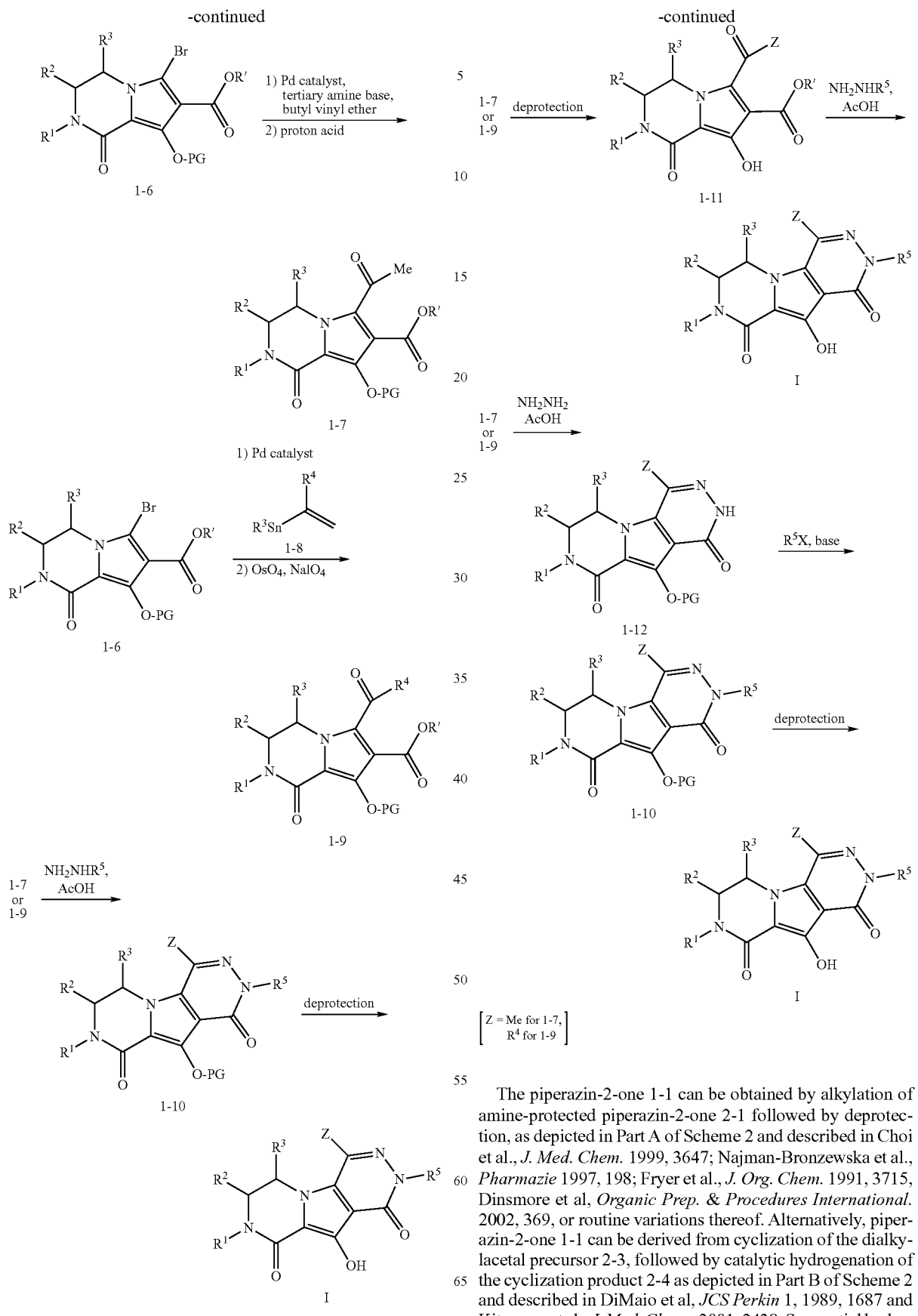

The piperazin-2-one 1-1 can be obtained by alkylation of amine-protected piperazin-2-one 2-1 followed by deprotection, as depicted in Part A of Scheme 2 and described in Choi et al., *J. Med. Chem.* 1999, 3647; Najman-Bronzewska et al., *Pharmazie* 1997, 198; Fryer et al., *J. Org. Chem.* 1991, 3715, Dinsmore et al, *Organic Prep. & Procedures International.* 2002, 369, or routine variations thereof. Alternatively, piperazin-2-one 1-1 can be derived from cyclization of the dialkylacetal precursor 2-3, followed by catalytic hydrogenation of the cyclization product 2-4 as depicted in Part B of Scheme 2 and described in DiMaio et al, *JCS Perkin* 1, 1989, 1687 and Kitamura et al., *J. Med. Chem.*, 2001, 2438. Sequential hydrogenation of the olefin (e.g., a Pd or Pt catalyst such as Pt on charcoal) followed by cleavage of the CBZ protecting group (e.g., Pd on charcoal or Pd hydroxide on charcoal) in a suitable protic solvent such as an alcohol (e.g., methanol or ethanol) under an atmosphere of hydrogen gas provided the required piperazin-2-one 1-1. Similarly, reaction of glycinamde 2-5 with pyruvic aldehyde provided the key pyrazinone 2-6, which was hydrogenated to provide piperazin-2-one 1-1 as depicted in Part C of Scheme 2, and as described in Wilfred et al., *JCS Chem Comm.,* 1980, 334. Hydrogenation in the presence of appropriate catalyst, chiral ligands, and additives provided optically enriched piperazin-2-one 1-1 in a manner similar those described in Zhang et al, *Chem. Rev,* 2003, 3029 and *Angew. Chem. Int. Ed.* 2001, 3425. Alternatively, stepwise reductive alkylation of aldehyde 2-7 with a suitably substituted amine and treatment of the resultant material with haloacetyl halide (such as chloroacetyl chloride or bromo acetylbromide) provided the intermediate 2-8. Based induced cyclization, followed by deprotection of the amino group provided piperazin-2-one 1-1 as depicted in Part D of Scheme 2 and described in Williams, et al., *J. Med. Chem.,* 1999, 3779, and Lewis, et al., *J. Med. Chem.,* 1995, 923. Alternatively, stepwise reduction of N-Boc aminoacid carboxamide 2-9 with an appropriate reducing reagent such as lithium aluminum hydride and coupling of the resultant amine with haloacetic acid can afford the intermediate amide 2-10. Based induced cyclization, followed by deprotection of the amino group provided piperazin-2-one 1-1 as depicted in Part E of Scheme 2 and described in Schanen et al., *Tetrahedron Lett,* 1994, 2533 & *Synthesis,* 1996, 833; Pohlmann et al., *J. Org. Chem.,* 1997, 1016. Piperazin-2-one 1-1 can alternatively be also prepared using methods described in Bernotas et al., *Tetrahedron Lett.* 1996, 7339; Saari et al., *J. Med. Chem.* 1990, 2590; Sugihara et al., *J. Med. Chem.* 1998, 489, Dinsmore et al, *Organic Prep. & Procedures International.* 2002, 369, or routine variations thereof.

Scheme 2

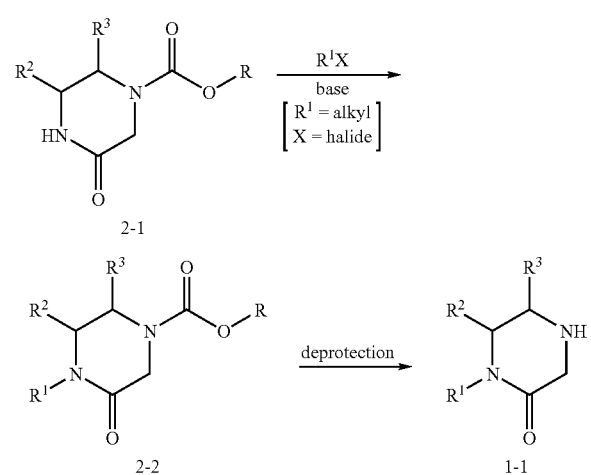

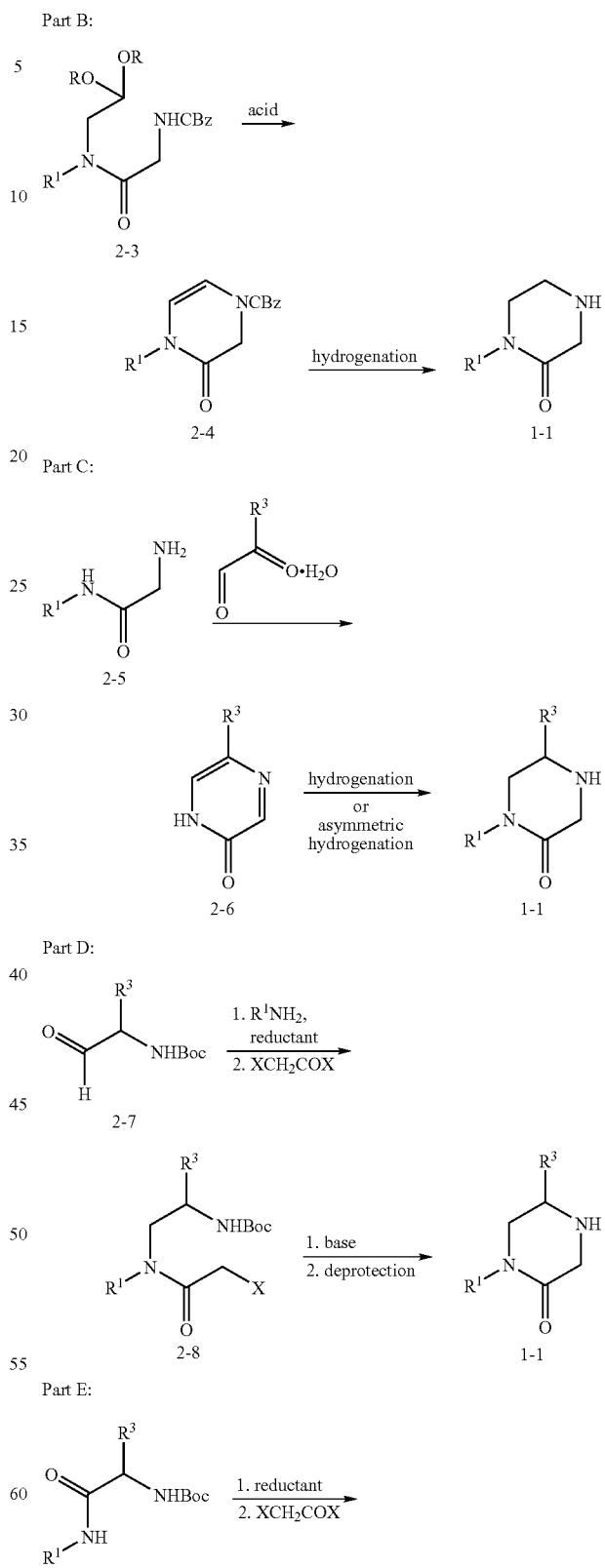

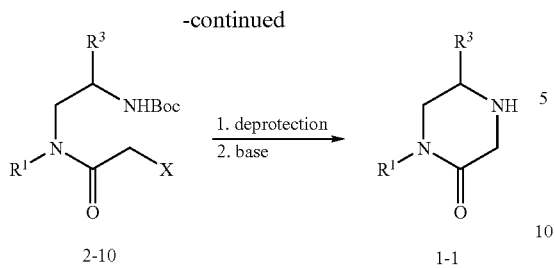

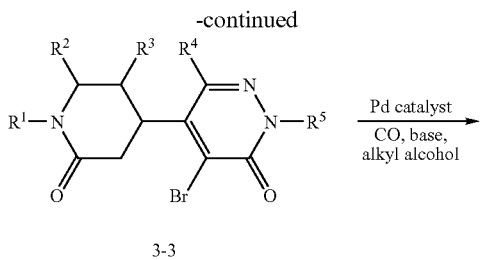

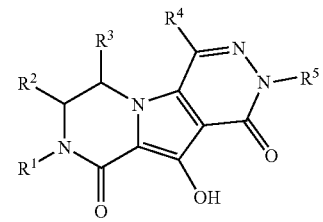

An alternative method for the preparation of compounds of the present invention embraced by Formula I is shown in Scheme 3, wherein dibromopyridazinone 3-1 is treated with base and alkylating reagent in an anhydrous, non-protic solvent such as DMF to give alkyl dibromopyridazinone 3-2. Reaction of the dibromide with piperazinone 1-1 in a solvent (e.g., an alkyl alcohol such as ethanol) provides the addition product 3-3 (Betti et al *J. Med. Chem.* 2003, 3555). Conversion of bromide 3-3 to the corresponding tricyclic product can be achieved via a palladium catalyzed carbonylation followed by a base catalyzed cyclization (Zhuang et al *J. Med. Chem.* 2003, 453).

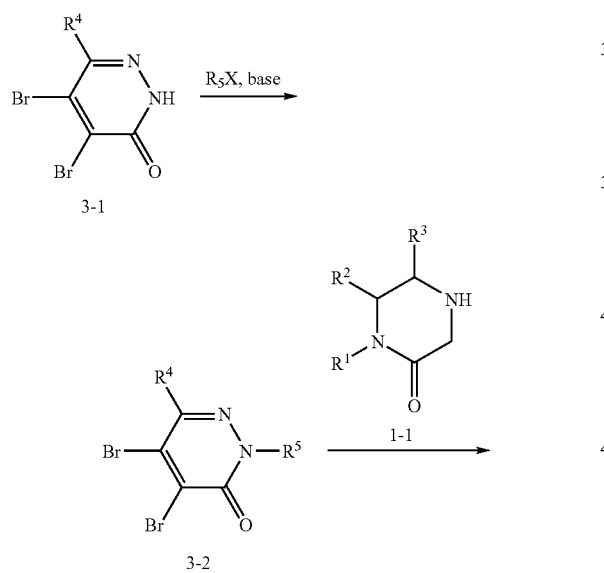

A general method for the preparation of compounds of Formula I in which the $R^4$ substituent bears an amino group linked directly to the tricyclic system is shown in Scheme 4, wherein the bicyclic bromo ester 1-6 is treated with zinc cyanide in the presence of palladium catalyst as described in Maddaford S. P. et al *SynLett,* 2236, 2003 to provide the corresponding nitrile 4-1. Reaction of the nitrile 4-1 with substituted hydrazines provides the tricyclic intermediate 4-2. Removal of the protecting group affords compound 4-3. The appropriate sequence of alkylation/acylation or alkylation/allylation or bisalkylation of 4-2 can provide 4-4, followed by deprotection to give 4-5. When $R^5$ is benzyl or substituted benzyl, nitrile 4-1 is alternatively and preferably treated with hydrazine to provide the corresponding tricyclic intermediate 4-6, which can be regio-selectively benzylated to provide intermediate 4-2 (see Scheme 4A).

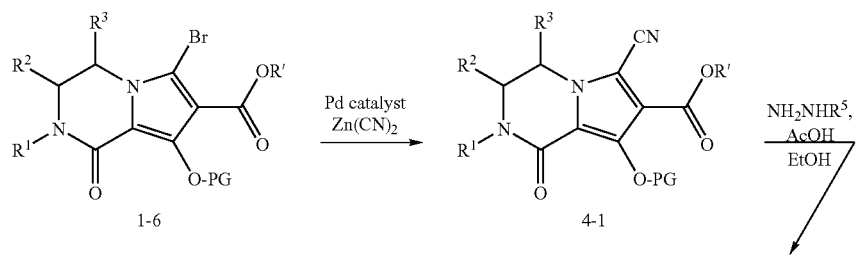

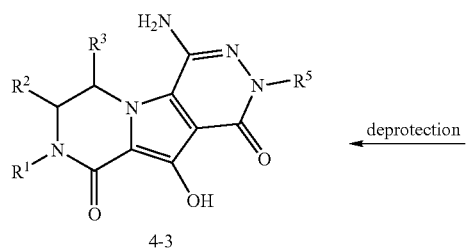

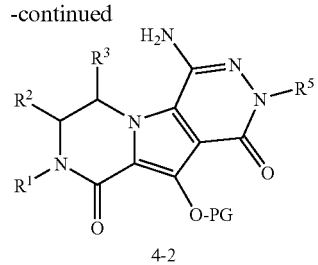

4-3    4-2

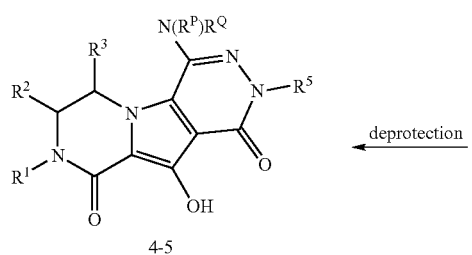

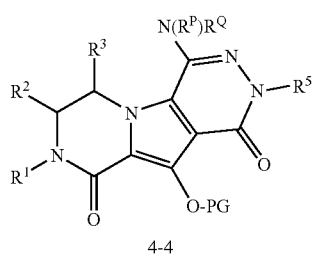

4-5    4-4

$$\begin{bmatrix} R^P = R^A \\ R^Q = R^B, C(O)R^B, \\ \quad CO_2R^B, SO_2R^B, \\ \quad SO_2N(R^A)R^B, \text{ or} \\ \quad C(O)C(O)N(R^A)R^B \end{bmatrix}$$

Scheme 4A

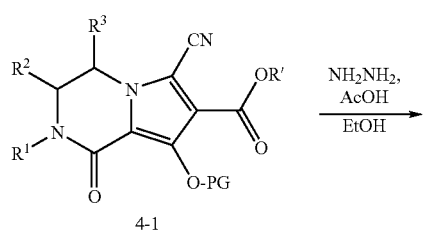

4-1

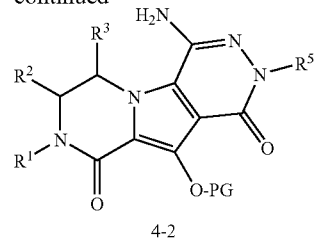

4-2

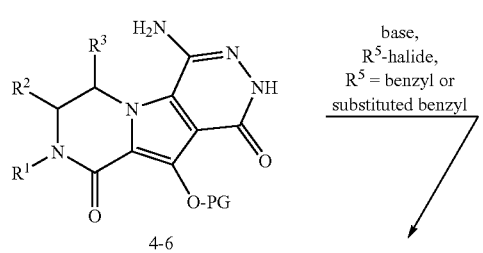

4-6

A general method for the preparation of compounds of Formula I in which the $R^4$ substituent bears an oxygen linker connected to the tricyclic system as is shown in Scheme 5, wherein the bicyclic ester 1-5 is hydrolyzed to the corresponding acid and converted to the corresponding acid chloride 5-1. Treatment of the acid chloride with appropriate substituted hydrazine provides the required hydrazine amide 5-2 (Fassler A. et al, *J. Med Chem.* 1996, 3203-2316). Bromination of 5-2 and selective removal of the protecting group on the hydrazine amide provides intermediate 5-3. Palladium (0) catalyzed carbonylation and cyclization provides the tricyclic intermediate 5-4. Removal of the protecting group leads to analog 5-5. The tricyclic intermediate 5-4 can be further elaborated by treatment with alkylating reagents/base or diazoalkanes to provide a mixture of O- and N-alkylated products. The O-alkylation product can be separated and the protecting group removed to provide analog 5-7.

Scheme 5

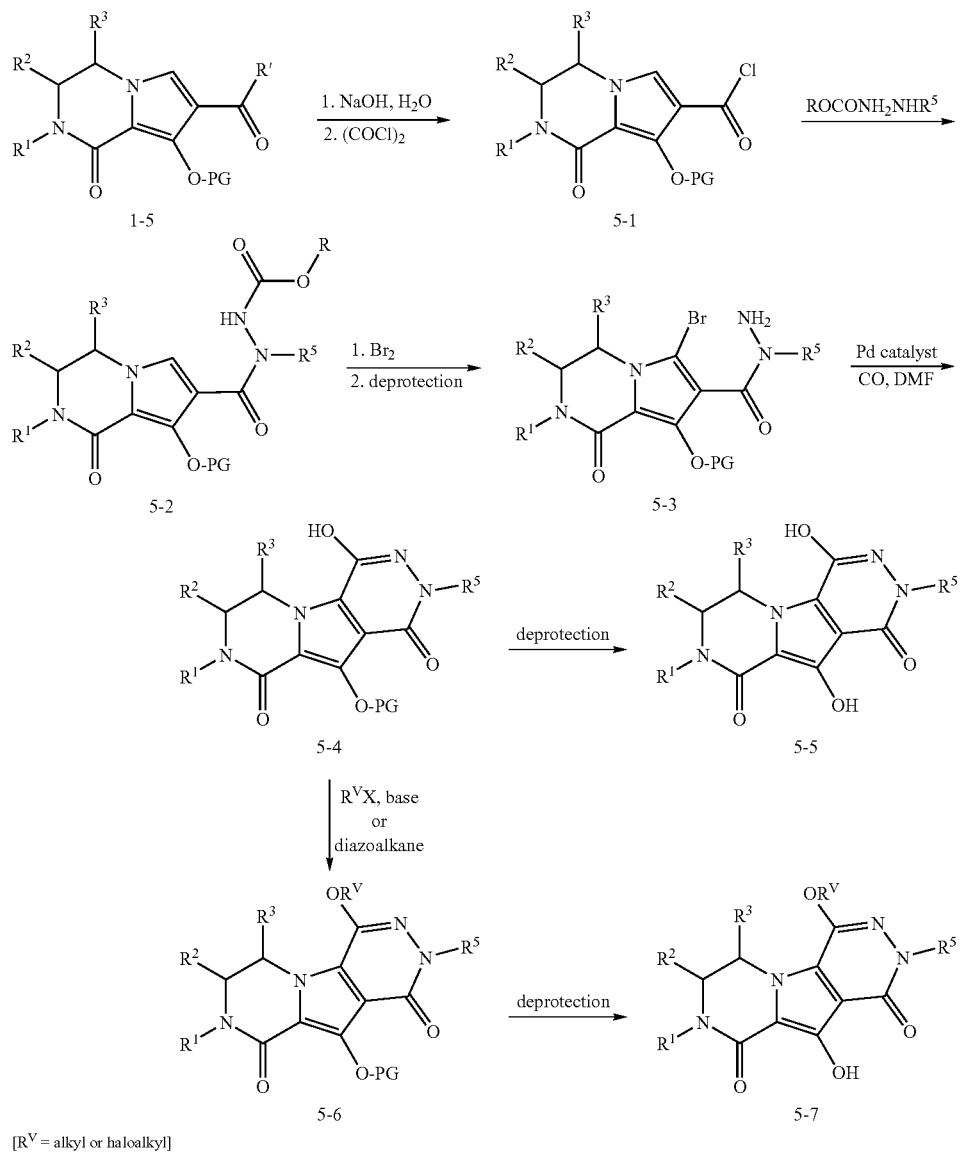

[$R^V$ = alkyl or haloalkyl]

Scheme 6 depicts a general method for preparing compounds of Formula I in which the $R^4$ substituent is a carboxylic derivative such as an amide or ester, wherein the bicyclic bromide 1-6 is lithiated with alkyl lithium followed by treatment with dialkyl oxalate to provide the corresponding keto-ester 6-1 in a manner similar to that described in Engler et al., Bioorganic & Medicinal Chem. Lett., 2003, 2261. The keto-ester can be treated with hydrazine to provide the corresponding tricyclic hydrazine amide 6-2, using conditions similar to those described in Bethune et al., *JCS, Perkin Trans.* 1: *Org & Bio-Org Chem.*, 1994, 1925. Oxidative activation of the hydrazine carboxamide in the presence of an alcohol or amine provides the corresponding ester or amide 6-3, respectively, using procedures and conditions similar to those described in Cheung et al., *J. Org. Chem.*, 1965, 315 and Wolman et al., *JACS.*, 1962, 1889. Subsequent selective alkylation provides the tricyclic intermediate 6-4. Removal of the protecting group leads to desired analog 6-5.

Scheme 6

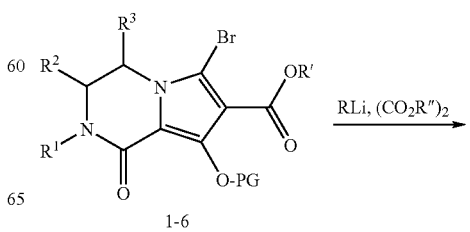

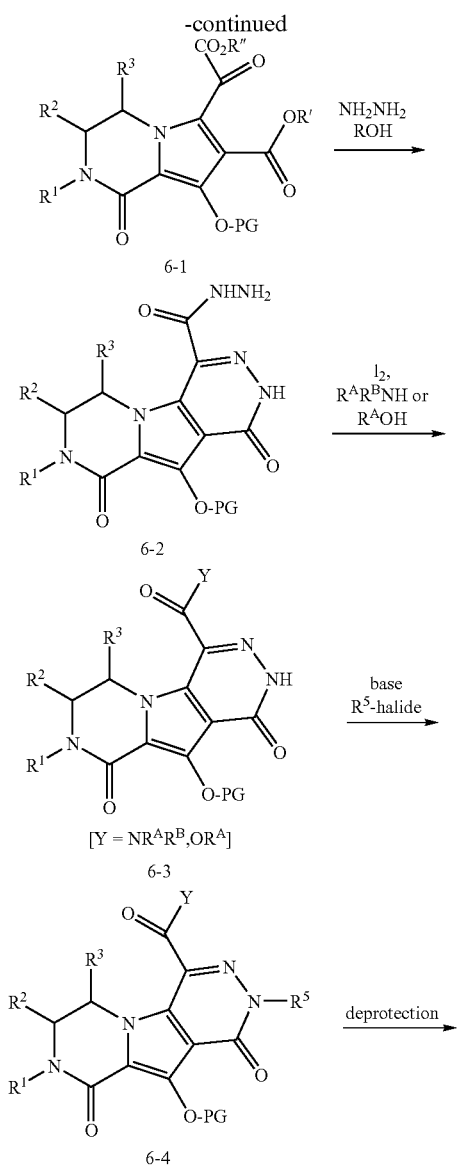

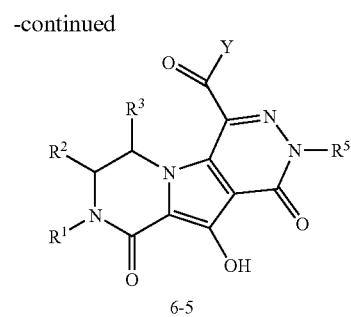

[R,R'R" = alkyl]

Scheme 7 depicts a general method for preparing compounds of Formula I in which R⁴ is a heterocycle, sulfide, or sulfone attached to the tricyclic core via a methylene or substituted methylene linker, wherein the bicyclic keto-ester 6-1 is treated with hydrazine acetate in glacial acetic acid to provide the corresponding tricyclic ester 7-1 using conditions similar to those described in Bethune at al., *JCS, Perkin Trans. 1: Org & Bio-Org Chem.*, 1994, 1925. The ester 7-1 can be alkylated to provide the tricyclic intermediate 7-2, which can be selectively reduced to the corresponding alcohol 7-3 (Brown et al *J. Org. Chem.*, 1963, 3261). Treatment of the alcohol 7-3 with thionyl chloride provides the corresponding chloride 7-5 (with $R^Y$=H; *Tetrahedron Lett.*, 1970, 2931; 1971, 71). Primary alcohol 7-3 can be readily converted to the corresponding secondary alcohol 7-4 via an oxidation (Swern et al., *Tetrahedron*, 1978, 1651)/Grignard reaction sequence (March, *Advanced Organic Chemistry*, 4th edition, p 920, John Wiley & Sons). Similarly, the secondary alcohol 7-4 can be treated with thionyl chloride to provide the corresponding secondary chloride 7-5 ($R^Y$=$R^X$). Reaction of various heterocycles or thiol alcohols with chloride 7-5 in the presences of base provides the corresponding tricyclic intermediate 7-6. Sulfide analogs can be oxidized to the corresponding sulfones with an oxidant such as m-chlorobenzoic acid (March, *Advanced Organic Chemistry*, 4th edition, p 1201, John Wiley & Sons). Removal of the protecting group affords desired analog 7-7.

Scheme 7

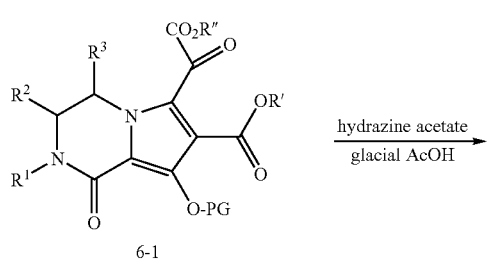

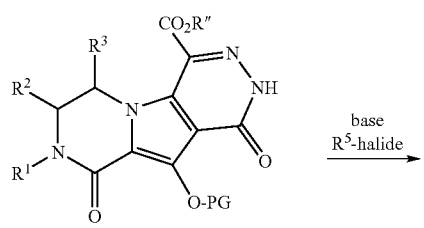

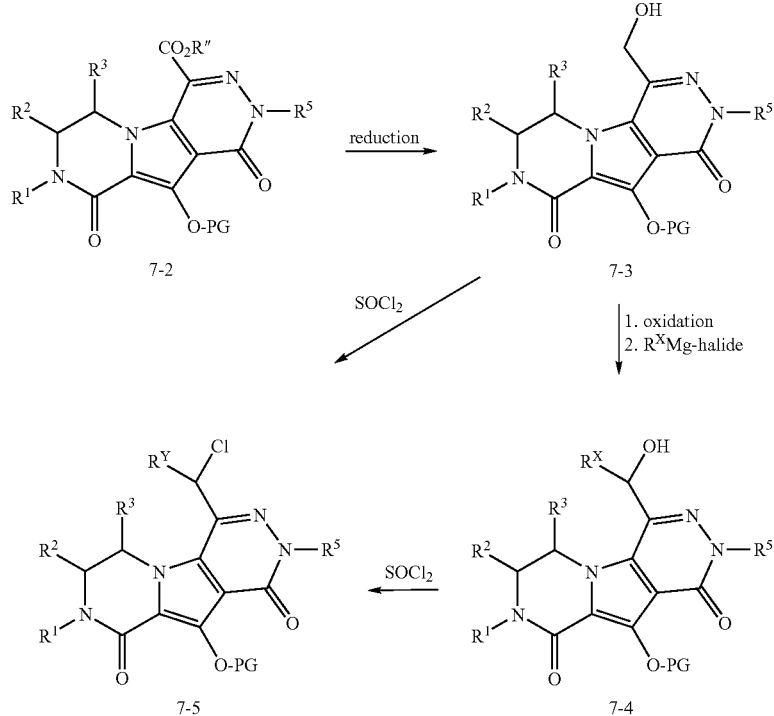

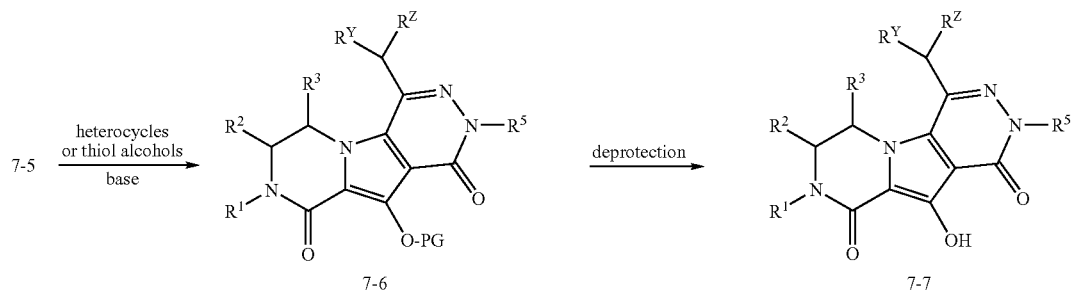

Scheme 8 depicts a general method for preparing compounds of Formula I in which $R^4$ is heterocycle attached to the tricyclic core via a methylene linker, wherein the bicyclic ketone 1-7 is treated with bromine and hydrogen bromide in glacial acetic acid to provide the corresponding bromo ketone 8-1 (March, *Advanced Organic Chemistry*, 4th edition, p 587, John Wiley & Sons). Reaction of the bromide with heterocycle in the presence of an appropriate base provides the corresponding substituted ketone 8-2. Ketone 8-2 can be reacted with hydrazine to afford tricyclic intermediate 8-3 (adapted from conditions described Bethune et al., *JCS, Perkin Trans.* 1: *Org & Bio-Org Chem.*, 1994, 1925), which can be selectively alkylated to provide compound 8-4. Removal of the protecting group leads to desired analog 8-5.

Scheme 8

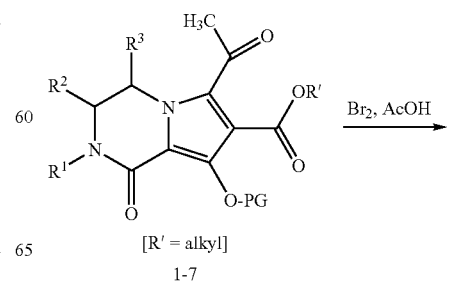

-continued

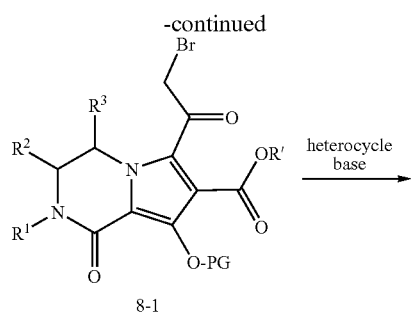
8-1

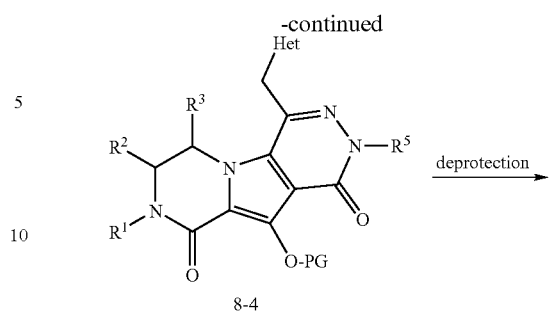
8-4 heterocycle base → deprotection →

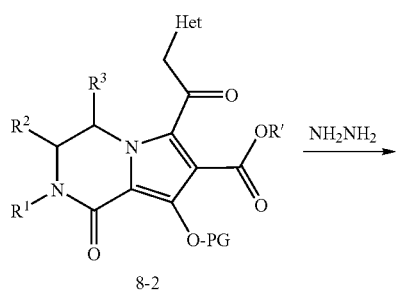
8-2

NH₂NH₂ →

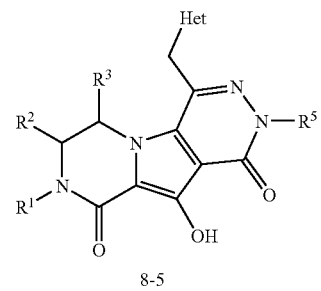
8-5

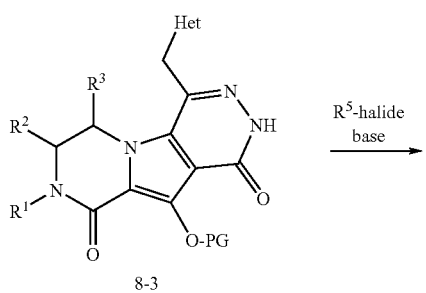
8-3

R⁵-halide base →

Scheme 9 depicts a general method for preparing compounds of Formula I in which R⁴ substituent is a secondary or tertiary alcohol, wherein the primary alcohol 7-3 can be oxidized (using, e.g., $(COCl)_2$, DMSO, $Et_3N$, $CH_2Cl_2$) to provide the corresponding aldehyde 9-1 (Swern et al., *Tetrahedron*, 1978, 1651). The aldehyde can be reacted with an appropriate Grignard reagent or alkyl lithium to provide the corresponding secondary alcohol 9-2 (March, *Advanced Organic Chemistry*, 4th edition, p 920, John Wiley & Sons). Removal of the protecting group from 9-2 leads to the desired analog 9-3. Repeating the same sequence of steps with 9-2 can provide the desired tertiary alcohol 9-4.

Scheme 9

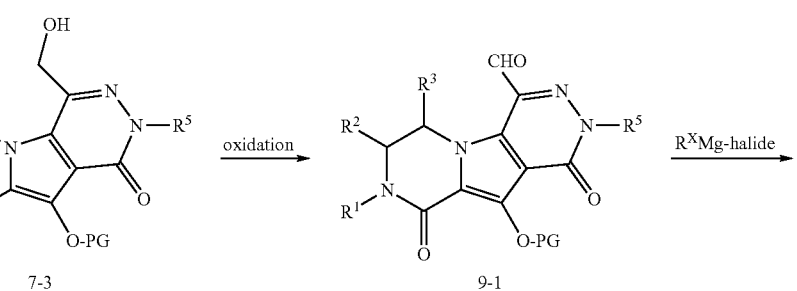

7-3    oxidation →    9-1    R$^X$Mg-halide →

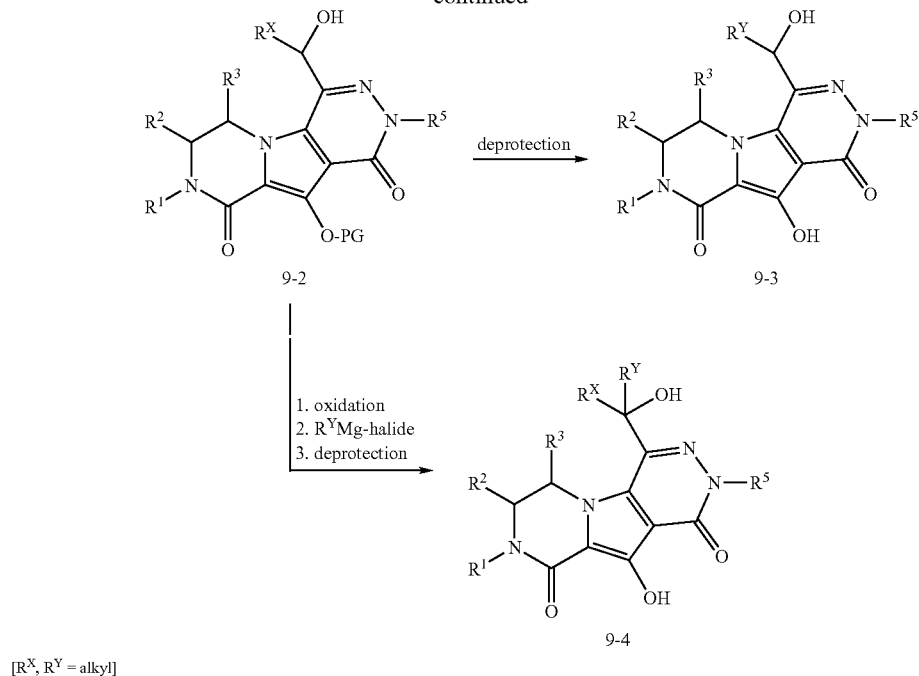

[R^X, R^Y = alkyl]

Scheme 10 depicts a general method for preparing compounds of Formula I in which $R^4$ is a heterocyclyl, alkylthio, alkylsulfonyl, or amine, wherein the amino intermediate 4-2 is diazotized with tert-butylnitrite in the presence of copper (II) bromide (Doyle et al., *J. Org. Chem.*, 1980, 2570) or sodium nitrite in the presence of hydrogen fluoride-pyridine (Zhang et al., *J. Med. Chem.*, 2004, 2453) to provide the corresponding bromide or fluoride 10-1, respectively. Reaction of the bromide with a suitable heteroboronic acid in the presence of a palladium catalyst provides the corresponding heterocyclic substituted intermediate 10-2 (Littke et al., *JACS.*, 2000, 4020). Removal of the protecting group leads to analog 10-3. Treatment of the bromide 10-1 with a nucleophile such as amines, sodium thiolate, heterocycles with or without the addition of copper (I) iodide or a palladium catalyst (Wu et al., *Tetrahedron Lett.*, 2003, 3385; Steinhuebel et al., *Tetrahedron Lett.*, 2004, 3305) affords the appropriately substituted intermediate 10-2. The intermediate sulfide can be oxidized to the corresponding sulfone (March, *Advanced Organic Chemistry*, 4th edition, p 1201, John Wiley & Sons). Some of these compounds can also be prepared by treatment of the fluoride 10-1 with nucleophilic heterocyclic systems in the presence of base. Removal of the protecting group leads to the desired analog 10-3.

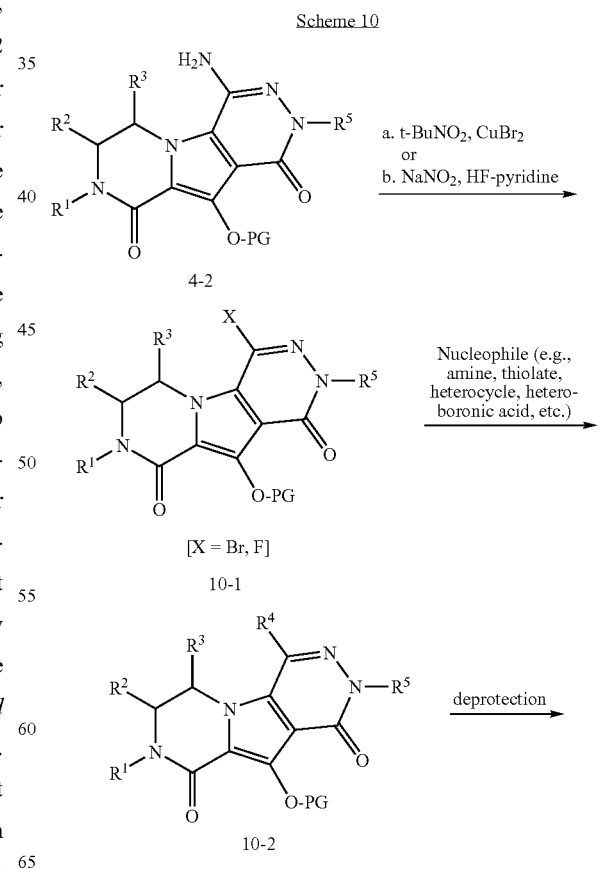

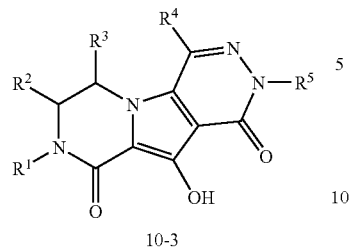

10-3

[R⁴ = amino, thio, sulfinyl sulfonyl, or heterocyclyl group]

A general method for the preparation of compounds of Formula I in which the R⁴ substituent is a heterocycle connected to the tricyclic system as is shown in Scheme 11, wherein the bicyclic bromide 1-6 is lithiated with alkyl lithium followed by treatment with heterocyclic carboxylic ester to provide the corresponding keto-ester 11-1 (March, *Advanced Organic Chemistry*, 4th edition, p 488, John Wiley & Sons). Treatment of the keto-ester with hydrazine provides the corresponding tricyclic intermediate 11-2 (adapted from conditions described in Bethune et al., *JCS, Perkin Trans. 1: Org & Bio-Org Chem.*, 1994, 1925), which can be selectively alkylated and then deprotected to afford the desired analog 11-3.

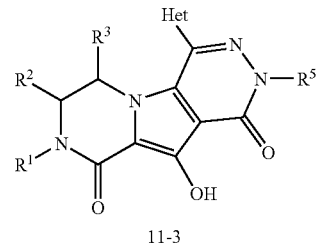

11-3

[R, R' = alkyl
Het = heterocyclyl]

Scheme 12 depicts a general method for preparing compounds of Formula I in which R⁴ is a heterocycle connected to the tricyclic core directly or via a carboxylmethyl linker. Bromide 10-1 is treated with trialkyl(1-alkoxyvinyl)tin in the presence of a palladium catalyst, followed by aqueous acid hydrolysis to provide the corresponding methyl ketone 12-1 (Murali Dhar et al., *J. Med. Chem.*, 2002, 2127). Intermediate 12-1 can be brominated to provide the bromomethyl ketone 12-2 (March, *Advanced Organic Chemistry*, 4th edition, p 587, John Wiley & Sons). Treatment of the bromide 12-2 with a nucleophile such as an amine, sodium thiolate, or heterocycle, followed by deprotection affords the appropriately substituted compound of interest 12-3. Some of these intermediates can be further elaborated to alternative heterocyclic systems under specific conditions (Gilchrist et al., *JCS, Perkin Trans. 1: Org & Bio-Org Chem.*, 2001, 2491).

Scheme 11

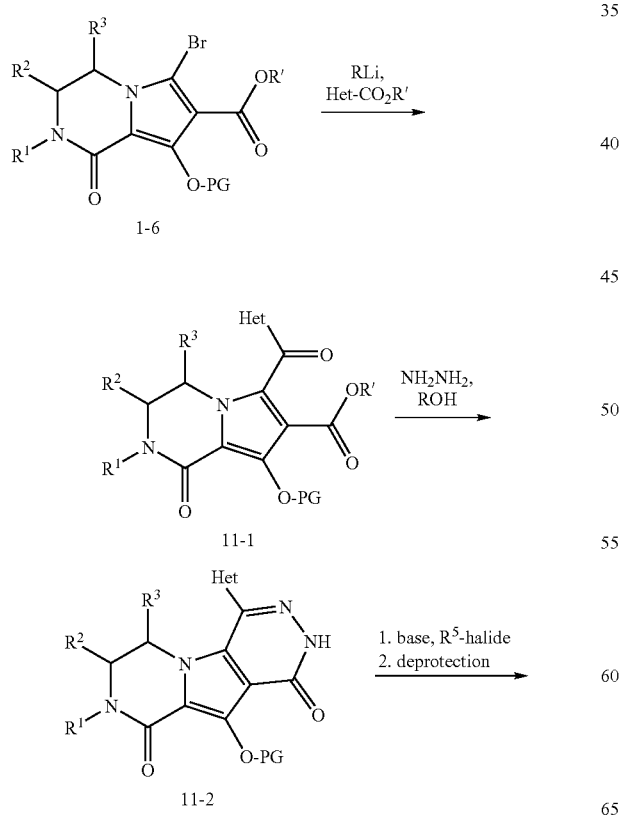

Scheme 12

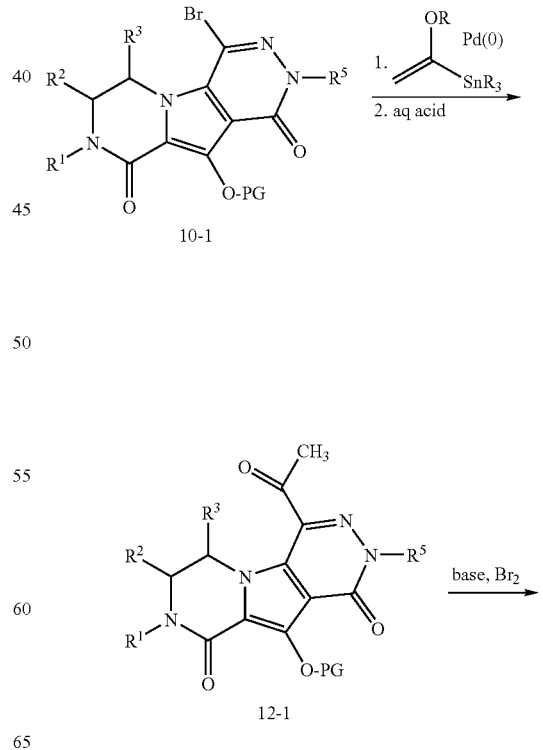

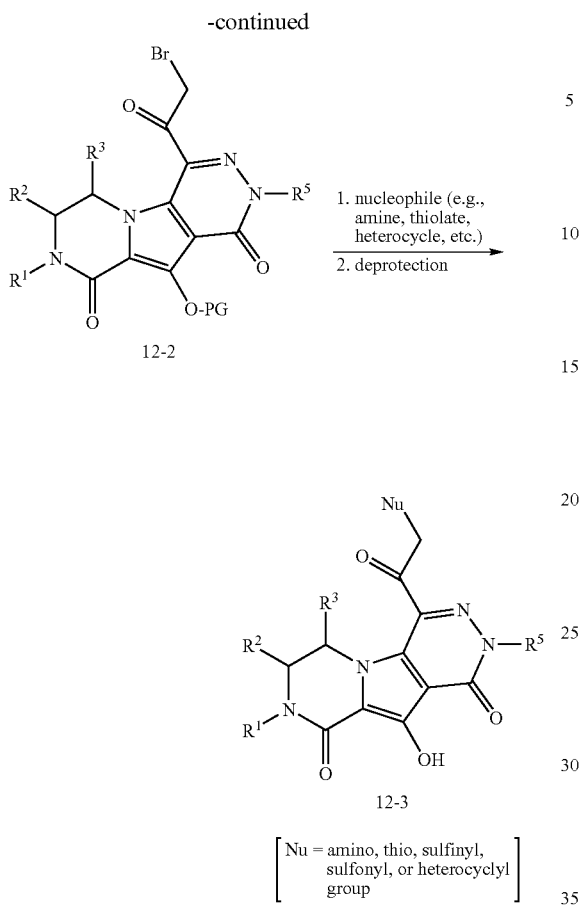

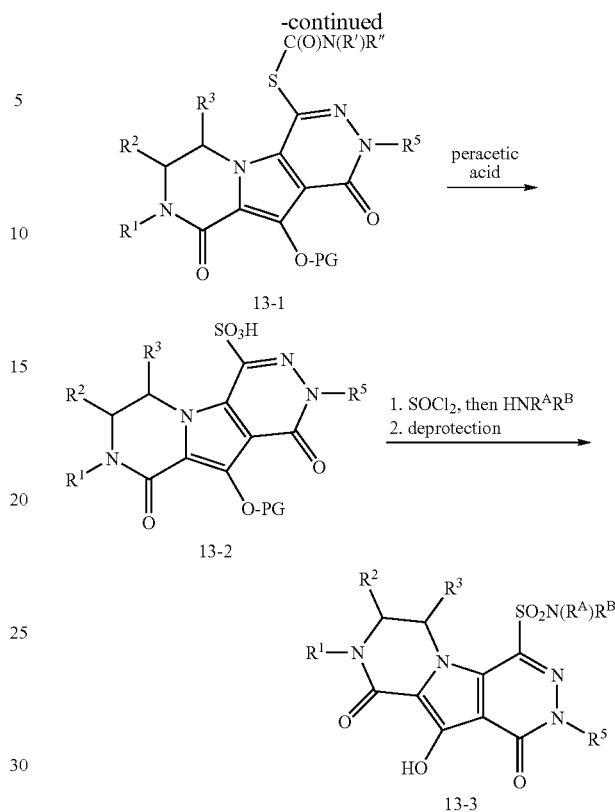

[R', R" = alkyl]

The following examples serve only to illustrate the invention and its practice. The examples are not to be construed as limitations on the scope or spirit of the invention.

EXAMPLE 1

8-(4-Fluorobenzyl)-10-hydroxy-2,4-dimethyl-7,8-dihydropyrazino[1',2':1,5]pyrrolo[2,3-d]pyridazine-1,9(2H,6H)-dione

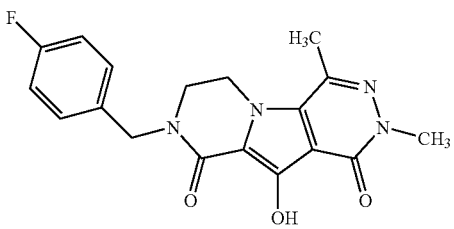

Scheme 13 depicts a general method for preparing compounds of Formula I in which R⁴ is a sulfonamide. Bromide 10-1 is treated with copper (II) dialkyldithiocarbamate to provide the corresponding tricyclic carbamate 13-1 in a manner similar to that described in Dureja et al., *J. Indian Chemical Society*, 1980, 1017. Oxidation of 13-1 provides the corresponding sulfonic acid 13-2 (Sartori et al., *J. Fluorine Chemistry*, 1979, 201). Treating the sulfonic acid 13-2 with thionyl chloride, followed by addition of a solution of amine and then deprotection affords the appropriately substituted sulfonamide of interest 13-3 (Ikemoto et al., *Tetrahedron*, 2003, 1317).

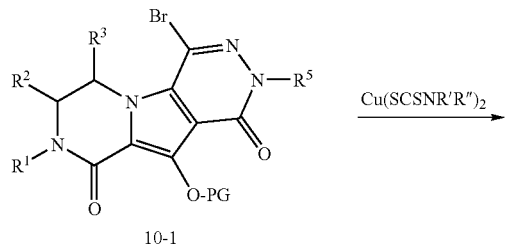

Step 1:
N-(2,2-Dimethoxyethyl)-N-(4-fluorobenzyl)amine

A mixture of 4-fluorobenzaldehyde (227.6 g, 1.83 mol) and dimethoxy-ethylamine (192.6 g, 1.83 mol) in methanol (2.5 L) was heated at 65° C. for 1.5 hours. The solution was allowed to cool to room temperature overnight and treated with sodium borohydride (47.6 g 1.26 mol) in portions over a period of 2 hours. The resultant mixture was stirred at room temperature for 3 hours and quenched with water (1 L). The product mixture was concentrated to about 1 L and extracted with diethyl ether (3×). The ethereal extracts were combined, washed with brine, dried over anhydrous sodium sulfate, filtered, and concentrated under vacuum to provide the titled compound as yellow oil.

$^1$H NMR (400 MHz, CDCl$_3$) δ 7.28 (dd, J=5.5, 8.6 Hz, 2H), 7.00 (t, J=6.8 Hz, 2H), 4.48 (t, J=5.5 Hz, 1H), 3.77 (s, 2H), 3.37 (s, 6H), 2.73 (d, J=5.5 Hz, 2H).

ES MS M+1=214

Step 2: N$^2$-Benzyloxycarbonyl-N$^1$-(2,2-dimethoxyethyl)-N$^1$-(4-fluorobenzyl)-glycinamide To a solution of N-(2,2-dimethoxyethyl)-N-(4-fluorobenzyl)amine (50.6 g, 237.3 mmol), N-CBZ-glycine (54.6 g, 260.8 mmol), EDC (50.0 g, 260.8 mmol), and HOBt (4.2 g, 27 mmol) in anhydrous DMF (500 mL), N,N-diisopropylethylamine (~10 mL) was added until the solution is about pH 7. The reaction mixture was stirred at room temperature overnight and concentrated under vacuum. The residue was partitioned between dichloromethane (1 L) and water (250 mL). The organic extract was washed with brine, dried over anhydrous sodium sulfate, filtered, and concentrated under vacuum to provide the titled compound.

ES MS M−OCH$_3$=374

Step 3: 4-Benzyloxycarbonyl-1-(4-fluorobenzyl)-3,4-dihydropyrazin-2(1H)-one

A solution of N$^2$-benzyloxycarbonyl-N$^1$-(2,2-dimethoxyethyl)-N$^1$-(4-fluorobenzyl)glycinamide (61.5 g, 152 mmol) and p-toluenesulfonic acid monohydrate (3 g) in toluene (450 mL) was stirred at 75° C. for 5 days. Each day an additional 3 g of toluenesulfonic acid was added. The resultant reaction mixture was cooled to room temperature and filtered through a pad of Celite. The filtrate was concentrated under vacuum, and the residue dissolved in dichloromethane. The organic solution was washed successively with saturated aqueous sodium bicarbonate, brine, dried over anhydrous sodium sulfate, filtered, and concentrated under vacuum. The residual solid was subjected to column chromatography on silica gel eluted first with dichloromethane and then 5% ethyl acetate in dichloromethane. Appropriate fractions were collected and concentrated under vacuum. Residual ethyl acetate and dichloromethane was removed by co-evaporation with toluene 3 times for subsequent hydrogenation. The residue was triturated with hexane, and filtered to provide the cyclization product as an off-white solid.

$^1$H NMR (400 MHz, CDCl$_3$) δ 7.37 (br s, 5H), 7.23 (m, 2H), 7.02 (t, J=8.6 Hz, 2H), 6.44 (d, J=6.0 Hz, ½H), 6.32 (d, J=6.0 Hz, ½H), 5.53 (d, J=6.0 Hz, ½H), 5.42 (d, J=6.0 Hz, ½H), 5.21 (s, 2H), 4.65 (s, 2H), 4.38 (s, 2H).

ES MS M+1=341

Step 4: 1-(4-Fluorobenzyl)piperazin-2-one

A mixture of 4-benzyloxycarbonyl-1-(4-fluorobenzyl)-3,4-dihydro-pyrazin-2(1H)-one (0.5 g, 1.45 mmol) and Pearlman's catalyst (26 mg; 20% palladium hydroxide on carbon) in methanol (25 mL) was stirred under an atmosphere of hydrogen (1 atm) at room temperature overnight. The product mixture was filtered through a pad of Celite, and then concentrated under vacuum to provide 1-(4-fluorobenzyl)piperazin-2-one.

$^1$H NMR (400 MHz, d$_6$ DMSO) δ 7.29 (dd, J=8.4, 5.7 Hz, 2H), 7.16 (t, J=9.0 Hz, 2H), 4.48 (s, 2H), 3.28 (s, 2H), 3.14 (t, J=5.3 Hz, 2H) 2.84 (t, J=5.3 Hz, 2H).

ES MS M+1=209

Step 5: Ethyl 2-(4-fluorobenzyl)-8-hydroxy-1-oxo-1,2,3,4-tetrahydropyrrolo[1,2-a]-pyrazine-7-carboxylate A mixture of 1-(4-fluorobenzyl)piperazin-2-one (10.0 g, 48.0 mmol) and diethyl ethoxymethylenemalonate (10.9 g, 50.4 mmol) in toluene (250 mL) was heated in a sealed tube at 80° C. for 4 hours. The resultant mixture was concentrated under vacuum. The residue was dissolved in anhydrous DMF (350 mL), cooled to 0° C. under an atmosphere of nitrogen, and treated with a solution of lithium bis(trimethylsilyl)amide in THF (1 M, 57.4 mL, 57.4 mmol). The reaction mixture was stirred at room temperature overnight and concentrated under vacuum. The residue was partitioned between ethyl acetate and dilute aqueous HCl. The organic extract was washed with brine, dried over anhydrous magnesium sulfate, filtered, and concentrated under vacuum. The residue was triturated with diethyl ether, and the solid precipitated was filtered to provide the titled compound.

$^1$H NMR (400 MHz, DMSO-d$_6$) δ 8.54 (s, 1H), 7.40 (dd, J=8.3, 5.8 Hz, 2H), 7.36 (s, 1H), 7.17 (t, J=8.3 Hz, 2H), 4.59 (s, 2H), 4.18 (q, J=7.1 Hz, 2H), 4.01 (t, J=5.3 Hz, 2H), 3.53 (t, J=5.3 Hz, 2H), 1.24 (t, J=7.1 Hz, 3H).

ES MS M+1=333

Step 6: Ethyl 8-(benzyloxy)-2-(4-fluorobenzyl)-1-oxo-1,2,3,4-tetrahydro-pyrrolo[1,2-a]-pyrazine-7-carboxylate To a solution of ethyl 2-(4-fluorobenzyl)-8-hydroxy-1-oxo-1,2,3,4-tetrahydropyrrolo[1,2-a]-pyrazine-7-carboxylate (8.2 g, 24.6 mmol) in DMF (200 mL), cesium carbonate (10.4 g, 32.0 mmol) and benzyl bromide (3.2 mL, 27.1 mmol) were added. The reaction mixture was stirred at room temperature over night. The mixture was filtered and the filtrate concentrated under vacuum. The residue was partitioned between ethyl acetate and brine. The organic extract was washed with brine, dried over sodium sulfate, filtered, and concentrated under vacuum. The residue was subjected to column chromatography on silica gel eluted with hexanes and ethyl acetate gradient to give titled material.

$^1$H NMR (400 MHz, CDCl$_3$) δ 7.62 (br d, J=7.5 Hz, 2H), 7.24-7.38 (m, 5H), 7.14 (s, 1H), 7.02 (t, J=8.6 Hz, 2H), 5.33 (s, 2H), 4.72 (s, 2H), 4.28 (q, J=7.0 Hz, 2H), 4.07 (t, J=5.8 Hz, 2H), 3.49 (t, J=5.7 Hz, 2H), 1.30 (t, J=7.2 Hz, 3H).

ES MS M+1=423.2

Step 7: Ethyl 8-(benzyloxy)-6-bromo-2-(4-fluorobenzyl)-1-oxo-1,2,3,4-tetrahydropyrrolo[1,2-a]-pyrazine-7-carboxylate To a mixture of ethyl 8-(benzyloxy)-2-(4-fluorobenzyl)-1-oxo-1,2,3,4-tetrahydro-pyrrolo[1,2-a]-pyrazine-7-carboxylate (8.0 g, 18.9 mmol) and sodium bicarbonate (4.8 g, 56.8 mmol) in dichloromethane (100 mL) at room temperature, a solution of bromine (3.5 g, 21.7 mmol) in dichloromethane (30 mL) was added dropwise. The reaction mixture was stirred at room temperature for 30 minutes, filtered, and concentrated under vacuum. The residue was subjected to column chromatography on silica gel eluted with a hexanes and ethyl acetate gradient to provide the titled product.

$^1$H NMR (400 MHz, CDCl$_3$) δ 7.60 (br d, J=7.1 Hz, 2H), 7.24-7.38 (m, 5H), 7.02 (t, J=8.0 Hz, 2H), 5.27 (s, 2H), 4.72 (s, 2H), 4.30 (q, J=7.2 Hz, 2H), 4.05 (t, J=5.9 Hz, 2H), 3.51 (t, J=5.7 Hz, 2H), 1.31 (t, J=7.2 Hz, 3H).

ES MS M+1=501, 503 (1:1)

Step 8: Ethyl 6-acetyl-8-(benzyloxy)-2-(4-fluorobenzyl)-1-oxo-1,2,3,4-tetrahydropyrrolo[1,2-a]-pyrazine-7-carboxylate A solution of ethyl 8-(benzyloxy)-6-bromo-2-(4-fluorobenzyl)-1-oxo-1,2,3,4-tetrahydropyrrolo[1,2-a]-pyrazine-7-carboxylate (0.32 g, 0.64 mmol) and N-methyldicyclohexylamine (0.20 mL, 0.96 mmol) in dioxane (1 mL) was purged with nitrogen for 5 minutes, n-butyl vinyl ether (0.83 mL, 6.4 mmol), tris(dibenzylidene-acetone)dipalladium (0.12 g, 0.13 mmol), and tri-tert-butylphosphine (0.065 g, 0.32 mmol) were added. After stirring at room temperature for 2 days, the reaction mixture was treated with 1 N HCl and stirred at room temperature overnight. The reaction mixture was partitioned between chloroform and brine. The organic extract was dried over sodium sulfate, filtered and concentrated. The residue was subjected to column chromatography on silica gel eluted with a hexanes and ethyl acetate gradient to provide titled product.

$^1$H NMR (400 MHz, CDCl$_3$) δ 7.53 (br d, J=6.8 Hz, 2H), 7.24-7.38 (m, 5H), 7.02 (t, J=8.7 Hz, 2H), 5.26 (s, 2H), 4.70 (s, 2H), 4.34 (t, J=5.8 Hz, 2H), 4.28 (q, J=7.1 Hz, 2H), 3.51 (t, J=5.8 Hz, 2H), 2.46 (s, 3H), 1.29 (t, J=7.2 Hz, 3H).

ES MS M+1=465.2

Step 9: Ethyl 6-acetyl-2-(4-fluorobenzyl)-8-hydroxy-1-oxo-1,2,3,4-tetrahydropyrrolo[1,2-a]-pyrazine-7-carboxylate A mixture of ethyl 6-acetyl-8-(benzyloxy)-2-(4-fluorobenzyl)-1-oxo-1,2,3,4-tetrahydropyrrolo[1,2-a]-pyrazine-7-carboxylate (140 mg, 0.30 mmol) and Pearlman's catalyst (5.0 mg, 20% Pd(OH)$_2$ on carbon) in ethanol (20 mL) was stirred under an atmosphere of hydrogen gas (1 atm) at room temperature overnight. The reaction mixture was filtered through a pad of Celite. The filtrate was concentrated under vacuum to provide the titled product.

$^1$H NMR (400 MHz, CDCl$_3$) δ8.68 (br s, 1H), 7.28(d, J=8.4, 2H), 7.03 (t, J=8.6 Hz, 2H), 4.66 (s, 2H), 4.39 (q, J=7.1 Hz, 2H), 4.26 (t, J=5.8 Hz, 2H), 3.49 (t, J=5.6 Hz, 2H), 2.57 (s, 3H), 1.27 (t, J=7.0 Hz, 3H).

ES MS M+1=375.2

Step 10: 8-(4-Fluorobenzyl)-10-hydroxy-2,4-dimethyl-7,8-dihydropyrazino-[1',2':1,5]pyrrolo[2,3-d]pyridazine-1,9(2H,6H)-dione A mixture of ethyl 6-acetyl-2-(4-fluorobenzyl)-8-hydroxy-1-oxo-1,2,3,4-tetrahydropyrrolo[1,2-a]-pyrazine-7-carboxylate (75 mg, 0.2 mmol), methylhydrazine (46 mg, 1 mmol), and a drop of acetic acid in ethanol (4 mL) was heated in a sealed tube at 105° C. overnight. The product mixture was concentrated under vacuum. The residue was recrystallized from methanol to provide the titled product.

$^1$H NMR (400 MHz, CDCl$_3$) δ8.40 (br s, 1H), 7.32 (dd, J=8.4, 5.3 Hz, 2H), 7.06 (t, J=8.8 Hz, 2H), 4.71 (s, 2H), 4.36 (t, J=6.0 Hz, 2H), 3.72 (s, 3H), 3.63 (t, J=6.0 Hz, 2H), 2.52 (s, 3H).

ES MS M+1=357

EXAMPLES 2-6

The compounds in the following table were prepared in accordance with the procedure set forth in Example 1 using the appropriate hydrazine in place of methyl hydrazine.

| Example | Compound | Data |
|---|---|---|
| 2 | 8-(4-Fluorobenzyl)-10-hydroxy-2-ethyl-4-methyl-7,8-dihydropyrazino-[1',2':1,5]pyrrolo[2,3-d]pyridazine-1,9(2H,6H)-dione | ES MS M + 1 = 371 |
| 3 | 8-(4-Fluorobenzyl)-10-hydroxy-2-benzyl-4-methyl-7,8-dihydropyrazino-[1',2':1,5]pyrrolo[2,3-d]pyridazine-1,9(2H,6H)-dione | ES MS M + 1 = 433 |

| Example | Compound | Data |
|---|---|---|
| 4 | 8-(4-Fluorobenzyl)-10-hydroxy-2-cyclohexyl-4-methyl-7,8-dihydropyrazino-[1',2':1,5]pyrrolo[2,3-d]pyridazine-1,9(2H,6H)-dione | ES MS M + 1 = 425 |
| 5 | 8-(4-Fluorobenzyl)-10-hydroxy-2-cyanoethyl-4-methyl-7,8-dihydropyrazino-[1',2':1,5]pyrrolo[2,3-d]pyridazine-1,9(2H,6H)-dione | ES MS M + 1 = 396 |
| 6 | 8-(4-Fluorobenzyl)-10-hydroxy-2-hydroxyethyl-4-methyl-7,8-dihydropyrazino-[1',2':1,5]pyrrolo[2,3-d]pyridazine-1,9(2H,6H)-dione | ES MS M + 1 = 387 |

EXAMPLE 7

2-(4-Fluorobenzyl)-10-hydroxy-4,8-dimethyl-7,8-dihydropyrazino[1',2':1,5]pyrrolo[2,3-d]pyridazine-1,9(2H,6H)-dione

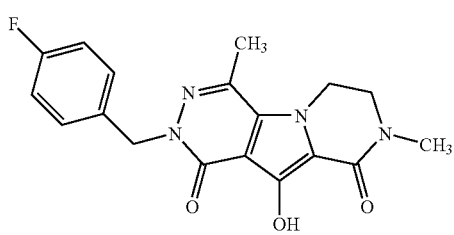

Step 1: $N^2$-Benzyloxycarbonyl-$N^1$-(2,2-dimethoxyethyl)-$N^1$-methylglycinamide A solution of N-(2,2-dimethoxyethyl)-N-methylamine (760 g, 6.38 mmol), N-CBZ-glycine (1337.6 g, 6.39 mol), EDC (1225.8 g, 6.39 mol), and HOBt (107.7 g, 0.70 mol), and N,N-diisopropylethylamine (172 mL) in anhydrous DMF (12 L) was stirred at room temperature overnight. The reaction mixture was diluted with water (24 L) and extracted with dichloromethane (3×10 L). The organic extracts were combined, dried over anhydrous magnesium sulfate, filtered, and concentrated under vacuum to provide the title compound.

ES MS M+1=311

Step 2: 4-Benzyloxycarbonyl-1-methyl-3,4-dihydropyrazin-2(1H)-one

A solution of $N^2$-benzyloxycarbonyl-$N^1$-(2,2-dimethoxyethyl)-$N^1$-methylglycinamide (1.9 Kg, 6.1 mol) and p-toluenesulfonic acid monohydrate (270 g) in toluene (29.4 L) was stirred at 80° C. for 4 hours. The resultant reaction mixture was cooled to room temperature, washed with water (4×2 L), dried over anhydrous magnesium sulfate, filtered, and concentrated under vacuum. The residual solid was subjected to column chromatography on silica gel eluting with heptane-ethyl acetate. Concentration of appropriate fractions provide the cyclization product as off-white solid.

$^1$H NMR (400 MHz, CDCl$_3$) δ 7.37 (br s, 5H), 6.44 (d, J=6.0 Hz, ½H), 6.32 (d, J=6.0 Hz, ½H), 5.53 (d, J=6.0 Hz, ½H), 5.42 (d, J=6.0 Hz, ½H), 5.21 (s, 2H), 4.31 (s, 2H), 3.08 (s, 3H).

ES MS M+1=247

Step 3: 1-methylpiperazin-2-one

A mixture of 4-benzyloxycarbonyl-1-methyl-3,4-dihydropyrazin-2(1H)-one (510 g, 2.1 mol) and 10% Pt/C (40 g) in ethanol (12 L) was stirred under an atmosphere of hydrogen (1 atm) at room temperature overnight. Pearlman's catalyst (50 g; 20% Pd(OH)$_2$ on C) was added and stirred under an atmosphere of hydrogen gas for additional 24 hours. The product mixture was filtered through a pad of Celite, and then concentrated under vacuum to provide 1-methylpiperazin-2-one.

$^1$H NMR (400 MHz, CDCl$_3$) δ 3.52 (s, 2H), 3.32 (t, J=5.7 Hz, 2H) 3.09 (t, J=5.7 Hz, 2H), 2.97 (s, 3H).

Step 4: Ethyl 8-hydroxy-2-methyl-1-oxo-1,2,3,4-tetrahydropyrrolo[1,2-a]-pyrazine-7-carboxylate A mixture of 1-methylpiperazin-2-one (183 g, 1.6 mol) and diethyl ethoxymethylenemalonate (346 g, 1.6 mol) in toluene (12 L) was heated at 100° C. overnight. The resultant mixture was concentrated under vacuum. The residue was dissolved in anhydrous THF (8 L), brought to reflux under an atmosphere of nitrogen, and treated with a solution of lithium bis(trimethylsilyl)amide in THF (1 M, 1.05 eq). The reaction mixture was allowed to cool to room temperature and concentrated under vacuum. The residue was partitioned between methylene chloride and dilute aqueous HCl. The organic extract was washed with brine, dried over anhydrous magnesium sulfate, filtered, and concentrated under vacuum. The residue was triturated with ethyl acetate, cooled to −20° C., and the solid precipitated was filtered to provide the title compound.

$^1$H NMR (400 MHz, DMSO-d$_6$) δ 8.50 (s, 1H), 7.33 (s, 1H), 4.18 (q, J=7.1 Hz, 2H), 4.11 (t, J=5.5 Hz, 2H), 3.59 (t, J=5.5 Hz, 2H), 2.92 (s, 3H), 1.24 (t, J=7.1 Hz, 3H).

ES MS M+1=239

Step 5: Ethyl 8-(benzyloxy)-2-methyl-1-oxo-1,2,3,4-tetrahydro-pyrrolo[1,2-a]-pyrazine-7-carboxylate To a solution of ethyl 8-hydroxy-2-methyl-1-oxo-1,2,3,4-tetrahydro-pyrrolo[1,2-a]-pyrazine-7-carboxylate (25.0 g, 104.9 mmol) in DMF (500 mL), potassium carbonate (58 g, 420 mmol) and benzyl bromide (14.9 mL, 126 mmol) was added. The reaction mixture was stirred at room temperature overnight. The mixture was filtered and the filtrate concentrated under vacuum. The residue was partitioned between dichloromethane and brine. The organic extract was washed with brine, dried over sodium sulfate, filtered, and concentrated under vacuum. The residue was subjected to column chromatography on silica gel eluted with ethyl acetate to give titled material.

$^1$H NMR (400 MHz, CDCl$_3$) δ 7.62 (br d, J=7.5 Hz, 2H), 7.34-7.27 (m, 3H), 7.15 (s, 1H), 5.29 (s, 2H), 4.29 (q, J=7.0 Hz, 2H), 4.11 (t, J=5.8 Hz, 2H), 3.62 (t, J=5.7 Hz, 2H), 3.12 (s, 3H), 1.31 (t, J=7.2 Hz, 3H).

ES MS M+1=329

Step 6: Ethyl 8-(benzyloxy)-6-bromo-2-methyl-1-oxo-1,2,3,4-tetrahydro-pyrrolo[1,2-a]-pyrazine-7-carboxylate To a mixture of ethyl 8-(benzyloxy)-2-methyl-1-oxo-1,2,3,4-tetrahydro-pyrrolo[1,2-a]-pyrazine-7-carboxylate (5.0 g, 15.2 mmol) and sodium bicarbonate (19.2 g, 228 mmol) in dichloromethane (150 mL) at 0° C., a solution of bromine in dichloromethane (0.5 M, 32 mL, 16 mmol) was added dropwise. The reaction mixture was stirred at room temperature for 2 hours, filtered, and concentrated under vacuum. The residue was subjected to column chromatography on silica gel eluted with a hexane-ethyl acetate gradient to provide the titled product.

$^1$H NMR (400 MHz, CDCl$_3$) δ 7.59 (br d, J=7.1 Hz, 2H), 7.37-7.29 (m, 3H), 5.23 (s, 2H), 4.30 (q, J=7.3 Hz, 2H), 4.14 (t, J=5.9 Hz, 2H), 3.64 (t, J=5.9 Hz, 2H), 3.12 (s, 3H), 1.31 (t, J=7.3 Hz, 3H).

ES MS M+1=407, 409 (1:1)

Step 7: Ethyl 6-acetyl-8-(benzyloxy)-2-methyl-1-oxo-1,2,3,4-tetrahydro-pyrrolo[1,2-a]-pyrazine-7-carboxylate A mixture of ethyl 8-(benzyloxy)-6-bromo-2-methyl-1-oxo-1,2,3,4-tetrahydro-pyrrolo[1,2-a]-pyrazine-7-carboxylate (0.42 g, 1.03 mmol), palladium acetate (29 mg, 0.13 mmol), thallium acetate (0.34 g, 1.29 mmol), diisopropyl ethylamine (0.58 mL, 4.12 mmol), 1,3-bis(diphenylphosphino)propane (60 mg, 0.14 mol), n-butyl vinyl ether (0.67 mL, 5.2 mmol) in DMF (3 mL) was purged with nitrogen for 5 minutes. The mixture was sealed and heated at 100° C. overnight. The reaction mixture was concentrated under vacuum, and the residue was treated with 1 N aq HCl and stirred at room temperature for one hour. The reaction mixture was diluted with dichloromethane. The organic extract was dried over sodium sulfate, filtered and concentrated. The residue was subjected to column chromatography on silica gel eluted with ethyl acetate to provide titled product.

$^1$H NMR (400 MHz, CDCl$_3$) δ 7.52 (br d, J=7.1 Hz, 2H), 7.37-7.28 (m, 3H), 5.22 (s, 2H), 4.47 (t, J=5.9 Hz, 2H), 4.29 (q, J=7.1 Hz, 2H), 3.60 (t, J=5.9 Hz, 2H), 3.13 (s, 3H), 2.48 (s, 3H), 1.31 (t, J=7.1 Hz, 3H).

ES MS M+1=371

Step 8: 10-(Benzyloxy)-2-(4-fluorobenzyl)-4,8-dimethyl-7,8-dihydropyrazino-[1',2':1,5]pyrrolo-[2,3-d] pyridazine-1,9(2H,6H)-dione A mixture of ethyl 6-acetyl-8-(benzyloxy)-2-methyl-1-oxo-1,2,3,4-tetrahydro-pyrrolo[1,2-a]-pyrazine-7-carboxylate (65 mg, 0.18 mmol) and 4-fluorobenzyl hydrazine (0.12 g, 0.88 mmol), and acetic acid (3 drops) in toluene (40 mL) was heated in a sealed tube at 120° C. overnight. The reaction mixture was concentrated under vacuum, and the residue was subjected to column chromatography on silica gel eluted with 1-5% methanol in ethyl acetate gradient to provide titled product.

$^1$H NMR (400 MHz, CDCl$_3$) δ 7.66 (d, J=8.6 Hz, 2H), 7.39 (dd, J=8.4, 5.3 Hz, 2H), 7.33-7.24 (m, 3H), 7.98 (t, J=8.8 Hz, 2H), 5.45 (s, 2H), 5.25 (s, 2H), 4.36 (t, J=6.0 Hz, 2H), 3.62 (t, J=6.0 Hz, 2H), 3.08 (s, 3H), 2.55 (s, 3H).

ES MS M+1=467

Step 9: 2-(4-Fluorobenzyl)-10-hydroxy-4,8-dimethyl-7,8-dihydropyrazino-[1',2':1,5]pyrrolo[2,3-d] pyridazine-1,9(2H,6H)-dione A mixture of 10-(benzyloxy)-2-(4-fluorobenzyl)-4,8-dimethyl-7,8-dihydropyrazino-[1',2':1,5]pyrrolo-[2,3-d]pyridazine-1,9(2H,6H)-dione (17 mg, 38 μmol) and Pearlman's catalyst (6.0 mg, 20% Pd(OH)$_2$ on carbon) in ethanol (20 mL) was stirred under an atmosphere of hydrogen gas (1 atm) at room temperature for 30 minutes. The reaction mixture was diluted with acetonitrile and filtered through a pad of Celite. The filtrate was concentrated under vacuum, and the residue triturated with a mixture of methanol and diethyl ether. A solid precipitate was obtained by filtration to provide the titled compound.

$^1$H NMR (400 MHz, CDCl$_3$) δ 8.48 (br s, 1H), 7.44 (dd, J=8.4, 5.3 Hz, 1H), 6.96 (t, J=8.8 Hz, 2H), 5.25 (s, 2H), 4.41 (t, J=6.0 Hz, 2H), 3.72 (t, J=6.0 Hz, 2H), 3.11 (s, 3H).

ES MS M+1=357

EXAMPLE 8

2-(3,4-Dichlorobenzyl)-10-hydroxy-4,8-dimethyl-7,8-dihydropyrazino[1',2':1,5]-pyrrolo[2,3-d]pyridazine-1,9(2H,6H)-dione

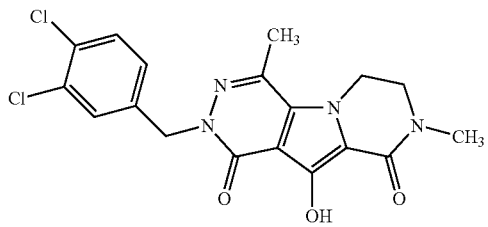

Step 1: 10-(Benzyloxy)-4,8-dimethyl-7,8-dihydropyrazino[1',2':1,5]pyrrolo[2,3-d]pyridazine-1,9(2H,6H)-dione A solution of ethyl 6-acetyl-8-(benzyloxy)-2-methyl-1-oxo-1,2,3,4-tetrahydropyrrolo[1,2-a]-pyrazine-7-carboxylate (0.44 g,1.2 mmol; see Example 7, Step 7), and hydrazine monohydrate (0.37 mL, 11.9 mmol) in glacial acetic acid (2 mL) was heated in a microwave oven at 180° C. for 20 minutes. The reaction mixture was concentrated under vacuum and the residue partitioned between dichloromethane and aqueous sodium bicarbonate. The organic extract was dried over MgSO$_4$, filtered, and concentrated to provide the titled dione.

$^1$H NMR (400 MHz, CDCl$_3$) δ 9.64 (s, 1H), 7.65 (d, J=6.9 Hz, 2H), 7.33 (t, J=7.1 Hz, 2H), 5.54 (s, 2H), 5.29 (s, 1H), 4.45 (t, J=5.6 Hz, 2H), 3.68 (t, J=5.6 Hz, 2H), 3.14 (s, 3H), 2.58 (s, 3H).

ES MS M+1=339

Step 2: 2-(3,4-Dichlorobenzyl)-10-hydroxy-4,8-dimethyl-7,8-dihydropyrazino-[1',2':1,5]-pyrrolo[2,3-d]pyridazine-1,9(2H,6H)-dione A solution of 10-(benzyloxy)-4,8-dimethyl-7,8-dihydropyrazino[1',2':1,5]-pyrrolo[2,3-d]pyridazine-1,9(2H,6H)-dione (0.05 g, 0.15 mmol) in DMF (1 mL) was treated with sodium hydride (5 mg, 0.17 mmol). The resultant mixture was stirred at room temperature for 5 minutes. After bubbling ceased, 3,4-dichlorobenzyl chloride (0.02 mL, 0.16 mmol) was added and the reaction mixture was stirred at room temperature for overnight. The reaction was then treated with 33% HBr solution in acetic acid (2 mL) and stirred at room temperature overnight. The reaction mixture was concentrated under vacuum. The residue was treated with water and the solid precipitated was collected by filtration to provide the titled compound as white solid.

$^1$H NMR (500 MHz, CD$_3$OD) δ7.46 (m, 2H), 7.27 (m, 1H), 5.25 (s, 2H), 4.53 (t, J=5.9 Hz, 2H), 3.77 (t, J=5.9 Hz, 2H), 3.09 (s, 3H), 2.62 (s, 3H).

ES MS M+1=407.0640 (Found); 407.0670 (Calculated)

EXAMPLES 9-32

The compounds in the following table were prepared in accordance with the procedure set forth in Example 8 using the appropriate benzyl hydrazine.

| Example | Compound | Data |
|---|---|---|
| 9 | 2-(3-Chlorobenzyl)-10-hydroxy-4,8-dimethyl-7,8-dihydropyrazino-[1',2':1,5]-pyrrolo[2,3-d]pyridazine-1,9(2H,6H)-dione | ES MS M + 1 = 373.1060 (Found); 373.1060 (Calculated) |
| 10 | 2-(4-Chlorobenzyl)-10-hydroxy-4,8-dimethyl-7,8-dihydropyrazino-[1',2':1,5]-pyrrolo[2,3-d]pyridazine-1,9(2H,6H)-dione | ES MS M + 1 = 373.1074 (Found); 373.1062 (Calculated) |

-continued

| Example | Compound | Data |
|---------|----------|------|
| 11 | 2-(1,3-Benzodioxol-5-ylmethyl)-10-hydroxy-4,8-dimethyl-7,8-dihydropyrazino-[1',2':1,5]pyrrolo[2,3-d]pyridazine-1,9(2H,6H)-dione | ES MS M + 1 = 383.1344 (Found); 383.1350 (Calculated) |
| 12 | 2-(2,3,4-Trifluorobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 393.1169 (Found); 393.1169 (Calculated) |
| 13 | 2-(2,4-Difluorobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 375.1243 (Found); 375.1263 (Calculated) |
| 14 | 2-(2-Chloro-4-fluorobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 391.0975 (Found); 391.0968 (Calculated) |
| 15 | 2-(3-Methylbenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 353.1603 (Found); 353.1608 (Calculated) |

-continued

| Example | Compound | Data |
|---|---|---|
| 16 | 2-(2-Cyanobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 364.1396 (Found); 364.1404 (Calculated) |
| 17 | 2-(4-Methylbenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 353.1611 (Found); 353.1608 (Calculated) |
| 18 | 2-(3-Methoxybenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 369.1553 (Found); 369.1558 (Calculated) |
| 19 | 2-(4-Methoxylbenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 368.1601 (Found); 368.1605 (Calculated) |
| 20 | 2-(Benzyl)-10-hydroxy-4,8-dimethyl-7,8-dihydropyrazino[1',2':1,5]-pyrrolo[2,3-d]pyridazine-1,9(2H,6H)-dione | ES MS M + 1 = 339.1457 (Found); 339.1452 (Calculated) |

-continued

| Example | Compound | Data |
| --- | --- | --- |
| 21 | 2-(4-Fluoro-2-methoxycarbonyllbenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 415.1393 (Found); 415.1412 (Calculated) |
| 22 | 2-(4-Fluoro-2-methylaminocarbonyllbenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 414.1558 (Found); 414.5172 (Calculated) |
| 23 | 2-(2,3-Dichlorobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 407.0658 (Found); 407.0672 (Calculated) |
| 24 | 2-(2-Fluorobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 357.1337 (Found); 357.1350 (Calculated) |
| 25 | 2-(3-Fluorobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 357.1342 (Found); 357.1358 (Calculated) |

| Example | Compound | Data |
|---|---|---|
| 26 | 2-(2,3-Difluorobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 375.1244 (Found); 375.1263 (Calculated) |
| 27 | 2-(3,4-Difluorobenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 375.1247 (Found); 375.1263 (Calculated) |
| 28 | 2-(2-Methoxybenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 369.1536 (Found); 369.1558 (Calculated) |
| 29 | 2-(2-Methylbenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 353.1592 (Found); 353.1608 (Calculated) |
| 30 | 2-(3,4-Dimethylbenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 367.1746 (Found); 367.1765 (Calculated) |

| Example | Compound | Data |
|---|---|---|
| 31 | 2-(3-Trifluoromethylbenzyl)-10-hydroxy-4,8-dimethyl-7,8-dihydropyrazino[1',2':1,5]-pyrrolo[2,3-d]pyridazine-1,9(2H,6H)-dione | ES MS M + 1 = 407.1311 (Found); 407.1326 (Calculated) |
| 32 | 2-(1,3-Benzodioxol-4-ylmethyl)-10-hydroxy-4,8-dimethyl-7,8-dihydropyrazino-[1',2':1,5]pyrrolo[2,3-d]pyridazine-1,9(2H,6H)-dione | ES MS M + 1 = 383.1334 (Found); 383.1350 (Calculated) |

EXAMPLE 33

2-(4-Fluorobenzyl)-10-hydroxy-6,8-dimethyl-7,8-dihydropyrazino[1',2':1,5]-pyrrolo[2,3-d]pyridazine-1,9(2H,6H)-dione

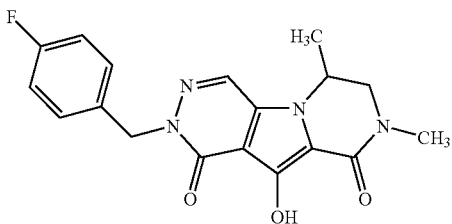

Step 1: 1,5-Dimethylpyrazin-2(1H)-one

A mixture of N'-methylglycinamide (6.34 g, 71.9 mmol), pyruvic aldehyde (40% wt solution in water, 12.9 mL, 71.9 mmol), and sodium hydroxide (2.88 g, 71.9 mmol) in water (250 mL) was heated at 100° C. for 30 minutes. The solution was cooled to 0° C. and saturated with solid sodium chloride. The resultant mixture was extracted with dichloromethane (3×). The organic extracts were combined, dried over anhydrous sodium sulfate, filtered, and concentrated under vacuum to provide the titled compound.

$^1$H NMR (400 MHz, CDCl$_3$) δ8.12 (1H, s); 6.93 (1H, s); 3.50 (3H, s); 2.28 (3H, s).
ES MS M+1=125

Step 2: 1,5-Dimethylpiperazin-2-one

A mixture of 1,5-dimethylpyrazin-2(1H)-one (5.7 g, 45.9 mmol) and platinum oxide (0.57 g) in ethyl acetate (100 mL) was stirred under an atmosphere of hydrogen (1 atm) at room temperature overnight. The product mixture was filtered through a pad of Celite, and concentrated under vacuum to provide 1,5-dimethyl-piperazin-2-one.

$^1$H NMR (400 MHz, CDCl$_3$) δ 3.55 (2H, d, J=6 Hz); 3.07-3.19 (3H, m); 2.95 (3H, s); 1.17 (3H, d, J=6 Hz)
ES MS M+1=129

Step 3: Ethyl 8-(benzyloxy)-6-bromo-2,4-dimethyl-1-oxo-1,2,3,4-tetrahydro-pyrrolo[1,2-a]-pyrazine-7-carboxylate Following the procedures described in Example 7, Steps 4 to 6, substituting 1-methylpiperazin-2-one with 1,5-dimethylpiperazin-2-one, the titled carboxylate was prepared.

$^1$H NMR (400 MHz, CDCl$_3$) δ 7.58 (2H, d, J=7 Hz), 7.35 (2H, t, J=7 Hz), 7.29-7.31 (1H, m), 5.23 (2H, s), 4.57-4.60 (1H, m), 4.30 (2H, q, J=7 Hz), 3.96 (1H, dd, J=4, 13 Hz), 3.24 (1H, d, J=13 Hz), 3.14 (3H, s), 1.44 (3H, d, J=7 Hz), 1.30 (3H, t, J=7 Hz).
ES MS M+1=421, 423

Step 4: Ethyl 8-(benzyloxy)-2,4-dimethyl-1-oxo-6-vinyl-1,2,3,4-tetrahydro-pyrrolo[1,2-a]-pyrazine-7-carboxylate A mixture of ethyl 8-(benzyloxy)-6-bromo-2,4-dimethyl-1-oxo-1,2,3,4-tetrahydro-pyrrolo[1,2-a]-pyrazine-7-carboxylate (0.5 g, 1.19 mmol), tri-n-butyl vinyltin (0.46 mL, 1.42 mmol), and bis(tri-tert-butylphosphine)palladium(0) (0.12 g, 0.24 mmol) in toluene (6 mL) was purged with nitrogen for 2 minutes and sealed. The mixture was heated in a microwave oven at 100° C. for 10 minutes. The reaction mixture was concentrated under vacuum. The residue was subjected to column chromatography on silica gel eluted with a hexanes and ethyl acetate gradient to provide titled product.

$^1$H NMR (400 MHz, CDCl$_3$) δ 7.59 (2H, d, J=7 Hz), 7.35 (2H, t, J=7 Hz), 7.27-7.30 (1H, m), 6.97 (1H, dd), 5.61 (1H, dd), 5.22 (2H, q), 4.60-4.63 (1H, m), 4.23-4.29 (2H, m), 3.92 (1H, dd, J=4, 13 Hz), 3.21 (1H, dd, J=1, 13 Hz), 3.15 (3H, s), 1.44 (3H, d, J=7 Hz), 1.27 (3H, t, J=7 Hz).
ES MS M+1=369

Step 5: Ethyl 8-(benzyloxy)-2,4-dimethyl-1-oxo-6-formyl-1,2,3,4-tetrahydro-pyrrolo[1,2-a]-pyrazine-7-carboxylate A mixture of ethyl 8-(benzyloxy)-2,4-dimethyl-1-oxo-6-vinyl-1,2,3,4-tetrahydro-pyrrolo[1,2-a]-pyrazine-7-carboxylate (0.11 g, 0.29 mmol), osmium tetroxide (2.5% in t-butanol, 0.59 mL, 0.058 mmol), sodium periodate (0.19 g, 0.87 mmol) in aqueous THF (6 mL, 1:2 v/v) was stirred at room temperature for 4 hours. The reaction mixture was treated with 10% aqueous sodium sulfite and diluted with ethyl acetate. The organic extract was washed with brine, dried over anhydrous magnesium sulfate, filtered, and concentrated under vacuum. The residue was subjected to column chromatography on silica gel eluted with a hexanes and ethyl acetate gradient to provide the titled product.

$^1$H NMR (400 MHz, CDCl$_3$) δ 10.33 (1H, s), 7.56-7.58 (2H, m), 7.31-7.39 (3H, m), 5.40-5.53 (1H, m), 5.22 (2H, q, J=10 Hz), 4.34 (2H, q, J=7 Hz), 3.96 (2H, dd, J=4, 13 Hz), 3.23 (1H, dd, J=1, 13 Hz), 3.17 (3H, s), 1.47 (3H, d, J=7 Hz), 1.32 (3H, t, J=7 Hz).

ES MS M+1=371

Step 6: 10-(Benzyloxy)-6,8-dimethyl-7,8-dihydropyrazino[1',2':1,5]pyrrolo[2,3-d]pyridazine-1,9(2H,6H)-dione A solution of ethyl 8-(benzyloxy)-2,4-dimethyl-1-oxo-6-formyl-1,2,3,4-tetrahydro-pyrrolo[1,2-a]-pyrazine-7-carboxylate (0.29 g, 0.79 mmol), and hydrazine monohydrate (0.20 mL, 3.96 mmol) in glacial acetic acid (2 mL) was heated in a microwave oven at 100° C. for 5 minutes. The reaction mixture was concentrated under vacuum and the residue partitioned between dichloromethane and aqueous sodium bicarbonate. The organic extract was dried over MgSO$_4$, filtered, and concentrated to provide the titled dione.

$^1$H NMR (400 MHz, CDCl$_3$) δ 8.09 (1H, s), 7.58-7.60 (2H, m), 7.42 (1H, s), 7.24-7.35 (3H, m), 5.56 (2H, dd, J=11, 24 Hz), 4.69-4.72 (1H, m), 4.03 (1H, dd, J=4, 13 Hz), 3.36 (1H, dd, J=2, 13 Hz), 3.17 (3H, s), 1.50 (3H, d, J=7 Hz).

ES MS M+1=339

Step 7: 10-(Benzyloxy)-2-(4-fluorobenzyl)-6,8-dimethyl-7,8-dihydropyrazino-[1',2':1,5]pyrrolo-[2,3-d]pyridazine-1,9(2H,6H)-dione A mixture of 10-(benzyloxy)-6,8-dimethyl-7,8-dihydropyrazino[1',2':1,5]-pyrrolo[2,3-d]pyridazine-1,9(2H,6H)-dione (0.12 g, 0.34 mmol), 4-fluorobenzyl bromide (63 μL, 0.34 mmol), and cesium carbonate (0.22 g, 0.68 mmol) in anhydrous DMF (1 mL) was stirred at room temperature for 2 hours. The reaction mixture was concentrated under vacuum and the residue partitioned between ethyl acetate and aqueous citric acid. The organic extract was washed with brine, dried over MgSO$_4$, filtered, and concentrated to provide the titled dione. The residue was subjected to column chromatography on silica gel eluted with a methanol-chloroform gradient to provide the titled product.

$^1$H NMR (400 MHz, CDCl$_3$) δ 7.92 (1H, s), 7.63 (2H, d, J=7 Hz), 7.43 (2H, dd, J=5, 9 Hz), 7.32 (2H, t, J=7 Hz), 7.25-7.26 (1H, m), 7.00 (2H, t, J=9 Hz), 5.59 (2H), 5.36 (2H, d, J=5 Hz), 4.52-4.61 (1H, m), 3.99 (1H, dd, J=4, 13 Hz), 3.29 (1H, dd, J=2, 13 Hz), 3.17 (3H, s), 1.50 (3H, d, J=7 Hz).

ES MS M+1=447.

Step 8: 2-(4-Fluorobenzyl)-10-hydroxy-6,8-dimethyl-7,8-dihydropyrazino-[1',2':1,5]-pyrrolo[2,3-d]pyridazine-1,9(2H,6H)-dione A mixture of 10-(benzyloxy)-2-(4-fluorobenzyl)-6,8-dimethyl-7,8-dihydropyrazino-[1',2':1,5]pyrrolo-[2,3-d]pyridazine-1,9(2H,6H)-dione (99 mg, 0.22 mmol) and Pearlman's catalyst (20 mg, 20% Pd(OH)$_2$ on carbon) in methanol (2 mL) was stirred under an atmosphere of hydrogen gas (1 atm) at room temperature for one hour. The reaction mixture was filtered through a pad of Celite. The filtrate was concentrated under vacuum, and the residue triturated with diethyl ether. The solid precipitated was obtained by filtration to provide the titled product.

$^1$H NMR (400 MHz, CDCl$_3$) δ 8.30 (1H, s), 7.92 (1H, s), 7.46 (2H, dd, J=5.5, 8.5 Hz), 6.98 (2H, t, J=9 Hz), 5.32 (2H); 4.57-4.60 (1H, m), 3.96 (1H, dd, J=4, 13 Hz), 3.34 (1H, dd, J=3, 13 Hz), 3.14 (3H, s), 1.50 (3H, d, J=7 Hz).

ES MS M+1=357.1355 (Found); 357.1363 (Calculated)

EXAMPLES 34-35

The compounds in the following table were prepared in accordance with the procedure set forth in Example 33 using the appropriate 3-chloro-4-fluorobenzyl bromide in place of 4-fluorobenzyl bromide in Example 34 and in Example 35 also using 1-ethyl-5-methylpyrazin-2(1H)-one in place of 1,5-dimethylpyrazin-2(1H)-one.

| Example | Compound | Data |
|---|---|---|
| 34 | 2-(3-Chloro-4-fluorobenzyl)-10-hydroxy-6,8-dimethyl-7,8-dihydropyrazino[1',2':1,5]-pyrrolo[2,3-d]pyridazine-1,9(2H,6H)-dione | $^1$H NMR (400 MHz, CDCl$_3$) δ 8.32 (1H, br s), 7.93 (1H, s), 7.52 (1H, dd, J = 2, 7 Hz), 7.36-7.39 (1H, m), 7.06 (1H, t, J = 9 Hz), 5.28 (2H, dd), 4.58-4.61 (1H, m), 3.97 (1H, dd, J = 4.5, 13 Hz), 3.35 (1H, dd, J = 2.5, 13 Hz), 3.14 (3H, s), 1.51 (3H, d, J = 7 Hz). ES MS M + 1 = 391.0963 (Found); 391.0973 (Calculated) |

| Example | Compound | Data |
|---|---|---|
| 35 | 2-(3-Chloro-4-fluorobenzyl)-8-ethyl-10-hydroxy-6-dimethyl-7,8-dihydropyrazino-[1',2':1,5]-pyrrolo[2,3-d]pyridazine-1,9(2H,6H)-dione 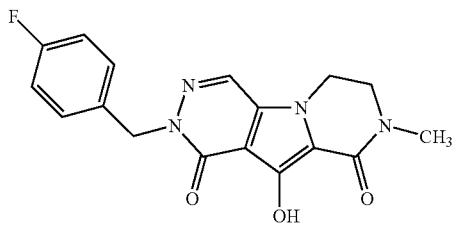 | $^1$H NMR (400 MHz, CDCl$_3$) δ 8.34 (1H, br s), 7.93 (1H, s), 7.52 (1H, dd, J = 2, 7 Hz), 7.35-7.39 (1H, m), 7.06 (1H, t, J = 9 Hz), 5.28 (2H, q, J = 14 Hz), 4.58-4.61 (1H, m), 4.96 (1H, dd, J = 4.14 Hz), 3.69-3.75 (1H, m), 3.47-3.53 (1H, m), 3.35 (1H, dd, J = 2, 13 Hz), 1.49 (3H, d, J = 7 Hz), 1.24 (3H, t, J = 7 Hz). ES MS M + 1 = 405.1113 (Found); 405.1124 (Calculated) |

EXAMPLE 36

2-(4-Fluorobenzyl)-10-hydroxy-8-methyl-7,8-dihydropyrazino[1',2':1,5]-pyrrolo[2,3-d]pyridazine-1,9(2H,6H)-dione

Step 1:
4,5-Dibromo-2-(4-fluorobenzyl)pyridazin-3(2H)-one

A mixture of 4,5-dibromopyridazin-3(2H)-one (1.0 g, 3.94 mmol), 4-fluorobenzyl bromide (0.89 g, 4.7 mmol), and cesium carbonate (1.67 g, 5,12 mmol) in anhydrous DMF (20 mL) was stirred at room temperature overnight. The mixture was filtered, and the filtrate concentrated under vacuum. The residue was partitioned between brine and ethyl acetate. The organic extract was washed with brine, dried over anhydrous sodium sulfate, filtered, and concentrated under vacuum. The residue was triturated with a mixture of dichloromethane and hexane. The solid precipitated was obtained by filtration to provide the titled dibromide.

$^1$H NMR (400 MHz, CDCl$_3$) δ 7.80 (s, 1H), 7.44 (dd, J=8.8, 5.5 Hz, 2H), 7.01 (t, J=8.6 Hz, 2Hz), 5.27 (s, 2H).
ES MS M+1=361.1, 363.1, 365.1.

Step 2: 4-Bromo-2-(4-fluorobenzyl)-5-(4-methyl-3-oxopiperazin-1-yl)pyridazin-3(2H)-one A mixture of 4,5-dibromo-2-(4-fluorobenzyl)pyridazin-3(2H)-one (0.8 g, 2.21 mmol), 1-methylpiperazin-2-one (0.33, 2.87 mmol; see Example 7, Step 3), and diisopropylethylamine (0.34 g, 3.32 mmol) in absolute ethanol (3 mL) was heated in a sealed tube in an oil bath at 100° C. overnight. The mixture was concentrated under vacuum. The residue was partitioned between ethyl acetate and brine. The organic extract was dried over sodium sulfate, filtered, and concentrated under vacuum. The residue was subjected to column chromatography on silica gel eluted with hexanes and ethyl acetate gradient to give titled material.

$^1$H NMR (400 MHz, CDCl$_3$) δ 7.50 (s, 1H), 7.44 (dd, J=8.6, 5.4 Hz, 2H), 7.00 (t, J=8.7 Hz, 2H), 5.27 (s, 2H), 4.00 (s, 2H), 3.71 (t, J=5.6 Hz, 2H), 3.51 (t, J=5.6 Hz, 2H), 3.03 (s, 3H).
ES MS M+1=395.2, 397.2

Step 3: 2-(4-Fluorobenzyl)-10-hydroxy-8-methyl-7,8-dihydropyrazino[1',2':1,5]-pyrrolo[2,3-d]pyridazine-1,9(2H,6H)-dione A mixture of 4-bromo-2-(4-fluorobenzyl)-5-(4-methyl-3-oxopiperazin-1-yl)pyridazin-3(2H)-one (0.2 g, 0.51 mmol), dicyclohexylmethylamine (0.15 g, 0.76 mmol), and bis-(tri-t-butylphosphine)palladium (0) (52 mg, 0.10 mmol) in anhydrous methanol (5 mL) was heated in a stainless steel pressure vessel under an atmosphere of carbon monoxide (250 psi) in an oil bath at 90° C. overnight. The resultant mixture was diluted with methanol, filtered through a pad of Celite. The filtrate was concentrated under vacuum. The residual oil was triturated with methanol. The white solid precipitated was filtered to provide the titled dione.

$^1$H NMR (400 MHz, d$_6$ DMSO) δ 8.98 (s, 1H), 8.35 (s, 1H), 7.31 (dd, J=8.4, 5.6 Hz, 2H), 7.13 (t, J=8.6 Hz, 2H), 5.22 (s, 2H), 4.33 (t, J=5.7 Hz, 2H), 3.71 (t, J=5.5 Hz, 2H), 2.99 (s, 3H).
ES MS M+1=343.3.

EXAMPLE 37

2-(4-Fluorobenzyl)-10-hydroxy-4,6,8-trimethyl-7,8-dihydropyrazino[1',2':1,5]-pyrrolo[2,3-d]pyridazine-1,9(2H,6H)-dione

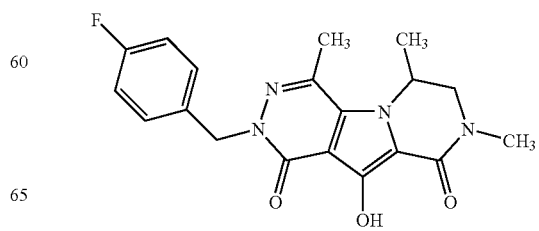

Following the procedures described in Example 33, Steps 1 to 3, and Example 7, Step 7, substituting ethyl 8-(benzyloxy)-6-bromo-2-methyl-1-oxo-1,2,3,4-tetrahydro-pyrrolo[1,2-a]-pyrazine-7-carboxylate with ethyl 8-(benzyloxy)-6-bromo-2,4-dimethyl-1-oxo-1,2,3,4-tetrahydro-pyrrolo[1,2-a]-pyrazine-7-carboxylate, and procedures described in Example 8, Steps 1 to 2, the titled dione was prepared.

¹H NMR (400 MHz, CDCl₃) δ8.51 (1H, br s), 7.45-7.48 (2H, m), 6.97 (2H, t, J=8 Hz), 5.26 (2H, dd), 4.81-4.83 (1H, m), 4.04 (1H, dd, J=4, 13 Hz), 3.29 (1H, d, J=13 Hz), 3.14 (3H, s), 2.57 (3H, s), 1.46 (3H, d, J=7 Hz).

ES MS M+1=371.1493 (Found); 371.1519 (Calculated)

EXAMPLE 38

8-Ethyl-2-(4-fluorobenzyl)-10-hydroxy-4,6-dimethyl-7,8-dihydropyrazino[1',2':1,5]-pyrrolo[2,3-d]pyridazine-1,9(2H,6H)-dione

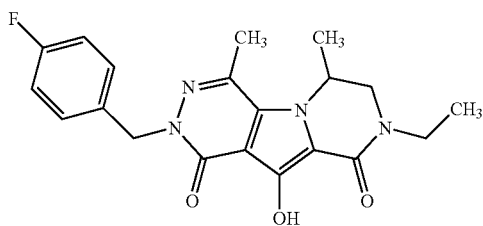

The title compound was prepared in accordance with the procedure set forth in Example 37 using 1-ethyl-5-methylpyrazin-2(1H)-one in place of 1,5-dimethylpyrazin-2(1H)-one.

¹H NMR (400 MHz, d₆ DMSO) δ7.27-7.30 (2H, m), 7.09 (2H, t, J=9 Hz), 5.15 (2H, s), 4.78-4.84 (1H, m), 3.74 (1H, dd, J=3, 13 Hz), 3.50-3.55 (1H, m), 3.37-3.42 (1H, m), 3.26-3.32 (1H, m), 2.49 (3H, s), 1.25 (3H, d, J=7 Hz), 1.08 (3H, t, J=7 Hz).

ES MS M+1=385.1668 (Found); 385.1676 (Calculated)

EXAMPLE 39

4-Amino-8-(4-Fluorobenzyl)-10-hydroxy-2-methyl-7,8-dihydropyrazino[1',2':1,5]-pyrrolo[2,3-d]pyridazine-1,9(2H,6H)-dione

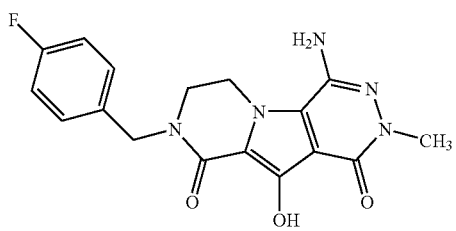

Step 1: Ethyl 8-(benzyloxy)-6-cyano-2-(4-fluorobenzyl)-1-oxo-1,2,3,4-tetrahydropyrrolo[1,2-a]-pyrazine-7-carboxylate A solution of ethyl 8-(benzyloxy)-6-bromo-2-(4-fluorobenzyl)-1-oxo-1,2,3,4-tetrahydropyrrolo[1,2-a]-pyrazine-7-carboxylate (1.40 g, 2.79 mmol; Example 1, Step 7), zinc cyanide (0.26 g, 2.23 mmol), tris(dibenzylideneacetone)dipalladium (0) (0.51 g, 0.56 mmol), triphenylphosphine (0.15 g, 0.56 mmol) in DMF (4.5 mL) was purged with nitrogen for 5 minutes. The reaction mixture was heated at 100° C. overnight and concentrated under vacuum. The reaction mixture was partitioned between dichloromethane and brine. The organic extract was dried over sodium sulfate, filtered and concentrated. The residue was subjected to column chromatography on silica gel eluted with 0-10% methanol in chloroform gradient to provide titled product.

¹H NMR (400 MHz, CDCl₃) δ 7.58 (br d, J=7.1 Hz, 2H), 7.39-7.28 (m, 5H), 7.03 (t, J=8.0 Hz, 2H), 5.27 (s, 2H), 4.68 (s, 2H), 4.35 (q, J=7.2 Hz, 2H), 4.14 (t, J=5.9 Hz, 2H), 3.54 (t, J=5.9 Hz, 2H), 1.36 (t, J=7.2 Hz, 3H).

ES MS M+1=448

Step 2: 4-Amino-8-(4-Fluorobenzyl)-10-hydroxy-2-methyl-7,8-dihydropyrazino-[1',2':1,5]-pyrrolo[2,3-d]pyridazine-1,9(2H,6H)-dione A mixture of ethyl 8-(benzyloxy)-6-cyano-2-(4-fluorobenzyl)-1-oxo-1,2,3,4-tetrahydropyrrolo[1,2-a]-pyrazine-7-carboxylate (0.50 g, 1.12 mmol) and methylhydrazine (0.30 mL, 5.59 mmol), and drop of acetic acid in ethanol (12 mL) was heated in a sealed tube at 105° C. overnight. The reaction mixture was concentrated under vacuum and the residue subjected to purification on reverse phase HPLC. Collection and lyophilization of appropriate fractions provided the intermediate aminopyridazine. A mixture of this aminopyridazine (113 mg, 0.25 mmol) and Pearlman's catalyst (5 mg, 20% Pd(OH)₂ on carbon) in ethanol-THF (12 mL, 1:1 v/v) was stirred under an atmosphere of hydrogen gas (1 atm) at room temperature overnight. The reaction mixture was diluted with DMF, filtered through a pad of Celite. The filtrate was concentrated under vacuum, and the residue triturated with diethyl ether. The solid precipitated was obtained by filtration to provide the titled product.

¹H NMR (400 MHz, CDCl₃) δ8.86 (br s, 1H), 7.39(dd, J=8.6, 5.7, 2H), 7.03 (t, J=9.0 Hz, 2H), 5.49 (s, 2H), 4.45 (t, J=5.7 Hz, 2H), 3.63 (t, J=5.7 Hz, 2H), 3.43 (s, 3H).

ES MS M+1=358.1308 (Found); 358.1310 (Calculated)

EXAMPLE 40

8-(4-Fluorobenzyl)-10-hydroxy-2-methyl-4-morpholin-4-yl-7,8-dihydropyrazino[1',2':1,5]-pyrrolo[2,3-d]pyridazine-1,9(2H,6H)-dione

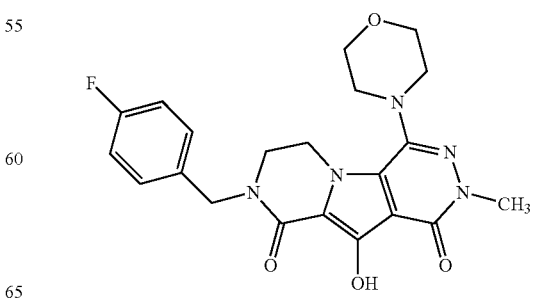

Step 1: 10-(Benzyloxy)-8-(4-fluorobenzyl)-2-methyl-4-morpholin-4-yl-7,8-dihydropyrazino[1',2':1,5]pyrrolo[2,3-d]]pyridazine-1,9(2H,6H)-dione A mixture of ethyl 8-(benzyloxy)-6-cyano-2-(4-fluorobenzyl)-1-oxo-1,2,3,4-tetrahydropyrrolo[1,2-a]-pyrazine-7-carboxylate (0.50 g, 1.12 mmol; Step 1, Example 39) and methylhydrazine (0.30 mL, 5.59 mmol), and drop of acetic acid in ethanol (12 mL) was heated in a sealed tube at 105° C. overnight. The reaction mixture was concentrated under vacuum and the residue subjected to purification on reverse phase HPLC. Collection and lyophilization of appropriate fractions provided the intermediate aminopyridazine. Residual water and TFA in the aminopyridazine sample were removed by concentration from solution in acetonitrile, and then from benzene under vacuum. A solution of this aminopyridazine (0.10 g, 0.22 mmol) in anhydrous DMF (2.5 mL) at room temperature under an atmosphere of nitrogen, a solution of sodium bis(trimethylsilylamide) in THF (0.67 mL, 1M) was added. After stirring at room temperature for 30 minutes, 2-bromoethyl ether (78 mg, 0.34 mmol) was added. The mixture was stirred at room temperature overnight and concentrated under vacuum. The residue was partitioned between ethyl acetate and brine. The organic extract was dried over anhydrous sodium sulfate, filtered, and concentrated under vacuum. The residue was subjected to column chromatography on silica gel eluting with 80-100% ethyl acetate in dichloromethane gradient. Collection and concentration of appropriate fractions provided the titled compound.

ES MS M+1=518

Step 2: 8-(4-Fluorobenzyl)-10-hydroxy-2-methyl-4-morpholin-4-yl-7,8-dihydropyrazino[1',2':1,5]-pyrrolo[2,3-d]pyridazine-1,9(2H,6H)-dione A mixture of 10-(benzyloxy)-8-(4-fluorobenzyl)-2-methyl-4-morpholin-4-yl-7,8-dihydropyrazino[1',2':1,5]pyrrolo[2,3-d]]pyridazine-1,9(2H,6H)-dione (50 mg, 0.097 mmol) and Pearlman's catalyst (2 mg, 20% Pd(OH)$_2$ on carbon) in methanol(20 mL) was stirred under an atmosphere of hydrogen gas (1 atm) at room temperature overnight. The reaction mixture was filtered through a pad of Celite. The filtrate was concentrated under vacuum, and the residue subjected to purification on reverse phase HPLC. Collection and lyophilization of appropriate fractions provided the titled product.

$^1$H NMR (400 MHz, CDCl$_3$) δ 7.31(dd, J=8.6, 5.7, 2H), 7.06 (t, J=9.0 Hz, 2H), 4.70 (s, 2H), 4.47 (t, J=5.7 Hz, 2H), 3.71 (s, 3H), 3.59 (t, J=5.7 Hz, 2H), 3.08 (br t, 8H).

ES MS M+1=428

EXAMPLE 41

4-Amino-2-(4-Fluorobenzyl)-10-hydroxy-8-methyl-7,8-dihydropyrazino[1',2':1,5]-pyrrolo[2,3-d]pyridazine-1,9(2H,6H)-dione

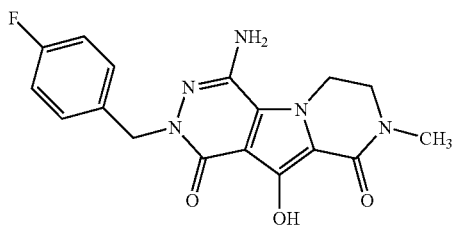

Step 1: 4-Amino-2-(4-Fluorobenzyl)-10-(benzyloxy)-8-methyl-7,8-dihydro-pyrazino[1',2':1,5]-pyrrolo[2,3-d]pyridazine-1,9(2H,6H)-dione Following the procedures described in Example 39, substituting ethyl 8-(benzyloxy)-6-bromo-2-(4-fluorobenzyl)-1-oxo-1,2,3,4-tetrahydropyrrolo[1,2-a]-pyrazine-7-carboxylate with ethyl 8-(benzyloxy)-6-bromo-2-methyl-1-oxo-1,2,3,4-tetrahydro-pyrrolo[1,2-a]-pyrazine-7-carboxylate (Example 7, Step 6) in Step 1 and substituting methylhydrazine with 4-fluorobenzyl hydrazine in Step 2, the titled dione was prepared.

ES MS M+1=448

Step 2: 4-Amino-2-(4-Fluorobenzyl)-10-hydroxy-8-methyl-7,8-dihydropyrazino-[1',2':1,5]-pyrrolo[2,3-d]pyridazine-1,9(2H,6H)-dione To a solution of 4-amino-2-(4-fluorobenzyl)-10-(benzyloxy)-8-methyl-7,8-dihydropyrazino[1',2':1,5]-pyrrolo[2,3-d]pyridazine-1,9(2H,6H)-dione (0.11 g, 0.25 mmol) in dichloromethane (10 mL) at 0° C., a solution of boron tribromide in dichloromethane (0.7 mL, 1M) was added. The resultant solution was stirred at room temperature overnight. The reaction mixture was concentrated under vacuum and the residue subjected to purification on reverse phase HPLC. Collection and lyophilization of appropriate fractions provided the titled compound.

$^1$H NMR (400 MHz, CDCl$_3$) δ7.39(dd, J=8.6, 5.5, 2H), 6.96 (t, J=8.8 Hz, 2H), 5.13 (s, 2H), 4.48 (t, J=5.9 Hz, 2H), 3.71 (t, J=5.9 Hz, 2H), 3.10 (s, 3H).

ES MS M+1=358

EXAMPLE 42

4-Amino-2-benzyl-10-hydroxy-8-methyl-7,8-dihydropyrazino[1',2':1,5]-pyrrolo[2,3-d]pyridazine-1,9(2H,6H)-dione

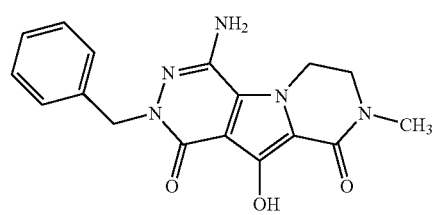

The title compound was prepared in accordance with the procedure set forth in Example 41 using benzyl hydrazine in place of 4-fluorobenzyl hydrazine. ES MS M+1=340

EXAMPLE 43

2-(4-Fluorobenzyl)-4,10-dihydroxy-8-methyl-7,8-dihydropyrazino[1',2':1,5]-pyrrolo[2,3-d]pyridazine-1,9(2H,6H)-dione

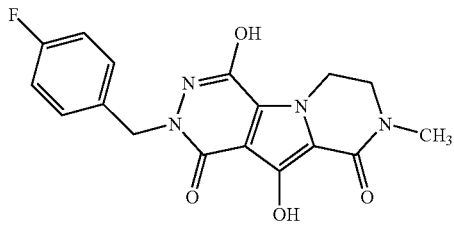

Step 1: tert-Butyl 2-(4-fluorobenzyl)-2-[(8-benzyloxy-2-methyl-1-oxo-1,2,3,4-tetrahydropyrrolo[1,2-a]pyrazin-7-yl)carbonyl]hydrazinecarboxylate To a cold (0° C.) solution of tert-butyl 2-(4-fluorobenzyl) hydrazinecarboxylate (7.30 g, 30.37 mmol; see Fassler et al., J. Med Chem. 1996, 3203) and diisopropylethylamine (10.70 g, 82.82 mmol) in dichloromethane (200 mL), a solution of 8-(benzyloxy)-2-methyl-1-oxo-1,2,3,4-tetrahydropyrrolo[1,2-a]pyrazine-7-carbonyl chloride (8.80 g, 27.61 mmol; derived from treatment of the corresponding acid with oxalyl chloride in dichloromethane in the presence of catalytic amount of DMF at room temperature) in dichloromethane was added. The resultant mixture was stirred at room temperature overnight. The resultant mixture was washed with aqueous ammonium chloride, and brine. The organic extract was dried over anhydrous sodium sulfate, filtered, and concentrated under vacuum to provide the titled amide. This was used with no further purification.

$^1$H NMR (400 MHz, CDCl$_3$) δ 7.30-6.87 (m, 10H), 5.20 (br signals, 4H), 4.08 (t, J=5.8 Hz, 2H), 3.62 (t, J=5.8 Hz, 2H), 3.12 (s, 3H), 1.60 (s, 9H).

ES MS M+1=523

Step 2: tert-Butyl 2-(4-fluorobenzyl)-2-[(8-benzyloxy-6-bromo-2-methyl-1-oxo-1,2,3,4-tetrahydropyrrolo[1,2-a]pyrazin-7-yl)carbonyl]hydrazinecarboxylate To a mixture of tert-butyl 2-(4-fluorobenzyl)-2-[(8-benzyloxy-2-methyl-1-oxo-1,2,3,4-tetrahydropyrrolo[1,2-a]pyrazin-7-yl)carbonyl]hydrazinecarboxylate (14.43 g, 27.61 mol) and solid sodium bicarbonate (25 g) in dichloromethane (300 mL), solution of bromine (77 mL, 0.5 M) in dichloromethane was added. After stirring at room temperature for one hour, the mixture was filtered, and the filtrate concentrated under vacuum. The residue was subjected to column chromatography on silica gel eluting with a dichloromethane-ethyl acetate gradient. Collection and concentration of appropriate fractions provided the titled bromide.

$^1$H NMR (400 MHz, CDCl$_3$) δ 7.30-6.87 (m, 9H), 5.20 (br signals, 4H), 4.09 (br s 2H), 3.63 (br s, 2H), 3.12 (s, 3H), 1.56 (s, 9H).

ES MS M+1=523

Step 3: 10-(Benzyloxy)-2-(4-fluorobenzyl)-4-hydroxy-8-methyl-7,8-dihydropyrazino-[1',2':1,5]-pyrrolo[2,3-d]pyridazine-1,9(2H,6H)-dione A cold (0° C.) solution of tert-butyl 2-(4-fluorobenzyl)-2-[(8-benzyloxy-6-bromo-2-methyl-1-oxo-1,2,3,4-tetrahydropyrrolo[1,2-a]pyrazin-7-yl)carbonyl]hydrazine-carboxylate (12.30 g, 20.45 mmol) in dichloromethane (150 mL) was saturated with anhydrous HCl gas. After stirring at 0° C. for half an hour, the mixture was treated with saturated aqueous sodium bicarbonate. The organic layer was separated, and the aqueous phase extracted with dichloromethane. The organic extracts were combined, washed with brine, dried over anhydrous sodium sulfate, filtered and concentrated under vacuum. The residue was dissolved in benzene and concentrated under vacuum. The residual white solid was used without further purification. A solution of the above 8-(benzyloxy)-6-bromo-N-(4-fluorobenzyl)-2-methyl-1-oxo-1,2,3,4-tetrahydropyrrolo[1,2-a]pyrazine-7-carbohydrazide (5.20 g, 10.37 mmol) and dicyclohexylmethylamine (3.03 g, 15.53 mmol) in anhydrous DMF (100 mL) was purged with nitrogen for 10 minutes. Bis-(tri-tert-butylphosphine)palladium (0) (0.74 g, 1.45 mmol) was added and mixture was heated under an atmosphere of carbon monoxide (400 psi) in a stainless vessel in an oil bath at 90° C. overnight. The mixture was filtered through a pad of Celite. The filtrate was concentrated under vacuum to remove~80 mL of the solvent. The residue was partitioned between dichloromethane (600 mL) and dilute aqueous HCl. The organic extract was washed with brine, dried over sodium sulfate, filtered, and concentrated under vacuum. As the solution was concentrated to about 20 mL, the solution was cooled in an ice-water bath. The solid precipitated was filtered, washed with cold (0° C.) dichloromethane, and dried in vacuum to provide the titled compound.

$^1$H NMR (400 MHz, CDCl$_3$) δ 7.60 (br d, 2H), 7.36-7.29 (m, 5H), 6.98 (br t, 2H), 5.49 (s, 2H), 5.10 (s, 2H), 4.58 (br t, 2H), 3.71 (br t, 2H), 3.15 (s, 3H).

ES MS M+1=449

Step 4: 2-(4-Fluorobenzyl)-4,10-dihydroxy-8-methyl-7,8-dihydropyrazino[1',2':1,5]-pyrrolo[2,3-d]pyridazine-1,9(2H,6H)-dione A mixture of 10-(benzyloxy)-2-(4-fluorobenzyl)-4-hydroxy-8-methyl-7,8-dihydropyrazino[1',2':1,5]-pyrrolo[2,3-d]pyridazine-1,9(2H,6H)-dione (23 mg, 0.05 mmol) and Pearlman's catalyst [25 mg, 20% Pd(OH)$_2$ on carbon] in methanol (10 mL) was stirred under an atmosphere of hydrogen gas (1 atm) at room temperature for 45 minutes. The reaction mixture was diluted with acetonitrile and filtered. The filtrate was concentrated under vacuum, and the residue was subjected to purification on reverse phase HPLC. Collection and lyophilization of appropriate fractions provided the titled compound.

$^1$H NMR (400 MHz, CDCl$_3$ with 10% d$_6$ DMSO) δ 8.35 (br s, 1H), 7.39(br m, 2H), 6.98 (br m, 2H), 5.15 (br d, 2H), 4.55 (br t, 2H), 3.63 (br t, 2H), 3.11 (s, 3H).

ES MS M+1=359

EXAMPLE 44

2-(4-Fluorobenzyl)-10-hydroxy-4-methoxy-8-methyl-7,8-dihydropyrazino[1',2':1,5]-pyrrolo[2,3-d]pyridazine-1,9(2H,6H)-dione

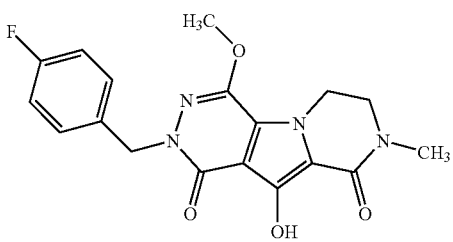

Step 1: 10-(Benzyloxy)-2-(4-fluorobenzyl)-4-methoxy-8-methyl-7,8-dihydropyrazino-[1',2':1,5]-pyrrolo[2,3-d]pyridazine-1,9(2H,6H)-dione A suspension of 10-(benzyloxy)-2-(4-fluorobenzyl)-4-hydroxy-8-methyl-7,8-dihydropyrazino[1',2':1,5]-pyrrolo[2,3-d]pyridazine-1,9(2H,6H)-dione (0.50 g, 1.11 mmol) in mixture of dichloromethane (20 mL) and methanol (1 mL) at room temperature was treated with a solution of (trimethylsilyl)diazomethane in hexane. After stirring for 30 minutes, the resultant homogeneous solution was treated with a few drops of acetic acid, and the mixture was concentrated under vacuum. The residue was partitioned between chloroform and brine. The organic extract was dried over anhydrous sodium sulfate, filtered, and concentrated under vacuum. The residue was subject to column chromatography on silica gel eluting with 2% methanol in chloroform. Collection and concentration of the faster eluting major product provide the titled compound.

ES MS M+1=463

Step 2: 2-(4-Fluorobenzyl)-10-hydroxy-4-methoxy-8-methyl-7,8-dihydropyrazino-[1',2':1,5]-pyrrolo[2,3-d]pyridazine-1,9(2H,6H)-dione A mixture of 10-(benzyloxy)-2-(4-fluorobenzyl)-4-methoxy-8-methyl-7,8-dihydropyrazino[1',2':1,5]-pyrrolo[2,3-d]pyridazine-1,9(2H,6H)-dione (23 mg, 0.05 mmol) and Pearlman's catalyst [23 mg, 20% Pd(OH)$_2$ on carbon] in methanol (20 mL) was stirred under an atmosphere of hydrogen gas (1 atm) at room temperature for 25 minutes. The reaction mixture was diluted with acetonitrile and filtered. The filtrate was concentrated under vacuum, and the residue was subjected to purification on reverse phase HPLC. Collection and lyophilization of appropriate fractions provided the titled compound.

$^1$H NMR (400 MHz, d$_6$ DMSO) δ 8.95 (br s, 1H), 7.30(dd, J=8.6, 5.5, 2H), 7.15 (t, J=8.8 Hz, 2H), 5.05 (s, 2H), 4.37 (t, J=5.9 Hz, 2H), 3.84 (s, 3H), 3.66 (t, J=5.9 Hz, 2H), 2.95 (s, 3H).

ES MS M+1=373

EXAMPLES 45-46

The compounds in the following table were prepared in accordance with the procedure set forth in Example 44.

| Example | Compound | ES MS M + 1 |
|---|---|---|
| 45 | 2-(3-Chloro-4-fluorobenzyl)-10-hydroxy-4-ethoxy-8-methyl-7,8-dihydropyrazino[1',2':1,5]pyrrolo[2,3-d]pyridazine-1,9(2H,6H)-dione | 421 |
| 46 | 8-(4-Fluorobenzyl)-10-hydroxy-4-methoxy-2-methyl-7,8-dihydropyrazino[1',2':1,5]pyrrolo[2,3-d]pyridazine-1,9(2H,6H)-dione | 373 |

EXAMPLE 47

6(S)-2-(4-Fluorobenzyl)-10-hydroxy-6-isopropyl-4,8-dimethyl-7,8-dihydropyrazino[1',2':1,5]pyrrolo[2,3-d]pyridazine-1,9(2H,6H)-dione

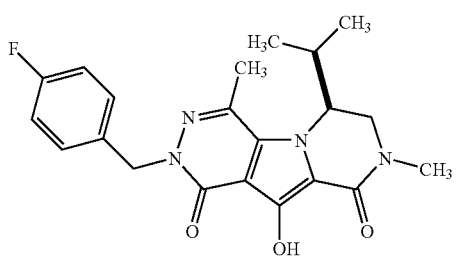

The title compound was prepared in accordance with the procedure set forth in Example 37 using (5S)-1-methyl-5-isopropylpyrazin-2(1H)-one (Williams et al., *J Med. Chem.*, 1999, 3779) in place of 1,5-dimethylpyrazin-2(1H)-one.

$^1$H NMR (400 MHz, CDCl$_3$) δ 8.51 (br s, 1H), 7.47(dd, J=8.6, 5.7, 2H), 7.03 (t, J=8.8 Hz, 2H), 5.30 (dd, J=13.9 Hz, 1H), 5.23 (dd, J=13.9 Hz, 1H), 4.35 (br m, 1H), 3.97 (d, J=4.3 Hz, 1H), 3.94 (d, J=4.3 Hz, 1H), 3.53 (d, J=13.2 Hz, 1H), 3.12 (s, 3H), 2.54 (s, 3H), 2.16 (heptet, J=6.9 Hz, 1H), 0.98 (d, J=7.1 Hz, 3H), 0.80 (d, J=7.1 Hz, 3H).

ES MS M+1=399.1826 (Found); 399.1827 (Calculated).

EXAMPLES 48-58

The compounds in the following table were prepared in accordance with the procedure set forth in Example 47.

| Ex. | Name | A | B | C & D | M + 1 |
|---|---|---|---|---|---|
| 48 | 6(S)-8-Ethyl-2-(4-fluorobenzyl)-10-hydroxy-6-isopropyl-4-methyl-7,8-dihydropyrazino[1',2':1,5]pyrrolo[2,3-d]pyridazine-1,9(2H,6H)-dione | H | Me-C(Me)- * | C = H<br>D = Et | 413 |
| 49 | 6(S)-8-Ethyl-2-(4-fluorobenzyl)-10-hydroxy-4,6-dimethyl-7,8-dihydropyrazino[1',2':1,5]pyrrolo[2,3-d]pyridazine-1,9(2H,6H)-dione | H | Me * | C = H<br>D = Et | 385 |
| 50 | 6(S)-2-(4-Fluorobenzyl)-10-hydroxy-8-isopropyl-4,6-dimethyl-7,8-dihydropyrazino[1',2':1,5]pyrrolo[2,3-d]pyridazine-1,9(2H,6H)-dione | H | Me * | C = H<br>D = i-Pr | 399 |
| 51 | 6(S)-2-(3-Chloro-4-fluorobenzyl)-10-hydroxy-8-isopropyl-4,6-dimethyl-7,8-dihydropyrazino[1',2':1,5]pyrrolo[2,3-d]pyridazine-1,9(2H,6H)-dione | Cl | Me * | C = H<br>D = i-Pr | 432 |
| 52 & 53 | 2-(4-Fluorobenzyl)-10-hydroxy-4,6,8-trimethyl-7,8-dihydropyrazino[1',2':1,5]pyrrolo[2,3-d]pyridazine-1,9(2H,6H)-dione<br>The resulting racemic mixture was seperated with preparative chiral HPLC to afford both enantiomers | H | Me | C = H<br>D = Me | 371 |
| 54 | (6aR)-2-(4-fluorobenzyl)-12-hydroxy-4-methyl-6a,7,8,9-tetrahydro-1H,6H-pyrrolo[1'',2'':4',5']pyrazino[1',2':1,5]pyrrolo[2,3-d]pyridazine-1,11(2H,6H)-dione | H | H | C = D: (cyclopentane ring) | 383 |
| 55 | (6aS)-2-(4-fluorobenzyl)-12-hydroxy-4-methyl-6a,7,8,9-tetrahydro-1H,6H-pyrrolo[1'',2'':4',5']pyrazino[1',2':1,5]pyrrolo[2,3-d]pyridazine-1,11(2H)-dione | H | H | C = D: (cyclopentane ring) | 383 |

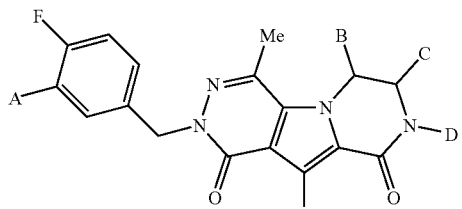

| Ex. | Name | A | B | C & D | M + 1 |
|---|---|---|---|---|---|
| 56 | (racemic) 8-Ethyl-2-(4-fluorobenzyl)-10-hydroxy-4-methyl-6-(hydroxymethyl)-7,8-dihydropyrazino[1',2':1,5]pyrrolo[2,3-d]pyridazine-1,9(2H,6H)-dione | H | HOH₂C\* | C = H<br>D = Et | 401 |
| 57 | (racemic) 8-Ethyl-2-(4-fluorobenzyl)-10-hydroxy-4-methyl-6-(hydroxymethyl)-7,8-dihydropyrazino[1',2':1,5]pyrrolo[2,3-d]pyridazine-1,9(2H,6H)-dione | H | CH₂SMe\* | C = H<br>D = Et | 431 |
| 58 | (racemic) 8-Ethyl-2-(4-fluorobenzyl)-10-hydroxy-4-methyl-6-[(methylsulfonyl)methyl]-7,8-dihydropyrazino[1',2':1,5]pyrrolo[2,3-d]pyridazine-1,9(2H,6H)-dione | H | CH₂SO₂Me\* | C = H<br>D = Et | 463 |

Note: M + 1 determined by ES MS.

EXAMPLE 59

4-Ethyl-2-(4-fluorobenzyl)-10-hydroxy-8-methyl-7,8-dihydropyrazino[1',2':1,5]pyrrolo[2,3-d]pyridazine-1,9(2H,6H)-dione

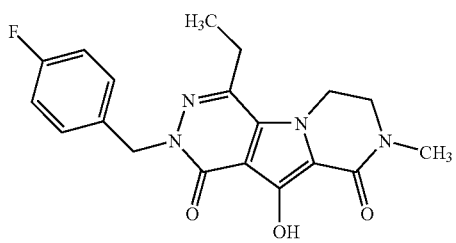

Step 1: Ethyl 8-(benzyloxy)-2-methyl-1-oxo-6-propionyl-1,2,3,4-tetrahydropyrrolo[1,2-a]pyrazine-7-carboxylate To a cold (−78° C.) solution of ethyl 6-acetyl-8-(benzyloxy)-2-methyl-1-oxo-1,2,3,4-tetrahydropyrrolo[1,2-a]pyrazine-7-carboxylate (0.60 g, 1.62 mmol; Example 7, step 7) in anhydrous DMF (17 mL), a solution of lithium bis(trimethylsilyl)amide (1.94 mL, 1.94 mmol) in MTBE was added. The mixture was stirred at −78° C. for 15 minutes, treated with iodomethane (0.12 mL, 1.94 mmol), allowed to slowly warm up to room temperature, and stirred at the temperature overnight. The product mixture was concentrated under vacuum. The residue was partitioned between chloroform and dilute hydrochloric acid. The organic extract was washed with brine, dried over anhydrous magnesium sulfate, filtered, and concentrated under vacuum. The residue was subjected to preparation HPLC on C-18 stationary phase eluting with a gradient of methanol in water in the presence of ammonium acetate (1 g/L). Collection and concentration of appropriate fractions provided the title compound. The corresponding bis-methylated ketone was also isolated and was used for the preparation of Examples 60 & 61.

ES MS M+1=385

Step 2: 4-Ethyl-2-(4-fluorobenzyl)-10-hydroxy-8-methyl-7,8-dihydropyrazino[1',2':1,5]pyrrolo[2,3-d]pyridazine-1,9(2H,6H)-dione The title compound was prepared in accordance with the procedure set forth in Example 7, steps 8 to 9.

$^1$H NMR (400 MHz, CDCl₃) δ 8.51 (br s, 1H), 7.46 (dd, J=8.4, 5.3 Hz, 2H), 6.96 (t, J=8.8 Hz, 2H), 5.25 (s, 2H), 4.39 (t, J=6.7 Hz, 2H), 3.71 (t, J=6.7 Hz, 2H), 3.10 (s, 3H), 2.87 (q, J=7.4 Hz, 2H), 1.32 (t, J=7.4 Hz, 3H). ES MS M+1=371.

EXAMPLES 60-61

The compounds in the following table were prepared in accordance with the procedure set forth in Example 59.

| Example | Compound | ES MS M + 1 |
|---|---|---|
| 60 | 2-(4-Fluorobenzyl)-10-hydroxy-4-isopropyl-8-methyl-7,8-dihydropyrazino[1',2':1,5]pyrrolo[2,3-d]pyridazine-1,9(2H,6H)-dione | 385 |
| 61 | 2-(3-Chloro-4-fluorobenzyl)-10-hydroxy-4-isopropyl-8-methyl-7,8-dihydropyrazino-[1',2':1,5]pyrrolo[2,3-d]pyridazine-1,9(2H,6H)-dione | 419 |

EXAMPLE 62

6(S)-2-(3-Chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide

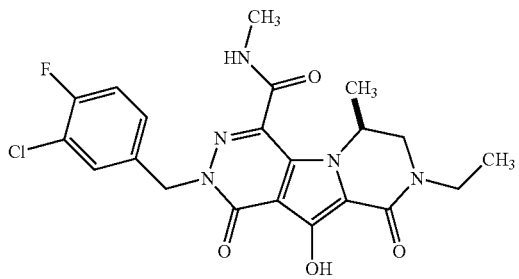

Step 1: tert-Butyl[(1S)-2-(ethylamino)-1-methylethyl]carbamate

To a cold (0° C.) solution of N-(tert-butoxycarbonyl)-L-alanine N'-methoxy-N'-methylamide (15.6 g, 67.2 mmol) in anhydrous THF (150 mL) and diethyl ether (400 mL), solid lithium aluminum hydride (5.1 g, 134.3 mmol) was added portionwise over a period of 30 minutes. The mixture was stirred at room temperature for 3 hours and cooled back to 0° C. The reaction was treated carefully with an aqueous solution of potassium hydrogen sulfate (250 mL, 1M). The resultant mixture was diluted with diethyl ether. The organic extract was washed successively with dilute hydrochloric acid, and brine, dried over anhydrous sodium sulfate, filtered, and concentrated under vacuum to provide the corresponding aldehyde as colorless solid. Without further purification, a cold (0° C.), stirred solution of the intermediate aldehyde (10.7 g, 61.8 mmol) and ethylamine hydrogen chloride (10.1 g, 123.5 mmol) in methanol (72 mL) was treated with sodium triacetoxyborohydride (17.2 g, 80.9 mmol) in one portion. The mixture was allowed to warm up to room temperature. After stirring at room temperature overnight, the solution was concentrated under vacuum. The residue was partitioned between diethyl ether and cold aqueous sodium hydroxide (1.5 M). The ethereal extract was washed with brine, dried over anhydrous sodium sulfate, filtered, and concentrated under vacuum to provide the titled compound.

$^1$H NMR (400 MHz, CDCl$_3$) δ 4.68 (br s, 1H), 3.75 (br t, 1H), 2.62 (m, 5 H), 1.13 (d, J=6.7 Hz, 3H), 1.09 (t, J=7.0 Hz, 3H). ES MS M+1=203

Step 2: tert-Butyl {(1S)-2-[(bromoacetyl)ethylamino]-1-methylethyl}carbamate To a cold (0° C.) stirred solution of tert-butyl[(1S)-2-(ethylamino)-1-methylethyl]carbamate (11.0 g, 54.6 mmol) in a mixture of ethyl acetate (107 mL) and saturated aqueous sodium bicarbonate (65 mL), bromoacetyl bromide (12.1 g, 60.0 mmol) was added portionwise under an atmosphere of nitrogen. The mixture was allowed to warm up to room temperature over a period of 3.5 hours. The organic phase was separated, washed successively with saturated aqueous sodium bicarbonate, and brine. The organic extract was dried over anhydrous sodium sulfate, filtered, and concentrated under vacuum. The residue was concentrated as a solution in toluene under vacuum to afford the title compound. ES MS M+1=323, 325.

Step 3: tert-Butyl (2S)-4-ethyl-2-methyl-5-oxopiperazine-1-carboxylate

To a stirred slurry of sodium hydride (1.7 g, 69.8 mmol) in anhydrous THF (800 mL), a solution of tert-butyl{(1S)-2-

[(bromoacetyl)ethylamino]-1-methylethyl}carbamate (17.4 g, 53.7 mmol) in anhydrous THF (100 mL) was added dropwise over a period of 1 hour under an atmosphere of nitrogen. The reaction mixture was stirred at room temperature for two hours, cooled in an ice-water bath, and quenched with dropwise addition of aqueous citric acid (80 mL, 1M). The mixture was concentrated under vacuum. The residue was partitioned between chloroform and saturated aqueous sodium bicarbonate. The organic extract was dried over anhydrous sodium sulfate, filtered, and concentrated under vacuum. The residue was subjected to column chromatography on silica gel eluting with a gradient of 0-15% acetonitrile in chloroform. Collection and concentration of appropriate fractions provided the title compound.

$^1$H NMR (400 MHz, CDCl$_3$) δ 4.46 (br s, 1H), 4.24 (d, J=18.4 Hz, 1 H), 3.78 (d, J=18.4 Hz, 1 H), 3.64 (dd, J=12.3, 4.2 Hz, 1 H), 3.54 (heptet, J=7.1 Hz, 1 H), 3.38 (heptet, J=7.1 Hz, 1 H), 2.99 (dd, J=12.3, 1.8 Hz, 1 H), 1.47 (s, 9H), 1.21 (d, J=6.8 Hz, 3H), 1.14 (t, J=7.1 Hz, 3H). ES MS M+1=243.

Step 4: (5S)-1-Ethyl-5-methylpiperazin-2-one hydrochloride

Anhydrous hydrogen chloride gas was bubbled into a cold (−20° C.) solution of tert-butyl (2S)-4-ethyl-2-methyl-5-oxopiperazine-1-carboxylate (10.5 g, 43.4 mmol) in ethyl acetate (250 mL) under nitrogen. After the solution was saturated with hydrogen chloride, the reaction mixture was stirred in an ice-water bath for 30 minutes. The product mixture was purged with nitrogen, concentrated under vacuum to provide the title hydrogen chloride salt as pale yellow solid.

$^1$H NMR (400 MHz, DMSO-d$_6$) δ 10.00 (br d, 2H), 3.72 (d, J=16.6 Hz, 1 H), 3.62(d, J=16.6 Hz, 1 H), 3.49-3.35 (m, 5 H), 3.29 (heptet, J=7.3 Hz, 1 H), 1.31 (d, J=6.6 Hz, 3H), 1.05 (t, J=7.1 Hz, 3H).

Step 5: Ethyl (4S)-2-ethyl-8-hydroxy-4-methyl-1-oxo-1,2,3,4-tetrahydropyrrolo[1,2-a]pyrazin-7-carboxylate Anhydrous ammonia gas was bubbled into a cold (0° C.) solution of (5S)-1-Ethyl-5-methylpiperazin-2-one hydrochloride (5.8 g, 32.3 mmol) in chloroform for 30 minutes. The resultant slurry was filtered and concentrated under vacuum. The residual oil was concentrated as a solution in toluene under vacuum, redissolved in toluene (120 mL) and treated with diethyl ethoxymethylenemalonate (7.0 g, 32.3 mmol) and heated in a sealed flask in an oil bath at 100° C. overnight. The resultant solution was concentrated under vacuum. The residual oil was concentrated as a solution in toluene under vacuum to provide the corresponding diethyl{[(2S)-4-ethyl-2-methyl-5-oxopiperazin-1-yl]methylene}malonate. Without further purification, to a solution of the malonate (10.5 g, 33.5 mmol) in anhydrous THF (330 mL) warmed with an external oil bath at 65° C. under an atmosphere of nitrogen, a solution of lithium bis(trimethylsilyl)amide (35.1 mL, 1 M, 35.1 mmol) was added. The solution was heated at the same temperature for one hour and concentrated under vacuum. The residue was partitioned between dichloromethane and hydrochloric acid (1M). The organic extract was washed with brine, dried over anhydrous magnesium sulfate, filtered, and concentrated under vacuum. The residue was triturated with diethyl ether. The solid precipitated was filtered, washed with diethyl ether to provide the title compound as pale brown solid.

$^1$H NMR (400 MHz, CDCl$_3$) δ 8.43 (s, 1H), 7.11 (s, 1H), 4.32 (q, J=7.1 Hz, 2H), 4.24 (m, 1H), 3.65-3.35 (m, 4H), 1.51 (d, J=6.4 Hz, 3H), 1.36 (t, J=7.0 Hz, 3H), 1.19 (t, J=7.0 Hz, 3H). ES MS M+1=267

Step 6: Ethyl (4S)-2-ethyl-8-methoxy-4-methyl-1-oxo-1,2,3,4-tetrahydropyrrolo[1,2-a]pyrazin-7-carboxylate A mixture of ethyl (4S)-2-ethyl-8-hydroxy-4-methyl-1-oxo-1,2,3,4-tetrahydropyrrolo[1,2-a]pyrazin-7-carboxylate (6.6 g, 24.8 mmol), anhydrous potassium carbonate (13.7 g, 99.1 mmol, 325 mesh), and iodomethane (4.2 g, 29.7 mmol) in anhydrous DMF (123 mL) was stirred at room temperature overnight. The mixture was filtered and concentrated under vacuum. The residue was partitioned between chloroform and dilute hydrochloric acid. The organic extract was washed with brine, dried over anhydrous sodium sulfate, filtered, and concentrated under vacuum. The residue was subjected to column chromatography on silica gel eluting with a gradient of 0-3% methanol in chloroform. Collection and concentration of appropriate fractions provided the title compound. Residual methanol was removed by concentrating from its solution in toluene under vacuum.

$^1$H NMR (400 MHz, CDCl$_3$) δ 7.19 (s, 1H), 4.29 (q, J=7.1 Hz, 2 H), 4.24 (m, 1H), 4.03 (s, 3H), 3.70-3.32 (m, 4 H), 1.52 (d, J=6.6 Hz, 3H), 1.35 (t, J=7.0 Hz, 3H), 1.19 (t, J=7.2 Hz, 3H). ES MS M+1=281

Step 7: Ethyl (4S)-6-bromo-2-ethyl-8-methoxy-4-methyl-1-oxo-1,2,3,4-tetrahydropyrrolo[1,2-a]pyrazin-7-carboxylate To a mixture of ethyl (4S)-2-ethyl-8-(methoxy)-4-methyl-1-oxo-1,2,3,4-tetrahydropyrrolo[1,2-a]pyrazine-7-carboxylate (6.2 g, 22.1 mmol) and sodium bicarbonate (20.0 g, 238.0 mmol) in dichloromethane (500 mL) at 0° C., a solution of bromine in dichloromethane (24.2 mmol, 0.5 M) was added over a period of 60 minutes. The reaction mixture was stirred at room temperature for 2 h, filtered, and concentrated under vacuum. The residue was subjected to column chromatography on silica gel eluted with ethyl acetate. Collection and concentration of appropriate fractions provided the corresponding bromide. Residual ethyl acetate was removed by concentrating from its solution in benzene under vacuum.

$^1$H NMR (400 MHz, CDCl$_3$) δ 4.58 (br m, 1H), 4.34 (m, 1H), 3.99 (s, 3H), 3.92 (dd, J=13.0, 4.0 Hz, 1H), 3.67 (heptet, J=7.1 Hz, 1 H), 3.49 (heptet, J=7.1 Hz, 1 H), 3.23 (d, J=13.0 Hz, 1H), 1.40 (d, J=7.1 Hz, 3H), 1.38 (t, J=7.0 Hz, 3H), 1.20 (t, J=7.0 Hz, 3H). ES MS M+1=359, 361.

Step 8: Ethyl (4S)-2-ethyl-8-(methoxy)-6-[methoxy (oxo)acetyl]-4-methyl-1-oxo-1,2,3,4-tetrahydropyrrolo[1,2-a]pyrazine-7-carboxylate To a cold (−78° C.) solution of ethyl (4S)-6-bromo-2-ethyl-8-methoxy-4-methyl-1-oxo-1,2,3,4-tetrahydropyrrolo[1,2-a]pyrazin-7-carboxylate (8.51 g, 23.7 mmol) in anhydrous THF (800 mL) under an atmosphere of dry nitrogen, a solution of n-BuLi in hexane (10.5 mL, 26.3 mmol, 2.5 M) was added. The resultant mixture was stirred at −78° C. for 20 minutes. A solution of dimethyl oxalate (6.4 g, 53.8 mmol; dried from concentration from benzene under vac) in anhydrous THF (30 mL) was added. The reaction mixture was stirred at −78° C. for 1 hour and cannulated into a mixture of aqueous sulfuric acid (240 mL, 2M) and THF (200 mL) maintained between at −5 to −35° C. The mixture was extracted with ethyl acetate (3 times). The organic extracts were combined, washed with brine, dried over anhydrous sodium sulfate, filtered and concentrated under vacuum. The residue was subjected to column chromatography on silica gel eluted with 40 to 100% ethyl acetate-hexane gradient. Collection and concentration of appropriate fractions provided the titled compound.

$^1$H NMR (400 MHz, CDCl$_3$) δ 5.07 (m, 1H), 4.29 (q, J=7.2 Hz, 2H), 4.00 (s, 3H), 3.99-3.93 (m, 1H), 3.89 (s, 3H), 3.74-3.66 (m, 1H), 3.53-3.48 (m, 1H), 3.23 (dd, J=1.3, 13.2 Hz, 1H), 1.46 (d, J=6.6 Hz, 3H), 1.36 (t, J=7.2 Hz, 3H), 1.22 (t, J=7.1 Hz, 3H). ES MS M+1=367

Step 9: (6S)-8-Ethyl-10-methoxy-6-methyl-1,9-dioxo-1,2,6,7,8,9-hexahydropyrazino[1',2':1,5]pyrrolo[2,3-d]pyridazine-4-carbohydrazide A mixture of ethyl (4S)-2-ethyl-8-(methoxy)-6-[methoxy(oxo)acetyl]-4-methyl-1-oxo-1,2,3,4-tetrahydropyrrolo[1,2-a]pyrazine-7-carboxylate (3.3 g, 8.9 mmol) and anhydrous hydrazine (1.7 mL, 53.7 mmol) in methanol (400 mL) was stirred at room temperature for one hour. The reaction mixture was concentrated under vacuum. The residue was concentrated from toluene. The resultant gummy solid was treated with methanol (20 mL). Diethyl ether was added to the resultant slurry which was filtered to provide the title compound as white solid.

$^1$H NMR (400 MHz, CDCl$_3$) δ 8.99 (br s, 2H), 5.54 (br m, 1H), 4.12 (m, 1H), 4.10 (s, 3H), 3.81 (m, 1H), 3.39 (m, 1H), 3.21 (d, J=12.6 Hz, 1H), 1.44 (d, J=6.4 Hz, 3H), 1.23 (t, J=7.3 Hz, 3H). ES MS M+1=335

Step 10: (6S)-8-Ethyl-10-methoxy-N,6-dimethyl-1,9-dioxo-1,2,6,7,8,9-hexahydropyrazino[1',2':1,5]pyrrolo[2,3-d]pyridazine-4-carboxamide To a solution of (6S)-8-ethyl-10-methoxy-6-methyl-1,9-dioxo-1,2,6,7,8,9-hexahydropyrazino[1',2':1,5]pyrrolo[2,3-d]pyridazine-4-carbohydrazide (0.39 g, 1.2 mmol) and methylamine (5.9 mL, 11.8 mmol; 2 M in THF) in anhydrous dichloromethane (25 mL) in a water bath at room temperature, a solution of iodine (0.60 g, 2.4 mmol) in dichloromethane was added dropwise. After the addition was completed, an aqueous solution of sodium sulfite was added and the mixture was stirred vigorously for 10 minutes. The organic phase was separated, diluted with chloroform, and washed with brine. The organic extract was dried over anhydrous sodium sulfate, filtered, and concentrated under vacuum. The residue was triturated with a mixture of ethanol (7 mL) and diethyl ether (25 mL). The white solid precipitated was obtained by filtration and dried from its solution in toluene under vacuum.

$^1$H NMR (400 MHz, CDCl$_3$) δ 11.57 (s, 1H), 7.38 (m, 1H), 5.95 (br m, 1H), 4.17 (s, 3H), 4.03 (dd, J=13.4, 3.8 Hz, 1 H), 3.76 (heptet, J=7.1 Hz, 1 H), 3.50 (heptet, J=7.1 Hz, 1 H), 2.99 (dd, J=12.9, 1.0 Hz, 1 H), 3.03 (d, J=5.0 Hz, 3H), 1.44 (d, J=6.6 Hz, 3H), 1.23 (t, J=7.2 Hz, 3H). ES MS M+1=334

Step 11: (6S)-2-(3-Chloro-4-fluorobenzyl)-8-ethyl-10-methoxy-N,6-dimethyl-1,9-dioxo-1,2,6,7,8,9-hexahydropyrazino[1',2':1,5]pyrrolo[2,3-d]pyridazine-4-carboxamide To a cold (0° C.) solution of (6S)-8-ethyl-10-methoxy-N,6-dimethyl-1,9-dioxo-1,2,6,7,8,9-hexahydropyrazino[1',2':1,5]pyrrolo[2,3-d]pyridazine-4-carboxamide (1.58 g, 4.73 mmol) in anhydrous DMF (50 mL), a solution of lithium bis(trimethylsilyl)amide (4.97 mL, 4.97 mmol, 1 M in THF) was added. After stirring at the same temperature for 25 minutes, 3-chloro-4-fluorobenzyl bromide (1.27 g, 5.68 mmol) was added. The reaction mixture was stirred at room temperature for 10 minutes and concentrated under vacuum. The residue was partitioned between chloroform and brine. The organic extract was dried over anhydrous sodium sulfate, filtered, and concentrated under vacuum. The residue was subjected to column chromatography on silica gel eluting with a 1-5% methanol in ethyl acetate gradient. Collection and concentration of appropriate fractions provided the title compound.

$^1$H NMR (400 MHz, CDCl$_3$) δ 7.46 (dd, J=6.9, 2.2 Hz, 1H), 7.32 (m, 1H), 7.09 (t, J=7.6 Hz, 1H), 7.03 (br signal, 1H), 5.92 (m, 1H), 5.32 (d, J=14.1 Hz, 1H), 5.26 (d, J=14.1 Hz, 1H), 4.14 (s, 3H), 3.97 (dd, J=13.2, 3.7 Hz, 1H), 3.73 (heptet, J=7.2 Hz, 1 H), 3.51 (heptet, J=7.1 Hz, 1H), 3.21 (dd, J=13.2, 1.7 Hz, 1H), 3.03 (d, J=5.0 Hz, 3H), 1.42 (d, J=6.6 Hz, 3H), 1.23 (t, J=7.1 Hz, 3H). ES MS M+1=476

Step 12: (6S)-2-(3-Chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide To a solution of (6S)-2-(3-chloro-4-fluorobenzyl)-8-ethyl-10-methoxy-N,6-dimethyl-1,9-dioxo-1,2,6,7,8,9-hexahydropyrazino[1',2':1,5]pyrrolo[2,3-d]pyridazine-4-carboxamide (1.15 g, 2.41 mmol) in anhydrous dichloromethane (800 mL), a solution of boron tribromide in dichloromethane (3.14 mL, 3.14 mmol; 1 M) was added. After stirring at room temperature for 5 minutes, the reaction mixture was treated with anhydrous methanol, stirred for 30 minutes, and concentrated under vacuum. The procedure was repeated twice. The residue was dissolved in a mixture of methanol and acetonitrile and treated with aqueous sodium hydroxide. The mixture was subjected to purification on preparative reverse phase high pressure column chromatography. Collection and lyophilization of appropriate fractions provided the title compound as white amorphous solid.

$^1$H NMR (400 MHz, CDCl$_3$) δ 7.48 (dd, J=7.0, 2.2 Hz, 1H), 7.33 (m, 1H), 7.09 (t, J=8.7 Hz, 1H), 6.01 (m, 1H), 5.33 (d, J=14.1 Hz, 1H), 5.27 (d, J=14.1 Hz, 1H), 3.99 (dd, J=12.8, 4.0 Hz, 1 H), 3.71 (heptet, J=7.1 Hz, 1 H), 3.49 (heptet, J=7.1 Hz, 1 H), 3.24 (dd, J=13.2, 1.5 Hz, 1 H), 3.03 (d, J=5.1 Hz, 3H), 1.42 (d, J=6.6 Hz, 3H), 1.24 (t, J=7.3 Hz, 3H). ES MS M+1=462

The amorphous product was dissolved in boiling methanol (1.4 g/200 mL). Upon cooling in an ice-water bath, a precipitate formed which was separated by obtained by filtration to afford a white crystalline solid.

The corresponding sodium salt was prepared by treatment of a solution of (6S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide (920 mg, 1.99 mmol) in aqueous acetonitrile with aqueous sodium hydroxide (1.03 equivalent), followed by lyophilization of the resultant solution.

(5S)-1-Ethyl-5-methylpiperazin-2-one was alternatively prepared as follows:

Step 1: N$^2$-tert-Butoxycarbonyl-N$^1$-ethylglycinamide

Ethylamine (37 g, 0.82 mol) was condensed into a pressure vessel at 0° C. N-(tert-butoxycarbonyl)glycine methyl ester (50 mL, 0.34 mol) was added. The vessel was sealed and the mixture was stirred at room temperature overnight. The product mixture was concentrated under vacuum and the residue was passed through a pad of silica gel eluting with ethyl acetate. The solution was concentrated under vacuum to provide the title compound as a clear oil.

$^1$H NMR (400 MHz, CDCl$_3$) δ 6.11 (br s, 1H), 5.18 (br s, 1H), 3.77 (d, J=5.7 Hz, 2H), 3.31 (q, J=7.1 Hz, 2H), 1.15 (t, J=7.1 Hz, 3H).

Step 2: 1-Ethyl-5-methylpyrazin-2(1H)-one

A cold (0° C.) solution of N$^2$-tert-butoxycarbonyl-N$^1$-ethylglycinamide (68.0 g, 0.33 mol) in anhydrous dichloromethane (500 mL) was saturated with anhydrous hydrogen chloride gas. After stirring at the same temperature for 1.5 hours, the solution was recharged with more hydrogen chloride gas and stirred for additional 15 minutes. The reaction mixture was concentrated under vacuum. The residue was dissolved in methanol, diluted with toluene, and concentrated under vacuum to afford the intermediate N-ethylglycinamide HCl salt. This was stored under vacuum overnight and used without further purification. A solution of N-ethylglycinamide HCl salt (44.2 g, 0.32 mol), aqueous sodium hydroxide (640 mL, 1M), water (350 mL), pyruvic aldehyde (20.9 mL, 40% solution in water) was heated in an oil bath at 120° C. for one hour. The reaction mixture was cooled and saturated with solid sodium chloride. The mixture was extracted with chloroform (4×250 mL). The combined organic extract was dried over anhydrous sodium sulfate, filtered, and passed through a plug of silica gel. The silica gel was rinsed successively with ethyl acetate and then 2% methanol in ethyl acetate. The eluted fractions were combined and concentrated under vacuum. The residual solid was recrystallized from diethyl ether to afford the title compound as pale yellow solid.

$^1$H NMR (400 MHz, CDCl$_3$) δ 8.11 (s, 1H), 6.92 (s, 1H), 3.92 (q, J=7.2 Hz, 2H), 2.28 (s, 3H), 1.37 (t, J=7.2 Hz, 3H).

Step 3: (5S)-1-Ethyl-5-methylpiperazin-2-one

A mixture of chloro-1,5-cyclooctadiene iridium (I) dimer (34 mg, 51 μmol) and (S)-1-[(R)-2-di-(3,5-bis(trifluoromethyl)phenyl)phosphino)ferrocenyl]ethyldicyclohexylphosphine (44 mg, 51 μmol; Solvias AG, SL-J006-2) in a mixture of 1:2 toluene and methanol (100 mL; purged with nitrogen for 15 minutes) was sonicated under an atmosphere of nitrogen for 15 minutes. To the resultant mixture, iodine (0.39 g, 1.52 mmol) and 1-ethyl-5-methylpyrazin-2(1H)-one (7.0 g, 50.66 mmol) was added. The resultant mixture was heated in an oil bath at 50° C. under an atmosphere of hydrogen gas at 800 psi for 48 hours. The product mixture was filtered through a pad of Celite. The filtrate was concentrated under vacuum. The residue was treated with chloroform saturated with ammonia gas (100 mL). The resultant suspension was filtered through a pad of Celite, which was the rinsed with chloroform saturated with ammonia gas. The combined filtrate was concentrated under vacuum. The residue was concentrated as a solution in toluene for subsequent reaction.

$^1$H NMR (400 MHz, CDCl$_3$) δ 3.58 (d, J=17.2 Hz, 1H), 3.53(d, J=17.2 Hz, 1H), 3.49-3.35 (m, 2H), 1.19 (d, J=5.9 Hz, 3H), 1.14 (t, J=7.2 Hz, 3H).

EXAMPLES 63-94

The compounds in the following table were prepared in accordance with the procedure set forth in Example 62.

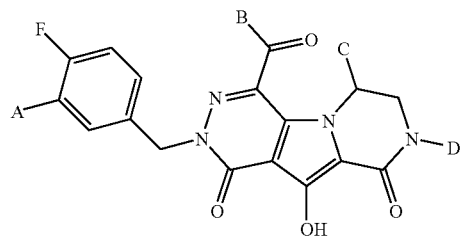

| Ex. | Name | A | B | C | D | M + 1 |
|---|---|---|---|---|---|---|
| 63 | 6(R)-2-(3-Chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide | Cl | NH(Me) | Me | Et | 462 |
| 64 | 2-(4-Fluorobenzyl)-10-hydroxy-N,N,8-trimethyl-1,9-dioxo-1,2,6,7,8,9-hexahydropyrazino[1',2':1,5]pyrrolo[2,3-d]pyridazine-4-carboxamide | H | NMe$_2$ | H | Me | 414 |
| 65 | 2-(4-Fluorobenzyl)-10-hydroxy-8-methyl-4-(morpholin-4-ylcarbonyl)-7,8-dihydropyrazino[1',2':1,5]pyrrolo[2,3-d]pyridazine-1,9(2H,6H)-dione | H | (morpholine) | H | Me | 456 |
| 66 | Ethyl 2-(4-fluorobenzyl)-10-hydroxy-8-methyl-1,9-dioxo-1,2,6,7,8,9-hexahydropyrazino[1',2':1,5]pyrrolo[2,3-d]pyridazine-4-carboxylate | H | OEt | H | Me | 415 |
| 67 | 2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazine-4-carboxamide | Cl | NH$_2$ | H | Me | 420 |

-continued

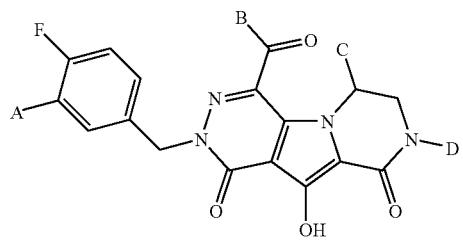

| Ex. | Name | A | B | C | D | M + 1 |
|---|---|---|---|---|---|---|
| 68 | 2-(3-Chloro-4-fluorobenzyl)-10-hydroxy-N,8-dimethyl-1,9-dioxo-1,2,6,7,8,9-hexahydropyrazino[1',2':1,5]pyrrolo[2,3-d]pyridazine-4-carboxamide | Cl | NHMe | H | Me | 434 |
| 69 | 2-(3-Chloro-4-fluorobenzyl)-N-ethyl-10-hydroxy-8-methyl-1,9-dioxo-1,2,6,7,8,9-hexahydropyrazino[1',2':1,5]pyrrolo[2,3-d]pyridazine-4-carboxamide | Cl | NHEt | H | Me | 448 |
| 70 | 2-(3-Chloro-4-fluorobenzyl)-N-cyclopropyl-10-hydroxy-8-methyl-1,9-dioxo-1,2,6,7,8,9-hexahydropyrazino[1',2':1,5]pyrrolo[2,3-d]pyridazine-4-carboxamide | Cl | HN-cyclopropyl | H | Me | 460 |
| 71 | 2-(3-Chloro-4-fluorobenzyl)-N-(2-fluoroethyl)-10-hydroxy-8-methyl-1,9-dioxo-1,2,6,7,8,9-hexahydropyrazino[1',2':1,5]pyrrolo[2,3-d]pyridazine-4-carboxamide | Cl | NHCH$_2$CH$_2$F | H | Me | 466 |
| 72 | 2-(3-Chloro-4-fluorobenzyl)-N-(2,2-difluoroethyl)-10-hydroxy-8-methyl-1,9-dioxo-1,2,6,7,8,9-hexahydropyrazino[1',2':1,5]pyrrolo[2,3-d]pyridazine-4-carboxamide | Cl | NHCH$_2$CHF$_2$ | H | Me | 484 |
| 73 | 2-(3-Chloro-4-fluorobenzyl)-N-(2,2,2-trifluoroethyl)-10-hydroxy-8-methyl-1,9-dioxo-1,2,6,7,8,9-hexahydropyrazino[1',2':1,5]pyrrolo[2,3-d]pyridazine-4-carboxamide | Cl | NHCH$_2$CF$_3$ | H | Me | 502 |
| 74 | 2-(3-Chloro-4-fluorobenzyl)-N-[2-(dimethylamino)ethyl]-10-hydroxy-8-methyl-1,9-dioxo-1,2,6,7,8,9-hexahydropyrazino[1',2':1,5]pyrrolo[2,3-d]pyridazine-4-carboxamide | Cl | NH(CH$_2$)$_2$NMe$_2$ | H | Me | 491 |
| 75 | 2-(3-Chloro-4-fluorobenzyl)-N-[3-(dimethylamino)propyl]-10-hydroxy-8-methyl-1,9-dioxo-1,2,6,7,8,9-hexahydropyrazino[1',2':1,5]pyrrolo[2,3-d]pyridazine-4-carboxamide | Cl | NH(CH$_2$)$_3$NMe$_2$ | H | Me | 505 |
| 76 | 2-(3-Chloro-4-fluorobenzyl)-10-hydroxy-N,N,8-trimethyl-1,9-dioxo-1,2,6,7,8,9-hexahydropyrazino[1',2':1,5]pyrrolo[2,3-d]pyridazine-4-carboxamide | Cl | NMe$_2$ | H | Me | 448 |
| 77 | 2-(3-Chloro-4-fluorobenzyl)-N-ethyl-10-hydroxy-N,8-dimethyl-1,9-dioxo-1,2,6,7,8,9-hexahydropyrazino[1',2':1,5]pyrrolo[2,3-d]pyridazine-4-carboxamide | Cl | N(Me)Et | H | Me | 462 |
| 78 | 2-(3-Chloro-4-fluorobenzyl)-10-hydroxy-N-isopropyl-N,8-dimethyl-1,9-dioxo-1,2,6,7,8,9-hexahydropyrazino[1',2':1,5]pyrrolo[2,3-d]pyridazine-4-carboxamide | Cl | N(Me)-i-Pr | H | Me | 476 |
| 79 | 2-(3-Chloro-4-fluorobenzyl)-10-hydroxy-8-methyl-4-(morpholin-4-ylcarbonyl)-7,8-dihydropyrazino[1',2':1,5]pyrrolo[2,3-d]pyridazine-1,9(2H,6H)-dione | Cl | morpholin-4-yl | H | Me | 490 |

-continued

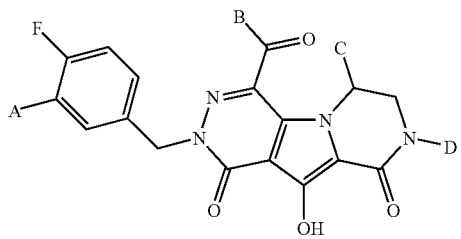

| Ex. | Name | A | B | C | D | M + 1 |
|---|---|---|---|---|---|---|
| 80 | 2-(3-Chloro-4-fluorobenzyl)-10-hydroxy-8-methyl-4-(piperidin-1-ylcarbonyl)-7,8-dihydropyrazino[1',2':1,5]pyrrolo[2,3-d]pyridazine-1,9(2H,6H)-dione | Cl | piperidin-1-yl | H | Me | 488 |
| 81 | 2-(3-Chloro-4-fluorobenzyl)-10-hydroxy-8-methyl-4-[(4-methylpiperazin-1-yl)carbonyl]-7,8-dihydropyrazino[1',2':1,5]pyrrolo[2,3-d]pyridazine-1,9(2H,6H)-dione | Cl | 4-methylpiperazin-1-yl | H | Me | 503 |
| 82 | 2-(3-Chloro-4-fluorobenzyl)-10-hydroxy-8-methyl-4-[(4-allylpiperazin-1-yl)carbonyl]-7,8-dihydropyrazino[1',2':1,5]pyrrolo[2,3-d]pyridazine-1,9(2H,6H)-dione | Cl | 4-allylpiperazin-1-yl | H | Me | 529 |
| 83 | 2-(3-Chloro-4-fluorobenzyl)-10-hydroxy-8-methyl-4-[(1,1-dioxidothiomorpholin-4-yl)carbonyl]-7,8-dihydropyrazino[1',2':1,5]pyrrolo[2,3-d]pyridazine-1,9(2H,6H)-dione | Cl | 1,1-dioxidothiomorpholin-4-yl | H | Me | 538 |
| 84 | 2-(3-Chloro-4-fluorobenzyl)-10-hydroxy-8-methyl-4-[(4-methyl-3-oxopiperazin-1-yl)carbonyl]-7,8-dihydropyrazino[1',2':1,5]pyrrolo[2,3-d]pyridazine-1,9(2H,6H)-dione | Cl | 4-methyl-3-oxopiperazin-1-yl | H | Me | 517 |
| 85 | 6(S)-2-(3-Chloro-4-fluorobenzyl)-10-hydroxy-8-isopropyl-N,6-dimethyl-1,9-dioxo-1,2,6,7,8,9-hexahydropyrazino[1',2':1,5]pyrrolo[2,3-d]pyridazine-4-carboxamide | Cl | NHMe | Me | i-Pr | 476 |
| 86 | 6(S)-2-(3-Chloro-4-fluorobenzyl)-10-hydroxy-8-isopropyl-N-ethyl-6-methyl-1,9-dioxo-1,2,6,7,8,9-hexahydropyrazino[1',2':1,5]pyrrolo[2,3-d]pyridazine-4-carboxamide | Cl | NHEt | Me | i-Pr | 490 |
| 87 | 6(S)-2-(4-Fluorobenzyl)-10-hydroxy-8-isopropyl-N-ethyl-6-methyl-1,9-dioxo-1,2,6,7,8,9-hexahydropyrazino[1',2':1,5]pyrrolo[2,3-d]pyridazine-4-carboxamide | H | NHEt | Me | i-Pr | 456 |
| 88 | 6(S)-2-(3-Chloro-4-fluorobenzyl)-10-hydroxy-8-isopropyl-N,N,6-trimethyl-1,9-dioxo-1,2,6,7,8,9-hexahydropyrazino[1',2':1,5]pyrrolo[2,3-d]pyridazine-4-carboxamide | Cl | $NMe_2$ | Me | i-Pr | 490 |
| 89 | 6(S)-2-(3-Chloro-4-fluorobenzyl)-10-hydroxy-N,8-diethyl-6-methyl-1,9-dioxo-1,2,6,7,8,9-hexahydropyrazino[1',2':1,5]pyrrolo[2,3-d]pyridazine-4-carboxamide | Cl | NHEt | Me | Et | 476 |

-continued

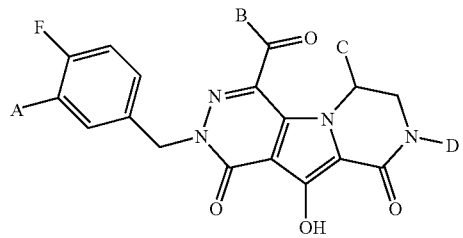

| Ex. | Name | A | B | C | D | M + 1 |
|---|---|---|---|---|---|---|
| 90 | 6(S)-2-(3-Chloro-4-fluorobenzyl)-8-ethyl-10-hydroxy-6-methyl-1,9-dioxo-N-(2,2,2-trifluoroethyl)-1,2,6,7,8,9-hexahydropyrazino[1',2':1,5]pyrrolo[2,3-d]pyridazine-4-carboxamide | Cl | NHCH$_2$CF$_3$ | Me (*) | Et | 530 |
| 91 | 6(S)-2-(3-Chloro-4-fluorobenzyl)-8-ethyl-10-hydroxy-N,N,6-trimethyl-1,9-dioxo-1,2,6,7,8,9-hexahydropyrazino[1',2':1,5]pyrrolo[2,3-d]pyridazine-4-carboxamide | Cl | NMe$_2$ | Me (*) | Et | 476 |
| 92 | 6(S)-N,2-bis(3-Chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide | Cl | 3-Cl-4-F-C$_6$H$_3$CH$_2$N(Me)– | Me (*) | Et | 604 |
| 93 | 6(S)-2-(3-Chloro-4-fluorobenzyl)-8-(cyclopropylmethyl)-10-hydroxy-N,6-dimethyl-1,9-dioxo-1,2,6,7,8,9-hexahydropyrazino[1',2':1,5]pyrrolo[2,3-d]pyridazine-4-carboxamide | Cl | NHMe | Me (*) | CH$_2$-cyclopropyl | 488 |
| 94 | 6(S)-2-(3-Chloro-4-fluorobenzyl)-10-hydroxy-8-isobutyl-N,6-dimethyl-1,9-dioxo-1,2,6,7,8,9-hexahydropyrazino[1',2':1,5]pyrrolo[2,3-d]pyridazine-4-carboxamide | Cl | NHMe | Me (*) | i-Bu | 490 |

Note: M + 1 determined by ES MS.

EXAMPLES 95-96

The compounds in the following table were prepared in accordance with the procedure set forth in Example 62.

| Example | Compound | ES MS M + 1 |
|---|---|---|
| 95 | N-(2,3-Dihydro-1H-inden-2-yl)-10-hydroxy-8-methyl-1,9-dioxo-2-(2-phenylethyl)-1,2,6,7,8,9-hexahydropyrazino[1',2':1,5]pyrrolo[2,3-d]pyridazine-4-carboxamide | 498 |

| Example | Compound | ES MS M + 1 |
|---|---|---|
| 96 | 8-(4-Fluorobenzyl)-10-hydroxy-N,N,2-trimethyl-1,9-dioxo-1,2,6,7,8,9-hexahydropyrazino[1',2':1,5]pyrrolo[2,3-d]pyridazine-4-carboxamide | 414 |

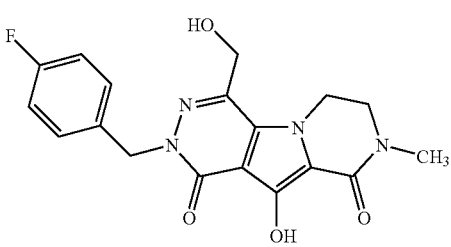

EXAMPLE 97

2-(4-Fluorobenzyl)-10-hydroxy-4-(hydroxymethyl)-8-methyl-7,8-dihydropyrazino[1',2':1,5]pyrrolo[2,3-d]pyridazine-1,9(2H,6H)-dione

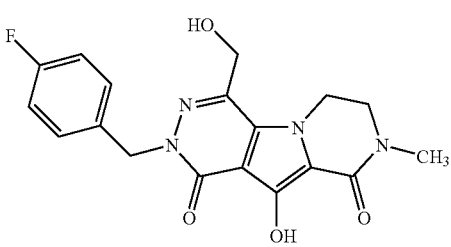

Step 1: Methyl 10-methoxy-8-methyl-1,9-dioxo-1,2,6,7,8,9-hexahydropyrazino[1',2':1,5]pyrrolo[2,3-d]pyridazine-4-carboxylate A solution of ethyl 2-methyl-8-(methoxy)-6-[methoxy(oxo)acetyl]-1-oxo-1,2,3,4-tetrahydropyrrolo[1,2-a]pyrazine-7-carboxylate (1.28 g, 3.78 mmol; prepared in a manner similar to that described in Example 62, step 5 to 8, starting with 1-methylpiperazin-2-one (Example 7, step 1 to 3) and hydrazine acetate (1.05 g, 11.36 mmol) in glacial acetic acid (8 mL) was heated at 160° C. in an microwave oven for 20 minutes. The mixture was concentrated under vacuum. The residue was partitioned between chloroform and brine. The organic extract was dried over anhydrous magnesium sulfate, filtered, and concentrated under vacuum. The residue was triturated in a 4:1 mixture of ethanol and diethyl ether. The precipitate was filtered to afford the title compound. ES MS M+1=321

Step 2: Methyl 2-(4-fluorobenzyl)-10-methoxy-8-methyl-1,9-dioxo-1,2,6,7,8,9-hexahydropyrazino[1',2':1,5]pyrrolo[2,3-d]pyridazine-4-carboxylate The title compound was prepared in accordance with the procedure set forth in Example 62, step 11. ES MS M+1=415

Step 3: 2-(4-Fluorobenzyl)-4-(hydroxymethyl)-10-methoxy-8-methyl-7,8-dihydropyrazino[1',2':1,5]pyrrolo[2,3-d]pyridazine-1,9(2H,6H)-dione A solution of methyl 2-(4-fluorobenzyl)-10-methoxy-8-methyl-1,9-dioxo-1,2,6,7,8,9-hexahydropyrazino[1',2':1,5]pyrrolo[2,3-d]pyridazine-4-carboxylate (0.10 g, 0.24 mmol) in methanol (4 mL) was treated with sodium borohydride (9 mg, 0.24 mmol). After stirring at room temperature for 30 minutes, the reaction mixture was concentrated under vacuum to half the volume. The white solid precipitated was filtered and air dried to provide the title alcohol.

$^1$H NMR (400 MHz, CDCl$_3$) δ 7.8 (dd, J=8.4, 5.3 Hz, 1H), 6.96 (t, J=8.8 Hz, 2H), 5.24 (s, 2H), 4.76 (d, J=6.4 Hz, 2H), 4.63 (t, J=6.7 Hz, 2H), 4.37 (t, J=6.4 Hz, 1H), 3.97 (s, 3H), 3.81 (t, J=6.7 Hz, 2H), 3.11 (s, 3H). ES MS M+1=387.

Step 4: 2-(4-Fluorobenzyl)-10-hydroxy-4-(hydroxymethyl)-8-methyl-7,8-dihydropyrazino[1',2':1,5]pyrrolo[2,3-d]pyridazine-1,9(2H,6H)-dione To a solution of 2-(4-fluorobenzyl)-4-(hydroxymethyl)-10-methoxy-8-methyl-7,8-dihydropyrazino[1',2':1,5]pyrrolo[2,3-d]pyridazine-1,9(2H,6H)-dione (27 mg g, 70 μmol) in anhydrous dichloromethane (1 mL), a solution of boron tribromide in dichloromethane (90 μL, 90 μmol; 1 M) was added. After stirring at room temperature for one hour, the reaction mixture was treated with anhydrous methanol (2 mL), stirred for 30 minutes, and concentrated under vacuum. The procedure was repeated twice. The residue was subjected to purification on preparative reverse phase high pressure column chromatography. Collection and lyophilization of appropriate fractions provided the title compound.

$^1$H NMR (400 MHz, DMSO-d$_6$) δ 8.97 (s, 1H), 7.46 (dd, J=8.8, 5.2 Hz, 2H), 7.14 (t, J=9.0 Hz, 2H), 5.75 (t, J=5.6 Hz, 1H), 5.20 (s, 2H), 4.59 (d, J=5.6 Hz, 2H), 4.53 (t, J=5.6 Hz, 2H), 3.73 (t, J=5.6 Hz, 2H), 3.00 (s, 3H). ES MS M+1=373

EXAMPLE 98

2-(4-Fluorobenzyl)-10-hydroxy-4-[(1,1-dioxido-1,2-thiazinan-2-yl)methyl]-8-methyl-7,8-dihydropyrazino[1',2':1,5]pyrrolo[2,3-d]pyridazine-1,9(2H,6H)-dione

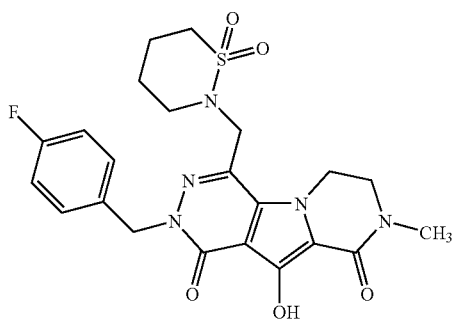

Step 1: Ethyl 6-(bromoacetyl)-8-(benzyloxy)-2-methyl-1-oxo-1,2,3,4-tetrahydropyrrolo[1,2-a]pyrazine-7-carboxylate A solution of ethyl 6-acetyl-8-(benzyloxy)-2-methyl-1-oxo-1,2,3,4-tetrahydropyrrolo[1,2-a]pyrazine-7-carboxylate (0.50 g, 1.35 mmol; Example 7, step 7), bromine (0.24 g, 1.49 mmol), 33% hydrobromide in glacial acetic acid (10 drops) in chloroform (15 mL) was stirred at room temperature for 6 hours. The mixture was treated with aqueous sodium bicarbonate and diluted with chloroform. The organic extract was dried over anhydrous magnesium sulfate, filtered, and concentrated under vacuum. The residue was subjected to column chromatography on silica gel eluting with a 20 to 80% ethyl acetate in hexane to afford the title compound. ES MS M+1=407, 409

Step 2: Ethyl 8-(benzyloxy)-6-[(1,1-dioxido-1,2-thiazinan-2-yl)acetyl]-2-methyl-1-oxo-1,2,3,4-tetrahydropyrrolo[1,2-a]pyrazine-7-carboxylate A mixture of 1,2-thiazinane 1,1-dioxide (70 mg, 0.51 mmol) and sodium hydride (0.51 mmol) in anhydrous DMF (2 mL) was stirred at room temperature for 30 minutes. The mixture was treated with a solution of ethyl 6-(bromoacetyl)-8-(benzyloxy)-2-methyl-1-oxo-1,2,3,4-tetrahydropyrrolo[1,2-a]pyrazine-7-carboxylate (0.23 g, 0.51 mmol) in DMF. The reaction mixture was stirred at room temperature overnight and concentrated under vacuum. The residue was partitioned between ethyl acetate and saturated aqueous ammonium chloride. The organic extract was washed with brine, dried over anhydrous magnesium sulfate, filtered, and concentrated under vacuum. The residue was subjected to column chromatography on silica gel eluting with a 20 to 100% ethyl acetate in hexane gradient to afford the title compound.
$^1$H NMR (400 MHz, CDCl$_3$) δ 7.52 (d, J=6.9 Hz, 2H), 7.36 (t, J=6.9 Hz, 2H), 7.29 (t, 1H), 5.23 (s, 2H), 4.37 (s, 2), 4.28-4.23 (m, 4H), 3.58 (t, J=5.8 Hz, 2H), 3.45 (t, J=5.8 Hz, 2H), 3.12 (s, 3H), 2,98 (t, J=6.0 Hz, 2H), 2.19 (m, 2H), 1.68 (m, 2H), 1.29 (t, J=6.9 Hz, 3H). ES MS M+1=504

Step 3: 8-(Benzyloxy)-4-[(1,1-dioxido-1,2-thiazinan-2-yl)methyl]-8-methyl-7,8-dihydropyrazino[1',2':1,5]pyrrolo[2,3-d]pyridazine-1,9(2H,6H)-dione A solution of ethyl 8-(benzyloxy)-6-[(1,1-dioxido-1,2-thiazinan-2-yl)acetyl]-2-methyl-1-oxo-1,2,3,4-tetrahydropyrrolo[1,2-a]pyrazine-7-carboxylate (50 mg, 99 μmol) and hydrazine (20 mg, 0.39 mmol) in ethanol (9 mL) was heated at 140° C. in an microwave oven for 45 minutes. The mixture was cooled to 0° C. and the solid precipitated was filtered to afford the title compound. ES MS M+1=472

Step 4: 2-(4-Fluorobenzyl)-10-hydroxy-4-[(1,1-dioxido-1,2-thiazinan-2-yl)methyl]-8-methyl-7,8-dihydropyrazino[1',2':1,5]pyrrolo[2,3-d]pyridazine-1,9(2H,6H)-dione The title compound was prepared in accordance with the procedure set forth in Example 97.
$^1$H NMR (400 MHz, DMSO-d$_6$) δ 9.00 (br s, 1H), 7.32 (dd, J=8.8, 5.5 Hz, 2H), 7.14 (t, J=8.8 Hz, 2H), 5.23 (s, 2H), 4.51 (s, 2H), 4.48 (t, J=5.5 Hz, 2H), 3.73 (t, J=5.5 Hz, 2H), 3.26 (t, J=5.5 Hz, 2H), 3.05 (t, J=5.5 Hz, 2H), 2.99 (s, 3H), 2.00 (m, 2H), 1.51 (m, 2H). ES MS M+1=490

EXAMPLE 99

2-(4-Fluorobenzyl)-10-hydroxy-4-[(2-oxopyridine-1(2H)-yl)methyl]-8-methyl-7,8-dihydropyrazino[1',2':1,5]pyrrolo[2,3-d]pyridazine-1,9(2H,6H)-dione

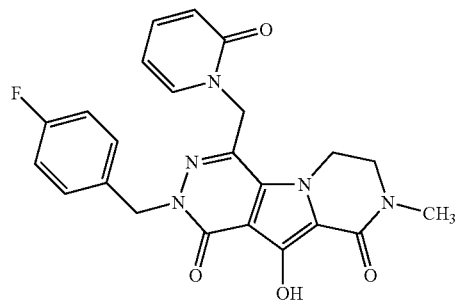

The title compound was prepared in accordance with the procedure set forth in Example 98 replacing 1,2-thiazinane 1,1-dioxide with pyridinone in step 2. ES MS M+1=450

EXAMPLE 100

2-(4-Fluorobenzyl)-10-hydroxy-4-(morpholin-4-ylmethyl)-8-methyl-7,8-dihydropyrazino[1',2':1,5]pyrrolo[2,3-d]pyridazine-1,9(2H,6H)-dione

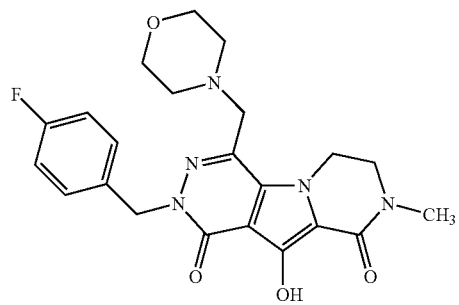

Step 1: 2-(4-Fluorobenzyl)-4-(chloromethyl)-10-methoxy-8-methyl-7,8-dihydropyrazino[1',2':1,5]pyrrolo[2,3-d]pyridazine-1,9(2H,6H)-dione 2-(4-Fluorobenzyl)-4-(hydroxymethyl)-10-methoxy-8-methyl-7,8-dihydropyrazino[1',2':1,5]pyrrolo[2,3-d]pyridazine-1,9(2H,6H)-dione (0.24 g, 0.62 mmol; Example 97) was dissolved in thionyl chloride (4.8 mL) at 0° C. The solution was allowed to warmed up slowly to room temperature and was stirred at room temperature overnight. The product mixture was concentrated under vacuum. The residue was concentrated from its solution in benzene to afford the title chloride.

$^1$H NMR (400 MHz, CDCl$_3$) δ 7.43 (dd, J=8.4, 5.3 Hz, 1H), 6.98 (t, J=8.8 Hz, 2H), 5.28 (s, 2H), 4.74 (s, 3H), 4.53 (t, J=5.5 Hz, 2H), 4.16 (s, 3H), 3.73 (t, J=5.5 Hz, 2H), 3.14 (s, 3H). ES MS M+1=405.

Step 2: 2-(4-Fluorobenzyl)-10-hydroxy-4-(morpholin-4-ylmethyl)-8-methyl-7,8-dihydropyrazino[1',2':1,5]pyrrolo[2,3-d]pyridazine-1,9(2H,6H)-dione A mixture of 2-(4-fluorobenzyl)-4-(chloromethyl)-10-methoxy-8-methyl-7,8-dihydropyrazino[1',2':1,5]pyrrolo[2,3-d]pyridazine-1,9(2H,6H)-dione (0.50 mg 0.12 mmol) and morpholine (43 mg, 0.49 mmol) in 2-propanol (1 mL) was heated under reflux for one hour. The product mixture was concentrated under vacuum. The residue was partitioned between dichloromethane and brine. The organic extract was dried over anhydrous sodium sulfate, filtered, and concentrated under vacuum to afford the alkylation intermediate. Without further purification, the residue was dissolved in anhydrous dichloromethane (3 mL), cooled to 0° C., and treated with a solution of boron tribromide in dichloromethane (0.25 mL, 1M). The mixture was stirred at room temperature for one hour, treated with anhydrous methanol (5 mL), and concentrated under vacuum. The residue was subjected to purification on preparative reverse phase high pressure column chromatography. Collection and lyophilization of appropriate fractions provided the title compound as TFA salt $^1$H NMR (400 MHz, CD$_3$OD) δ 7.39 (dd, J=8.5, 5.5 Hz, 2H), 7.06 (t, J=8.7 Hz, 2H), 5.32 (s, 2H), 4.50 (br signal, 4H), 3.86 (br signal, 4H), 3.80 (br signal, 2H), 3.13 (broad signal, 2H), 3.10 (s, 3H). ES MS M+1=442

EXAMPLES 101-112

The compounds in the following table were prepared in accordance with the procedure set forth in Example 100.

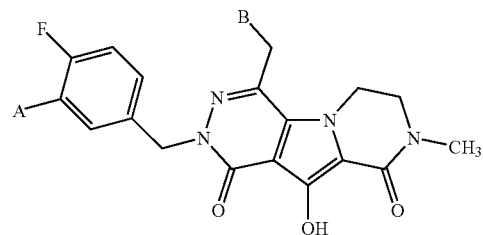

| Ex. | Name | A | B | M + 1 |
|---|---|---|---|---|
| 101 | 2-(4-Fluorobenzyl)-10-hydroxy-4-(pyrrolidin-1-ylmethyl)-8-methyl-7,8-dihydropyrazino[1',2':1,5]pyrrolo[2,3-d]pyridazine-1,9(2H,6H)-dione | H | pyrrolidin-1-yl | 426 |
| 102 | 2-(4-Fluorobenzyl)-10-hydroxy-4-{[(ethyl)methyl)amino]methyl}-8-methyl-7,8-dihydropyrazino[1',2':1,5]pyrrolo[2,3-d]pyridazine-1,9(2H,6H)-dione | H | N(Me)Et | 414 |
| 103 | 2-(4-Fluorobenzyl)-10-hydroxy-4-(1H-1,2,4-triazol-1-ylmethyl)-8-methyl-7,8-dihydropyrazino[1',2':1,5]pyrrolo[2,3-d]pyridazine-1,9(2H,6H)-dione | H | 1,2,4-triazol-1-yl | 424 |
| 104 | 2-(4-Fluorobenzyl)-10-hydroxy-4-(1H-imidazol-1-ylmethyl)-8-methyl-7,8-dihydropyrazino[1',2':1,5]pyrrolo[2,3-d]pyridazine-1,9(2H,6H)-dione | H | imidazol-1-yl | 423 |

-continued

| Ex. | Name | A | B | M + 1 |
|---|---|---|---|---|
| 105 | 2-(4-Fluorobenzyl)-10-hydroxy-4-[(2-oxopiperidin-1-yl)methyl]-8-methyl-7,8-dihydropyrazino[1',2':1,5]pyrrolo[2,3-d]pyridazine-1,9(2H,6H)-dione | H | 2-oxopiperidin-1-yl | 454 |
| 106 | 2-(4-Fluorobenzyl)-10-hydroxy-4-[(4-ethyl-2,3-dioxopiperazin-1-yl)methyl]-8-methyl-7,8-dihydropyrazino[1',2':1,5]pyrrolo[2,3-d]pyridazine-1,9(2H,6H)-dione | H | 4-ethyl-2,3-dioxopiperazin-1-yl | 497 |
| 107 | 2-(4-Fluorobenzyl)-10-hydroxy-4-[(methylthio)methyl]-8-methyl-7,8-dihydropyrazino[1',2':1,5]pyrrolo[2,3-d]pyridazine-1,9(2H,6H)-dione | H | SMe | 403 |
| 108 | 2-(4-Fluorobenzyl)-10-hydroxy-4-[(methylsulfonyl)methyl]-8-methyl-7,8-dihydropyrazino[1',2':1,5]pyrrolo[2,3-d]pyridazine-1,9(2H,6H)-dione | H | SO$_2$Me | 435 |
| 109 | 2-(4-Fluorobenzyl)-10-hydroxy-4-[(phenylthio)methyl]-8-methyl-7,8-dihydropyrazino[1',2':1,5]pyrrolo[2,3-d]pyridazine-1,9(2H,6H)-dione | H | S-Ph | 465 |
| 110 | 2-(4-Fluorobenzyl)-10-hydroxy-4-[(phenylsulfonyl)methyl]-8-methyl-7,8-dihydropyrazino[1',2':1,5]pyrrolo[2,3-d]pyridazine-1,9(2H,6H)-dione | H | SO$_2$Ph | 497 |
| 111 | 2-(3-Chloro-4-fluorobenzyl)-10-hydroxy-4-[(2-oxopyridine-1(2H)-yl)methyl]-8-methyl-7,8-dihydropyrazino[1',2':1,5]pyrrolo[2,3-d]pyridazine-1,9(2H,6H)-dione | Cl | 2-oxopyridin-1(2H)-yl | 484 |
| 112 | 2-(3-Chloro-4-fluorobenzyl)-10-hydroxy-4-[(2-oxopyrrolidin-1-yl)methyl]-8-methyl-7,8-dihydropyrazino[1',2':1,5]pyrrolo[2,3-d]pyridazine-1,9(2H,6H)-dione | Cl | 2-oxopyrrolidin-1-yl | 474 |

Note: M + 1 determined by ES MS.

EXAMPLE 113

2-(4-Fluorobenzyl)-10-hydroxy-4-(1-hydroxyethyl)-8-methyl-7,8-dihydropyrazino[1',2':1,5]pyrrolo[2,3-d]pyridazine-1,9(2H,6H)-dione

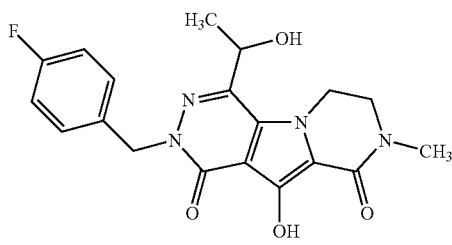

Step 1: 2-(4-Fluorobenzyl)-8-methyl-10-methoxy-1,9-dioxo-1,2,6,7,8,9-hexahydropyrazino[1',2':1,5]pyrrolo[2,3-d]pyridazine-4-carboxaldehyde To a cold (−78° C.) solution of oxalyl chloride (0.25 mL, 2.8 mmol) in anhydrous dichloromethane (15 mL) under an atmosphere of nitrogen, a solution of anhydrous DMSO (0.21 mL, 2.93 mmol) in anhydrous dichloromethane (5 mL) was added. The resultant mixture was stirred at the same temperature for 10 minutes. A solution of 2-(4-fluorobenzyl)-4-(hydroxymethyl)-10-methoxy-8-methyl-7,8-dihydropyrazino[1',2':1,5]pyrrolo[2,3-d]pyridazine-1,9(2H,6H)-dione (0.47 g, 1.22 mmol) in a mixture of anhydrous dichloromethane (3 mL) and DMSO (5 mL) was added. After stirring at the same temperature for 2 hours, the reaction mixture was allowed to warm to −35° C., and treated with triethylamine (8 mL). The reaction mixture was allowed to warm to room temperature and pour into water (40 mL). The product mixture was diluted with dichloromethane. The organic extract was dried over anhydrous magnesium sulfate, filtered, and concentrated under vacuum. The residual oil was treated with hexane and cooled to 0° C. The solid precipitated was filtered and vacuum dried to provide the title compound.

$^1$H NMR (400 MHz, CDCl$_3$) δ 9.73 (S, 1H), 7.50 (dd, J=8.6, 5.5, 2H), 7.01 (t, J=8.8 Hz, 2H), 5.43(s, 2H), 4.85 (m, 2H), 4.15 (s, 3H), 3.67 (m, 2H), 3.15 (s, 3H). ES MS M+1=385

Step 2: 2-(4-Fluorobenzyl)-10-methoxy-4-(1-hydroxyethyl)-8-methyl-7,8-dihydropyrazino[1',2':1,5]pyrrolo[2,3-d]pyridazine-1,9(2H,6H)-dione To a solution of 2-(4-fluorobenzyl)-8-methyl-10-methoxy-1,9-dioxo-1,2,6,7,8,9-hexahydropyrazino[1',2':1,5]pyrrolo[2,3-d]pyridazine-4-carboxaldehyde (42 mg, 0.11 mmol) in anhydrous DME (10 mL), a solution of methyl magnesium bromide in butyl ether (0.26 mL, 0.26 mmol; 1 M) was added. After stirring at room temperature for 5 minutes, the reaction mixture was treated with dilute hydrochloric acid, and diluted with dichloromethane. The organic extract was washed with brine, dried over anhydrous magnesium sulfate, filtered and concentrated under vacuum to provide the title compound as yellow solid. ES MS M+1=401

Step 3: 2-(4-Fluorobenzyl)-10-hydroxy-4-(1-hydroxyethyl)-8-methyl-7,8-dihydropyrazino[1',2':1,5]pyrrolo[2,3-d]pyridazine-1,9(2H,6H)-dione The title compound was prepared in accordance with the procedure set forth in Example 62, step 12.

$^1$H NMR (400 MHz, CDCl$_3$) δ 8.56 (br s, 1H), 7.41 (dd, J=8.6, 5.5 Hz, 2H), 6.96 (t, J=8.6 Hz, 2H), 5.32 (d, J=13.6 Hz, 1H), 5.07 (d, J=13.6 Hz, 1H), 4.95 (q, J=6.2 Hz, 1H), 4.82 (m, 1H), 4.52 (m, 1H), 3.79 (m, 1H), 3.67 (m, 1H), 3.09 (s, 3H), 1.65 (d, J=6.2 Hz, 2H). ES MS M+1=387

EXAMPLE 114

2-(4-Fluorobenzyl)-10-hydroxy-4-[1-(1,1-dioxido-1,2-thiazinan-2-yl)ethyl]-8-methyl-7,8-dihydropyrazino[1',2':1,5]pyrrolo[2,3-d]pyridazine-1,9(2H,6H)-dione

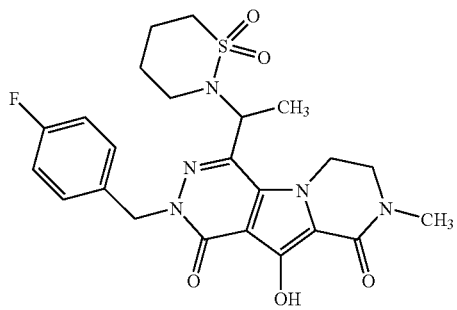

Step 1: 2-(4-Fluorobenzyl)-10-methoxy-4-(1-chloroethyl)-8-methyl-7,8-dihydropyrazino[1',2':1,5]pyrrolo[2,3-d]pyridazine-1,9(2H,6H)-dione A solution of 2-(4-fluorobenzyl)-10-methoxy-4-(1-hydroxyethyl)-8-methyl-7,8-dihydropyrazino[1',2':1,5]pyrrolo[2,3-d]pyridazine-1,9(2H,6H)-dione (0.12 g, 0.30 mmol) in thionyl chloride (3.3 mL) was stirred at room temperature for 3 hours. The reaction mixture was concentrated under vacuum. The residue was concentrated from a solution in benzene under vacuum and triturated with diethyl ether. The solid precipitated was filtered and vacuum dried to provide the title compound.

$^1$H NMR (400 MHz, CDCl$_3$) δ 7.45 (dd, J=8.6, 5.5 Hz, 2H), 6.98 (t, J=8.6 Hz, 2H), 5.45 (d, J=13.6 Hz, 1H), 5.25 (q, J=6.2 Hz, 1H), 5.14 (d, J=13.6 Hz, 1H), 4.81 (m, 1H), 4.37 (m, 1H), 4.15 (s, 3H), 3.79 (m, 1H), 3.64 (m, 1H), 3.13 (s, 3H), 1.98 (d, J=6.4 Hz, 2H). ES MS M+1=419

Step 2: 2-(4-Fluorobenzyl)-10-methoxy-4-[1-(1,1-dioxido-1,2-thiazinan-2-yl)ethyl]-8-methyl-7,8-dihydropyrazino[1',2':1,5]pyrrolo[2,3-d]pyridazine-1,9(2H,6H)-dione To a cold (0° C.) solution of 1,2-thiazinane 1,1-dioxide (32 mg, 0.24 mmol) in anhydrous DMF (2 mL) under an atmosphere of nitrogen, a solution of lithium bis(trimethylsilyl)amide in THF (0.18 mL, 1M) was added. After stirred at room temperature for 20 minutes, solid 2-(4-fluorobenzyl)-10-methoxy-4-(1-chloroethyl)-8-methyl-7,8-dihydropyrazino[1',2':1,5]pyrrolo[2,3-d]pyridazine-1,9(2H,6H)-dione (50 mg. 0.12 mmol) was added and the reaction mixture was stirred at room temperature overnight. The product mixture was concentrated under vacuum. The residue was partitioned between dichloromethane and dilute hydrochloric acid. The organic extract was washed with brine, dried over anhydrous magnesium sulfate, filtered, and concentrated under vacuum to afford the title compound. ES MS M+1=518

Step 3: 2-(4-Fluorobenzyl)-10-hydroxy-4-[1-(1,1-dioxido-1,2-thiazinan-2-yl)ethyl]-8-methyl-7,8-dihydropyrazino[1',2':1,5]pyrrolo[2,3-d]pyridazine-1,9(2H,6H)-dione The title compound was prepared in accordance with the procedure set forth in Example 62, step 12.
$^1$H NMR (400 MHz, CDCl$_3$) δ 7.42 (dd, J=8.5, 5.4 Hz, 2H), 6.98 (t, J=8.6 Hz, 2H), 5.56 (q, J=6.6 Hz, 1H), 5.38 (d, J=13.8 Hz, 1H), 5.287 (d, J=13.8 Hz, 1H), 4.73 (m, 1H), 4.47 (m, 1H), 3.72 (m, 2H), 3.13 (m, 2H), 3.11 (s, 3H), 2.94 (m, 2H), 2.20 (m, 2H), 1.61 (d, J=6.8 Hz, 2H), 1.34 (M, 1H).
ES MS M+1=504

EXAMPLE 115

2-(4-Fluorobenzyl)-10-hydroxy-4-(1-morpholin-4-ylethyl)-8-methyl-7,8-dihydropyrazino[1',2':1,5]pyrrolo[2,3-d]pyridazine-1,9(2H,6H)-dione

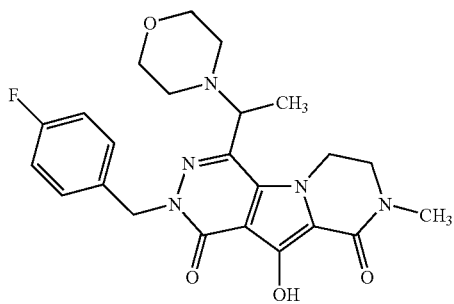

The title compound was prepared in accordance with the procedure set forth in Example 114 substituting 1,2-thiazinane 1,1-dioxide with morpholine in step 2. ES MS M+1=456

EXAMPLE 116

4-Acetyl-2-(3-chloro-4-fluorobenzyl)-1-hydroxy-8-methyl-7,8-dihydropyrazino[1',2':1,5]pyrrolo[2,3-d]pyridazine-1,9(2H,6H)-dione

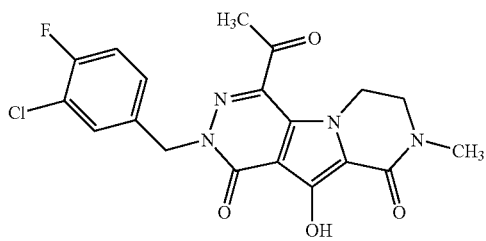

The title compound was prepared in accordance with the procedure set forth in Example 113, steps 1, 2, and 1 starting with 2-(3-chloro-4-fluorobenzyl)-4-(hydroxymethyl)-10-methoxy-8-methyl-7,8-dihydropyrazino[1',2':1,5]pyrrolo[2,3-d]pyridazine-1,9(2H,6H)-dione. The ketone intermediate can alternatively be prepared as described in Example 185, step 1.
$^1$H NMR (400 MHz, DMSO-d$_6$) δ 9.14 (s, 1H), 7.59 (dd, 1H), 7.40 (m, 2H), 5.32 (s, 2H), 4.16 (t, J=5.9 Hz, 2H), 3.66 (t, J=5.9 Hz, 2H), 2.99 (s, 3H), 2.56 (s, 3H). ES MS M+1=419

EXAMPLE 117

2-(3-Chloro-4-fluorobenzyl)-10-hydroxy-4-(1-hydroxy-1-methylethyl)-8-methyl-7,8-dihydropyrazino[1',2':1,5]pyrrolo[2,3-d]pyridazine-1,9(2H,6H)-dione

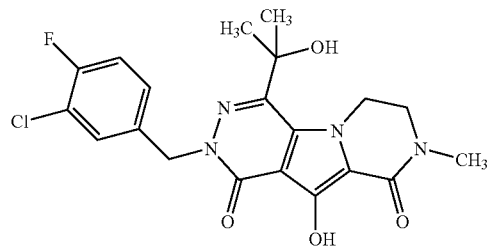

The title compound was prepared in accordance with the procedure set forth in Example 113, steps 1 and 2, and then steps 1 and 2 again, starting with 2-(3-chloro-4-fluorobenzyl)-4-(hydroxymethyl)-10-methoxy-8-methyl-7,8-dihydropyrazino[1',2':1,5]pyrrolo[2,3-d]pyridazine-1,9(2H,6H)-dione.
$^1$H NMR (400 MHz, DMSO-d$_6$) δ 9.07 (s, 1H), 7.52 (dd, J=7.1, 5.7 Hz, 1H), 7.33 (m, 2H), 5.83 (s, 1H), 5.18 (s, 2H), 4.86 (t, J=5.2 Hz, 2H), 3.69 (t, J=5.2 Hz, 2H), 2.99 (s, 3H), 1.51 (s, 6H), ES MS M+1=435

EXAMPLE 118

Methyl [2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]acetate

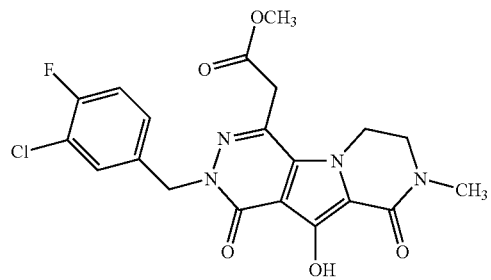

Step 1: 2-(3-Chloro-4-Fluorobenzyl)-4-(cyanomethyl)-10-methoxy-8-methyl-7,8-dihydropyrazino[1',2':1,5]pyrrolo[2,3-d]pyridazine-1,9(2H,6H)-dione A mixture of 2-(3-chloro-4-fluorobenzyl)-4-(chloromethyl)-10-methoxy-8-methyl-7,8-dihydropyrazino[1',2':1,5]pyrrolo[2,3-d]pyridazine-1,9(2H,6H)-dione (0.16 g, 0.37 mmol; Example 100) and sodium cyanide (30 mg, 0.61 mmol) in anhydrous DMF (2 mL) was heated in a sealed tube at room temperature overnight. The product mixture was concentrated under vacuum. The residue was partitioned between dichloromethane and brine. The organic extract was washed with brine, dried over anhydrous magnesium sulfate, filtered, and concentrated under vacuum. The residue was subjected to column chromatography on silica gel eluting with a 0 to 10% methanol in chloroform gradient. Collection and concentration of appropriate fractions afforded the title compound.

$^1$H NMR (400 MHz, CDCl$_3$) δ 7.50 (dd, J=7.2, 1.2 Hz, 1H), 7.35 (m, 1H), 7.08 (t, J=8.6 Hz, 1H), 5.23 (s, 2H), 4.47 (t, J=5.7 Hz, 2H), 4.16 (s, 3H), 4.01 (s, 2H), 3.76 (t, J=5.7 Hz, 2H), 3.14 (s, 3H).
ES MS M+1=430.

Step 2: Methyl [2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]acetate The title compound was prepared in accordance with the procedure set forth in Example 62, step 12. After treatment of 2-(4-fluorobenzyl)-4-(cyanomethyl)-10-methoxy-8-methyl-7,8-dihydropyrazino[1',2':1,5]pyrrolo[2,3-d]pyridazine-1,9 (2H,6H)-dione with boron tribromide in dichloromethane, followed by addition of methanol, in addition to the deprotection of the phenolic hydroxy group, the nitrile group was also converted to the corresponding methyl ester.

$^1$H NMR (400 MHz, CDCl$_3$) δ 7.48 (dd, J=7.0, 1.9 Hz, 1H), 7.35 (m, 1H), 7.05 (t, J=8.8 Hz, 1H), 5.25 (s, 2H), 4.35 (t, J=5.6 Hz, 2H), 3.76 (s, 3H), 3.71 (t, J=5.6 Hz, 2H), 3.11 (s, 3H). ES MS M+1=449

EXAMPLE 119

2-(3-Chloro-4-fluorobenzyl)-10-hydroxy-4-(5-oxopyrrolidin-3-yl)-8-methyl-7,8-dihydropyrazino[1',2':1,5]pyrrolo[2,3-d]pyridazine-1,9(2H,6H)-dione

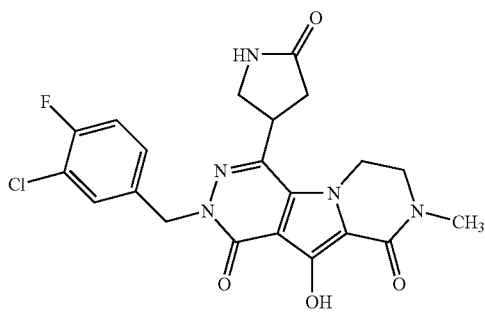

Step 1: Methyl 3-[2-(3-chloro-4-fluorobenzyl)-10-methoxy-8-methyl-1,9-dioxo-1,2,6,7,8,9-hexahydropyrazino[1',2':1,5]pyrrolo[2,3-d]pyridazin-4-yl]-3-cyanopropanoate To a cold (0° C.) solution of 2-(3-chloro-4-fluorobenzyl)-4-(cyanomethyl)-10-methoxy-8-methyl-7,8-dihydropyrazino[1',2':1,5]pyrrolo[2,3-d]pyridazine-1,9(2H,6H)-dione (0.11 g, 0.25 mmol; Example 118, step 1) in anhydrous DMF (1 mL), a solution of lithium bis(trimethylsilyl)amide (0.28 mL, 0.28 mmol; 1M) in THF was added over a period of 5 minutes. The reaction solution was stirred at the same temperature for 30 minutes and treated with methyl bromoacetate (43 mg, 0.28 mmol). After stirring at room temperature for two hours, the product mixture was concentrated under vacuum. The residue was partitioned between dichloromethane and aqueous ammonium chloride. The organic extract was washed with brine, dried over anhydrous magnesium sulfate, filtered, and concentrated under vacuum. The residue was subjected to column chromatography on silica gel eluting with a 0 to 10% methanol in chloroform gradient. Collection and concentration of appropriate fractions afforded the title compound.

$^1$H NMR (400 MHz, CDCl$_3$) δ 7.43 (dd, J=7.2, 2.2 Hz, 1H), 7.30 (m, 1H), 7.08 (t, J=8.6 Hz, 1H), 5.38 (d, J=14.0 Hz, 1H), 5.08 (d, J=14.0 Hz, 1H), 4.76-4.50 (m, 3H), 4.16 (s, 3H), 3.77 (m, 3 H), 3.16 (s, 3H). ES MS M+1=502

Step 2: 2-(3-Chloro-4-fluorobenzyl)-10-methoxy-4-(5-oxopyrrolidin-3-yl)-8-methyl-7,8-dihydropyrazino[1',2':1,5]pyrrolo[2,3-d]pyridazine-1,9(2H, 6H)-dione A mixture of methyl 3-[2-(3-chloro-4-fluorobenzyl)-10-methoxy-8-methyl-1,9-dioxo-1,2,6,7,8,9-hexahydropyrazino[1',2':1,5]pyrrolo[2,3-d]pyridazin-4-yl]-3-cyanopropanoate (0.12 g, 0.24 mmol) and Raney nickel (200 mg; washed successively with deionized water until neutral to pH paper and three times with absolute ethanol) in absolute ethanol (35 mL) was subjected to an atmosphere of hydrogen gas at 50 psi in a Parr hydrogenation vessel at room temperature for 48 hours. The product mixture was filtered through a pad of Celite. The filtrate was concentrated under vacuum. The residue was subjected to reverse phase preparative HPLC purification. Collection and lyophilization of appropriate fractions provide the title compound. ES MS M+1=474

Step 3: 2-(3-Chloro-4-fluorobenzyl)-10-hydroxy-4-(5-oxopyrrolidin-3-yl)-8-methyl-7,8-dihydropyrazino[1',2':1,5]pyrrolo[2,3-d]pyridazine-1,9(2H, 6H)-dione The title compound was prepared in accordance with the procedure set forth in Example 62, step 12.

$^1$H NMR (400 MHz, DMSO-d$_6$) δ 9.01 (br s, 1H), 7.65 (s, 1H), 7.49 (dd, J=7.1, 1.9 Hz, 1H), 7.37-7.29 (m, 2H), 5.18 (s, 2H), 4.47 (heptet, J=6.1 Hz, 1H), 4.40 (heptet, J=6.1 Hz, 1H), 4.16 (m, 1 H), 3.71 (t, J=6.1 Hz, 1H), 3.62 (t, J=9.8 Hz, 1H), 3.50 (m, 3 H), 3.03 (s, 3H), 2.64 to 2.52 (m, 2 H). ES MS M+1=460

EXAMPLE 120

(6S)-4-Amino-2-(3-chloro-4-fluorobenzyl)-10-hydroxy-8-ethyl-6-methyl-7,8-dihydropyrazino[1',2':1,5]pyrrolo[2,3-d]pyridazine-1,9(2H,6H)-dione

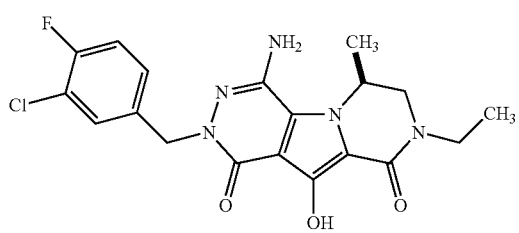

Step 1: Ethyl (4S)-6-cyano-2-ethyl-8-methoxy-4-methyl-1-oxo-1,2,3,4-tetrahydropyrrolo[1,2-a]pyrazin-7-carboxylate To a mixture of ethyl (4S)-6-bromo-2-ethyl-8-methoxy-4-methyl-1-oxo-1,2,3,4-tetrahydropyrrolo[1,2-a]pyrazin-7-carboxylate (4.1 g, 11.41 mmol; Example 62, step 7), zinc dust (0.15 g, 2.28 mmol), zinc cyanide (1.11 g, 9.47 mmol), triphenylphosphine (0.46 g, 1.77 mmol), and tris(dibenzylideneacetone)dipalladium (0) (1.57 g, 1.71 mmol) in anhydrous DMF (10 mL) was purged with argon gas for 15 minutes. The mixture was heated in a sealed tube in an oil bath at 140° C. overnight. The reaction mixture was filtered through a pad of Celite, and the filtrate concentrated under vacuum. The residue was partitioned between chloroform and aqueous EDTA monosodium salt. The mixture was stirred at room temperature for 30 minutes. The organic extract was washed with brine, dried over anhydrous magnesium sulfate, filtered, and concentrated under vacuum. The residue was subjected to column chromatography on silica gel eluted with 0 to 40% ethyl acetate in chloroform gradient. Collection and concentration of appropriate fractions provided the title nitrile.

$^1$H NMR (400 MHz, CDCl$_3$) δ 4.63 (br m, 1H), 4.37 (q, J=7.2 Hz, 2H), 4.03 (s, 3H), 3.99 (dd, J=12.3, 4.2 Hz, 1H), 3.70 (heptet, J=6.7 Hz, 1H), 3.51 (heptet, J=7.2 Hz, 1 H), 3.31 (dd, J=13.2, 1.4 Hz, 1H), 1.52 (d, J=6.7 Hz, 3H), 1.40 (t, J=7.2 Hz, 3H), 1.22 (t, J=7.2 Hz, 3H). ES MS M+1=306.

Step 2: (6S)-4-Amino-8-ethyl-10-methoxy-6-methyl-7,8-dihydropyrazino[1',2':1,5]pyrrolo[2,3-d]pyridazine-1,9(2H,6H)-dione A solution of ethyl (4S)-6-cyano-2-ethyl-8-methoxy-4-methyl-1-oxo-1,2,3,4-tetrahydropyrrolo[1,2-a]pyrazin-7-carboxylate (1.10 g, 3.60 mmol) in absolute ethanol (25 mL) was purged with argon gas for 15 minutes. The mixture was treated with hydrazine (1.16 g, 36.02 mmol) and 20 drops glacial acetic acid, and heated in a sealed tube in an oil bath at 110° C. overnight. The product mixture was cooled to 0° C. The solid precipitated collected by filtration, washed with cold ethanol and diethyl ether to afford the title compound. The filtrate was concentrated under vacuum, and the residue was subjected to preparative high pressure reverse phase column chromatography. Collection and lyophilization of appropriate fractions provided additional product, which was concentrated from its solution in acetonitrile and anhydrous DMF prior to the following benzylation. ES MS M+1=292.

Step 3: (6S)-4-Amino-2-(3-chloro-4-fluorobenzyl)-10-methoxy-8-ethyl-6-methyl-7,8-dihydropyrazino[1',2':1,5]pyrrolo[2,3-d]pyridazine-1,9(2H,6H)-dione To a solution of (6S)-4-amino-8-ethyl-10-methoxy-6-methyl-7,8-dihydropyrazino[1',2':1,5]pyrrolo[2,3-d]pyridazine-1,9(2H,6H)-dione (0.94 g, 3.23 mmol) in anhydrous DMF (32 mL) under an atmosphere of nitrogen, a solution of lithium bis(trimethylsilyl)amide in THF (3.87 mL, 1 M, 3.87 mmol) was added. The mixture was stirred at room temperature for 15 minutes and treated with 4-fluoro-3-chlorobenzyl bromide (0.72 g, 3.23 mmol). The reaction mixture was stirred at room temperature for 1 hour and concentrated under vacuum. The residue was partitioned between chloroform and dilute hydrochloric acid. The organic extract was washed with brine, dried over anhydrous sodium sulfate, filtered, and concentrated under vacuum. The residue was subjected to column chromatography on silica gel eluting with 0-20% methanol in ethyl acetate gradient. Collection and concentration of appropriate fractions provided the title material.

$^1$H NMR (400 MHz, DMSO-d$_6$) δ 7.46 (dd, J=7.2, 2.0 Hz, 1H), 7.37 (t, J=8.7 Hz, 1H), 7.27 (m, 1H), 5.57 (s, 2H), 5.19 (m, 1H), 5.11 (d, J=14.7 Hz, 1H), 5.03 (d, J=14.7 Hz, 1H), 3.91 (s, 3H), 3.89 (m, 1H), 3.65 (heptet, J=6.4 Hz, 1 H), 3.37 (m), 1.32 (d, J=6.6 Hz, 3H), 1.11 (t, J=7.2 Hz, 3H).

ES MS M+1=434

Step 4: (6S)-4-Amino-2-(3-chloro-4-fluorobenzyl)-10-hydroxy-8-ethyl-6-methyl-7,8-dihydropyrazino[1',2':1,5]pyrrolo[2,3-d]pyridazine-1,9(2H,6H)-dione To a solution of (6S)-4-amino-2-(3-chloro-4-fluorobenzyl)-10-methoxy-8-ethyl-6-methyl-7,8-dihydropyrazino[1',2':1,5]pyrrolo[2,3-d]pyridazine-1,9(2H,6H)-dione (62 mg, 0.14 mmol) in anhydrous dichloromethane (2 mL), a solution of boron tribromide in dichloromethane (0.43 mL, 0.43 mmol; 1 M) was added. After stirring at room temperature for 30 minutes, the reaction mixture was treated with anhydrous methanol, stirred for 30 minutes, and concentrated under vacuum. The procedure was repeated twice. The residue was subjected to purification on preparative reverse phase high pressure column chromatography. Collection and lyophilization of appropriate fractions provided the title compound.

$^1$H NMR (400 MHz, DMSO-d$_6$) δ 8.98 (s, 1H), 7.44 (dd, J=7.1, 2.0 Hz, 1H), 7.37 (t, J=8.9 Hz, 1H), 7.25 (m, 1H), 5.61 (s, 2H), 5.12 (m. 1H), 5.07 (d, J=14.8 Hz, 1H), 5.01 (d, J=14.8 Hz, 1H), 3.92 (dd, J=13.4, 3.9 Hz, 1H), 3.62 (heptet, J=6.9 Hz, 1 H), 3.48 (d, J=13.0 Hz, 1H), 3.41-3.30 (m), 1.28 (d, J=6.4 Hz, 3H), 1.13 (t, J=7.1 Hz, 3H). ES MS M+1=420

EXAMPLES 121-123

The compounds in the following table were prepared in accordance with the procedure set forth in Example 120.

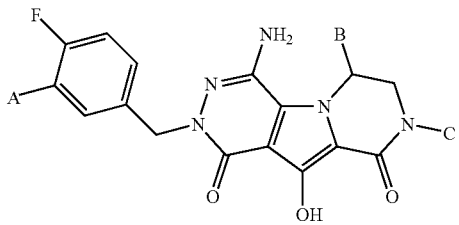

| Ex. | Name | A | B | C | M + 1 |
|---|---|---|---|---|---|
| 121 | 4-Amino-2-(3-chloro-4-fluorobenzyl)-10-hydroxy-8-methyl-7,8-dihydropyrazino[1',2':1,5]pyrrolo[2,3-d]pyridazine-1,9(2H,6H)-dione | Cl | H | Me | 392 |
| 122 | (6S)-4-Amino-2-(3-chloro-4-fluorobenzyl)-10-hydroxy-8-isopropyl-6-methyl-7,8-dihydropyrazino[1',2':1,5]pyrrolo[2,3-d]pyridazine-1,9(2H,6H)-dione | Cl | Me⎯* | i-Pr | 434 |
| 123 | (6S)-4-Amino-2-(4-fluorobenzyl)-10-hydroxy-8-isopropyl-6-methyl-7,8-dihydropyrazino[1',2':1,5]pyrrolo[2,3-d]pyridazine-1,9(2H,6H)-dione | H | Me⎯* | i-Pr | 400 |

Note: M + 1 determined by ES MS.

EXAMPLE 124

N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylacetamide

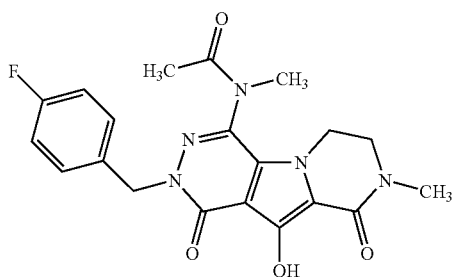

Step 1: N-[10-(Benzyloxy)-2-(4-fluorobenzyl)-8-methyl-1,9-dioxo-1,2,6,7,8,9-hexahydropyrazino[1',2':1,5]pyrrolo[2,3-d]pyridazin-4-yl]acetamide To a mixture of 4-amino-2-(4-fluorobenzyl)-10-benzyloxy-8-methyl-7,8-dihydropyrazino[1',2':1,5]pyrrolo[2,3-d]pyridazine-1,9(2H,6H)-dione (21 mg, 47 μmol) and diisopropylethylamine (10 μL, 56 μmol) in anhydrous chloroform (2 mL), acetyl chloride (8 μL, 104 μmol) was added. The mixture was stirred at room temperature for 30 minutes and concentrated under vacuum. The intermediate bisacetylated product was dissolved in methanol, stirred at room temperature overnight, and concentrated under vacuum. The residue was subjected to column chromatography on silica gel. Collection and concentration of appropriate fractions provided the title monoacetylated product.

$^1$H NMR (400 MHz, DMSO-d$_6$) δ 7.65 (d, J=7.33, 2H), 7.41(m, 5H), 7.03 (t, J=8.8 Hz, 2H), 5.36 (s, 2H), 5.31 (s, 2H), 4.35 (br s, 2H), 3.70 (m, 3H), 3.07 (s, 3H), 2.14 (d, J=5.2 Hz, 3H).

ES MS M+1=490

Step 2: N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylacetamide To a solution of N-[10-(benzyloxy)-2-(4-fluorobenzyl)-8-methyl-1,9-dioxo-1,2,6,7,8,9-hexahydropyrazino[1',2':1,5]pyrrolo[2,3-d]pyridazin-4-yl]acetamide (0.13 g, 0.27 mmol) in anhydrous DMF (5 mL), a solution of lithium bis(trimethylsilyl)amide (0.4 mL, 0.4 mmol; 1 M in THF) was added. The mixture was stirred at room temperature for 10 minutes, treated with iodomethane (25 μL, 0.40 mmol), and stirred at room temperature for 1 hour. The reaction mixture was concentrated under vacuum and the residue partitioned between chloroform and dilute hydrochloric acid. The organic extract was washed with brine, dried over anhydrous magnesium sulfate, filtered and concentrated under vacuum. The title compound was debenzylated in accordance with the procedure set forth in Example 62, step 12.

$^1$H NMR (400 MHz, DMSO-d$_6$) δ 7.33 (dd, J=8.6, 5.9, 2H), 7.15 (t, J=8.9 Hz, 2H), 5.31 (d, J=14.4 Hz, 1H), 5.13 (d, J=14.4 Hz, 1H), 4.16 (t, J=6.1 Hz, 2H), 3.72 (t, J=6.1 Hz, 2H), 3.10 (s, 3H), 2.99 (s, 3H), 1.79 (s, 3H). ES MS M+1=414

EXAMPLES 125-130

The compounds in the following table were prepared in accordance with the procedure set forth in Example 124.

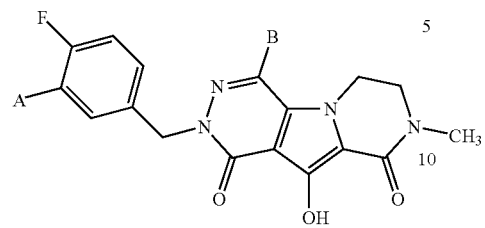

| Ex. | Name | A | B | M + 1 |
|---|---|---|---|---|
| 125 | N-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,2-dimethylpropanamide | Cl | Me\N—C(=O)—CH(Me)₂ (*-N(Me)-C(O)CH(Me)₂) | 476 |
| 126 | N-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-(N',N'-dimethylcarbonylmethyl)-2-methylpropanamide | Cl | (Me)₂N-C(O)-CH₂-N(*)-C(O)CH(Me)₂ | 547 |
| 127 | [2-(4-Fluorobenzyl)-10-hydroxy-8-methyl-4-(2-oxopiperidin-1-yl)-7,8-dihydropyrazino[1',2':1,5]pyrrolo[2,3-d]pyridazine-1,9(2H,6H)-dione (using 5-pentanoyl chloride in step 1) | H | 2-oxopiperidin-1-yl | 440 |
| 128 | N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N',N'-dimethylethanediamide | H | (Me)₂N-C(O)-C(O)-NH-* | 457 |
| 129 | N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N',N'-trimethylethanediamide | H | (Me)₂N-C(O)-C(O)-N(Me)-* | 471 |
| 130 | N-[2-(3-Chloro-4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N',N'-trimethylethanediamide | Cl | (Me)₂N-C(O)-C(O)-N(Me)-* | 505 |

Note: M + 1 determined by ES MS.

EXAMPLE 131

N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N'-dimethylurea

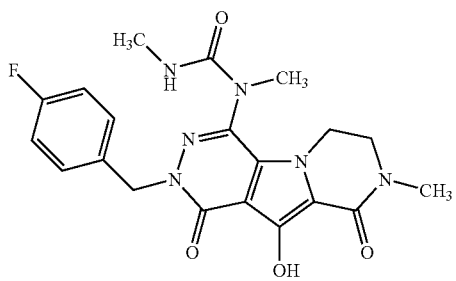

Step 1: N-[10-(Benzyloxy)-2-(4-fluorobenzyl)-8-methyl-1,9-dioxo-1,2,6,7,8,9-hexahydropyrazino[1',2':1,5]pyrrolo[2,3-d]pyridazin-4-yl]-N'-methylurea A mixture of 4-amino-2-(4-fluorobenzyl)-10-benzyloxy-8-methyl-7,8-dihydropyrazino[1',2':1,5]pyrrolo[2,3-d]pyridazine-1,9(2H,6H)-dione (75 mg, 168 µmol) and methylisocyanate (24 mg, 419 µmol) in anhydrous 1,2-dichloroethane (3 mL) was heated in a sealed tube in an oil bath at 100° C. overnight. The product mixture was concentrated under vacuum. The intermediate dicarbonimidic diamide was dissolved in methanol, treated with an aqueous solution of KOH (0.1 mL, 2 M), and stirred at room temperature for one hour, and concentrated under vacuum. The residue was partitioned between chloroform and dilute hydrochloric acid. The organic extract was washed with brine, dried over anhydrous magnesium sulfate, filtered, and concentrated under vacuum to provide the title compound. ES MS M+1=505

Step 2: N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N'-dimethylurea The title compound was prepared in accordance with the procedure set forth in Example 124, step 2.

$^1$H NMR (400 MHz, DMSO-$d_6$) δ 7.33 (dd, J=8.6, 5.6, 2H), 7.14 (t, J=8.9 Hz, 2H), 6.62 (br s, 1H), 5.28 (d, J=15.0 Hz, 1H), 5.05 (d, J=15.0 Hz, 1H), 4.21 (m, 1H), 4.00 (m, 1H), 3.70 (m, 1H), 3.64 (m, 1H), 3.11 (s, 3H), 2.98 (s, 3H), 2.57 (d, J=4.3 Hz, 3H). ES MS M+1=429

EXAMPLES 132-134

The compounds in the following table were prepared in accordance with the procedure set forth in Example 131.

| Ex. | Name | A | B | C | M + 1 |
|---|---|---|---|---|---|
| 132 | N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N'-methylurea | H | NHMe | H | 415 |
| 133 | N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N'-ethylurea | H | NHEt | H | 429 |
| 134 | N-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N',N'-trimethylurea | Cl | NMe$_2$ | Me | 477 |

Note: M + 1 determined by ES MS.

EXAMPLE 135

N'-[(6S)-2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N,N-dimethylethanimidamide

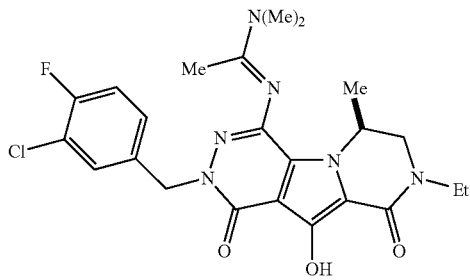

Step 1: N'-[(6S)-2-(3-Chloro-4-fluorobenzyl)-10-methoxy-8-ethyl-6-methyl-1,9-dioxo-1,2,6,7,8,9-hexahydropyrazino[1',2':1,5]pyrrolo[2,3-d]pyridazin-4-yl]-N,N-dimethylethanimidamide A solution of (6S)-4-amino-2-(3-chloro-4-fluorobenzyl)-10-methoxy-8-ethyl-6-methyl-7,8-dihydropyrazino[1',2':1,5]pyrrolo[2,3-d]pyridazine-1,9(2H,6H)-dione (0.20 g, 0.46 mmol; Example 120, step 3) and N,N-dimethylacetamide dimethyl acetal (0.37 mL, 2.51 mmol) in anhydrous DMF (50 mL) was stirred in an oil bath at 40° C. overnight. The reaction mixture was concentrated under vacuum. The residue was subjected to column chromatography on silica gel eluting with a 0-5% methanol in chloroform gradient. Collection and concentration of appropriate fractions provided the title compound.

$^1$H NMR (400 MHz, CDCl$_3$) δ 7.49 (dd, J=6.9, 2.0 Hz, 1H), 7.33 (m, 1H), 7.05 (t, J=8.6 Hz, 1H), 5.41 (m, 1H), 5.28 (d, J=14.3 Hz, 1H), 5.11 (d, J=14.3 Hz, 1H), 4.20 (s, 3H), 3.93 (dd, J=13.0, 4.0 Hz, 1 H), 3.71 (heptet, J=7.0 Hz, 1H), 3.51 (heptet, J=7.0 Hz, 1H), 3.19 (d, J=12.8 Hz, 1H), 3.14 (s, 6H), 2.06 (s, 3H), 1.40 (d, J=6.6 Hz, 3H), 1.21 (t, J=7.2 Hz, 3H). ES MS M+1=503

Step 2: N'-[(6S)-2-(3-Chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N,N-dimethylethanimidamide The title compound was prepared in accordance with the procedure set forth in Example 62, step 12.

$^1$H NMR (400 MHz, DMSO-d$_6$) δ 7.48 (dd, J=7.2, 1.9 Hz, 1H), 7.36 (t, J=8.8 Hz, 1H), 7.29 (m, 1H), 5.12 (s, 2H), 3.90 (dd, J=13.2, 4.2 Hz, 1H), 3.60 (heptet, J=6.7 Hz, 1H), 3.41 (d, J=13.4 Hz, 1H), 3.36 (heptet, J=6.7 Hz, 1H), 3.12 (s, 6H), 2.07 (s, 3H), 1.27 (d, J=6.6 Hz, 3H), 1.121 (t, J=7.0 Hz, 3H). ES MS M+1=489

EXAMPLES 136-137

The compounds in the following table were prepared in accordance with the procedure set forth in Example 135.

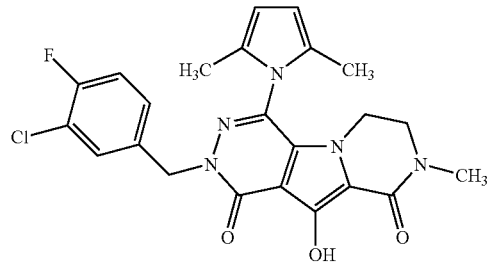

| Ex. | Name | A | B | M+1 |
|---|---|---|---|---|
| 136 | N'-[(6S)-2-(3-Chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N,N-dimethylimidoformamide | Me* | Et | 475 |
| 137 | N'-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N-dimethylimidoformamide | H | Me | 467 |

Note: M + 1 determined by ES MS.

EXAMPLE 138

2-(3-Chloro-4-fluorobenzyl)-10-hydroxy-4-(2,5-dimethyl-1H-pyrrol-yl)-8-methyl-7,8-dihydropyrazino[1',2':1,5]pyrrolo[2,3-d]pyridazine-1,9(2H,6H)-dione

Step 1: 2-(3-Chloro-4-fluorobenzyl)-10-hydroxy-4-(2,5-dimethyl-1H-pyrrol-yl)-8-methyl-7,8-dihydropyrazino[1',2':1,5]pyrrolo[2,3-d]pyridazine-1,9(2H,6H)-dione A mixture of 4-amino-2-(3-chloro-4-fluorobenzyl)-10-methoxy-8-methyl-7,8-dihydropyrazino[1',2':1,5]pyrrolo[2,3-d]pyridazine-1,9(2H,6H)-dione (100 mg, 246 μmol), hexan-2,5-dione (34 mg, 296 μmol), and toluenesulfonic acid (catalytic amount) in toluene (2 mL) was heated in a sealed tube in an oil bath at 120° C. for one hour. The product mixture was concentrated under vacuum. The residue was partitioned between dichloromethane and aqueous sodium bicarbonate. The organic extract was washed with brine, dried over anhydrous sodium sulfate, filtered, and concentrated under vacuum. The residue was subjected to column chromatography on silica gel eluting with a 0-30% methanol in ethyl acetate gradient. Collection and concentration of appropriate fractions provided the title compound.

¹H NMR (400 MHz, CDCl₃) δ 7.53 (dd, J=7.1, 2.2 Hz, 1H), 7.37 (m, 1H), 7.07 (t, J=8.8 Hz, 1H), 5.96 (s, 2H), 5.30 (s, 2H), 4.22 (s, 3H), 3.47 (t, J=6.0 Hz, 2H), 3.17 (t, J=6.0 Hz, 2H), 3.06 (s, 3H), 2.00 (s, 6H). ES MS M+1=484

Step 2: 2-(3-Chloro-4-fluorobenzyl)-10-hydroxy-4-(2,5-dimethyl-1H-pyrrol-yl)-8-methyl-7,8-dihydropyrazino[1',2':1,5]pyrrolo[2,3-d]pyridazine-1,9(2H,6H)-dione The title compound was prepared in accordance with the procedure set forth in Example 62, step 12.

¹H NMR (400 MHz, CDCl₃) δ 7.53 (dd, J=7.1, 2.2 Hz, 1H), 7.37 (m, 1H), 7.06 (t, J=8.8 Hz, 1H), 5.95 (s, 2H), 5.32 (s, 2H), 3.53 (t, J=5.5 Hz, 2H), 3.21 (t, J=5.5 Hz, 2H), 3.06 (s, 3H), 1.98 (s, 6H).
ES MS M+1=470

EXAMPLE 139

2-(3-Chloro-4-fluorobenzyl)-8-ethyl-4-fluoro-10-hydroxy-6-methyl-7,8-dihydropyrazino[1',2':1,5]pyrrolo[2,3-d]pyridazine-1,9(2H,6H)-dione

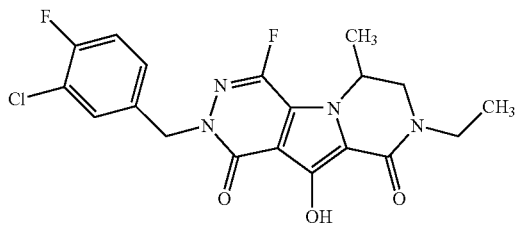

Step 1: 2-(3-Chloro-4-fluorobenzyl)-8-ethyl-4-fluoro-10-methoxy-6-methyl-7,8-dihydropyrazino[1',2':1,5]pyrrolo[2,3-d]pyridazine-1,9(2H,6H)-dione To a stirred, cold (0° C.) solution of 4-amino-2-(3-chloro-4-fluorobenzyl)-10-methoxy-8-ethyl-6-methyl-7,8-dihydropyrazino[1',2':1,5]pyrrolo[2,3-d]pyridazine-1,9(2H,6H)-dione (0.55 g, 1.26 mmol) in hydrogen fluoride-pyridine (9.5 mL) in a polyethylene tube, solid sodium nitrite (96 mg, 1.38 mmol) was added in small portions over a period of 10 minutes. The reaction mixture was stirred at room temperature for 1 hour. The product mixture was added dropwise into an ice-cold saturated aqueous sodium bicarbonate solution. The resultant mixture was extracted with ethyl acetate. The combined organic extract was washed with brine, dried over anhydrous sodium sulfate, filtered, and concentrated under vacuum to afford the title material.

¹H NMR (400 MHz, CDCl₃) δ 7.51 (dd, J=7.0, 2.2 Hz, 1H), 7.36 (m, 1H), 7.08 (t, J=8.7 Hz, 1H), 5.17 (d, J=14.2 Hz, 1H), 5.12 (d, J=14.2 Hz, 1H), 4.81 (m, 1H), 4.21 (s, 3H), 4.02 (dd, J=13.2, 3.9 Hz, 1H), 3.73 (heptet, J=6.7 Hz, 1H), 3.54 (heptet, J=6.7 Hz, 1 H), 3.30 (dd, J=13.2, 1.3 Hz, 1 H), 1.51 (d, J=6.7 Hz, 3H), 1.23 (t, J=7.2 Hz, 3H). ES MS M+1=437

Step 2: 2-(3-Chloro-4-fluorobenzyl)-8-ethyl-4-fluoro-10-hydroxy-6-methyl-7,8-dihydropyrazino[1',2':1,5]pyrrolo[2,3-d]pyridazine-1,9(2H,6H)-dione The title compound was prepared in accordance with the procedure set forth in Example 62, step 12.

¹H NMR (400 MHz, DMSO-d₆) δ 9.24 (s, 1H), 7.52 (dd, J=7.2, 2.1 Hz, 1H), 7.38 (t, J=8.6 Hz, 1H), 7.33 (m, 1H), 5.13 (d, J=15.1 Hz, 1H), 5.09 (d, J=15.1 Hz, 1H), 4.82 (m, 1H), 3.95 (dd, J=13.3, 3.9 Hz, 1H), 3.62 (heptet, J=7.1 Hz, 1H), 3.47 (d, J=13.1 Hz, 1H), 3.38 (heptet, J=7.1 Hz, 1H), 1.36 (d, J=6.6 Hz, 3H), 1.12 (t, J=7.1 Hz, 3H). ES MS M+1=423

EXAMPLE 140

2-(3-Chloro-4-fluorobenzyl)-8-ethyl-10-hydroxy-4-(1,1-dioxidoisothiazinan-2-yl)-6-methyl-7,8-dihydropyrazino[1',2':1,5]pyrrolo[2,3-d]pyridazine-1,9(2H,6H)-dione

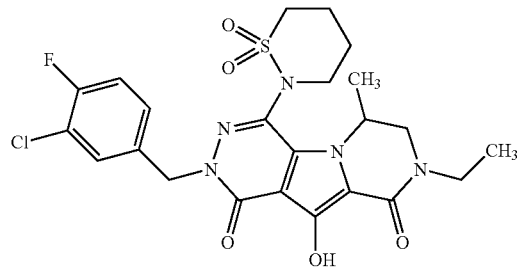

Step 1: 2-(3-Chloro-4-fluorobenzyl)-8-ethyl-10-methoxy-4-(1,1-dioxidoisothiazinan-2-yl)-6-methyl-7,8-dihydropyrazino[1',2':1,5]pyrrolo[2,3-d]pyridazine-1,9(2H,6H)-dione A solution of 2-(3-chloro-4-fluorobenzyl)-8-ethyl-4-fluoro-10-methoxy-6-methyl-7,8-dihydropyrazino[1',2':1,5]pyrrolo[2,3-d]pyridazine-1,9(2H,6H)-dione (0.10 g, 0.23 mmol; Example 139), 1,2-thiazinane 1,1-dioxide (45 mg, 0.33 mmol), and cesium carbonate (0.15 g, 0.46 mmol) in anhydrous DMSO (9.5 mL) was heated in an oil bath at 50° C. for 5 hours. The product mixture was filtered through a pad of Celite and the filtrate was subjected to purification on reverse phase preparative HPLC purification. Collection and lyophilization of appropriate fractions afforded the title material. Analytical HPLC indicated that the product is a 1:1 mixture of two isomers that arose from the relative stereochemistry of the 6-methyl group and restricted rotation between the sultam ring and the tricyclic core.

¹H NMR (400 MHz, CDCl₃) δ 7.48 (m 1H), 7.28 (m, 1H), 7.11 (t, J=8.5 Hz, 1H), 5.17 (d, J=14.2 Hz, ½H), 5.34 (m, ½H), 5.29 (d, J=14.2 Hz, ½H), 5.23 (d, J=14.2 Hz, ½H), 5.09 (d, J=14.2 Hz, ½H), 5.07 (m, ½H), 4.18 (s, 1.5H), 4.16 (s, 1.5H), 4.12-3.17 (m), 2.58-2.00 (m), 1.57 (d, J=6.6 Hz, 1.5H), 1.42 (d, J=6.8 Hz, 1.5H), 1.23 (t, J=6.8 Hz, 1.5H), 1.22 (t, J=7.1 Hz, 1.5H). ES MS M+1=552

Step 2: 2-(3-Chloro-4-fluorobenzyl)-8-ethyl-10-hydroxy-4-(1,1-dioxidoisothiazinan-2-yl)-6-methyl-7,8-dihydropyrazino[1',2':1,5]pyrrolo[2,3-d]pyridazine-1,9(2H,6H)-dione The title compound was prepared in accordance with the procedure set forth in Example 62, step 12. Analytical HPLC indicated that the product is a 1:1 mixture of two isomers that arose from the relative stereochemistry of the 6-methyl group and restricted rotation between the sultam ring and the tricyclic core.

¹H NMR (400 MHz, CDCl₃) δ 8.58 (br s, 1H), 7.49 (m 1H), 7.30 (m, 1H), 7.10 (t, J=8.4 Hz, 1H), 5.42 (d, J=14.1 Hz, ½H), 5.31 (d, J=13.9 Hz, ½H), 5.24 (m, ½ H), 5.18 (d, J=13.9 Hz, ½H), 5.10 (d, J=14.1 Hz, ½H), 4.99 (m, ½H), 4.11-3.17 (m), 2.45-1.57 (m), 1.53 (d, J=6.6 Hz, 1.5H), 1.37 (d, J=7.6 Hz, 1.5H), 1.24 (t, J=6.2 Hz, 1.5H), 1.23 (t, J=7.2 Hz, 1.5H). ES MS M+1=538

EXAMPLES 141-159

The compounds in the following table were prepared in accordance with the procedure set forth in Example 140.

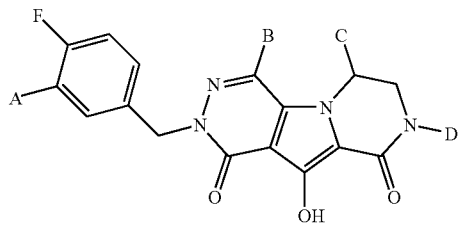

| Ex. | Name | A | B | C | D | M + 1 |
|---|---|---|---|---|---|---|
| 141 | N-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]propane-2-sulfonamide | Cl | NHSO₂CH(Me)₂ | H | Me | 498 |
| 142 | N-[2-(3-Chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]ethanesulfonamide | Cl | NHSO₂Et | Me | Et | 512 |
| 143 | N-[2-(4-Fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylmethanesulfonamide | H | N(Me)SO₂Me | H | Me | 450 |
| 144 | N-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylmethanesulfonamide | Cl | N(Me)SO₂Me | H | Me | 484 |
| 145 | N-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-ethylmethanesulfonamide | Cl | N(Et)SO₂Me | H | Me | 498 |
| 146 | N-(Cyclopropylmethyl)-N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]methanesulfonamide | H | Me—S(O)(O)—N(CH₂-cyclopropyl)* | H | Me | 490 |
| 147 | N-(Cyclopropylmethyl)-N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]methanesulfonamide | Cl | Me—S(O)(O)—N(CH₂-cyclopropyl)* | H | Me | 524 |
| 148 | N-Allyl-N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]methanesulfonamide | Cl | Me—S(O)(O)—N(allyl)* | H | Me | 510 |

-continued

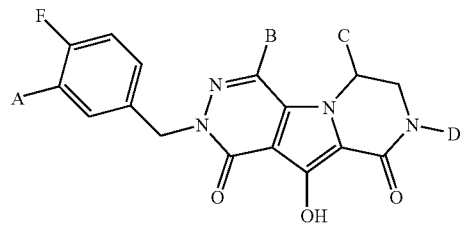

| Ex. | Name | A | B | C | D | M + 1 |
|---|---|---|---|---|---|---|
| 149 | N-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylcyclopropanesulfonamide | Cl | cyclopropyl-S(O)₂-N(Me)-* | H | Me | 510 |
| 150 | N-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylpropane-2-sulfonamide | Cl | N(Me)SO₂CH(Me)₂ | H | Me | 512 |
| 151 | N-[(6S)-2-(3-Chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N-methylmethanesulfonamide | Cl | N(Me)SO₂Me | Me (wedge) * | Et | 512 |
| 152 | N-[2-(3-Chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N-methylpropane-2-sulfonamide | Cl | N(Me)SO₂CH(Me)₂ | Me | Et | 540 |
| 153 | N-[(6S)-2-(3-Chloro-4-fluorobenzyl)-10-hydroxy-8-isopropyl-6-methyl-1,9-dioxo-1,2,6,7,8,9-hexahydropyrazino[1',2':1,5]pyrrolo[2,3-d]pyridazin-4-yl]-N-methylmethanesulfonamide | Cl | N(Me)SO₂Me | Me (wedge) * | i-Pr | 526 |
| 154 | N²-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N²-(isopropylsulfonyl)-N¹,N¹-dimethylglycinamide | Cl | (Me)₂CH-S(O)₂-N(CH₂C(O)N(Me)₂)-* | H | Me | 583 |
| 155 | N²-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N²-(methanesulfonyl)-N¹,N¹-dimethylglycinamide | Cl | Me-S(O)₂-N(CH₂C(O)N(Me)₂)-* | H | Me | 555 |
| 156 | 2-(3-Chloro-4-fluorobenzyl)-8-ethyl-10-hydroxy-4-(1,1-dioxidoisothiazolidin-2-yl)-6-methyl-7,8-dihydropyrazino[1',2':1,5]pyrrolo[2,3-d]pyridazine-1,9(2H,6H)-dione | Cl | 1,1-dioxidoisothiazolidin-2-yl * | Me | Et | 524 |
| 157 | 2-(3-Chloro-4-fluorobenzyl)-10-hydroxy-4-(1,1-dioxidoisothiazolidin-2-yl)-8-methyl-7,8-dihydropyrazino[1',2':1,5]pyrrolo[2,3-d]pyridazine-1,9(2H,6H)-dione | Cl | 1,1-dioxidoisothiazolidin-2-yl * | H | Me | 496 |
| 158 | 2-(3-Chloro-4-fluorobenzyl)-10-hydroxy-4-(1,1-dioxidoisothiazinan-2-yl)-8-methyl-7,8-dihydropyrazino[1',2':1,5]pyrrolo[2,3-d]pyridazine-1,9(2H,6H)-dione | Cl | 1,1-dioxidoisothiazinan-2-yl * | H | Me | 510 |

-continued

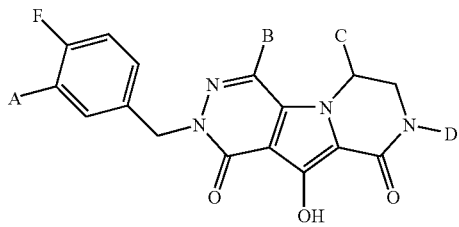

| Ex. | Name | A | B | C | D | M + 1 |
|---|---|---|---|---|---|---|
| 159 | 2-(4-Fluorobenzyl)-10-hydroxy-4-(1,1-dioxidoisothiazinan-2-yl)-8-methyl-7,8-dihydropyrazino[1',2':1,5]pyrrolo[2,3-d]pyridazine-1,9(2H,6H)-dione | H | 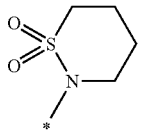 | H | Me | 476 |
| 159-A | N-[(6S)-2-(4-Fluorobenzyl)-10-hydroxy-8-isopropyl-6-methyl-1,9-dioxo-1,2,6,7,8,9-hexahydropyrazino[1',2':1,5]pyrrolo[2,3-d]pyridazin-4-yl]-N-methylmethanesulfonamide | H | N(Me)SO$_2$Me | Me | i-Pr | 492 |
| 159-B | (racemic) N-[2-(3-Chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N-ethylmethanesulfonamide | Cl | N(Et)SO$_2$Me | Me | Et | 526 |

Note: M + 1 determined by ES MS.

EXAMPLE 160

2-(4-Fluorobenzyl)-10-hydroxy-8-methyl-4-(methylsulfonyl)-7,8-dihydropyrazino[1',2':1,5]pyrrolo[2,3-d]pyridazine-1,9(2H,6H)-dione

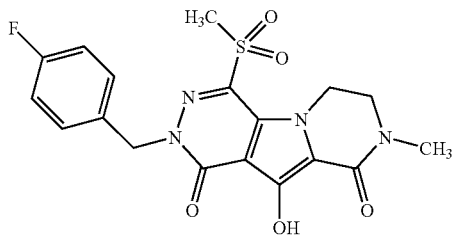

Step 1: 10-(Benzyloxy)-4-bromo-2-(4-fluorobenzyl)-8-methyl-7,8-dihydropyrazino[1',2':1,5]pyrrolo[2,3-d]pyridazine-1,9(2H,6H)-dione To a stirred mixture of copper (II) bromide (83 mg, 0.37 mmol) and tert-butyl nitrite (58 mg, 0.56 mmol) in anhydrous acetonitrile (4 mL) heated in an oil bath at 82° C., solid 10-(benzyloxy)-4-amino-2-(4-fluorobenzyl)-8-methyl-7,8-dihydropyrazino[1',2':1,5]pyrrolo[2,3-d]pyridazine-1,9(2H,6H)-dione (167 mg, 0.37 mmol) was added in small portions over a period of 10 minutes. The product mixture was allowed to cool to room temperature and concentrated under vacuum. The residue was treated with chloroform and a saturated aqueous solution of EDTA disodium salt and stirred at room temperature for 30 minutes. The organic phase was washed with brine, dried over anhydrous sodium sulfate, filtered, and concentrated under vacuum. The residue was subjected to column chromatography on silica gel eluting with ethyl acetate. Collection and concentration of appropriate fractions afforded the title bromide.

$^1$H NMR (400 MHz, CDCl$_3$) δ 7.63 (d, J=8.2 Hz, 2H), 7.43 (m, 2H), 7.35-7.26 (m, 3H), 7.00 (t, J=8.6 Hz, 2H), 5.47 (s, 2H), 5.30 (s, 2H), 4.74 (m, 2H), 3.65 (m, 2H), 3.14 (s, 3H). ES MS M+1=511

Step 2: 10-(Benzyloxy)-2-(4-fluorobenzyl)-8-methyl-4-(methylthio)-7,8-dihydropyrazino[1',2':1,5]pyrrolo[2,3-d]pyridazine-1,9(2H,6H)-dione A solution of 10-(benzyloxy)-4-bromo-2-(4-fluorobenzyl)-8-methyl-7,8-dihydropyrazino[1',2':1,5]pyrrolo[2,3-d]pyridazine-1,9(2H,6H)-dione (133 mg, 0.26 mmol) and sodium thiomethoxide (73 mg, 1.04 mmol) in anhydrous DMF (2.6 mL) was stirred at room temperature for 2 hours. The product mixture was concentrated under vacuum and the residue partitioned between chloroform and dilute hydrochloric acid. The organic phase was washed with brine, dried over anhydrous magnesium sulfate, filtered, and concentrated under vacuum. The residue was subjected to column chromatography on silica gel eluting with ethyl acetate. Collection and concentration of appropriate fractions afforded the title compound.

$^1$H NMR (400 MHz, CDCl$_3$) δ 7.65 (d, J=7.1 Hz, 2H), 7.42 (m, 2H), 7.32 (m, 2H), 7.25 (m, 1H), 6.99 (t, J=8.6 Hz, 2H), 5.51 (s, 2H), 5.32 (s, 2H), 4.62 (m, 2H), 3.64 (m, 2H), 3.14 (s, 3H), 2.53 (s, 3H).

ES MS M+1=479

Step 3: 10-(Benzyloxy)-2-(4-fluorobenzyl)-8-methyl-4-(methylsulfonyl)-7,8-dihydropyrazino[1',2':1,5]pyrrolo[2,3-d]pyridazine-1,9(2H,6H)-dione A solution of 10-(benzyloxy)-2-(4-fluorobenzyl)-8-methyl-4-(methylthio)-7,8-dihydropyrazino[1',2':1,5]pyrrolo[2,3-d]pyridazine-1,9(2H,6H)-dione (80 mg, 0.16 mmol) and m-chloroperbenzoic acid (119 mg, 0.62 mmol) in anhydrous dichloromethane (5 mL) was stirred at room temperature for 3 hours. The product mixture was diluted with dichloromethane, was washed with aqueous sodium carbonate, brine, dried over anhydrous magnesium sulfate, filtered, and concentrated under vacuum. The residue was used in the subsequent step without further purification.

Step 4: 2-(4-Fluorobenzyl)-10-hydroxy-8-methyl-4-(methylsulfonyl)-7,8-dihydropyrazino[1',2':1,5]pyrrolo[2,3-d]pyridazine-1,9(2H,6H)-dione The title compound was prepared in accordance with the procedure set forth in Example 62, step 12.

$^1$H NMR (400 MHz, DMSO-d$_6$) δ 9.27 (s, 1H), 7.42 (dd, J=6.4, 3.0 Hz, 2H), 7.18 (t, J=9.0 Hz, 2H), 5.28 (s, 2H), 4.54 (d, J=5.7 Hz, 2H), 3.76 (d, J=5.7 Hz, 2H), 3.51 (s, 3H), 2.99 (s, 3H).

ES MS M+1=421

EXAMPLES 161-167

The compounds in the following table were prepared in accordance with the procedure set forth in Example 160.

| Ex. | Name | A | B | C | D | M + 1 |
|---|---|---|---|---|---|---|
| 161 | 4-Bromo-2-(3-chloro-4-fluorobenzyl)-10-hydroxy-8-methyl-7,8-dihydropyrazino[1',2':1,5'pyrrolo[2,3-d]pyridazine-1,9(2H,6H)-dione | Cl | Br | H | Me | 455 |
| 162 | 2-(4-Fluorobenzyl)-10-hydroxy-8-methyl-4-(methylthio)-7,8-dihydropyrazino[1',2':1,5]pyrrolo[2,3-d]pyridazine-1,9(2H,6H)-dione | H | S-Me | H | Me | 389 |
| 163 | 2-(3-Chloro-4-fluorobenzyl)-10-hydroxy-8-methyl-4-(methylsulfonyl)-7,8-dihydropyrazino[1',2':1,5]pyrrolo[2,3-d]pyridazine-1,9(2H,6H)-dione | Cl | SO$_2$Me | H | Me | 455 |
| 164 | 2-(3-Chloro-4-fluorobenzyl)-10-hydroxy-8-methyl-4-(isopropylsulfonyl)-7,8-dihydropyrazino[1',2':1,5]pyrrolo[2,3-d]pyridazine-1,9(2H,6H)-dione | Cl | SO$_2$CH(Me)$_2$ | H | Me | 483 |
| 165 | 2-(3-Chloro-4-fluorobenzyl)-10-hydroxy-8-methyl-4-(cyclopentylsulfonyl)-7,8-dihydropyrazino[1',2':1,5]pyrrolo[2,3-d]pyridazine-1,9(2H,6H)-dione | Cl | 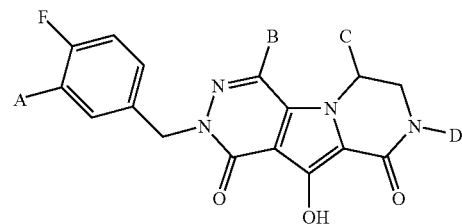 | H | Me | 509 |
| 166 | 6(S)-2-(3-Chloro-4-fluorobenzyl)-8-ethyl-10-hydroxy-4-(ethylsulfonyl)-6-methyl-7,8-dihydropyrazino[1',2':1,5]pyrrolo[2,3-d]pyridazine-1,9(2H,6H)-dione | Cl | SO$_2$Et | Me | Et | 497 |
| 167 | 6(S)-2-(3-Chloro-4-fluorobenzyl)-8-ethyl-10-hydroxy-4-(isopropylsulfonyl)-6-methyl-7,8-dihydropyrazino[1',2':1,5]pyrrolo[2,3-d]pyridazine-1,9(2H,6H)-dione | Cl | SO$_2$CH(Me)$_2$ | Me | Et | 511 |

Note: M + 1 determined by ES MS.

EXAMPLE 168

2-(4-Fluorobenzyl)-10-hydroxy-8-methyl-4-(4-methyl-3-oxopiperazin-1-yl)-7,8-dihydropyrazino[1',2':1,5]pyrrolo[2,3-d]pyridazine-1,9(2H,6H)-dione

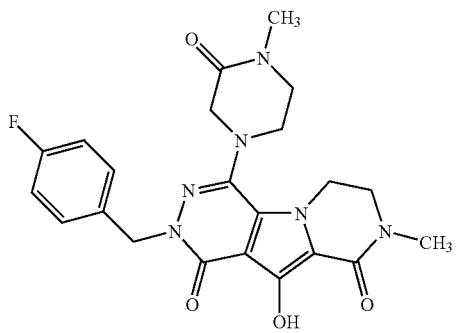

A mixture of 10-(benzyloxy)-4-bromo-2-(4-fluorobenzyl)-8-methyl-7,8-dihydropyrazino[1',2':1,5]pyrrolo[2,3-d]pyridazine-1,9(2H,6H)-dione (0.10 g, 0.19 mmol; Example 160, Step 1) and 1-methylpiperazin-2-one (2 mL) was heated in a sealed tube in an oil bath at 100° C. overnight. The benzyl protecting group was also cleaved in the process. The reaction mixture was subjected to reverse phase preparative HPLC purification. Collection and lyophilization of appropriate fractions provided the title compound.

$^1$H NMR (400 MHz, DMSO-d$_6$) δ 7.33 (dd, J=8.6, 5.7 Hz, 2H), 7.14 (t, J=9.0 Hz, 2H), 5.08 (s, 2H), 4.49 (br s, 2H), 3.68 (m, 2H), 3.30 (m, 2H), 2.99 (s, 3H), 2.83 (s, 3H). ES MS M+1=455

EXAMPLES 169-171

The compounds in the following table were prepared in accordance with the procedure set forth in Example 168.

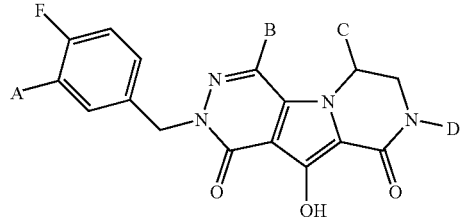

| Ex. | Name | A | B | C | D | M + 1 |
|---|---|---|---|---|---|---|
| 169 | 2-(4-Fluorobenzyl)-10-hydroxy-8-methyl-4-(4-methylpiperazin-1-yl)-7,8-dihydropyrazino[1',2':1,5]pyrrolo[2,3 d]pyridazine-1,9(2H,6H)-dione | H | ![piperazine-Me] | H | Me | 441 |
| 170 | 2-(4-Fluorobenzyl)-10-hydroxy-8-methyl-4-(4-acetylpiperazin-1-yl)-7,8-dihydropyrazino[1',2':1,5]pyrrolo[2,3-d]pyridazine-1,9(2H,6H)-dione | H | ![piperazine-C(O)Me] | H | Me | 469 |
| 171 | 6(S)-2-(3-Chloro-4-fluorobenzyl)-8-ethyl-10-hydroxy-4-(methylamino)-6-methyl-7,8-dihydropyrazino[1',2':1,5]pyrrolo[2,3-d]pyridazine-1,9(2H,6H)-dione | Cl | NHMe | Me | Et | 434 |

Note: M + 1 determined by ES MS.

EXAMPLE 172

2-(3-Chloro-4-fluorobenzyl)-10-hydroxy-4-(2-oxopyridinyl-1(2H)-yl)-8-methyl-7,8-dihydropyrazino[1',2':1,5]pyrrolo[2,3-d]pyridazine-1,9(2H,6H)-dione

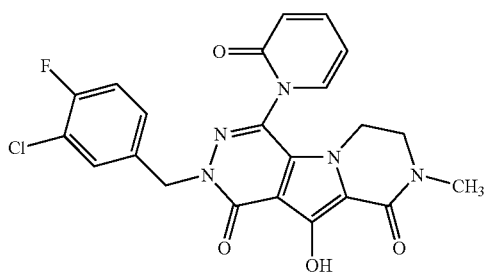

Step 1: 10-(Benzyloxy)-2-(3-chloro-4-fluorobenzyl)-8-methyl-4-(2-oxopyridin-1(2H)-yl)-7,8-dihydropyrazino[1',2':1,5]pyrrolo[2,3-d]pyridazine-1,9(2H,6H)-dione A mixture of 10-(benzyloxy)-2-(3-chloro-4-fluorobenzyl)-8-methyl-4-bromo-7,8-dihydropyrazino[1',2':1,5]pyrrolo[2,3-d]pyridazine-1,9(2H,6H)-dione (0.15 g, 0.28 mmol), copper (I) iodide (27 mg, 0.14 mmol), potassium carbonate (76 mg, 0.55 mmol), and 2-hydroxypyridine (52 mg, 0.55 mmol) in N-methyl-2-pyrrolidinone (2.7 mL) was stirred in an oil bath at 140° C. for 3 hours. The resultant mixture was filtered and concentrated under vacuum. The residue was subjected to column chromatography on silica gel eluting with a 1-5% methanol in chloroform gradient. Collection and concentration of appropriate fractions provided the title compound. ES MS M+1=560

Step 2: 2-(3-Chloro-4-fluorobenzyl)-10-hydroxy-4-(2-oxopyridinyl-1(2H)-yl)-8-methyl-7,8-dihydropyrazino[1',2':1,5]pyrrolo[2,3-d]pyridazine-1,9(2H,6H)-dione A mixture of 10-(benzyloxy)-2-(3-chloro-4-fluorobenzyl)-8-methyl-4-(2-oxopyridin-1(2H)-yl)-7,8-dihydropyrazino[1',2':1,5]pyrrolo[2,3-d]pyridazine-1,9(2H,6H)-dione (0.10 g, 0.21 mmol) and 10% palladium on charcoal (10 mg) in ethanol (20 mL) was stirred under a balloon of hydrogen gas at room temperature for 30 minutes. The resultant mixture was filtered and concentrated under vacuum. The residue was subjected to reverse phase preparative HPLC purification. Collection and lyophilization of appropriate fractions provided the title compound.

$^1$H NMR (400 MHz, DMSO-$d_6$) δ 8.21 (dd, J=5.6, 1.9 Hz, 1H), 7.96 (td, J=7.8, 2.0 Hz, 1H), 7.41 (dd, J=7.1, 1.9 Hz, 1H), 7.36 (t, J=8.7 Hz, 1H), 7.26 (m, 1H), 5.10 (s, 2H), 4.15 (t, J=5.2 Hz, 2H), 3.63 (t, J=5.2 Hz, 2H), 2.95 (s, 3H). ES MS M+1=470

EXAMPLES 173-174

The compounds in the following table were prepared in accordance with the procedure set forth in Example 172.

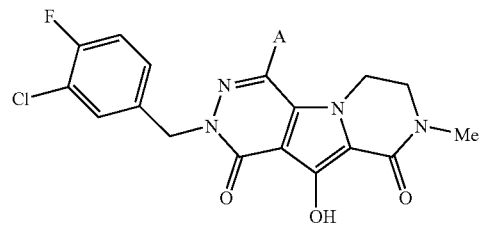

| Ex. | Name | A | M + 1 |
|---|---|---|---|
| 173 | 2-(3-Chloro-4-fluorobenzyl)-10-hydroxy-4-(2-oxo-4-cyanopyridinyl-1(2H)-yl)-8-methyl-7,8-dihydropyrazino[1',2':1,5]pyrrolo[2,3-d]pyridazine-1,9(2H,6H)-dione | CN-pyridinone | 495 |
| 174 | 2-(3-Chloro-4-fluorobenzyl)-10-hydroxy-4-(1H-1,2,4-triazol-1-yl)-8-methyl-7,8-dihydropyrazino[1',2':1,5]pyrrolo[2,3-d]pyridazine-1,9(2H,6H)-dione | triazole | 444 |

Note: M + 1 determined by ES MS.

EXAMPLE 175

2-(4-Fluorobenzyl)-10-hydroxy-4-pyrimidin-5-yl-8-methyl-7,8-dihydropyrazino[1',2':1,5]pyrrolo[2,3-d]pyridazine-1,9(2H,6H)-dione

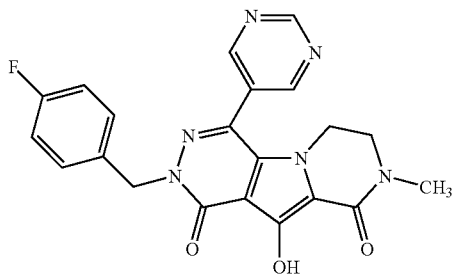

Step 1: 10-(Benzyloxy)-2-(4-fluorobenzyl)-8-methyl-4-pyrimidin-5-yl-7,8-dihydropyrazino[1',2':1,5]pyrrolo[2,3-d]pyridazine-1,9(2H,6H)-dione A mixture of 10-(benzyloxy)-4-bromo-2-(4-fluorobenzyl)-8-methyl-7,8-dihydropyrazino[1',2':1,5]pyrrolo[2,3-d]pyridazine-1,9(2H,6H)-dione (0.10 g, 0.19 mmol; Example 160, step 1), pyrimidine-5-boronic acid (73 mg, 0.59 mmol), cesium fluoride (0.12 g, 0.78 mmol), bis(tri-t-butylphosphine)palladium(0) (10 mg, 0.02 mmol), and tris(dibenzylideneacetone)dipalladium (18 mg, 0.02 mmol) in dioxane (3 mL) was purged with nitrogen for 2 minutes and heated in a sealed tube at 80° C. overnight. The reaction mixture was filtered through a pad of Celite, and the filtrate was concentrated under vacuum. The residue was subjected to column chromatography on silica gel eluting with 0 to 20% methanol in chloroform gradient. Collection and concentration of appropriate fractions afforded the title material.

$^1$H NMR (400 MHz, CDCl$_3$) δ 9.36 (s, 1H), 8.95 (s, 2H), 7.64 (d, J=8.7 Hz, 2H), 7.46 (dd, J=8.6, 5.5 Hz, 2H), 7.32 (t, J=6.9 Hz, 2H), 7.28 (t, 1H), 7.00 (t, J=8.6 Hz, 2H), 5.49 (s, 2H), 5.35 (s, 2H), 3.76 (t, J=6.1 Hz, 2H), 3.42 (t, J=6.1 Hz, 2H), 3.05 (s, 3H). ES MS M+1=511

Step 2: 2-(4-Fluorobenzyl)-10-hydroxy-4-pyrimidin-5-yl-8-methyl-7,8-dihydropyrazino[1',2':1,5]pyrrolo[2,3-d]pyridazine-1,9(2H,6H)-dione The title compound was prepared in accordance with the procedure set forth in Example 62, step 12.

$^1$H NMR (400 MHz, CD$_3$OD) δ 9.31 (s, 1H), 9.04 (s, 2H), 7.44 (br t, J=7.9 Hz, 2H), 7.00 (br t, J=8.6 Hz, 2H), 5.37 (s, 2H), 3.59 (br signal, 2H), 3.48 (br signal, 2H), 3.05 (s, 3H). ES MS M+1=421

EXAMPLES 176-182

The compounds in the following table were prepared in accordance with the procedure set forth in Example 175.

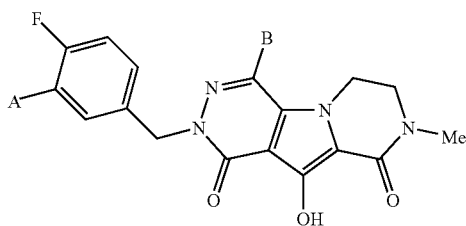

| Ex. | Name | A | B | M + 1 |
| --- | --- | --- | --- | --- |
| 176 | 2-(4-Fluorobenzyl)-10-hydroxy-4-pyridin-4-yl-8-methyl-7,8-dihydropyrazino[1',2':1,5]pyrrolo[2,3-d]pyridazine-1,9(2H,6H)-dione | H | 4-pyridyl | 420 |
| 177 | 2-(4-Fluorobenzyl)-10-hydroxy-4-(6-methoxypyridin-3-yl-8-methyl-7,8-dihydropyrazino[1',2':1,5]pyrrolo[2,3-d]pyridazine-1,9(2H,6H)-dione | H | 6-methoxypyridin-3-yl | 450 |

-continued

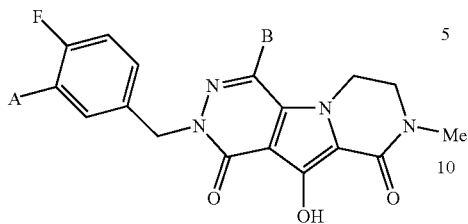

| Ex. | Name | A | B | M + 1 |
|---|---|---|---|---|
| 178 | 2-(3-Chloro-4-fluorobenzyl)-10-hydroxy-4-(6-methoxypyridin-3-yl-8-methyl-7,8-dihydropyrazino[1',2':1,5]pyrrolo[2,3-d]pyridazine-1,9(2H,6H)-dione | Cl | 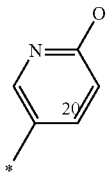 | 484 |
| 179 | 5-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]thiophene-2-carbonitrile | Cl | 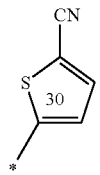 | 484 |
| 180 | 2-(3-Chloro-4-fluorobenzyl)-10-hydroxy-4-(5-methyl-2-thienyl)-8-methyl-7,8-dihydropyrazino[1',2':1,5]pyrrolo[2,3-d]pyridazine-1,9(2H,6H)-dione | Cl | 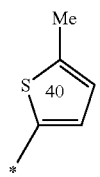 | 473 |
| 181 | 2-(3-Chloro-4-fluorobenzyl)-10-hydroxy-4-(1-methyl-6-oxo-1,6-dihydropyridin-3-yl)-8-methyl-7,8-dihydropyrazino[1',2':1,5]pyrrolo[2,3-d]pyridazine-1,9(2H,6H)-dione | Cl | 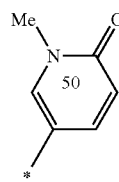 | 484 |
| 182 | 2-[5-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-2-oxopyridin-1(2H)-yl]-N,N-dimethylacetamide | Cl | 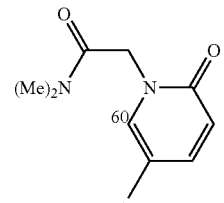 | 555 |

Note: M + 1 determined by ES MS.

EXAMPLE 183

2-(3-Chloro-4-fluorobenzyl)-10-hydroxy-4-pyrazin-2-yl-8-methyl-7,8-dihydropyrazino[1',2':1,5]pyrrolo[2,3-d]pyridazine-1,9(2H,6H)-dione

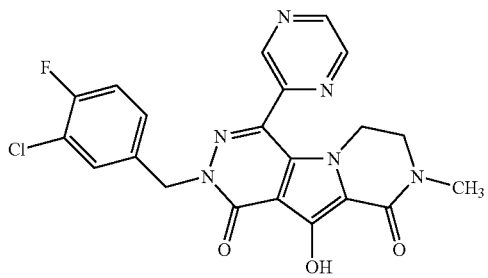

Step 1: Ethyl 8-methoxy-2-methyl-1-oxo-6-(pyrazin-2-ylcarbonyl)-1,2,3,4-tetrahydropyrrolo[1,2-a]-pyrazine-7-carboxylate To a cold (−78° C.) solution of ethyl 6-bromo-8-methoxy-2-methyl-1-oxo-1,2,3,4-tetrahydropyrrolo[1,2-a]-pyrazine-7-carboxylate (0.5 g, 1.51 mmol; Example 7, steps 1 to 6, substituting benzyl bromide with iodomethane in step 5) in anhydrous THF (15 mL) under an atmosphere of dry nitrogen, a solution of n-BuLi in hexane (1.81 mL, 1.81 mmol, 1 M) was added. The resultant mixture was stirred at −78° C. for 15 minutes, and treated with methyl pyrazine-2-carboxylate (0.21 g, 1.51 mmol). The reaction mixture was allowed to warm up to room temperature, treated with dilute hydrochloric acid, and concentrated under vacuum. The residue was extracted with ethyl acetate. The organic extracts were combined, washed with aqueous sodium carbonate, dried over anhydrous magnesium sulfate, filtered and concentrated under vacuum. The residue was subjected to column chromatography on silica gel eluted with 0 to 10% methanol in ethyl acetate gradient. Collection and concentration of appropriate fractions provided the title compound.

$^1$H NMR (400 MHz, CDCl$_3$) δ 9.25 (d, J=1.5 Hz, 1H), 8.75 (d, J=2.6 Hz, 1H), 8.57 (d, J=2.6, 1.5 Hz, 1H), 4.43 (m, 2H), 4.07 (s, 3H), 3.81 (q, J=7.1 Hz, 1H), 3.67 (m, 2H), 3.15 (s, 3H), 0.97 (t, J=7.1 Hz, 3H). ES MS M+1=359

Step 2: 2-(3-Chloro-4-fluorobenzyl)-10-hydroxy-4-pyrazin-2-yl-8-methyl-7,8-dihydropyrazino[1',2':1,5]pyrrolo[2,3-d]pyridazine-1,9(2H,6H)-dione The title compound was prepared in accordance with the procedure set forth in Example 62, step 9, 11, & 12. In Step 9, ethyl 8-methoxy-2-methyl-1-oxo-6-(pyrazin-2-ylcarbonyl)-1,2,3,4-tetrahydropyrrolo[1,2-a]-pyrazine-7-carboxylate was treated with hydrazine in ethanol with catalytic amount of glacial acetic acid at 110° C. in a sealed tube overnight.

$^1$H NMR (400 MHz, DMSO-d$_6$) δ 9.14 (br s, 1H), 9.02 (s, 1H), 8.80 (br d, J=2.6 Hz, 1H), 8.77 (br m, 1H), 7.58 (br d, J=6.7 Hz, 1H), 7.38 (br d, J=7.3 Hz, 2H), 5.32 (s, 2H), 4.00 (t, J=5.4 Hz, 2 H), 3.55 (t, J=5.4 Hz, 2 H), 2.96 (s, 3H). ES MS M+1=455

EXAMPLE 184

2-(3-Chloro-4-fluorobenzyl)-10-hydroxy-4-pyridin-2-yl-8-methyl-7,8-dihydropyrazino[1',2':1,5]pyrrolo[2,3-d]pyridazine-1,9(2H,6H)-dione

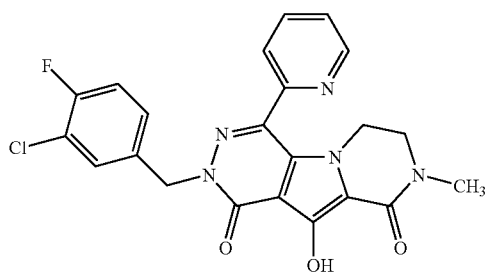

The title compound was prepared in accordance with the procedure set forth in Example 183 using a pyridin-2-ylcarbonyl analog in place of the pyrazin-2-ylcarbonyl pyrrolopyrazine. ES MS M+1=454

EXAMPLE 185

2-(3-Chloro-4-fluorobenzyl)-10-hydroxy-4-(3-oxo-1,2,3,6-tetrahydro-1,2,4-triazin-5-yl)-8-methyl-7,8-dihydropyrazino[1',2':1,5]pyrrolo[2,3-d]pyridazine-1,9(2H,6H)-dione

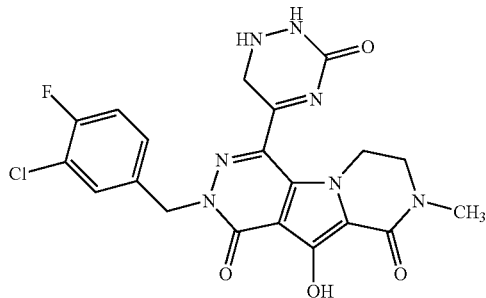

Step 1: 4-Acetyl-10-(benzyloxy)-2-(3-chloro-4-fluorobenzyl)-8-methyl-7,8-dihydropyrazino[1',2':1,5]pyrrolo[2,3-d]pyridazine-1,9(2H,6H)-dione A mixture of 4-bromo-10-(benzyloxy)-2-(3-chloro-4-fluorobenzyl)-8-methyl-7,8-dihydropyrazino[1',2':1,5]pyrrolo[2,3-d]pyridazine-1,9(2H,6H)-dione (1.00 g, 1.83 mmol), tributyl(1-ethoxyvinyl)tin (0.73 g, 2.01 mmol), and trans-dichlorobis(triphenylphosphine)palladium (II) (64 mg, 92 μmol) in dioxane (10 mL) was purged with nitrogen for 15 minutes. The reaction mixture was heated in a sealed tube at 100° C. overnight. The product mixture was filtered through a pad of Celite, and the filtrate concentrated under vacuum. The residue was subjected to column chromatography on silica gel eluting with a 1:1 mixture of ethyl acetate in chloroform. Collecting and concentration of appropriate fractions provided the intermediate ethoxyvinyl ether as off white solid. A solution of the ethoxyvinyl ether (0.70 g, 1.30 mmol) in acetone at room temperature was treated with hydrochloric acid (2 mL, 1 M) and stirred at the same temperature for 30 minutes. The resultant solution was concentrated under vacuum to provide the title ketone.

¹H NMR (400 MHz, CDCl₃) δ 7.64 (d, J=6.9 Hz, 2H), 7.52 (dd, J=7.0, 2.0 Hz, 1H), 7.49-7.28 (m, 3H), 7.11 (t, J=8.7 Hz, 1H), 5.44 (s, 2H), 5.37 (s, 2H), 4.56 (t, J=5.9 Hz, 2H), 3.59 (t, J=5.9 Hz, 2H), 3.15 (s, 3H), 2.64 (s, 3H). ES MS M+1=508

Step 2: 4-Bromoacetyl-10-(benzyloxy)-2-(3-chloro-4-fluorobenzyl)-8-methyl-7,8-dihydropyrazino[1',2': 1,5]pyrrolo[2,3-d]pyridazine-1,9(2H,6H)-dione To a cold (0° C.) solution of 4-acetyl-10-(benzyloxy)-2-(3-chloro-4-fluorobenzyl)-8-methyl-7,8-dihydropyrazino[1',2': 1,5]pyrrolo[2,3-d]pyridazine-1,9(2H,6H)-dione (0.50 g, 0.98 mmol) in anhydrous THF (20 mL) under an atmosphere of nitrogen, a solution of lithium bis(trimethylsilyl)amide (1.08 mL, 1.08 mmol) in THF was added. After stirring at the same temperature for 15 minutes, bromine (0.24 g, 1.47 mmol) was added and the reaction was stirred at room temperature. The reaction was monitored by LC-MS. Additional solution of lithium bis(trimethylsilyl)amide and bromine were added to drive the reaction to completion. The bromide generated as a solution in THF was used in the following reaction without further workup or purification. ES MS M+1=587

Step 3: 2-(3-Chloro-4-fluorobenzyl)-10-(benzyloxy)-4-(3-oxo-1,2,3,6-tetrahydro-1,2,4-triazin-5-yl)-8-methyl-7,8-dihydropyrazino[1',2':1,5]pyrrolo[2,3-d]pyridazine-1,9(2H,6H)-dione A solution of crude 4-bromoacetyl-10-(benzyloxy)-2-(3-chloro-4-fluorobenzyl)-8-methyl-7,8-dihydropyrazino[1',2': 1,5]pyrrolo[2,3-d]pyridazine-1,9(2H,6H)-dione (1.25 g, 2.13 mmol) in anhydrous THF, semicarbazide hydrochloride (0.35 g, 3.14 mmol), and diisopropylethylamine (0.66 mL, 3.77 mmol) was heated in a sealed tube at 100° C. for 30 minutes. The reaction mixture was concentrated under vacuum. The residue was dissolved in DMSO and subject to reverse phase preparative HPLC purification. Collection and lyophilization of appropriate fraction provided the intermediate 2-{2-[10-(benzyloxy)-2-(3-chloro-4-fluorobenzyl)-8-methyl-1,9-dioxo-1,2,6,7,8,9-hexahydropyrazino[1',2':1,5] pyrrolo[2,3-d]pyridazin-4-yl]-2-oxoethyl}hydrazinecarboxamide as white solid.

¹H NMR (400 MHz, DMSO-d₆) Broad signals δ 8.16 (1H), 7.63-7.42 (8H), 6.65 (2H), 5.40 (s, 2H), 5.35 (s, 2H), 4.33 (2H), 3.68 (2H), 3.08 (s, 3H), 2.13 (s). ES MS M+1=582

A solution of the above hydrazinecarboxamide (0.20 g, 0.34 mmol) and glacial acetic acid (0.1 mL) in absolute ethanol (5 mL) was heated in a sealed tube in an oil bath at 100° C. overnight. The reaction mixture was concentrated under vacuum. The residue was partitioned between chloroform and aqueous sodium bicarbonate. The organic extract was washed with brine, dried over anhydrous magnesium sulfate, filtered, and concentrated under vacuum to provide the corresponding cyclized trazinyl intermediate. ES MS M+1=564

Step 4: 2-(3-Chloro-4-fluorobenzyl)-10-hydroxy-4-(3-oxo-1,2,3,6-tetrahydro-1,2,4-triazin-5-yl)-8-methyl-7,8-dihydropyrazino[1',2':1,5]pyrrolo[2,3-d]pyridazine-1,9(2H,6H)-dione The title compound was prepared in accordance with the procedure set forth in Example 62, step 12.

¹H NMR (400 MHz, DMSO-d₆) Broad signals δ 13.47 (s, 1H), 9.21 (s, 1H), 8.48 (s, 1H), 7.7 (d, 1H), 7.41 (m, 2H), 5.36 (s, 2H), 4.47 (2H), 3.65 (2H), 2.99 (s, 3H), 2.69 (s, 2H). ES MS M+1=474

EXAMPLE 186

2-(3-Chloro-4-fluorobenzyl)-10-hydroxy-4-[(4-methyl-3-oxopiperazin-1-yl)acetyl]-8-methyl-7,8-dihydropyrazino[1',2':1,5]pyrrolo[2,3-d]pyridazine-1,9 (2H,6H)-dione

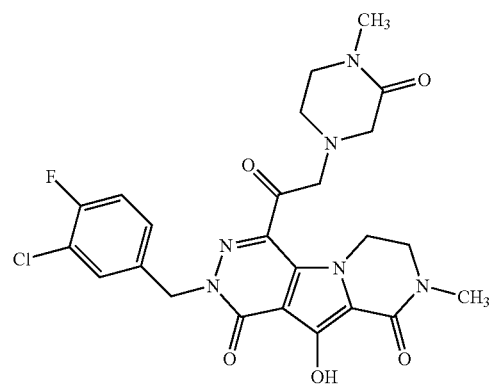

The title compound was prepared in accordance with the procedure set forth in Example 185, replacing semicarbazide hydrochloride with 1-methylpiperazin-2-one in step 3.

¹H NMR (400 MHz, DMSO-d₆) δ 9.20 (br s, 1H), 7.60 (d, J=6.8 Hz, 1H), 7.40 (m, 2H), 5.32 (s, 2H), 5.54 (br s, 2H), 4.49 (t, J=5.6 Hz, 2H), 3.69 (t, J=5.6 Hz, 2H), 3.65 (br s, 2H), 3.48 (br s, 2H), 3.29 (br s, 2H), 3.00 (s, 3H), 2.88 (s, 3H). ES MS M+1=531

EXAMPLE 187

[2-(3-Chloro-4-fluorobenzyl)-10-hydroxy-N,N,8-trimethyl-1,9-dioxo-1,2,6,7,8,9-hexahydropyrazino [1',2':1,5]pyrrolo[2,3-d]pyridazine-4-sulfonamide

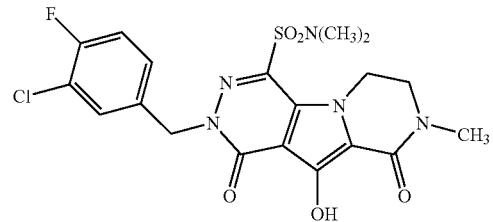

Step 1: S-[2-(3-Chloro-4-fluorobenzyl)-10-methoxy-8-methyl-1,9-dioxo-1,2,6,7,8,9-hexahydropyrazino [1',2':1,5]pyrrolo[2,3-d]pyridazin-4-yl]diethylthiocarbamate A mixture of 10-(methoxy)-2-(3-chloro-4-fluorobenzyl)-8-methyl-4-bromo-7,8-dihydropyrazino[1',2':1,5]pyrrolo[2, 3-d]pyridazine-1,9(2H,6H)-dione (0.50 g, 1.07 mmol) and copper (II) diethyldithiocarbamate (1.92 g, 5.32 mmol) in DMF (5 mL) was stirred at 110° C. overnight. The resultant mixture was concentrated under vacuum. The residue was partitioned between dichloromethane and brine. The organic extract was loaded directly onto a column of silica gel and eluted with 10% methanol in chloroform. Collection and concentration of appropriate fractions provided the title compound.

$^1$H NMR (400 MHz, CDCl$_3$) δ 7.48 (dd, J=7.1, 2.2 Hz, 1H), 7.33 (m, 1H), 7.06 (t, J=8.8 Hz, 1H), 5.32 (s, 2H), 4.68 (t, J=5.7 Hz, 2H), 4.14 (s, 3H), 3.65 (t, J=5.7 Hz, 2H), 3.44 (m, 4H), 1.34 (t, J=7.0 Hz, 3H), 1.18 (t, J=7.0 Hz, 3H). ES MS M+1=522

Step 2: 2-(3-Chloro-4-fluorobenzyl)-10-methoxy-8-methyl-1,9-dioxo-1,2,6,7,8,9-hexahydropyrazino[1',2':1,5]pyrrolo[2,3-d]pyridazine-4-sulfonic acid A mixture of S-[2-(3-chloro-4-fluorobenzyl)-10-methoxy-8-methyl-1,9-dioxo-1,2,6,7,8,9-hexahydropyrazino[1',2':1,5]pyrrolo[2,3-d]pyridazin-4-yl]dimethylthiocarbamate (0.10 g, 0.19 mmol) and 32% peracetic acid in acetic acid (0.62 mL, 9.29 mmol) in dichloromethane (8 mL) was stirred at room temperature for three hours. The resultant mixture was concentrated under vacuum. The residue was subjected to reverse phase preparative HPLC purification. Collection and lyophilization of appropriate fractions provided the title compound.

$^1$H NMR (400 MHz, DMSO-d$_6$) δ 7.48 (dd, J=7.1, 2.0 Hz, 1H), 7.38 (t, J=8.7 Hz, 1H), 7.26 (m, 1H), 5.23 (s, 2H), 4.89 (t, J=5.5 Hz, 2H), 3.89 (s, 3H), 3.65 (t, J=5.5 Hz, 2H), 2.99 (s, 3H).
ES MS M+1=471

Step 3: 2-(3-Chloro-4-fluorobenzyl)-10-methoxy-N,N,8-trimethyl-1,9-dioxo-1,2,6,7,8,9-hexahydropyrazino[1',2':1,5]pyrrolo[2,3-d]pyridazine-4-sulfonamide A mixture of 2-(3-chloro-4-fluorobenzyl)-10-methoxy-8-methyl-1,9-dioxo-1,2,6,7,8,9-hexahydropyrazino[1',2':1,5]pyrrolo[2,3-d]pyridazine-4-sulfonic acid (32 mg, 68 μmol), anhydrous DMF (11 μL, 0.14 mmol), and thionyl chloride (1.05 g, 8.84 mmol) in anhydrous acetonitrile (0.6 mL) was heated at 80° C. for 30 minutes. The resultant mixture was concentrated under vacuum. The residue was dissolved in anhydrous acetonitrile (3 mL) and treated with a solution of dimethylamine in THF (1 mL, 2 M). The mixture was stirred at room temperature for one hour and treated with aqueous sodium hydroxide (0.5 mL, 1 M). After stirring at room temperature for one hour, the product mixture was concentrated under vacuum. The residue was subjected to reverse phase preparative HPLC purification. Collection and lyophilization of appropriate fractions provided the title compound.

$^1$H NMR (400 MHz, CDCl$_3$) δ 7.44 (dd, J=7.0, 2.0 Hz, 1H), 7.29 (m, 1H), 7.11 (t, J=7.6 Hz, 1H), 5.29 (s, 2H), 4.69 (t, J=5.9 Hz, 2H), 4.16 (s, 3H), 3.69 (t, J=5.9 Hz, 2H), 3.16 (s, 3H), 3.04 (s, 6H).
ES MS M+1=498

Step 4: 2-(3-Chloro-4-fluorobenzyl)-10-hydroxy-N,N,8-trimethyl-1,9-dioxo-1,2,6,7,8,9-hexahydropyrazino[1',2':1,5]pyrrolo[2,3-d]pyridazine-4-sulfonamide The title compound was prepared in accordance with the procedure set forth in Example 62, step 12.

$^1$H NMR (400 MHz, DMSO-d$_6$) δ 9.25 (br s, 1H), 7.62 (dd, J=7.3, 2.0 Hz, 1H), 7.41 (t, J=9.0 Hz, 1H), 7.35 (m, 1H), 5.32 (s, 2H), 4.50 (t, J=5.7 Hz, 2H), 3.75 (t, J=5.7 Hz, 2H), 2.99 (s, 3H), 2.94 (s, 6H). ES MS M+1=484

EXAMPLE 188

S-[2-(3-Chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]diethylthiocarbamate

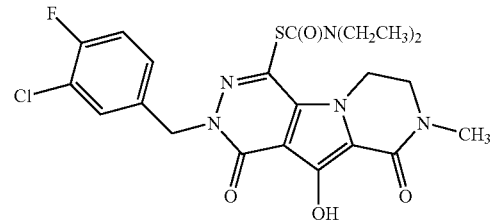

The title compound was prepared in accordance with the procedure set forth in Example 62, step 12, starting with S-[2-(3-chloro-4-fluorobenzyl)-10-methoxy-8-methyl-1,9-dioxo-1,2,6,7,8,9-hexahydropyrazino[1',2':1,5]pyrrolo[2,3-d]pyridazin-4-yl]dimethylthiocarbamate in Example 187, step 1.

$^1$H NMR (400 MHz, CDCl$_3$) δ 7.50 (dd, J=7.0, 2.0 Hz, 1H), 7.34 (m, 1H), 7.05 (t, J=8.7 Hz, 1H), 5.31 (s, 2H), 4.60 (t, J=5.9 Hz, 2H), 3.67 (t, J=5.9 Hz, 2H), 3.44 (m, 4H), 3.10 (s, 3H), 1.33 (t, J=6.9 Hz, 3H), 1.17 (t, J=6.9 Hz, 3H). ES MS M+1=508

EXAMPLE 189

6(S)-2-(3-Chloro-4-fluorobenzyl)-10-hydroxy-8-ethyl-6-methyl-7,8-dihydropyrazino[1',2':1,5]pyrrolo[2,3-d]pyridazine-1,9(2H,6H)-dione

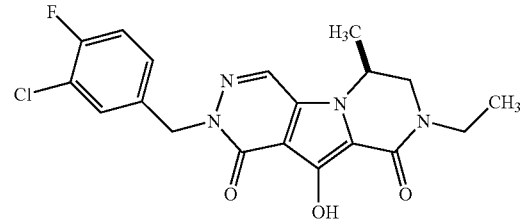

The title compound was prepared in accordance with the procedure set forth in Example 33 using (5S)-1-ethyl-5-methylpyrazin-2(1H)-one (Example 62, step 4) in place of 1,5-dimethylpyrazin-2(1H)-one.

$^1$H NMR (400 MHz, CDCl$_3$) δ 8.39 (s, 1H), 7.93(s, 1H), 7.52 (dd, J=7.1, 2.2 Hz, 1H), 7.36 (m, 1H), 7.06 (t, J=8.5 Hz, 1H), 5.31 (d, J=14.2 Hz, 1H), 5.25 (d, J=14.2 Hz, 1H), 4.59 (m, 1H), 3.96 (dd, J=12.9, 4.4 Hz, 1 H), 3.74 (m, 1 H), 3.51 (m, 1 H), 3.35 (dd, J=12.7, 2.2 Hz, 1H), 1.49 (d, J=6.6 Hz, 3H), 1.24 (t, J=7.3 Hz, 3H). ES MS M+1=405.

EXAMPLES 190-209

The compounds in the following table were prepared in accordance with the procedure set forth in Example 189.

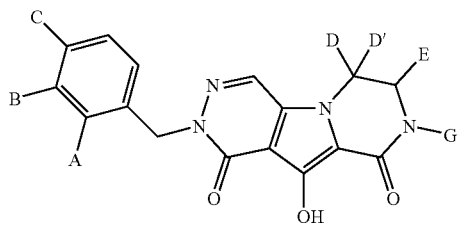

| Ex. | Name | A & B | C | D, D' & E | G | M + 1 |
|---|---|---|---|---|---|---|
| 190 | 6(S)-2-(4-Fluorobenzyl)-10-hydroxy-8-ethyl-6-methyl-7,8-dihydropyrazino[1',2':1,5]pyrrolo[2,3-d]pyridazine-1,9(2H,6H)-dione | A = H, B = H | F | D = Me, E = H | Et | 371 |
| 191 | 6(S)-2-(3-Chloro-4-fluorobenzyl)-10-hydroxy-6,8-dimethyl-7,8-dihydropyrazino[1',2':1,5]pyrrolo[2,3-d]pyridazine-1,9(2H,6H)-dione | A = H, B = Cl | F | D = Me, E = H | Me | 391 |
| 192 | 6(S)-2-(3-Chloro-4-fluorobenzyl)-10-hydroxy-8-isopropyl-6-methyl-7,8-dihydropyrazino[1',2':1,5]pyrrolo[2,3-d]pyridazine-1,9(2H,6H)-dione | A = H, B = Cl | F | D = Me, E = H | i-Pr | 419 |
| 193 | 6(S)-2-(4-Fluorobenzyl)-10-hydroxy-8-isopropyl-6-methyl-7,8-dihydropyrazino[1',2':1,5]pyrrolo[2,3-d]pyridazine-1,9(2H,6H)-dione | A = H, B = H | F | D = Me, E = H | i-Pr | 385 |
| 194 | 6(S)-2-(3,4-Difluorobenzyl)-10-hydroxy-8-isopropyl-6-methyl-7,8-dihydropyrazino[1',2':1,5]pyrrolo[2,3-d]pyridazine-1,9(2H,6H)-dione | A = H, B = F | F | D = Me, E = H | i-Pr | 403 |
| 195 | 6(S)-2-(3-Chlorobenzyl)-10-hydroxy-8-isopropyl-6-methyl-7,8-dihydropyrazino[1',2':1,5]pyrrolo[2,3-d]pyridazine-1,9(2H,6H)-dione | A = H, B = Cl | H | D = Me, E = H | i-Pr | 401 |
| 196 | 6(S)-2-(4-Fluoro-3-methylbenzyl)-10-hydroxy-8-isopropyl-6-methyl-7,8-dihydropyrazino[1',2':1,5]pyrrolo[2,3-d]pyridazine-1,9(2H,6H)-dione | A = H, B = Me | F | D = Me, E = H | i-Pr | 399 |
| 197 | 6(S)-2-(2,4-Difluorobenzyl)-10-hydroxy-8-isopropyl-6-methyl-7,8-dihydropyrazino[1',2':1,5]pyrrolo[2,3-d]pyridazine-1,9(2H,6H)-dione | A = F, B = H | F | D = Me, E = H | i-Pr | 403 |
| 198 | 6(S)-2-(4-Chloro-3-fluorobenzyl)-10-hydroxy-8-isopropyl-6-methyl-7,8-dihydropyrazino[1',2':1,5]pyrrolo[2,3-d]pyridazine-1,9(2H,6H)-dione | A = H, B = F | Cl | D = Me, E = H | i-Pr | 419 |
| 199 | 6(S)-2-(3-Chloro-4-fluorobenzyl)-10-hydroxy-8-tert-butyl-6-methyl-7,8-dihydropyrazino[1',2':1,5]pyrrolo[2,3-d]pyridazine-1,9(2H,6H)-dione | A = H, B = Cl | F | D = Me, E = H | t-Bu | 433 |
| 200 | 6(S)-2-(4-Fluorobenzyl)-10-hydroxy-8-tert-butyl-6-methyl-7,8-dihydropyrazino[1',2':1,5]pyrrolo[2,3-d]pyridazine-1,9(2H,6H)-dione | A = H, B = H | F | D = Me, E = H | t-Bu | 399 |

-continued

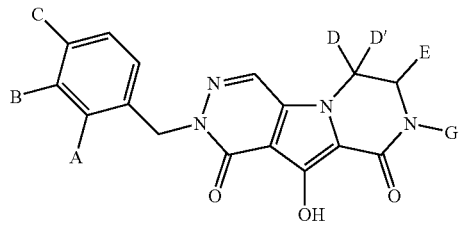

| Ex. | Name | A & B | C | D, D' & E | G | M + 1 |
|---|---|---|---|---|---|---|
| 201 | 6(S)-2-(4-Fluorobenzyl)-10-hydroxy-6-isopropyl-8-methyl-7,8-dihydropyrazino[1',2':1,5]pyrrolo[2,3-d]pyridazine-1,9(2H,6H)-dione | A = H<br>B = H | F | D = isopropyl (Me, Me)<br>E = H | Me | 385 |
| 202 | 6(S)-2-(4-Fluorobenzyl)-10-hydroxy-6-isopropyl-8-ethyl-7,8-dihydropyrazino[1',2':1,5]pyrrolo[2,3-d]pyridazine-1,9(2H,6H)-dione | A = H<br>B = H | F | D = isopropyl (Me, Me)<br>E = H | Et | 399 |
| 203 | 2-(4-Fluorobenzyl)-10-hydroxy-8-ethyl-6,6-dimethyl-7,8-dihydropyrazino[1',2':1,5]pyrrolo[2,3-d]pyridazine-1,9(2H,6H)-dione | A = H<br>B = H | F | D = Me<br>D' = Me<br>E = H | Et | 385 |
| 204 | 2-(4-Fluorobenzyl)-10-hydroxy-8-ethyl-6,6-dimethyl-7,8-dihydropyrazino[1',2':1,5]pyrrolo[2,3-d]pyridazine-1,9(2H,6H)-dione | A = H<br>B = Cl | F | D = Me<br>D' = Me<br>E = H | Et | 419 |
| 205 | 2-(4-Fluorobenzyl)-10-hydroxy-8-ethyl-6-hydroxymethyl-7,8-dihydropyrazino[1',2':1,5]pyrrolo[2,3-d]pyridazine-1,9(2H,6H)-dione | A = H<br>B = H | F | D = CH$_2$OH<br>E = H | Et | 387 |
| 206 | 6(R)-2-(4-Fluorobenzyl)-10-hydroxy-8-ethyl-6-hydroxymethyl-7,8-dihydropyrazino[1',2':1,5]pyrrolo[2,3-d]pyridazine-1,9(2H,6H)-dione | A = H<br>B = H | F | D = HOH$_2$C<br>E = H | Et | 387 |
| 207 | 6(R)-2-(3-Chloro-4-fluorobenzyl)-10-hydroxy-8-ethyl-6-hydroxymethyl-7,8-dihydropyrazino[1',2':1,5]pyrrolo[2,3-d]pyridazine-1,9(2H,6H)-dione | A = H<br>B = Cl | F | D = HOH$_2$C<br>E = H | Et | 421 |
| 208 | N-{[8-Ethyl-2-(4-fluorobenzyl)-10-hydroxy-1,9-dioxo-1,2,6,7,8,9-hexahydropyrazino[1',2':1,5]pyrrolo[2,3-d]pyridazin-6-yl]methyl}-N-methylmethanesulfonamide | A = H<br>B = H | F | D = CH$_2$N(Me)SO$_2$Me<br>E = H | Et | 478 |
| 209 | 6-(3-Chloro-4-fluorobenzyl)-4-hydroxy-2-ethyl-1a,9l-dihydro-1H-cyclopropa[5',6']pyrazino[1',2':1,5]pyrrolo[2,3-d]pyridazine-3,5(2H,6H)-dione | A = H<br>B = Cl | F | D + E = together form cyclopropyl | Et | 403 |

Notes:
1. Unless otherwise specified in the table, D' = H.
2. M + 1 determined by ES MS.

EXAMPLE 210

Encapsulated Oral Compositions

A capsule formulation is prepared by filling standard two-piece gelatin capsules each with 100 mg of the compound of Example 1, 150 mg of lactose, 50 mg of cellulose, and 3 mg of stearic acid. Encapsulated oral compositions containing any one of the compounds of Examples 2-209 can be similarly prepared.

EXAMPLE 211

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds prepared in Examples 1-44 and 47 were tested in the integrase assay and all were found to have $IC_{50}$'s less than 0.1 micromolar. More generally, the compounds prepared in Examples 1-209 were found to have $IC_{50}$ values of less than 1 micromolar in the integrase assay.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 212

Assay for Inhibition of HIV Replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds prepared in Examples 1-209 were found to have $IC_{95}$'s less than 10 micromolar in the present assay.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula I, or a pharmaceutically acceptable salt thereof:

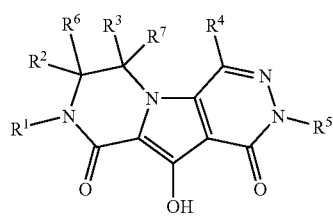

(I)

wherein:

$R^1$ is:
(1) —$C_{1-6}$ alkyl,
(2) —$C_{1-6}$ alkyl substituted with —OH, —O—$C_{1-6}$ alkyl, —O—$C_{1-6}$ haloalkyl, —CN, —NO$_2$, —N($R^A$)$R^B$, —C(O)N($R^A$)$R^B$, —C(O)$R^A$, —CO$_2R^A$, —SR$^A$, —S(O)$R^A$, —SO$_2R^A$, —SO$_2$N($R^A$)$R^B$, —N($R^A$)C(O)$R^B$, —N($R^A$)CO$_2R^B$, —N($R^A$)SO$_2R^B$, —N($R^A$)SO$_2$N($R^A$)$R^B$, —OC(O)N($R^A$)$R^B$, —N($R^A$)C(O)N($R^A$)$R^B$, or —N($R^A$)C(O)C(O)N($R^A$)$R^B$, (3) —$C_{3-8}$ cycloalkyl, which is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl, (4) —$C_{1-6}$ alkyl substituted with $C_{3-8}$ cycloalkyl, wherein the $C_{3-8}$ cycloalkyl is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl, (5) heteroaryl, which is optionally substituted with from 1 to 5 substituents each of which is independently any one of substituents (1) to (26) as defined below in part (i) of Part B of the definition of $R^J$, (6) —$C_{1-6}$ alkyl substituted with $R^J$, wherein $R^J$ is:
(A) aryl which is:
(i) optionally substituted with from 1 to 5 substituents each of which is independently:
(1) —$C_{1-6}$ alkyl, which is optionally substituted with —OH, —O—$C_{1-6}$ alkyl, —O—$C_{1-6}$ haloalkyl, —CN, —NO$_2$, —N($R^A$)$R^B$, —C(O)N($R^A$)$R^B$, —C(O)$R^A$, —CO$_2R^A$, —SR$^A$, —S(O)$R^A$, —SO$_2R^A$, —SO$_2$N($R^A$)$R^B$, —N($R^A$)C(O)$R^B$, —N($R^A$)CO$_2R^B$, —N($R^A$)SO$_2R^B$, —N($R^A$)SO$_2$N($R^A$)$R^B$, —OC(O)N($R^A$)$R^B$, —N($R^A$)C(O)N($R^A$)$R^B$, or —N($R^A$)C(O)C(O)N($R^A$)$R^B$,
(2) —O—$C_{1-6}$ alkyl,
(3) —$C_{1-6}$ haloalkyl,
(4) —O—$C_{1-6}$ haloalkyl,
(5) —OH,
(6) halogen,
(7) —CN,
(8) —NO$_2$,
(9) —N($R^A$)$R^B$,
(10) —C(O)N($R^A$)$R^B$,
(11) —C(O)$R^A$,
(12) —CO$_2R^A$,
(13) —SR$^A$,
(14) —S(O)$R^A$,
(15) —SO$_2R^A$,
(16) —SO$_2$N($R^A$)$R^B$,
(17) —N($R^A$)SO$_2R^B$,
(18) —N($R^A$)SO$_2$N($R^A$)$R^B$,
(19) —N($R^A$)C(O)$R^B$,
(20) —N($R^A$)C(O)—C(O)N($R^A$)$R^B$, or
(21) —N($R^A$)CO$_2R^B$, and (ii) optionally substituted with 1 or 2 substituents each of which is independently:
(1) —$C_{3-8}$ cycloalkyl,
(2) aryl,
(3) —$C_{1-6}$ alkyl substituted with aryl, —$C_{3-8}$ cycloalkyl, HetA, or HetB,
(4) -HetA,
(5) —C(O)-HetA; or
(6) -HetB;
wherein:
each cycloalkyl is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl, each aryl is optionally substituted with from 1 to 5 substituents each of which is independently any one of the substituents (1) to (21) as defined above in part (i) of Part A of the definition of $R^J$,
each HetA is independently (i) a —$C_{4-7}$ azacycloalkyl or oxacycloalkyl or thiacycloalkyl or (ii) a —$C_{3-6}$ diazacycloalkyl or oxazacycloalkyl or thiazacycloalkyl, wherein the S in the thiacycloalkyl or thiazacycloalkyl is optionally oxidized to S(O) or $SO_2$, and wherein any of the rings defined in (i) or (ii) is optionally substituted with from 1 to 4 substituents each of which is independently oxo, —$C_{1-6}$ alkyl, —C(O)$R^A$, —$CO_2R^A$, —$SR^A$, —S(O)$R^A$, or —S(O)$_2R^A$; and each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently any one of the substituents (1) to (26) as defined below in part (i) of Part B of the definition of $R^J$, or (B) heteroaryl which is:
(i) optionally substituted with from 1 to 6 substituents each of which is independently:
(1) —$C_{1-6}$ alkyl,
(2) —$C_{1-6}$ alkyl substituted with —OH, —O—$C_{1-6}$ alkyl, —O—$C_{1-6}$ haloalkyl, —CN, —$NO_2$, —N($R^A$)$R^B$, —C(O)N($R^A$)$R^B$, —C(O)$R^A$, —$CO_2R^A$, —$SR^A$, —S(O)$R^A$, —S(O)$_2R^A$, —S(O)$_2$N($R^A$)$R^B$, —N($R^A$)C(O)$R^B$, —N($R^A$)$CO_2R^B$, —N($R^A$)S(O)$_2R^B$, —N($R^A$)S(O)$_2$N($R^A$)$R^B$, —OC(O)N($R^A$)$R^B$, —N($R^A$)C(O)N($R^A$)$R^B$, or —N($R^A$)C(O)C(O)N($R^A$)$R^B$,
(3) —O—$C_{1-6}$ alkyl,
(4) —$C_{1-6}$ haloalkyl,
(5) —O—$C_{1-6}$ haloalkyl,
(6) —OH,
(7) -oxo,
(8) halogen,
(9) —CN,
(10) —$NO_2$,
(11) —N($R^A$)$R^B$,
(12) —C(O)N($R^A$)$R^B$,
(13) —C(O)$R^A$,
(14) —C(O)—$C_{1-6}$ haloalkyl,
(15) —C(O)O$R^A$,
(16) —OC(O)N($R^A$)$R^B$,
(17) —$SR^A$,
(18) —S(O)$R^A$,
(19) —S(O)$_2R^A$,
(20) —S(O)$_2$N($R^A$)$R^B$,
(21) —N($R^A$)S(O)$_2R^B$,
(22) —N($R^A$)S(O)$_2$N($R^A$)$R^B$,
(23) —N($R^A$)C(O)$R^B$,
(24) —N($R^A$)C(O)N($R^A$)$R^B$,
(25) —N($R^A$)C(O)—C(O)N($R^A$)$R^B$, or
(26) —N($R^A$)$CO_2R^B$, and (ii) optionally substituted with 1 or 2 substituents each of which is independently:
(1) —$C_{3-8}$ cycloalkyl,
(2) aryl,
(3) —$C_{1-6}$ alkyl substituted with aryl, —$C_{3-8}$ cycloalkyl, HetA, or HetB,
(4) -HetA,
(5) —C(O)-HetA; or
(6) -HetB;
wherein:
each cycloalkyl is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl,
each aryl is optionally substituted with from 1 to 5 substituents each of which is independently any one of the substituents (1) to (21) as defined above in part (i) of Part A of the definition of $R^J$,
each HetA is independently as defined in Part (A)(ii) of the definition of $R^J$, and
each HetB is independently as defined in Part (A)(ii) of the definition of $R^J$;

(7) aryl, which is optionally substituted with from 1 to 5 substituents each of which is independently any one of the substituents (1) to (21) as defined above in part (i) of Part A of the definition of $R^J$;

$R^2$ is:
(1) —H,
(2) —$C_{1-6}$ alkyl,
(3) —$C_{1-6}$ haloalkyl,
(4) —$C_{1-6}$ alkyl substituted with —OH, —O—$C_{1-6}$ alkyl, —O—$C_{1-6}$ haloalkyl, —CN, —$NO_2$, —N($R^A$)$R^B$, —C(O)N($R^A$)$R^B$, —C(O)$R^A$, —$CO_2R^A$, —$SR^A$, —S(O)$R^A$, —S(O)$_2R^A$, —S(O)$_2$N($R^A$)$R^B$, —N($R^A$)C(O)$R^B$, —N($R^A$)$CO_2R^B$, —N($R^A$)S(O)$_2R^B$, —N($R^A$)S(O)$_2$N($R^A$)$R^B$, —OC(O)N($R^A$)$R^B$, —N($R^A$)C(O)N($R^A$)$R^B$, or —N($R^A$)C(O)C(O)N($R^A$)$R^B$, or (5) —$C_{1-6}$ alkyl substituted with HetC, —C(O)-HetC, —$SO_2$-HetC, —N($R^A$)C(O)-HetC, or —N($R^A$)C(O)C(O)-HetC;
wherein HetC is a 4- to 7-membered, saturated or mono-unsaturated heterocyclic ring containing from 1 to 3 heteroatoms independently selected from 1 to 3 N atoms, zero to 1 O atom, and zero to 1 S atom, where the S is optionally oxidized to S(O) or S(O)$_2$, with the proviso that the ring is attached to the rest of the molecule via a ring N atom, and wherein the saturated or mono-unsaturated heterocyclic ring is optionally substituted with from 1 to 4 substituents each of which is independently halogen, —CN, —$C_{1-6}$ alkyl, —OH, oxo, —C(O)$R^A$, —$CO_2R^A$, —S(O)$R^A$, —$SR^A$, —S(O)$_2R^A$, —$CH_2$—CH=$CH_2$, —O—$C_{1-6}$ alkyl, —$C_{1-6}$ haloalkyl, —$C_{1-6}$ alkylene-CN, —$C_{1-6}$ alkylene-OH, or —$C_{1-6}$ alkylene-O—$C_{1-6}$ alkyl;

or alternatively $R^1$ and $R^2$ together with the ring nitrogen to which $R^1$ is attached and the ring carbon to which $R^2$ is attached form a 5- to 7-membered, saturated heterocyclic ring in which the portion of the ring formed from $R^1$ and $R^2$ is a 3- to 5-membered methylene chain in which one of the methylene moieties is optionally replaced with N(H), wherein the chain is optionally substituted with from 1 to 3 substituents each of which is independently —$C_{1-6}$ alkyl, —OH, or oxo;

$R^3$ is:
(1) —H,
(2) —$C_{1-6}$ alkyl,
(3) —$C_{1-6}$ haloalkyl,
(4) —$C_{1-6}$ alkyl substituted with —OH, —O—$C_{1-6}$ alkyl, —O—$C_{1-6}$ haloalkyl, —CN, —$NO_2$, —N($R^A$)$R^B$, —C(O)N($R^A$)$R^B$, —C(O)$R^A$, —$CO_2R^A$, —$SR^A$, —S(O)$R^A$, —S(O)$_2R^A$, —S(O)$_2$N($R^A$)$R^B$, —N($R^A$)C(O)$R^B$, —N($R^A$)$CO_2R^B$, —N($R^A$)S(O)$_2R^B$, —N($R^A$)S(O)$_2$N($R^A$)$R^B$, —OC(O)N($R^A$)$R^B$, —N($R^A$)C(O)N($R^A$)$R^B$, or —N($R^A$)C(O)C(O)N($R^A$)$R^B$, (5) —$C_{1-6}$ alkyl substituted with HetD, —C(O)-HetD, —$SO_2$-HetD, —N($R^A$)C(O)-HetD, or —N($R^A$)C(O)C(O)-HetD,
(6) CycM, AryM, or HetM, or
(7) —$C_{1-6}$ alkyl substituted with CycM, AryM, or HetM;
wherein:
  HetD independently has the same definition as HetC;
  CycM is —$C_{3-8}$ cycloalkyl which is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl;
  AryM is aryl, which is optionally substituted with from 1 to 5 substituents each of which is independently any one of the substituents (1) to (21) as defined above in part (i) of Part A of the definition of $R^J$; and
  HetM is heteroaryl, which is optionally substituted with from 1 to 5 substituents each of which is independently any one of the substituents (1) to (26) as defined above in part (i) of Part B of the definition of $R^J$;
or alternatively $R^2$ and $R^3$ together with the carbon atoms to which they are attached form:
(i) a 3- to 8-membered saturated carbocyclic ring which is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl,
(ii) a benzene ring, which is optionally substituted with from 1 to 4 substituents each of which is independently any one of the substituents (1) to (21) as defined above in part (i) of Part A of the definition of $R^J$,
(iii) a 4- to 7-membered, saturated or mono-unsaturated heterocyclic ring containing from 1 to 3 heteroatoms independently selected from N, O and S, where each S is optionally oxidized to S(O) or S(O)$_2$, and wherein the saturated or mono-unsaturated heterocyclic ring is optionally substituted with from 1 to 4 substituents each of which is independently halogen, —CN, —$C_{1-6}$ alkyl, —OH, oxo, —C(O)$R^A$, —CO$_2R^A$, —S(O)$R^A$, —S$R^A$, —S(O)$_2R^A$, —CH$_2$—CH=CH$_2$, —O—$C_{1-6}$ alkyl, —$C_{1-6}$ haloalkyl, —$C_{1-6}$ alkylene-CN, —$C_{1-6}$ alkylene-OH, or —$C_{1-6}$ alkylene-O—$C_{1-6}$ alkyl, or
(iv) a 5- or 6-membered heteroaromatic ring, which is optionally substituted with from 1 to 3 substituents each of which is independently any one of the substituents (1) to (26) as defined above in part (i) of Part B of the definition of $R^J$;
wherein $R^6$ and $R^7$ are absent, when $R^2$ and $R^3$ together with the carbon atoms to which they are attached form a benzene ring or a heteroaromatic ring;
$R^4$ is:
(1) —H,
(2) —$C_{1-6}$ alkyl,
(3) —$C_{1-6}$ haloalkyl,
(4) —$C_{1-6}$ alkyl substituted with —OH, —O—$C_{1-6}$ alkyl, —O—$C_{1-6}$ haloalkyl, —CN, —NO$_2$, —N($R^A$)$R^B$, —C(O)N($R^A$)$R^B$, —C(O)$R^A$, —CO$_2R^A$, —S$R^A$, —S(O)$R^A$, —SO$_2R^A$, —SO$_2$N($R^A$)$R^B$, —N($R^A$)C(O)$R^B$, —N($R^A$)CO$_2R^B$, —N($R^A$)SO$_2R^B$, —N($R^A$)SO$_2$N($R^A$)$R^B$, —OC(O)N($R^A$)$R^B$, —N($R^A$)C(O)N($R^A$)$R^B$, or —N($R^A$)C(O)C(O)N($R^A$)$R^B$,
(5) —OH,
(6) —O—$C_{1-6}$ alkyl,
(7) —O—$C_{1-6}$ haloalkyl,
(8) —CN,
(9) —NO$_2$,
(10) —N($R^C$)$R^D$,
(11) —C(O)N($R^C$)$R^D$,
(12) —C(O)$R^A$,
(13) —CO$_2R^A$,
(14) —S$R^A$,
(15) —S(O)$R^A$,
(16) —SO$_2R^A$,
(17) —SO$_2$N($R^A$)$R^B$,
(18) —N($R^A$)C(O)$R^B$,
(19) —N($R^A$)CO$_2R^B$,
(20) —N($R^A$)SO$_2R^B$,
(21) —N($R^A$)SO$_2$N($R^A$)$R^B$,
(22) —OC(O)N($R^A$)$R^B$,
(23) —N($R^A$)C(O)N($R^A$)$R^B$,
(24) —N($R^A$)C(O)C(O)N($R^A$)$R^B$,
(25) halogen,
(26) —S—C(O)N($R^C$)$R^D$,
(27) —N=C($R^A$)—N($R^C$)$R^D$,
(28) —C(O)N($R^A$)—$C_{1-6}$ alkylene-N($R^C$)$R^D$,
(29) —C(O)—$C_{1-6}$ alkylene-N($R^C$)$R^D$,
(30) —C(O)N($R^A$)—$C_{1-6}$ alkylene-$C_{1-6}$ haloalkyl,
(31) —C(O)—$C_{1-6}$ alkylene-$C_{1-6}$ haloalkyl,
(32) —N(SO$_2R^A$)—V,
(33) —N[C(O)$R^A$]—V,
(34) —$C_{1-6}$ alkyl substituted HetE, —C(O)-HetE, —SO$_2$-HetE, —N($R^A$)C(O)-HetE, or —N($R^A$)C(O)C(O)-HetE,
(35) —$C_{1-6}$ alkyl substituted with CycL, AryL, HetL, or HetS, or
(36) —T—$R^L$,
wherein:
  T is a single bond, O, C(O), C(O)N($R^A$), N($R^A$)C(O), S, S(O), S(O)$_2$, N($R^A$)S(O)$_2$, S(O)$_2$N($R^A$), O—$C_{1-6}$ alkylene, C(O)—$C_{1-6}$ alkylene, C(O)N($R^A$)—$C_{1-6}$ alkylene, N($R^A$)C(O)—$C_{1-6}$ alkylene, S—$C_{1-6}$ alkylene, S(O)—$C_{1-6}$ alkylene, S(O)$_2$—$C_{1-6}$ alkylene, $C_{1-6}$ alkylene-S, $C_{1-6}$ alkylene-S(O), $C_{1-6}$ alkylene-S(O)$_2$, $C_{1-6}$ alkylene-O, $C_{1-6}$ alkylene-C(O), $C_{1-6}$ alkylene-C(O)N($R^A$), $C_{1-6}$ alkylene-N($R^A$)C(O), $C_{1-6}$ alkylene-N($R^A$)S(O)$_2$, or $C_{1-6}$ alkylene-S(O)$_2$N($R^A$);
  V is (i) —CH$_2$—$C_{2-6}$ alkenyl or (ii) —$C_{1-6}$ alkyl substituted with C(O)N($R^C$)$R^D$, CycL, AryL, HetL, or HetS; and
  $R^L$ is CycL, AryL, HetL, or HetS;
CycL is —$C_{3-8}$ cycloalkyl which is optionally substituted with from 1 to 6 substituents each of which is independently halogen, —CN, —$C_{1-6}$ alkyl, —OH, —O—$C_{1-6}$ alkyl, —$C_{1-6}$ haloalkyl, or —O—$C_{1-6}$ haloalkyl;
AryL is aryl, which is optionally substituted with from 1 to 5 substituents each of which is independently any one of the substituents (1) to (21) as defined above in part (i) of Part A of the definition of $R^J$;
HetE independently has the same definition as HetC;
HetL is heteroaryl, which is optionally substituted with from 1 to 5 substituents each of which is independently any one of the substituents (1) to (26) as defined above in part (i) of Part B of the definition of $R^J$;
HetS is a 4- to 7-membered, saturated or mono-unsaturated heterocyclic ring containing at least one carbon atom and from 1 to 4 heteroatoms independently selected from N, O and S, where each S is optionally oxidized to S(O) or S(O)$_2$, with the proviso that HetS is attached to the rest of the molecule via a ring carbon atom; and wherein the saturated or mono-unsaturated heterocyclic ring is optionally substituted with from 1 to 4 substituents each of which is independently halogen, —CN, —C$_{1-6}$ alkyl, —OH, oxo, —C(O)R$^A$, —CO$_2$R$^A$, —S(O)R$^A$, —SR$^A$, —S(O)$_2$R$^A$, —CH$_2$—CH=CH$_2$, —O—C$_{1-6}$ alkyl, —C$_{1-6}$ haloalkyl, —C$_{1-6}$ alkylene-C(O)N(R$^A$)R$^B$, —C$_{1-6}$ alkylene-CN, —C$_{1-6}$ alkylene-OH, or —C$_{1-6}$ alkylene-O—C$_{1-6}$ alkyl;

R$^5$ is:

(1) —C$_{1-6}$ alkyl, (2) —C$_{1-6}$ alkyl substituted with —OH, —O—C$_{1-6}$ alkyl, —O—C$_{1-6}$ haloalkyl, —CN, —NO$_2$, —N(R$^A$)R$^B$, —C(O)N(R$^A$)R$^B$, —C(O)R$^A$, —CO$_2$R$^A$, —SR$^A$, —S(O)R$^A$, —SO$_2$R$^A$, —SO$_2$N(R$^A$)R$^B$, —N(R$^A$)C(O)R$^B$, —N(R$^A$)CO$_2$R$^B$, —N(R$^A$)SO$_2$R$^B$, —N(R$^A$)SO$_2$N(R$^A$)R$^B$, —OC(O)N(R$^A$)R$^B$, —N(R$^A$)C(O)N(R$^A$)R$^B$, or —N(R$^A$)C(O)C(O)N(R$^A$)R$^B$, (3) —C$_{3-8}$ cycloalkyl, which is optionally substituted with from 1 to 6 substituents each of which is independently halogen, —CN, —C$_{1-6}$ alkyl, —OH, —O—C$_{1-6}$ alkyl, —C$_{1-6}$ haloalkyl, or —O—C$_{1-6}$ haloalkyl, (4) —C$_{1-6}$ alkyl substituted with —C$_{3-8}$ cycloalkyl, wherein the —C$_{3-8}$ cycloalkyl is optionally substituted with from 1 to 6 substituents each of which is independently halogen, —CN, —C$_{1-6}$ alkyl, —OH, —O—C$_{1-6}$ alkyl, —C$_{1-6}$ haloalkyl, or —O—C$_{1-6}$ haloalkyl, (5) heteroaryl, which is optionally substituted with from 1 to 5 substituents each of which is independently any one of the substituents (1) to (26) as defined above in part (i) of Part B of the definition of R$^J$, (6) —C$_{1-6}$ alkyl substituted with R$^K$, wherein R$^K$ independently has the same definition as R$^J$ as set forth above in the definition of R$^1$, or (7) aryl, which is optionally substituted with from 1 to 5 substituents each of which is independently any one of the substituents (1) to (21) as defined above in part (i) of Part A of the definition of R$^J$;

and with the proviso that R$^5$ is —C$_{1-6}$ alkyl substituted with R$^K$, when R$^1$ is other than —C$_{1-6}$ alkyl substituted with R$^J$;

R$^6$ and R$^7$ are each independently —H or —C$_{1-6}$ alkyl;

or alternatively R$^3$ and R$^7$ together with the carbon atom to which they are attached form (i) a 3- to 8-membered saturated carbocyclic ring which is optionally substituted with from 1 to 6 substituents each of which is independently halogen, —CN, —C$_{1-6}$ alkyl, —OH, —O—C$_{1-6}$ alkyl, —C$_{1-6}$ haloalkyl, or —O—C$_{1-6}$ haloalkyl or (ii) a 4- to 7-membered, saturated or mono-unsaturated heterocyclic ring containing from 1 to 3 heteroatoms independently selected from N, O and S, where each S is optionally oxidized to S(O) or S(O)$_2$, and wherein the saturated or mono-unsaturated heterocyclic ring is optionally substituted with from 1 to 4 substituents each of which is independently halogen, —CN, —C$_{1-6}$ alkyl, —OH, oxo, —C(O)R$^A$, —CO$_2$R$^A$, —S(O)R$^A$, —SR$^A$, —S(O)$_2$R$^A$, —CH$_2$—CH=CH$_2$, —O—C$_{1-6}$ alkyl, —C$_{1-6}$ haloalkyl, —C$_{1-6}$ alkylene-CN, —C$_{1-6}$ alkylene-OH, or —C$_{1-6}$ alkylene-O—C$_{1-6}$ alkyl, each aryl is independently (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic;

each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or S(O)$_2$;

each R$^A$ is independently —H or —C$_{1-6}$ alkyl;
each R$^B$ is independently —H or —C$_{1-6}$ alkyl;
each R$^C$ is independently —H or —C$_{1-6}$ alkyl; and
each R$^D$ is independently —H or —C$_{1-6}$ alkyl;

or alternatively R$^C$ and R$^D$ together with the N to which they are both attached form a 4- to 7-membered, saturated or mono-unsaturated heterocyclic ring containing the N to which they are both attached and optionally containing 1 or 2 additional heteroatoms independently selected from N, O and S, where each S is optionally oxidized to S(O) or S(O)$_2$, and wherein the saturated or mono-unsaturated heterocyclic ring is optionally substituted with from 1 to 4 substituents each of which is independently halogen, —CN, —C$_{1-6}$ alkyl, —OH, oxo, —C(O)R$^A$, —CO$_2$R$^A$, —S(O)R$^A$, —SR$^A$, —S(O)$_2$R$^A$, —CH$_2$—C$_{2-6}$ alkenyl, —O—C$_{1-6}$ alkyl, —C$_{1-6}$ haloalkyl, —C$_{1-6}$ alkylene-CN, —C$_{1-6}$ alkylene-OH, or —C$_{1-6}$ alkylene-O—C$_{1-6}$ alkyl.

2. The compound according to claim 1, or a pharmaceutically acceptable salt thereof, wherein:

R$^1$ is:

(1) —C$_{1-4}$ alkyl, or (2) —C$_{1-4}$ alkyl substituted with R$^J$, wherein R$^J$ is:

(A) an optionally substituted phenyl of formula:

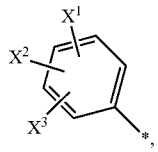

wherein the asterisk * denotes the point of attachment to the rest of the compound, X$^1$ and X$^2$ are each independently selected from the group consisting of —H, halogen, —C$_{1-4}$ alkyl, —O—C$_{1-4}$ alkyl, —C$_{1-4}$ fluoroalkyl, —CN, —CO$_2$H, —CO$_2$—C$_{1-4}$ alkyl, —SO$_2$—C$_{1-4}$ alkyl, —C(O)—NH(C$_{1-4}$ alkyl), —C(O)—N(C$_{1-4}$ alkyl)$_2$, —NHC(O)—C$_{1-4}$ alkyl, and —N(C$_{1-4}$ alkyl)C(O)—C$_{1-4}$ alkyl, and X$^3$ is —H, halogen, —C$_{1-4}$ alkyl, —O—C$_{1-4}$ alkyl, —C$_{1-4}$ fluoroalkyl, —SO$_2$—C$_{1-4}$ alkyl, —C(O)—NH(C$_{1-4}$ alkyl), —C(O)—N(C$_{1-4}$ alkyl)$_2$, or HetB, or (B) a heteroaryl which is (i) 5- or 6-membered heteroaromatic ring containing from 1 to 4 heteroatoms independently selected from N, O and S, wherein the ring is optionally substituted with from 1 to 3 substituents each of which is independently —C$_{1-4}$ alkyl or —OH, or (ii) a benzene ring fused to a 5- or 6-membered saturated or unsaturated heterocyclic ring containing from 1 to 3 heteroatoms independently selected from N, O and S, wherein the fused bicyclic ring system is optionally substituted with from 1 to 4 substituents each of which is independently —C$_{1-4}$ alkyl, oxo, or —OH;

R$^5$ is:

(1) —C$_{1-4}$ alkyl, (2) —C$_{1-4}$ alkyl substituted with —OH, —O—C$_{1-4}$ alkyl, —CN, —NH$_2$, —NH(C$_{1-4}$ alkyl), or —N(C$_{1-4}$ alkyl)$_2$, (3) —C$_{3-7}$ cycloalkyl, which is optionally substituted with from 1 to 4 substituents each of which is independently —C$_{1-4}$ alkyl, —OH, —O—C$_{1-4}$ alkyl, or —C$_{1-4}$ haloalkyl, (4) —C$_{1-4}$ alkyl substituted with —C$_{3-7}$ cycloalkyl, wherein the —C$_{3-7}$ cycloalkyl is optionally substituted with from 1 to 4 substituents each of which is independently —C$_{1-4}$ alkyl, —OH, —O—C$_{1-4}$ alkyl, or —C$_{1-4}$ haloalkyl, (5) 5- or 6-membered heteroaromatic ring containing from 1 to 4 heteroatoms independently selected from N, O and S, wherein the ring is optionally substituted with from 1 to 3 substituents each of which is independently —C$_{1-4}$ alkyl or —OH, or (6) —C$_{1-4}$ alkyl substituted with R$^K$, wherein R$^K$ is (A) an optionally substituted phenyl of formula:

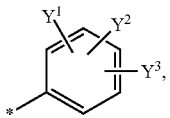

wherein the asterisk * denotes the point of attachment to the rest of the compound, Y$^1$ and Y$^2$ are each independently selected from the group consisting of —H, halogen, —C$_{1-4}$ alkyl, —O—C$_{1-4}$ alkyl, —C$_{1-4}$ fluoroalkyl, —CN, —CO$_2$H, —CO$_2$—C$_{1-4}$ alkyl, —SO$_2$—C$_{1-4}$ alkyl, —C(O)—NH(C$_{1-4}$ alkyl), —C(O)—N(C$_{1-4}$ alkyl)$_2$, —NHC(O)—C$_{1-4}$ alkyl, and —N(C$_{1-4}$ alkyl)C(O)—C$_{1-4}$ alkyl, and Y$^3$ is —H, halogen, —C$_{1-4}$ alkyl, —O—C$_{1-4}$ alkyl, —C$_{1-4}$ fluoroalkyl, —SO$_2$—C$_{1-4}$ alkyl, —C(O)—NH(C$_{1-4}$ alkyl), —C(O)—N(C$_{1-4}$ alkyl)$_2$, or HetB, or (B) a heteroaryl which is (i) 5- or 6-membered heteroaromatic ring containing from 1 to 4 heteroatoms independently selected from N, O and S, wherein the ring is optionally substituted with from 1 to 3 substituents each of which is independently —C$_{1-4}$ alkyl or —OH, or (ii) a benzene ring fused to a 5- or 6-membered saturated or unsaturated heterocyclic ring containing from 1 to 3 heteroatoms independently selected from N, O and S, wherein the fused bicyclic ring system is optionally substituted with from 1 to 4 substituents each of which is independently —C$_{1-4}$ alkyl, oxo, or —OH; and each HetB is independently a 5- or 6-membered heteroaromatic ring containing from 1 to 4 heteroatoms independently selected from N, O and S, wherein the heteroaromatic ring is optionally substituted with 1 or 2 substituents each of which is independently a —C$_{1-3}$ alkyl;

and with the proviso that R$^5$ is —C$_{1-4}$ alkyl substituted with R$^K$, when R$^1$ is —C$_{1-4}$ alkyl.

3. The compound according to claim 2, or a pharmaceutically acceptable salt thereof, wherein:

R$^1$ is:

(1) —C$_{1-4}$ alkyl, or (2) —CH$_2$—R$^J$; and

R$^5$ is:

(1) —C$_{1-4}$ alkyl, (2) —(CH$_2$)$_{1-3}$-Q, wherein Q is —OH, —O—C$_{1-4}$ alkyl, —CN, —NH$_2$, —NH(C$_{1-4}$ alkyl), or —N(C$_{1-4}$ alkyl)$_2$, (3) —C$_{3-7}$ cycloalkyl, which is optionally substituted with from 1 to 4 substituents each of which is independently —C$_{1-4}$ alkyl, —OH, —O—C$_{1-4}$ alkyl, or —C$_{1-4}$ haloalkyl, (4) —CH$_2$—C$_{3-7}$ cycloalkyl, wherein the —C$_{3-7}$ cycloalkyl is optionally substituted with from 1 to 4 substituents each of which is independently —C$_{1-4}$ alkyl, —OH, —O—C$_{1-4}$ alkyl, or —C$_{1-4}$ haloalkyl, (5) 5- or 6-membered heteroaromatic ring containing from 1 to 4 heteroatoms independently selected from N, O and S, wherein the ring is optionally substituted with from 1 to 3 substituents each of which is independently —C$_{1-4}$ alkyl or —OH, or (6) —CH$_2$—R$^K$;

and with the proviso that R$^5$ is —CH$_2$—R$^K$, when R$^1$ is —C$_{1-4}$ alkyl.

4. A compound according to claim 1, or a pharmaceutically acceptable salt thereof, which is a compound of Formula II:

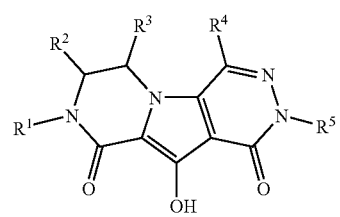

(II)

wherein:

R$^1$ is —CH$_2$—R$^J$, wherein R$^J$ is:

(A) an optionally substituted phenyl of formula:

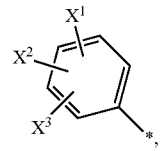

wherein the asterisk * denotes the point of attachment to the rest of the compound, X$^1$ and X$^2$ are each independently selected from the group consisting of —H, halogen, —C$_{1-4}$ alkyl, —O—C$_{1-4}$ alkyl, —C$_{1-4}$ fluoroalkyl, —CN, —CO$_2$H, —CO$_2$—C$_{1-4}$ alkyl, —SO$_2$—C$_{1-4}$ alkyl, —C(O)—NH(C$_{1-4}$ alkyl), —C(O)—N(C$_{1-4}$ alkyl)$_2$, —NHC(O)—C$_{1-4}$ alkyl, and —N(C$_{1-4}$ alkyl)C(O)—C$_{1-4}$ alkyl, and X$^3$ is —H, halogen, —C$_{1-4}$ alkyl, —O—C$_{1-4}$ alkyl, —C$_{1-4}$ fluoroalkyl, —SO$_2$—C$_{1-4}$ alkyl, —C(O)—NH(C$_{1-4}$ alkyl), —C(O)—N(C$_{1-4}$ alkyl)$_2$, or HetB, or (B) a 9- or 10-membered benzofused heterocyclic ring containing 1 or 2 heteroatoms independently selected from N, O and S;

R$^2$ and R$^3$ are each independently —H or —C$_{1-4}$ alkyl;

R$^4$ is —H, —C$_{1-4}$ alkyl, —OH, —O—C$_{1-4}$ alkyl, —O—C$_{1-4}$ haloalkyl, —CN, —NO$_2$, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, or —SO$_2$N(R$^A$)R$^B$;

R$^5$ is:

(1) —C$_{1-4}$ alkyl, (2) —(CH$_2$)$_{1-3}$-Q, wherein Q is —OH, —O—C$_{1-4}$ alkyl, —CN, —NH$_2$, —NH(C$_{1-4}$ alkyl), or —N(C$_{1-4}$ alkyl)$_2$, (3) —$C_{3-7}$ cycloalkyl, which is optionally substituted with from 1 to 4 substituents each of which is independently —$C_{1-4}$ alkyl, —OH, —O—$C_{1-4}$ alkyl, or —$C_{1-4}$ haloalkyl, (4) —$CH_2$—$C_{3-7}$ cycloalkyl, wherein the —$C_{3-7}$ cycloalkyl is optionally substituted with from 1 to 4 substituents each of which is independently —$C_{1-4}$ alkyl, —OH, —O—$C_{1-4}$ alkyl, or —$C_{1-4}$ haloalkyl, (5) 5- or 6-membered heteroaromatic ring containing from 1 to 4 heteroatoms independently selected from N, O and S, wherein the ring is optionally substituted with from 1 to 3 substituents each of which is independently —$C_{1-4}$ alkyl or —OH, or (6) —$CH_2$—$R^K$, wherein $R^K$ is (A) an optionally substituted phenyl of formula:

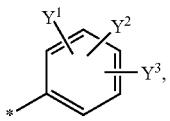

wherein the asterisk * denotes the point of attachment to the rest of the compound, $Y^1$ and $Y^2$ are each independently selected from the group consisting of —H, halogen, —$C_{1-4}$ alkyl, —O—$C_{1-4}$ alkyl, —$C_{1-4}$ fluoroalkyl, —CN, —$CO_2H$, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, and —N($C_{1-4}$ alkyl)C(O)—$C_{1-4}$ alkyl, and $Y^3$ is —H, halogen, —$C_{1-4}$ alkyl, —O—$C_{1-4}$ alkyl, —$C_{1-4}$ fluoroalkyl, —$SO_2$—$C_{1-4}$ alkyl, —C(O)—NH($C_{1-4}$ alkyl), —C(O)—N($C_{1-4}$ alkyl)$_2$, or HetB, or (B) a heteroaryl which is (i) 5- or 6-membered heteroaromatic ring containing from 1 to 4 heteroatoms independently selected from N, O and S, wherein the ring is optionally substituted with from 1 to 3 substituents each of which is independently —$C_{1-4}$ alkyl or —OH, or (ii) a 9- or 10-membered benzofused saturated or unsaturated heterocyclic ring containing from 1 to 3 heteroatoms independently selected from N, O and S;

each HetB is independently a 5- or 6-membered heteroaromatic ring containing from 1 to 4 heteroatoms independently selected from N, O and S, wherein the heteroaromatic ring is optionally substituted with 1 or 2 substituents each of which is independently a —$C_{1-3}$ alkyl;

each $R^A$ is independently —H or —$C_{1-4}$ alkyl;
each $R^B$ is independently —H or —$C_{1-4}$ alkyl;
each $R^C$ is independently —H or —$C_{1-4}$ alkyl; and
each $R^D$ is independently —H or —$C_{1-4}$ alkyl;

or alternatively $R^C$ and $R^D$ together with the N to which they are both attached form a 5- or 6-membered saturated heterocyclic ring containing the N to which they are both attached and optionally containing 1 or 2 additional heteroatoms independently selected from 1 or 2 N atoms, zero or 1 O atom, and zero or 1 S atom.

5. A compound according to claim 1, or a pharmaceutically acceptable salt thereof,
wherein:

$R^1$ is —$C_{1-4}$ alkyl or —$C_{1-4}$ alkyl substituted with —$C_{3-6}$ cycloalkyl, wherein the cycloalkyl is optionally substituted with from 1 to 3 substituents each of which is independently —$C_{1-4}$ alkyl, —OH, —O—$C_{1-4}$ alkyl, or —$C_{1-4}$ haloalkyl;

$R^2$ is —H or —$C_{1-4}$ alkyl;

or alternatively $R^1$ and $R^2$ together with the ring nitrogen to which $R^1$ is attached and the ring carbon to which $R^2$ is attached form a 5- to 7-membered, saturated heterocyclic ring in which the portion of the ring formed from $R^1$ and $R^2$ is a methylene chain of formula $(CH_2)_{3-5}$, wherein the methylene chain is optionally substituted with —$C_{1-4}$ alkyl, —OH, or oxo;

$R^3$ is:
(1) —H,
(2) —$C_{1-4}$ alkyl, or
(3) —$C_{1-4}$ alkyl substituted with —OH, —O—$C_{1-4}$ alkyl, —C(O)$R^A$, —$CO_2R^A$, —$SR^A$, —S(O)$R^A$, —$SO_2R^A$, or —N($R^A$)$SO_2R^B$;

or alternatively $R^2$ and $R^3$ together with the carbon atoms to which they are attached form:
(i) a 3- to 6-membered saturated carbocyclic ring which is optionally substituted with from 1 to 2 substituents each of which is independently —$C_{1-4}$ alkyl, —OH, or —O—$C_{1-4}$ alkyl,
(ii) a benzene ring, which is optionally substituted is optionally substituted with from 1 to 4 substituents each of which is independently halogen, —$C_{1-4}$ alkyl, —O—$C_{1-4}$ alkyl, —$C_{1-4}$ fluoroalkyl, —O—$C_{1-4}$ fluoroalkyl, —CN, —$CO_2H$, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl, or
(iii) a 6-membered heteroaromatic ring containing a total of from 1 to 2 N atoms, wherein the heteroaromatic ring is optionally substituted with from 1 to 3 substituents each of which is independently —$C_{1-4}$ alkyl, —O—$C_{1-4}$ alkyl or —OH;

wherein $R^7$ is absent, when $R^2$ and $R^3$ together with the carbon atoms to which they are attached form a benzene ring or a heteroaromatic ring;

$R^4$ is:
(1) —H,
(2) —$C_{1-4}$ alkyl,
(3) —$C_{1-4}$ haloalkyl,
(4) —$C_{1-4}$ alkyl substituted with —OH, —O—$C_{1-4}$ alkyl, —N($R^A$)$R^B$, —C(O)N($R^A$)$R^B$, —C(O)$R^A$, —$CO_2R^A$, —$SR^A$, —S(O)$R^A$, —$SO_2R^A$, or —$SO_2$N($R^A$)$R^B$,
(5) —OH,
(6) —O—$C_{1-4}$ alkyl,
(7) —O—$C_{1-4}$ haloalkyl,
(8) —CN,
(9) —$NO_2$,
(10) —N($R^C$)$R^D$,
(11) —C(O)N($R^C$)$R^D$,
(12) —C(O)$R^A$,
(13) —$CO_2R^A$,
(14) —$SR^A$,
(15) —S(O)$R^A$,
(16) —$SO_2R^A$,
(17) —$SO_2$N($R^A$)$R^B$,
(18) —N($R^A$)C(O)$R^B$,
(20) —N($R^A$)$SO_2R^B$,
(21) —N($R^A$)C(O)N($R^A$)$R^B$,
(22) —N($R^A$)C(O)C(O)N($R^A$)$R^B$,
(23) halogen,
(24) —S—C(O)N($R^C$)$R^D$,
(25) —N=C($R^A$)—N($R^C$)$R^D$,
(26) —C(O)N($R^A$)—($CH_2$)$_{1-3}$—N($R^C$)$R^D$,
(27) —C(O)—($CH_2$)$_{1-3}$—N($R^C$)$R^D$,

(28) —C(O)N($R^A$)—($CH_2$)$_{1-3}$—$C_{1-4}$ fluoroalkyl,
(29) —N($SO_2R^A$)—($CH_2$)$_{1-2}$C(O)N($R^C$)$R^D$,
(30) —N[C(O)$R^A$]—($CH_2$)$_{1-2}$C(O)N($R^C$)$R^D$,
(31) —N($SO_2R^A$)—$CH_2$—CH=$CH_2$,
(32) —N($SO_2R^A$)—($CH_2$)$_{1-2}$-CycL,
(33) —$C_{1-4}$ alkyl substituted HetE,
(34) —$C_{1-4}$ alkyl substituted CycL, AryL, HetL, or HetS,
(35) HetL or HetS,
(36) —C(O)N($R^A$)-CycL,
(37) —C(O)N($R^A$)-AryL, with the proviso that AryL is dihydroindenyl or tetrahydronaphthyl and is attached to the rest of the molecule via a non-aromatic ring carbon,
(38) —C(O)N($R^A$)—($CH_2$)$_{1-2}$-AryL,
(39) —($CH_2$)$_{1-2}$—S-AryL,
(40) —($CH_2$)$_{1-2}$—S(O)$_2$-AryL,
(41) —N($R^A$)$SO_2$-CycL, or
(42) —$SO_2$-CycL;

CycL is —$C_{3-6}$ cycloalkyl which is optionally substituted with from 1 to 2 substituents each of which is independently —$C_{1-4}$ alkyl, —OH, or —O—$C_{1-4}$ alkyl;

AryL is dihydroindenyl, tetrahydronaphthyl, naphthyl, or phenyl, wherein the dihydroindenyl, tetrahydronaphthyl, naphthyl, or phenyl is optionally substituted with from 1 to 3 substituents each of which is independently halogen, —$C_{1-4}$ alkyl, —O—$C_{1-4}$ alkyl, —$C_{1-4}$ fluoroalkyl, —O—$C_{1-4}$ fluoroalkyl, —CN, —$CO_2H$, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl;

HetE is a 5- or 6-membered, saturated heterocyclic ring containing from 1 to 2 heteroatoms independently selected from 1 to 2 N atoms, zero to 1 O atom, and zero to 1 S atom, where the S is optionally oxidized to S(O) or S(O)$_2$, with the proviso that the ring is attached to the rest of the molecule via a ring N atom, and wherein the saturated heterocyclic ring is optionally substituted with from 1 to 4 substituents each of which is independently —$C_{1-4}$ alkyl, oxo, —C(O)$R^A$, or —S(O)$_2R^A$;

HetL is a 5- or 6-membered heteroaromatic ring containing a total of from 1 to 4 heteroatoms independently selected from zero to 4 N atoms, zero to 1 O atom, and zero to 1 S atom, wherein the heteroaromatic ring is optionally substituted with from 1 to 3 substituents each of which is independently —CN, —$C_{1-4}$ alkyl, —O—$C_{1-4}$ alkyl, oxo, —OH, or —($CH_2$)$_{1-2}$C(O)N($R^A$)$R^B$;

HetS is a saturated or mono-unsaturated 5- or 6-membered heterocyclic ring, wherein the ring contains a total of from 1 to 3 heteroatoms independently selected from 1 to 3 N atoms, zero to 1 O atom, and zero to 1 S atom, where the S is optionally oxidized to S(O) or S(O)$_2$, with the proviso that HetS is attached to the rest of the molecule via a ring carbon atom; and wherein the heterocyclic ring is optionally substituted with from 1 to 4 substituents each of which is independently —$C_{1-4}$ alkyl, oxo, —C(O)$R^A$, —$CO_2R^A$, —S(O)$R^A$, —$SR^A$, —S(O)$_2R^A$, or —($CH_2$)$_{1-2}$C(O)N($R^A$)$R^B$;

$R^5$ is ($CH_2$)$_{1-2}$—$R^K$ or —CH($CH_3$)—$R^K$, wherein $R^K$ is:
(A) an optionally substituted phenyl of formula:

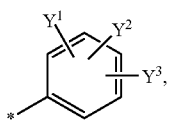

wherein the asterisk * denotes the point of attachment to the rest of the compound, $Y^1$ and $Y^2$ are each independently selected from the group consisting of —H, halogen, —$C_{1-4}$ alkyl, —O—$C_{1-4}$ alkyl, —$C_{1-4}$ fluoroalkyl, —O—$C_{1-4}$ fluoroalkyl, —CN, —$CO_2H$, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, and —N($C_{1-4}$ alkyl)C(O)—$C_{1-4}$ alkyl, and $Y^3$ is —H, halogen, —$C_{1-4}$ alkyl, —O—$C_{1-4}$ alkyl, —$C_{1-4}$ fluoroalkyl, —$SO_2$—$C_{1-4}$alkyl, —C(O)—NH ($C_{1-4}$ alkyl), —C(O)—N($C_{1-4}$ alkyl)$_2$, or HetB, or (B) a 9- or 10-membered benzofused heterocyclic ring containing 1 or 2 heteroatoms independently selected from N, O and S;

$R^6$ is —H;
$R^7$ is —H or —$C_{1-4}$ alkyl;

or alternatively $R^3$ and $R^7$ together with the carbon atom to which they are attached form a 3 to 6-membered saturated carbocyclic ring optionally substituted with from 1 to 2 $C_{1-4}$ alkyl;

HetB is a 5- or 6-membered heteroaromatic ring containing from 1 to 4 heteroatoms independently selected from N, O and S, wherein the heteroaromatic ring is optionally substituted with 1 or 2 substituents each of which is independently a —$C_{1-3}$ alkyl;

each $R^A$ is independently —H or —$C_{1-4}$ alkyl;
each $R^B$ is independently —H or —$C_{1-4}$ alkyl;
each $R^C$ is independently —H or —$C_{1-4}$ alkyl; and
each $R^D$ is independently —H or —$C_{1-4}$ alkyl;

or alternatively $R^C$ and $R^D$ together with the N to which they are both attached form a 5- or 6-membered saturated heterocyclic ring containing the N to which they are both attached and optionally containing 1 or 2 additional heteroatoms independently selected from 1 or 2 N atoms, zero or 1 O atom, and zero or 1 S atom, where the S is optionally oxidized to S(O) or S(O)$_2$, and wherein the saturated heterocyclic ring is optionally substituted with from 1 to 4 substituents each of which is independently —$C_{1-4}$ alkyl, oxo, —C(O)$R^A$, —$CO_2R^A$, S(O)$_2R^A$, or —$CH_2$—CH=$CH_2$.

6. The compound according to claim 5, or a pharmaceutically acceptable salt thereof, wherein
$R^1$ is —$C_{1-4}$ alkyl or —$CH_2$-cyclopropyl;
$R^2$ is —H;
or alternatively $R^1$ and $R^2$ together with the ring nitrogen to which $R^1$ is attached and the ring carbon to which $R^2$ is attached form a 5- or 6-membered, saturated heterocyclic ring in which the portion of the ring formed from $R^1$ and $R^2$ is ($CH_2$)$_3$ or ($CH_2$)$_4$;
$R^3$ is —H, —$C_{1-3}$ alkyl, —($CH_2$)$_{1-2}$OH, —($CH_2$)$_{1-2}SCH_3$, —($CH_2$)$_{1-2}$S(O)$CH_3$, —($CH_2$)$_{1-2}SO_2CH_3$, —($CH_2$)$_{1-2}$NHSO$_2CH_3$ or —($CH_2$)$_{1-2}$N($CH_3$)$SO_2CH_3$;
or alternatively $R^2$ and $R^3$ together with the carbon atoms to which they are attached form a 3-membered carbocyclic ring;
$R^4$ is:
(1) —H,
(2) —$C_{1-3}$ alkyl,
(3) —($CH_2$)$_{1-2}$OH, —CH($CH_3$)OH, —C($CH_3$)$_2$OH, —($CH_2$)$_{1-2}NH_2$, —($CH_2$)$_{1-2}$NH—$C_{1-3}$ alkyl, —($CH_2$)$_{1-2}$N($C_{1-3}$ alkyl)$_2$, —($CH_2$)$_{1-2}OCH_3$, —($CH_2$)$_{1-2}CO_2CH_3$, —($CH_2$)$_{1-2}SCH_3$, —($CH_2$)$_{1-2}$S(O)$CH_3$, or —($CH_2$)$_{1-2}SO_2CH_3$,
(4) —O—$C_{1-3}$ alkyl,
(5) —$NH_2$, —N(H)—$C_{1-3}$ alkyl, or —N($C_{1-3}$ alkyl)$_2$,
(6)

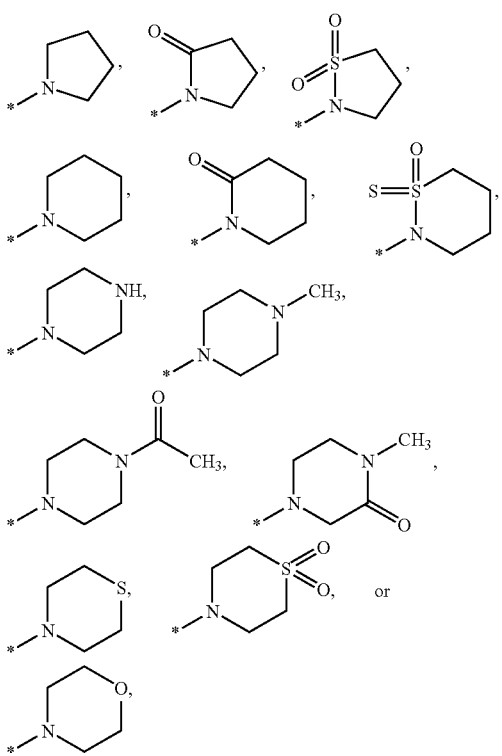

wherein * denotes the point of attachment to the rest of the molecule, (7) —C(O)NH₂, —C(O)N(H)—C₁₋₃ alkyl, or —C(O)N(C₁₋₃ alkyl)₂, (8)

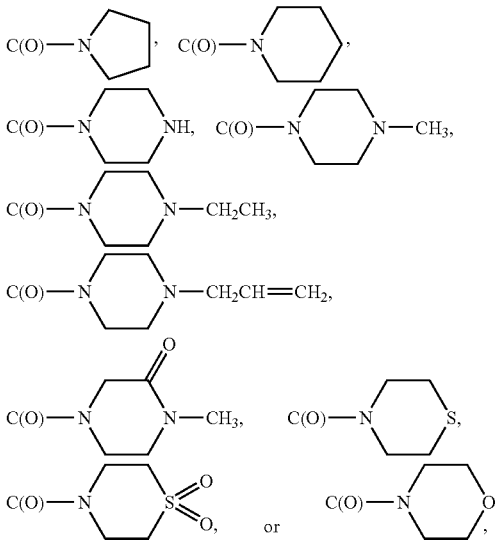

(9) —C(O)—C₁₋₃ alkyl,
(10) —CO₂—C₁₋₃ alkyl,
(11) —S—C₁₋₃ alkyl,
(12) —S(O)—C₁₋₃ alkyl,
(13) —SO₂—C₁₋₃ alkyl,
(14) —SO₂N(C₁₋₃ alkyl)₂,

(15) —NHC(O)—C₁₋₃ alkyl or —N(C₁₋₃ alkyl)C(O)—C₁₋₃ alkyl,
(16) —NHSO₂—C₁₋₃ alkyl or —N(C₁₋₃ alkyl)SO₂—C₁₋₃ alkyl,
(17) —NHC(O)NH(C₁₋₃ alkyl), —NHC(O)N(C₁₋₃ alkyl)₂, —N(C₁₋₃ alkyl)C(O)NH(C₁₋₃ alkyl), or —N(C₁₋₃ alkyl)C(O)N(C₁₋₃ alkyl)₂,
(18) —NHC(O)C(O)NH(C₁₋₃ alkyl), —NHC(O)C(O)N(C₁₋₃ alkyl)₂, —N(C₁₋₃ alkyl)C(O)C(O)NH(C₁₋₃ alkyl), or —N(C₁₋₃ alkyl)C(O)C(O)N(C₁₋₃ alkyl)₂,
(19) —Cl, —Br, or —F,
(20) —S—C(O)N(C₁₋₃ alkyl)₂,
(21) —N═CH—N(C₁₋₃ alkyl)₂ or —N═C(C₁₋₃ alkyl)-N(C₁₋₃ alkyl)₂,
(22) —C(O)NH—(CH₂)₂₋₃—N(C₁₋₃ alkyl)₂ or —C(O)N(C₁₋₃ alkyl)-(CH₂)₂₋₃—N(C₁₋₃ alkyl)₂,
(23)

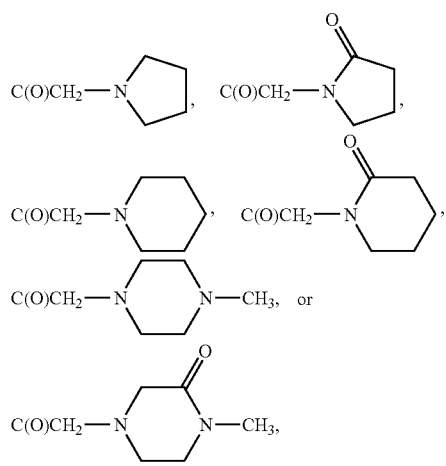

(24) —C(O)NHCH₂CH₂F, —C(O)NHCH₂CHF₂, or —C(O)NHCH₂CF₃,
(25) —N(SO₂—C₁₋₃ alkyl)-(CH₂)₁₋₂C(O)N(C₁₋₃ alkyl)₂,
(26) —N[C(O)—C₁₋₃ alkyl]-(CH₂)₁₋₂C(O)N(C₁₋₃ alkyl)₂,
(27) —N(SO₂—C₁₋₃ alkyl)-CH₂—CH═CH₂,
(28) —N(SO₂—C₁₋₃ alkyl)-CH₂-CycL,
(29)

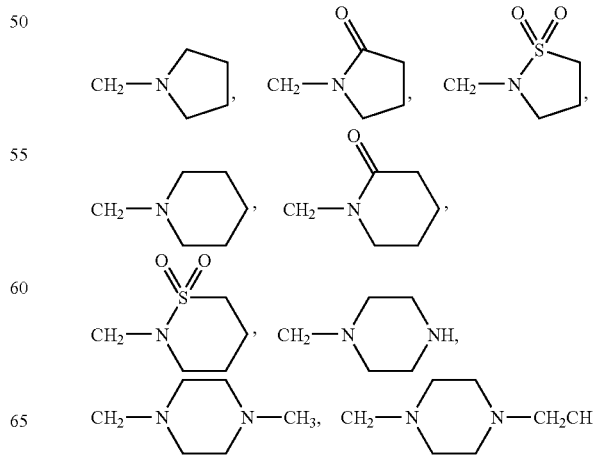

-continued

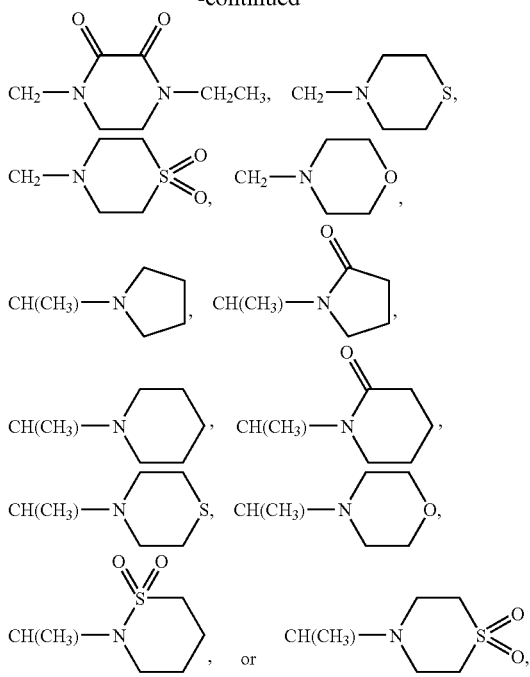

(30) —CH$_2$-HetL,
(31) HetL,
(32)

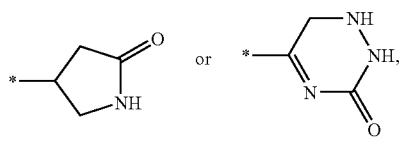

(33) —C(O)NH-CycL or —C(O)N(C$_{1-3}$ alkyl)-CycL,
(34)

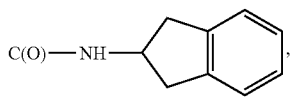

(35) —C(O)NH—CH$_2$-AryL or —C(O)N(CH$_3$)—CH$_2$-AryL,
(36) —CH$_2$—S-AryL,
(37) —CH$_2$—S(O)$_2$-AryL,
(38) —N(C$_{1-3}$ alkyl)SO$_2$-CycL, or
(39) —SO$_2$-CycL;

CycL is cyclopropyl, cyclobutyl, cyclopentyl, or cyclohexyl;

AryL is phenyl, which is optionally substituted with from 1 to 3 substituents each of which is independently —Cl, —Br, —F, —C$_{1-3}$ alkyl, —O—C$_{1-3}$ alkyl, —CF$_3$, —OCF$_3$, —CO$_2$CH$_3$, —SO$_2$CH$_3$, —C(O)NH(CH$_3$), —C(O)N(CH$_3$)$_2$, —NHC(O)CH$_3$, or —N(CH$_3$)C(O)CH$_3$;

HetL is (i) a 5- or 6-membered heteroaromatic ring selected from the group consisting of pyrrolyl, pyrazolyl, imidazolyl, triazolyl, tetrazolyl, furyl, thienyl, oxazolyl, isoxazolyl, thiazolyl, isothiazolyl, pyridinyl, pyrimidinyl, and pyrazinyl, wherein the heteroaromatic ring is optionally substituted with from 1 to 3 substituents each of which is independently —CN, —C$_{1-4}$ alkyl, —O—C$_{1-4}$ alkyl, —OH, or (CH$_2$)$_{1-2}$C(O)N(C$_{1-3}$ alkyl)$_2$, (ii) 2-oxo-pyridin-1(2H)-yl, (iii) 4-cyano-2-oxo-pyridin-1(2H)-yl, (iv) 1-(C$_{1-4}$ alkyl)-6-oxo-1,6-dihydropyridin-3-yl, or (v) 1-{[(di-C$_{1-3}$ alkylamino)carbonyl]methyl}-6-oxo-1,6-dihydropyridin-3-yl;

R$^5$ is

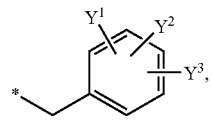

wherein the asterisk * denotes the point of attachment to the rest of the compound;

Y$^1$ and Y$^2$ are each independently selected from the group consisting of —H, —Cl, —Br, —F, —C$_{1-4}$ alkyl, —O—C$_{1-4}$ alkyl, —CF$_3$, —OCF$_3$, —CO$_2$CH$_3$, —SO$_2$CH$_3$, —C(O)NH(CH$_3$), —C(O)N(CH$_3$)$_2$, —NHC(O)CH$_3$ and —N(CH$_3$)C(O)CH$_3$; and Y$^3$ is —H, —Cl, —Br, —F, —C$_{1-4}$ alkyl, —O—C$_{1-4}$ alkyl, —CF$_3$, —SO$_2$CH$_3$, —C(O)NH(CH$_3$), or —C(O)N(CH$_3$)$_2$;

R$^6$ is —H; and

R$^7$ is —H or —C$_{1-3}$ alkyl.

7. A compound according to claim 5, or a pharmaceutically acceptable salt thereof, which is a compound of Formula II:

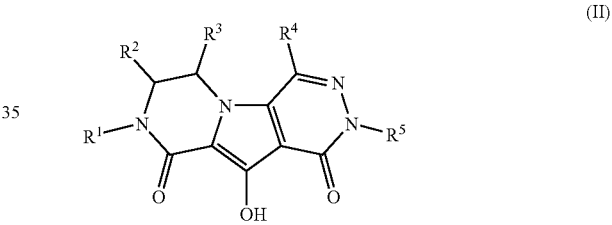

(II)

wherein:

R$^1$ is —C$_{1-4}$ alkyl;

R$^2$ and R$^3$ are each independently —H or —C$_{1-4}$ alkyl;

R$^4$ is —H, —C$_{1-4}$ alkyl, —OH, —O—C$_{1-4}$ alkyl, —O—C$_{1-4}$ haloalkyl, —CN, —NO$_2$, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, or —SO$_2$N(R$^A$)R$^B$;

R$^5$ is —CH$_2$—R$^K$, wherein R$^K$ is:

(A) an optionally substituted phenyl of formula:

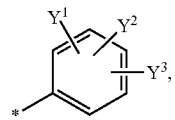

wherein the asterisk * denotes the point of attachment to the rest of the compound, Y$^1$ and Y$^2$ are each independently selected from the group consisting of —H, halogen, —C$_{1-4}$ alkyl, —O—C$_{1-4}$ alkyl, —C$_{1-4}$ fluoroalkyl, —CN, —CO$_2$H, —CO$_2$—C$_{1-4}$ alkyl, —SO$_2$—C$_{1-4}$ alkyl, —C(O)—NH(C$_{1-4}$ alkyl), —C(O)—N(C$_{1-4}$ alkyl)$_2$, —NHC(O)—C$_{1-4}$ alkyl, and —N(C$_{1-4}$ alkyl)C(O)—C$_{1-4}$ alkyl, and Y³ is —H, halogen, —C₁₋₄ alkyl, —O—C₁₋₄ alkyl, —C₁₋₄ fluoroalkyl, —SO₂—C₁₋₄ alkyl, —C(O)—NH (C₁₋₄ alkyl), —C(O)—N(C₁₋₄ alkyl)₂, or HetB, or (B) a 9- or 10-membered benzofused heterocyclic ring containing 1 or 2 heteroatoms independently selected from N, O and S;

R⁷ is —H;

HetB is a 5- or 6-membered heteroaromatic ring containing from 1 to 4 heteroatoms independently selected from N, O and S, wherein the heteroaromatic ring is optionally substituted with 1 or 2 substituents each of which is independently a —C₁₋₃ alkyl;

each R^A is independently —H or —C₁₋₄ alkyl;
each R^B is independently —H or —C₁₋₄ alkyl;
each R^C is independently —H or —C₁₋₄ alkyl; and
each R^D is independently —H or —C₁₋₄ alkyl;

or alternatively R^C and R^D together with the N to which they are both attached form a 5- or 6-membered saturated heterocyclic ring containing the N to which they are both attached and optionally containing 1 or 2 additional heteroatoms independently selected from 1 or 2 N atoms, zero or 1 O atom, and zero or 1 S atom.

8. The compound according to claim 5, or a pharmaceutically acceptable salt thereof, wherein R¹ is —CH₃, —CH₂CH₃, or —CH(CH₃)₂;
R² is H;
R³ is —CH₃ or —CH₂OH;
R⁴ is —H, —CH₃, —C(O)N(H)CH₃, —C(O)N(H)CH₂CH₃, —C(O)N(CH₃)₂, —N(CH₃)SO₂CH₃, —N(CH₂CH₃)SO₂CH₃, or SO₂CH₃;
R⁵ is 4-fluorobenzyl or 3-chloro-4-fluorobenzyl;
R⁶ is H; and
R⁷ is H.

9. A compound, or a pharmaceutically acceptable salt thereof, selected from the group consisting of:

8-(4-fluorobenzyl)-10-hydroxy-2,4-dimethyl-7,8-dihydropyrazino[1',2':1,5]pyrrolo[2,3-d]pyridazine-1,9(2H,6H)-dione;

8-(4-fluorobenzyl)-10-hydroxy-2-ethyl-4-methyl-7,8-dihydropyrazino-[1',2':1,5]pyrrolo[2,3-d]pyridazine-1,9(2H,6H)-dione;

8-(4-fluorobenzyl)-10-hydroxy-2-benzyl-4-methyl-7,8-dihydropyrazino-[1',2':1,5]pyrrolo[2,3-d]pyridazine-1,9(2H,6H)-dione;

8-(4-fluorobenzyl)-10-hydroxy-2-cyclohexyl-4-methyl-7,8-dihydropyrazino-[1',2':1,5]pyrrolo[2,3-d]pyridazine-1,9(2H,6H)-dione;

8-(4-fluorobenzyl)-10-hydroxy-2-cyanoethyl-4-methyl-7,8-dihydropyrazino-[1',2':1,5]pyrrolo[2,3-d]pyridazine-1,9(2H,6H)-dione;

8-(4-fluorobenzyl)-10-hydroxy-2-hydroxyethyl-4-methyl-7,8-dihydropyrazino-[1',2':1,5]pyrrolo[2,3-d]pyridazine-1,9(2H,6H)-dione;

2-(4-fluorobenzyl)-10-hydroxy-4,8-dimethyl-7,8-dihydropyrazino[1',2':1,5]pyrrolo[2,3-d]pyridazine-1,9(2H,6H)-dione;

2-(3,4-dichlorobenzyl)-10-hydroxy-4,8-dimethyl-7,8-dihydropyrazino[1',2':1,5]-pyrrolo[2,3-d]pyridazine-1,9(2H,6H)-dione;

2-(3-chlorobenzyl)-10-hydroxy-4,8-dimethyl-7,8-dihydropyrazino[1',2':1,5]-pyrrolo[2,3-d]pyridazine-1,9(2H,6H)-dione;

2-(4-chlorobenzyl)-10-hydroxy-4,8-dimethyl-7,8-dihydropyrazino[1',2':1,5]-pyrrolo[2,3-d]pyridazine-1,9(2H,6H)-dione;

2-(1,3-benzodioxol-5-ylmethyl)-10-hydroxy-4,8-dimethyl-7,8-dihydropyrazino-[1',2':1,5]pyrrolo[2,3-d]pyridazine-1,9(2H,6H)-dione;

2-(2,3,4-trifluorobenzyl)-10-hydroxy-4,8-dimethyl-7,8-dihydropyrazino[1',2':1,5]-pyrrolo[2,3-d]pyridazine-1,9(2H,6H)-dione;

2-(2,4-difluorobenzyl)-10-hydroxy-4,8-dimethyl-7,8-dihydropyrazino[1',2':1,5]-pyrrolo[2,3-d]pyridazine-1,9(2H,6H)-dione;

2-(2-chloro-4-fluorobenzyl)-10-hydroxy-4,8-dimethyl-7,8-dihydropyrazino[1',2':1,5]-pyrrolo[2,3-d]pyridazine-1,9(2H,6H)-dione;

2-(3-methylbenzyl)-10-hydroxy-4,8-dimethyl-7,8-dihydropyrazino[1',2':1,5]-pyrrolo[2,3-d]pyridazine-1,9(2H,6H)-dione;

2-(2-cyanobenzyl)-10-hydroxy-4,8-dimethyl-7,8-dihydropyrazino[1',2':1,5]-pyrrolo[2,3-d]pyridazine-1,9(2H,6H)-dione;

2-(4-methylbenzyl)-10-hydroxy-4,8-dimethyl-7,8-dihydropyrazino[1',2':1,5]-pyrrolo[2,3-d]pyridazine-1,9(2H,6H)-dione;

2-(3-methoxybenzyl)-10-hydroxy-4,8-dimethyl-7,8-dihydropyrazino[1',2':1,5]-pyrrolo[2,3-d]pyridazine-1,9(2H,6H)-dione;

2-(4-methoxybenzyl)-10-hydroxy-4,8-dimethyl-7,8-dihydropyrazino[1',2':1,5]-pyrrolo[2,3-d]pyridazine-1,9(2H,6H)-dione;

2-(benzyl)-10-hydroxy-4,8-dimethyl-7,8-dihydropyrazino[1',2':1,5]-pyrrolo[2,3-d]pyridazine-1,9(2H,6H)-dione;

2-(4-fluoro-2-methoxycarbonyllbenzyl)-10-hydroxy-4,8-dimethyl-7,8-dihydropyrazino[1',2':1,5]-pyrrolo[2,3-d]pyridazine-1,9(2H,6H)-dione;

2-(4-fluoro-2-methylaminocarbonyllbenzyl)-10-hydroxy-4,8-dimethyl-7,8-dihydropyrazino[1',2':1,5]-pyrrolo[2,3-d]pyridazine-1,9(2H,6H)-dione;

2-(2,3-dichlorobenzyl)-10-hydroxy-4,8-dimethyl-7,8-dihydropyrazino[1',2':1,5]-pyrrolo[2,3-d]pyridazine-1,9(2H,6H)-dione;

2-(2-fluorobenzyl)-10-hydroxy-4,8-dimethyl-7,8-dihydropyrazino[1',2':1,5]-pyrrolo[2,3-d]pyridazine-1,9(2H,6H)-dione;

2-(3-fluorobenzyl)-10-hydroxy-4,8-dimethyl-7,8-dihydropyrazino[1',2':1,5]-pyrrolo[2,3-d]pyridazine-1,9(2H,6H)-dione;

2-(2,3-difluorobenzyl)-10-hydroxy-4,8-dimethyl-7,8-dihydropyrazino[1',2':1,5]-pyrrolo[2,3-d]pyridazine-1,9(2H,6H)-dione;

2-(3,4-difluorobenzyl)-10-hydroxy-4,8-dimethyl-7,8-dihydropyrazino[1',2':1,5]-pyrrolo[2,3-d]pyridazine-1,9(2H,6H)-dione;

2-(2-methoxybenzyl)-10-hydroxy-4,8-dimethyl-7,8-dihydropyrazino[1',2':1,5]-pyrrolo[2,3-d]pyridazine-1,9(2H,6H)-dione;

2-(2-methylbenzyl)-10-hydroxy-4,8-dimethyl-7,8-dihydropyrazino[1',2':1,5]-pyrrolo[2,3-d]pyridazine-1,9(2H,6H)-dione;

2-(3,4-dimethylbenzyl)-10-hydroxy-4,8-dimethyl-7,8-dihydropyrazino[1',2':1,5]-pyrrolo[2,3-d]pyridazine-1,9(2H,6H)-dione;

2-(3-trifluoromethylbenzyl)-10-hydroxy-4,8-dimethyl-7,8-dihydropyrazino[1',2':1,5]-pyrrolo[2,3-d]pyridazine-1,9(2H,6H)-dione;

2-(1,3-benzodioxol-4-ylmethyl)-10-hydroxy-4,8-dimethyl-7,8-dihydropyrazino-[1',2':1,5]pyrrolo[2,3-d]pyridazine-1,9(2H,6H)-dione;

2-(4-fluorobenzyl)-10-hydroxy-6,8-dimethyl-7,8-dihydropyrazino[1',2':1,5]-pyrrolo[2,3-d]pyridazine-1,9(2H,6H)-dione;

2-(3-chloro-4-fluorobenzyl)-10-hydroxy-6,8-dimethyl-7,8-dihydropyrazino[1',2':1,5]-pyrrolo[2,3-d]pyridazine-1,9(2H,6H)-dione;

2-(3-chloro-4-fluorobenzyl)-8-ethyl-10-hydroxy-6-dimethyl-7,8-dihydropyrazino-[1',2':1,5]-pyrrolo[2,3-d]pyridazine-1,9(2H,6H)-dione;

2-(4-fluorobenzyl)-10-hydroxy-8-methyl-7,8-dihydropyrazino[1',2':1,5]-pyrrolo[2,3-d]pyridazine-1,9(2H,6H)-dione;

2-(4-fluorobenzyl)-10-hydroxy-4,6,8-trimethyl-7,8-dihydropyrazino[1',2':1,5]-pyrrolo[2,3-d]pyridazine-1,9(2H,6H)-dione;

8-ethyl-2-(4-fluorobenzyl)-10-hydroxy-4,6-dimethyl-7,8-dihydropyrazino[1',2':1,5]-pyrrolo[2,3-d]pyridazine-1,9(2H,6H)-dione;

4-amino-8-(4-fluorobenzyl)-10-hydroxy-2-methyl-7,8-dihydropyrazino[1',2':1,5]-pyrrolo[2,3-d]pyridazine-1,9(2H,6H)-dione;

8-(4-fluorobenzyl)-10-hydroxy-2-methyl-4-morpholin-4-yl-7,8-dihydropyrazino[1',2':1,5]-pyrrolo[2,3-d]pyridazine-1,9(2H,6H)-dione;

4-amino-2-(4-fluorobenzyl)-10-hydroxy-8-methyl-7,8-dihydropyrazino[1',2':1,5]-pyrrolo[2,3-d]pyridazine-1,9(2H,6H)-dione;

4-amino-2-benzyl-10-hydroxy-8-methyl-7,8-dihydropyrazino[1',2':1,5]-pyrrolo[2,3-d]pyridazine-1,9(2H,6H)-dione;

2-(4-fluorobenzyl)-4,10-dihydroxy-8-methyl-7,8-dihydropyrazino[1',2':1,5]-pyrrolo[2,3-d]pyridazine-1,9(2H,6H)-dione;

2-(4-fluorobenzyl)-10-hydroxy-4-methoxy-8-methyl-7,8-dihydropyrazino[1',2':1,5]-pyrrolo[2,3-d]pyridazine-1,9(2H,6H)-dione;

6(S)-8-methyl-2-(4-fluorobenzyl)-10-hydroxy-6-isopropyl-4-methyl-7,8-dihydropyrazino[1',2':1,5]-pyrrolo[2,3-d]pyridazine-1,9(2H,6H)-dione;

2-(3-chloro-4-fluorobenzyl)-10-hydroxy-4-ethoxy-8-methyl-7,8-dihydropyrazino[1',2':1,5]pyrrolo[2,3-d]pyridazine-1,9(2H,6H)-dione;

8-(4-fluorobenzyl)-10-hydroxy-4-methoxy-2-methyl-7,8-dihydropyrazino[1',2':1,5]pyrrolo[2,3-d]pyridazine-1,9(2H,6H)-dione;

6(S)-8-ethyl-2-(4-fluorobenzyl)-10-hydroxy-6-isopropyl-4-methyl-7,8-dihydropyrazino[1',2':1,5]pyrrolo[2,3-d]pyridazine-1,9(2H,6H)-dione;

6(S)-8-ethyl-2-(4-fluorobenzyl)-10-hydroxy-4,6-dimethyl-7,8-dihydropyrazino[1',2':1,5]pyrrolo[2,3-d]pyridazine-1,9(2H,6H)-dione;

6(S)-2-(4-fluorobenzyl)-10-hydroxy-8-isopropyl-4,6-dimethyl-7,8-dihydropyrazino[1',2':1,5]pyrrolo[2,3-d]pyridazine-1,9(2H,6H)-dione;

6(S)-2-(3-chloro-4-fluorobenzyl)-10-hydroxy-8-isopropyl-4,6-dimethyl-7,8-dihydropyrazino[1',2':1,5]pyrrolo[2,3-d]pyridazine-1,9(2H,6H)-dione;

2-(4-fluorobenzyl)-10-hydroxy-4,6,8-trimethyl-7,8-dihydropyrazino[1',2':1,5]pyrrolo[2,3-d]pyridazine-1,9(2H,6H)-dione;

(+)-2-(4-fluorobenzyl)-10-hydroxy-4,6,8-trimethyl-7,8-dihydropyrazino[1',2':1,5]pyrrolo[2,3-d]pyridazine-1,9(2H,6H)-dione;

(−)-2-(4-fluorobenzyl)-10-hydroxy-4,6,8-trimethyl-7,8-dihydropyrazino[1',2':1,5]pyrrolo[2,3-d]pyridazine-1,9(2H,6H)-dione;

(6aR)-2-(4-fluorobenzyl)-12-hydroxy-4-methyl-6a,7,8,9-tetrahydro-1H,6H-pyrrolo[1'',2'':4',5']pyrazino[1',2':1,5]pyrrolo[2,3-d]pyridazine-1,11(2H)-dione;

(6aS)-2-(4-fluorobenzyl)-12-hydroxy-4-methyl-6a,7,8,9-tetrahydro-1H,6H-pyrrolo[1'',2'':4',5']pyrazino[1',2':1,5]pyrrolo[2,3-d]pyridazine-1,11(2H)-dione;

8-ethyl-2-(4-fluorobenzyl)-10-hydroxy-4-methyl-6-(hydroxymethyl)-7,8-dihydropyrazino[1',2':1,5]pyrrolo[2,3-d]pyridazine-1,9(2H,6H)-dione;

8-ethyl-2-(4-fluorobenzyl)-10-hydroxy-4-methyl-6-[(methylthio)methyl]-7,8-dihydropyrazino[1',2':1,5]pyrrolo[2,3-d]pyridazine-1,9(2H,6H)-dione;

8-ethyl-2-(4-fluorobenzyl)-10-hydroxy-4-methyl-6-[(methylsulfonyl)methyl]-7,8-dihydropyrazino[1',2':1,5]pyrrolo[2,3-d]pyridazine-1,9(2H,6H)-dione;

4-ethyl-2-(4-fluorobenzyl)-10-hydroxy-8-methyl-7,8-dihydropyrazino[1',2':1,5]pyrrolo[2,3-d]pyridazine-1,9(2H,6H)-dione;

2-(4-fluorobenzyl)-10-hydroxy-4-isopropyl-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-isopropyl-8-methyl-7,8-dihydropyrazino-[1',2':1,5]pyrrolo[2,3-d]pyridazine-1,9(2H,6H)-dione;

6(S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide;

6(R)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide;

2-(4-fluorobenzyl)-10-hydroxy-N,N,8-trimethyl-1,9-dioxo-1,2,6,7,8,9-hexahydropyrazino[1',2':1,5]pyrrolo[2,3-d]pyridazine-4-carboxamide;

2-(4-fluorobenzyl)-10-hydroxy-8-methyl-4-(morpholin-4-ylcarbonyl)-7,8-dihydropyrazino[1',2':1,5]pyrrolo[2,3-d]pyridazine-1,9(2H,6H)-dione;

ethyl 2-(4-fluorobenzyl)-10-hydroxy-8-methyl-1,9-dioxo-1,2,6,7,8,9-hexahydropyrazino[1',2':1,5]pyrrolo[2,3-d]pyridazine-4-carboxylate;

2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-10-hydroxy-N,8-dimethyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-ethyl-10-hydroxy-8-methyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-cyclopropyl-10-hydroxy-8-methyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-(2-fluoroethyl)-10-hydroxy-8-methyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-(2,2-difluoroethyl)-10-hydroxy-8-methyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-(2,2,2-trifluoroethyl)-10-hydroxy-8-methyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-[2-(dimethylamino)ethyl]-10-hydroxy-8-methyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-[3-(dimethylamino)propyl]-10-hydroxy-8-methyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-10-hydroxy-N,N,8-trimethyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-ethyl-10-hydroxy-N,8-dimethyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-10-hydroxy-N-isopropyl-N,8-dimethyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-10-hydroxy-8-methyl-4-(morpholin-4-ylcarbonyl)-7,8-dihydropyrazino[1',2':1,5]pyrrolo[2,3-d]pyridazine-1,9(2H,6H)-dione;

2-(3-chloro-4-fluorobenzyl)-10-hydroxy-8-methyl-4-(piperidin-1-ylcarbonyl)-7,8-dihydropyrazino[1',2':1,5]pyrrolo[2,3-d]pyridazine-1,9(2H,6H)-dione;

2-(3-chloro-4-fluorobenzyl)-10-hydroxy-8-methyl-4-[(4-methylpiperazin-1-yl)carbonyl]-7,8-dihydropyrazino[1',2':1,5]pyrrolo[2,3-d]pyridazine-1,9(2H,6H)-dione;

2-(3-chloro-4-fluorobenzyl)-10-hydroxy-8-methyl-4-[(4-allylpiperazin-1-yl)carbonyl]-7,8-dihydropyrazino[1',2':1,5]pyrrolo[2,3-d]pyridazine-1,9(2H,6H)-dione;

2-(3-chloro-4-fluorobenzyl)-10-hydroxy-8-methyl-4-[(1,1-dioxidothiomorpholin-4-yl)carbonyl]-7,8-dihydropyrazino[1',2':1,5]pyrrolo[2,3-d]pyridazine-1,9(2H,6H)-dione;

2-(3-chloro-4-fluorobenzyl)-10-hydroxy-8-methyl-4-[(4-methyl-3-oxopiperazin-1-yl)carbonyl]-7,8-dihydropyrazino[1',2':1,5]pyrrolo[2,3-d]pyridazine-1,9(2H,6H)-dione;

6(S)-2-(3-chloro-4-fluorobenzyl)-10-hydroxy-8-isopropyl-N,6-dimethyl-1,9-dioxo-1,2,6,7,8,9-hexahydropyrazino[1',2':1,5]pyrrolo[2,3-d]pyridazine-4-carboxamide;

6(S)-2-(3-chloro-4-fluorobenzyl)-10-hydroxy-8-isopropyl-N-ethyl-6-methyl-1,9-dioxo-1,2,6,7,8,9-hexahydropyrazino[1',2':1,5]pyrrolo[2,3-d]pyridazine-4-carboxamide;

6(S)-2-(4-fluorobenzyl)-10-hydroxy-8-isopropyl-N-ethyl-6-methyl-1,9-dioxo-1,2,6,7,8,9-hexahydropyrazino[1',2':1,5]pyrrolo[2,3-d]pyridazine-4-carboxamide;

6(S)-2-(3-chloro-4-fluorobenzyl)-10-hydroxy-8-isopropyl-N,N,6-trimethyl-1,9-dioxo-1,2,6,7,8,9-hexahydropyrazino[1',2':1,5]pyrrolo[2,3-d]pyridazine-4-carboxamide;

6(S)-2-(3-chloro-4-fluorobenzyl)-10-hydroxy-N,8-diethyl-6-methyl-1,9-dioxo-1,2,6,7,8,9-hexahydropyrazino[1',2':1,5]pyrrolo[2,3-d]pyridazine-4-carboxamide;

6(S)-2-(3-chloro-4-fluorobenzyl)-8-ethyl-10-hydroxy-6-methyl-1,9-dioxo-N-(2,2,2-trifluoroethyl)-1,2,6,7,8,9-hexahydropyrazino[1',2':1,5]pyrrolo[2,3-d]pyridazine-4-carboxamide;

6(S)-2-(3-chloro-4-fluorobenzyl)-8-ethyl-10-hydroxy-N,N,6-trimethyl-1,9-dioxo-1,2,6,7,8,9-hexahydropyrazino[1',2':1,5]pyrrolo[2,3-d]pyridazine-4-carboxamide;

6(S)-N,2-bis(3-chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide;

6(S)-2-(3-chloro-4-fluorobenzyl)-8-(cyclopropylmethyl)-10-hydroxy-N,6-dimethyl-1,9-dioxo-1,2,6,7,8,9-hexahydropyrazino[1',2':1,5]pyrrolo[2,3-d]pyridazine-4-carboxamide;

6(S)-2-(3-chloro-4-fluorobenzyl)-10-hydroxy-8-isobutyl-N,6-dimethyl-1,9-dioxo-1,2,6,7,8,9-hexahydropyrazino[1',2':1,5]pyrrolo[2,3-d]pyridazine-4-carboxamide;

N-(2,3-dihydro-1H-inden-2-yl)-10-hydroxy-8-methyl-1,9-dioxo-2-(2-phenylethyl)-1,2,6,7,8,9-hexahydropyrazino[1',2':1,5]pyrrolo[2,3-d]pyridazine-4-carboxamide;

8-(4-fluorobenzyl)-10-hydroxy-N,N,2-trimethyl-1,9-dioxo-1,2,6,7,8,9-hexahydropyrazino[1',2':1,5]pyrrolo[2,3-d]pyridazine-4-carboxamide;

2-(4-fluorobenzyl)-10-hydroxy-4-(hydroxymethyl)-8-methyl-7,8-dihydropyrazino[1',2':1,5]pyrrolo[2,3-d]pyridazine-1,9(2H,6H)-dione;

2-(4-fluorobenzyl)-10-hydroxy-4-[(1,1-dioxido-1,2-thiazinan-2-yl)methyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-[(2-oxopyridine-1(2H)-yl)methyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-(morpholin-4-ylmethyl)-8-methyl-7,8-dihydropyrazino[1',2':1,5]pyrrolo[2,3-d]pyridazine-1,9(2H,6H)-dione;

2-(4-fluorobenzyl)-10-hydroxy-4-(pyrrolidin-1-ylmethyl)-8-methyl-7,8-dihydropyrazino[1',2':1,5]pyrrolo[2,3-d]pyridazine-1,9(2H,6H)-dione;

2-(4-fluorobenzyl)-10-hydroxy-4-{[ethyl)methyl]amino]methyl}-8-methyl-7,8-dihydropyrazino[1',2':1,5]pyrrolo[2,3-d]pyridazine-1,9(2H,6H)-dione;

2-(4-fluorobenzyl)-10-hydroxy-4-(1H-1,2,4-triazol-1-ylmethyl)-8-methyl-7,8-dihydropyrazino[1',2':1,5]pyrrolo[2,3-d]pyridazine-1,9(2H,6H)-dione;

2-(4-fluorobenzyl)-10-hydroxy-4-(1H-imidazol-1-ylmethyl)-8-methyl-7,8-dihydropyrazino[1',2':1,5]pyrrolo[2,3-d]pyridazine-1,9(2H,6H)-dione;

2-(4-fluorobenzyl)-10-hydroxy-4-[(2-oxopiperidin-1-yl)methyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-[(4-ethyl-2,3-dioxopiperazin-1-yl)methyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-[(methylthio)methyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-[(methylsulfonyl)methyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-[(phenylthio)methyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-[(phenylsulfonyl)methyl]-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-[(2-oxopyridine-1(2H)-yl)methyl]-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-[(2-oxopyrrolidin-1-yl)methyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-(1-hydroxyethyl)-8-methyl-7,8-dihydropyrazino[1',2':1,5]pyrrolo[2,3-d]pyridazine-1,9(2H,6H)-dione;

2-(4-fluorobenzyl)-10-hydroxy-4-[1-(1,1-dioxido-1,2-thiazinan-2-yl)ethyl]-8-methyl-7,8-dihydropyrazino[1',2':1,5]pyrrolo[2,3-d]pyridazine-1,9(2H,6H)-dione;

2-(4-fluorobenzyl)-10-hydroxy-4-(1-morpholin-4-ylethyl)-8-methyl-7,8-dihydropyrazino[1',2':1,5]pyrrolo[2,3-d]pyridazine-1,9(2H,6H)-dione;

4-acetyl-2-(3-chloro-4-fluorobenzyl)-10-hydroxy-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(1-hydroxy-1-methylethyl)-8-methyl-7,8-dihydropyrazino[1',2':1,5]pyrrolo[2,3-d]pyridazine-1,9(2H,6H)-dione;

methyl [2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]acetate;

2-(3-chloro-4-fluorobenzyl)-10-hydroxy-4-(5-oxopyrrolidin-3-yl)-8-methyl-7,8-dihydropyrazino[1',2':1,5]pyrrolo[2,3-d]pyridazine-1,9(2H,6H)-dione;

(6S)-4-amino-2-(3-chloro-4-fluorobenzyl)-10-hydroxy-8-ethyl-6-methyl-7,8-dihydropyrazino[1',2':1,5]pyrrolo[2,3-d]pyridazine-1,9(2H,6H)-dione;

4-amino-2-(3-chloro-4-fluorobenzyl)-10-hydroxy-8-methyl-7,8-dihydropyrazino[1',2':1,5]pyrrolo[2,3-d]pyridazine-1,9(2H,6H)-dione;

(6S)-4-amino-2-(3-chloro-4-fluorobenzyl)-10-hydroxy-8-isopropyl-6-methyl-7,8-dihydropyrazino[1',2':1,5]pyrrolo[2,3-d]pyridazine-1,9(2H,6H)-dione;

(6S)-4-amino-2-(4-fluorobenzyl)-10-hydroxy-8-isopropyl-6-methyl-7,8-dihydropyrazino[1',2':1,5]pyrrolo[2,3-d]pyridazine-1,9(2H,6H)-dione;

N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylacetamide;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,2-dimethylpropanamide;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-(N',N'-dimethylcarbonylmethyl)-2-methylpropanamide;

[2-(4-fluorobenzyl)-10-hydroxy-8-methyl-4-(2-oxopiperidin-1-yl)-7,8-dihydropyrazino[1',2':1,5]pyrrolo[2,3-d]pyridazine-1,9(2H,6H)-dione;

N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N',N'-dimethylethanediamide;

N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N',N'-trimethylethanediamide;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N',N'-trimethylethanediamide;

N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N'-dimethylurea;

N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N'-methylurea;

N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N'-ethylurea;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N',N'-trimethylurea;

N'-[(6S)-2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N,N-dimethylethanimidamide;

N'-[(6S)-2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N,N-dimethylimidoformamide;

N'-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N,N-dimethylimidoformamide;

2-(3-chloro-4-fluorobenzyl)-10-hydroxy-4-(2,5-dimethyl-1H-pyrrol-yl)-8-methyl-7,8-dihydropyrazino[1',2':1,5]pyrrolo[2,3-d]pyridazine-1,9(2H,6H)-dione;

2-(3-chloro-4-fluorobenzyl)-8-ethyl-4-fluoro-10-hydroxy-6-methyl-7,8-dihydropyrazino[1',2':1,5]pyrrolo[2,3-d]pyridazine-1,9(2H,6H)-dione;

2-(3-chloro-4-fluorobenzyl)-8-ethyl-10-hydroxy-4-(1,1-dioxidoisothiazinan-2-yl)-6-methyl-7,8-dihydropyrazino[1',2':1,5]pyrrolo[2,3-d]pyridazine-1,9(2H,6H)-dione;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]propane-2-sulfonamide;

N-[2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]ethanesulfonamide;

N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylmethanesulfonamide;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylmethanesulfonamide;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-ethylmethanesulfonamide;

N-(cyclopropylmethyl)-N-[2-(4-fluorobenzyl)-10-hydroxy-8-methyl-1,9-dioxo-1,2,6,7,8,9-hexahydropyrazino[1',2':1,5]pyrrolo[2,3-d]pyridazin-4-yl]methanesulfonamide;

N-(cyclopropylmethyl)-N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]methanesulfonamide;

N-allyl-N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]methanesulfonamide;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylcyclopropanesulfonamide;

N-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-N-methylpropane-2-sulfonamide;

N-[(6S)-2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N-methylmethanesulfonamide;

N-[2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N-methylpropane-2-sulfonamide;

N-[(6S)-2-(3-chloro-4-fluorobenzyl)-10-hydroxy-8-isopropyl-6-methyl-1,9-dioxo-1,2,6,7,8,9-hexahydropyrazino[1',2':1,5]pyrrolo[2,3-d]pyridazin-4-yl]-N-methylmethanesulfonamide;

$N^2$-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-$N^2$-(isopropylsulfonyl)-$N^1$,$N^1$-dimethylglycinamide;

$N^2$-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-$N^2$-(methanesulfonyl)-$N^1$,$N^1$-dimethylglycinamide;

2-(3-chloro-4-fluorobenzyl)-8-ethyl-10-hydroxy-4-(1,1-dioxidoisothiazolidin-2-yl)-6-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(1,1-dioxidoisothiazolidin-2-yl)-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(1,1-dioxidoisothiazinan-2-yl)-8-methyl-7,8-dihydropyrazino[1',2':1,5]pyrrolo[2,3-d]pyridazine-1,9(2H,6H)-dione;

2-(4-fluorobenzyl)-10-hydroxy-4-(1,1-dioxidoisothiazinan-2-yl)-8-methyl-7,8-dihydropyrazino[1',2':1,5]pyrrolo[2,3-d]pyridazine-1,9(2H,6H)-dione;

N-[(6S)-2-(4-fluorobenzyl)-10-hydroxy-8-isopropyl-6-methyl-1,9-dioxo-1,2,6,7,8,9-hexahydropyrazino[1',2':1,5]pyrrolo[2,3-d]pyridazin-4-yl]-N-methylmethanesulfonamide;

N-[2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N-ethylmethanesulfonamide;

2-(4-fluorobenzyl)-10-hydroxy-8-methyl-4-(methylsulfonyl)-7,8-dihydropyrazino[1',2':1,5]pyrrolo[2,3-d]pyridazine-1,9(2H,6H)-dione;

4-bromo-2-(3-chloro-4-fluorobenzyl)-10-hydroxy-8-methyl-7,8-dihydropyrazino[1',2':1,5]pyrrolo[2,3-d]pyridazine-1,9(2H,6H)-dione;

2-(4-fluorobenzyl)-10-hydroxy-8-methyl-4-(methylthio)-7,8-dihydropyrazino[1',2':1,5]pyrrolo[2,3-d]pyridazine-1,9(2H,6H)-dione;

2-(3-chloro-4-fluorobenzyl)-10-hydroxy-8-methyl-4-(methylsulfonyl)-7,8-dihydropyrazino[1',2':1,5]pyrrolo[2,3-d]pyridazine-1,9(2H,6H)-dione;

2-(3-chloro-4-fluorobenzyl)-10-hydroxy-8-methyl-4-(isopropylsulfonyl)-7,8-dihydropyrazino[1',2':1,5]pyrrolo[2,3-d]pyridazine-1,9(2H,6H)-dione;

2-(3-chloro-4-fluorobenzyl)-10-hydroxy-8-methyl-4-(cyclopentylsulfonyl)-7,8-dihydropyrazino[1',2':1,5]pyrrolo[2,3-d]pyridazine-1,9(2H,6H)-dione;

6(S)-2-(3-chloro-4-fluorobenzyl)-8-ethyl-10-hydroxy-4-(ethylsulfonyl)-6-methyl-7,8-dihydropyrazino[1',2':1,5]pyrrolo[2,3-d]pyridazine-1,9(2H,6H)-dione;

6(S)-2-(3-chloro-4-fluorobenzyl)-8-ethyl-10-hydroxy-4-(isopropylsulfonyl)-6-methyl-7,8-dihydropyrazino[1',2':1,5]pyrrolo[2,3-d]pyridazine-1,9(2H,6H)-dione;

2-(4-fluorobenzyl)-10-hydroxy-8-methyl-4-(4-methyl-3-oxopiperazin-1-yl)-7,8-dihydropyrazino[1',2':1,5]pyrrolo[2,3-d]pyridazine-1,9(2H,6H)-dione;

2-(4-fluorobenzyl)-10-hydroxy-8-methyl-4-(4-methylpiperazin-1-yl)-7,8-dihydropyrazino[1',2':1,5]pyrrolo[2,3-d]pyridazine-1,9(2H,6H)-dione;

2-(4-fluorobenzyl)-10-hydroxy-8-methyl-4-(4-acetylpiperazin-1-yl)-7,8-dihydropyrazino[1',2':1,5]pyrrolo[2,3-d]pyridazine-1,9(2H,6H)-dione;

6(S)-2-(3-chloro-4-fluorobenzyl)-8-ethyl-10-hydroxy-4-(methylamino)-6-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(2-oxopyridinyl-1(2H)-yl)-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(2-oxo-4-cyanopyridinyl-1(2H)-yl)-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(1H-1,2,4-triazol-1-yl)-8-methyl-7,8-dihydropyrazino[1',2':1,5]pyrrolo[2,3-d]pyridazine-1,9(2H,6H)-dione;

2-(4-fluorobenzyl)-10-hydroxy-4-pyrimidin-5-yl-8-methyl-7,8-dihydropyrazino[1',2':1,5]pyrrolo[2,3-d]pyridazine-1,9(2H,6H)-dione;

2-(4-fluorobenzyl)-10-hydroxy-4-pyridin-4-yl-8-methyl-7,8-dihydropyrazino[1',2':1,5]pyrrolo[2,3-d]pyridazine-1,9(2H,6H)-dione;

2-(4-fluorobenzyl)-10-hydroxy-4-(6-methoxypyridin-3-yl-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(6-methoxypyridin-3-yl-8-methyl-7,8-dihydropyrazino[1',2':1,5]pyrrolo[2,3-d]pyridazine-1,9(2H,6H)-dione;

5-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]thiophene-2-carbonitrile;

2-(3-chloro-4-fluorobenzyl)-10-hydroxy-4-(5-methyl-2-thienyl)-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(1-methyl-6-oxo-1,6-dihydropyridin-3-yl)-8-methyl-7,8-dihydropyrazino[1',2':1,5]pyrrolo[2,3-d]pyridazine-1,9(2H,6H)-dione;

2-[5-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]-2-oxopyridin-1(2H)-yl]-N,N-dimethylacetamide;

2-(3-chloro-4-fluorobenzyl)-10-hydroxy-4-pyrazin-2-yl-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-pyridin-2-yl-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-(3-oxo-1,2,3,6-tetrahydro-1,2,4-triazin-5-yl)-8-methyl-7,8-dihydropyrazino[1',2':1,5]pyrrolo[2,3-d]pyridazine-1,9(2H,6H)-dione;

2-(3-chloro-4-fluorobenzyl)-10-hydroxy-4-[(4-methyl-3-oxopiperazin-1-yl)acetyl]-8-methyl-7,8-dihydropyrazino[1',2':1,5]pyrrolo[2,3-d]pyridazine-1,9(2H,6H)-dione;

[2-(3-chloro-4-fluorobenzyl)-10-hydroxy-N,N,8-trimethyl-1,9-dioxo-1,2,6,7,8,9-hexahydropyrazino[1',2':1,5]pyrrolo[2,3-d]pyridazine-4-sulfonamide;

S-[2-(3-chloro-4-fluorobenzyl)-10-hydroxy-8-methyl-1,9-dioxo-1,2,6,7,8,9-hexahydropyrazino[1',2':1,5]pyrrolo[2,3-d]pyridazin-4-yl]diethylthiocarbamate;

6(S)-2-(3-chloro-4-fluorobenzyl)-10-hydroxy-8-ethyl-6-methyl-7,8-dihydropyrazino[1',2':1,5]pyrrolo[2,3-d]pyridazine-1,9(2H,6H)-dione;

6(S)-2-(4-fluorobenzyl)-10-hydroxy-8-ethyl-6-methyl-7,8-dihydropyrazino[1',2':1,5]pyrrolo[2,3-d]pyridazine-1,9(2H,6H)-dione;

6(S)-2-(3-chloro-4-fluorobenzyl)-10-hydroxy-6,8-dimethyl-7,8-dihydropyrazino[1',2':1,5]pyrrolo[2,3-d]pyridazine-1,9(2H,6H)-dione;

6(S)-2-(3-chloro-4-fluorobenzyl)-10-hydroxy-8-isopropyl-6-methyl-7,8-dihydropyrazino[1',2':1,5]pyrrolo[2,3-d]pyridazine-1,9(2H,6H)-dione;

6(S)-2-(4-fluorobenzyl)-10-hydroxy-8-isopropyl-6-methyl-7,8-dihydropyrazino[1',2':1,5]pyrrolo[2,3-d]pyridazine-1,9(2H,6H)-dione;

6(S)-2-(3,4-difluorobenzyl)-10-hydroxy-8-isopropyl-6-methyl-7,8-dihydropyrazino[1',2':1,5]pyrrolo[2,3-d]pyridazine-1,9(2H,6H)-dione;

6(S)-2-(3-chlorobenzyl)-10-hydroxy-8-isopropyl-6-methyl-7,8-dihydropyrazino[1',2':1,5]pyrrolo[2,3-d]pyridazine-1,9(2H,6H)-dione;

6(S)-2-(4-fluoro-3-methylbenzyl)-10-hydroxy-8-isopropyl-6-methyl-7,8-dihydropyrazino[1',2':1,5]pyrrolo[2,3-d]pyridazine-1,9(2H,6H)-dione;

6(S)-2-(2,4-Difluorobenzyl)-10-hydroxy-8-isopropyl-6-methyl-7,8-dihydropyrazino[1',2':1,5]pyrrolo[2,3-d]pyridazine-1,9(2H,6H)-dione;

6(S)-2-(4-chloro-3-fluorobenzyl)-10-hydroxy-8-isopropyl-6-methyl-7,8-dihydropyrazino[1',2':1,5]pyrrolo[2,3-d]pyridazine-1,9(2H,6H)-dione;

6(S)-2-(3-chloro-4-fluorobenzyl)-10-hydroxy-8-tert-butyl-6-methyl-7,8-dihydropyrazino[1',2':1,5]pyrrolo[2,3-d]pyridazine-1,9(2H,6H)-dione;

6(S)-2-(4-fluorobenzyl)-10-hydroxy-8-tert-butyl-6-methyl-7,8-dihydropyrazino[1',2':1,5]pyrrolo[2,3-d]pyridazine-1,9(2H,6H)-dione;

6(S)-2-(4-fluorobenzyl)-10-hydroxy-6-isopropyl-8-methyl-7,8-dihydropyrazino[1',2':1,5]pyrrolo[2,3-d]pyridazine-1,9(2H,6H)-dione;

6(S)-2-(4-fluorobenzyl)-10-hydroxy-6-isopropyl-8-ethyl-7,8-dihydropyrazino[1',2':1,5]pyrrolo[2,3-d]pyridazine-1,9(2H,6H)-dione;

2-(4-fluorobenzyl)-10-hydroxy-8-ethyl-6,6-dimethyl-7,8-dihydropyrazino[1',2':1,5]pyrrolo[2,3-d]pyridazine-1,9(2H,6H)-dione;

2-(4-fluorobenzyl)-10-hydroxy-8-ethyl-6,6-dimethyl-7,8-dihydropyrazino[1',2':1,5]pyrrolo[2,3-d]pyridazine-1,9(2H,6H)-dione;

2-(4-fluorobenzyl)-10-hydroxy-8-ethyl-6-hydroxymethyl-7,8-dihydropyrazino[1',2':1,5]pyrrolo[2,3-d]pyridazine-1,9(2H,6H)-dione;

6(R)-2-(4-fluorobenzyl)-10-hydroxy-8-ethyl-6-hydroxymethyl-7,8-dihydropyrazino[1',2':1,5]pyrrolo[2,3-d]pyridazine-1,9(2H,6H)-dione;

6(R)-2-(3-chloro-4-fluorobenzyl)-10-hydroxy-8-ethyl-6-hydroxymethyl-7,8-dihydropyrazino[1',2':1,5]pyrrolo[2,3-d]pyridazine-1,9(2H,6H)-dione;

N-{[8-ethyl-2-(4-fluorobenzyl)-10-hydroxy-1,9-dioxo-1,2,6,7,8,9-hexahydropyrazino[1',2':1,5]pyrrolo[2,3-d]pyridazin-6-yl]methyl}-N-methylmethanesulfonamide; and 6-(3-chloro-4-fluorobenzyl)-4-hydroxy-2-ethyl-1a,9l-dihydro-1H-cyclopropa[5',6']pyrazino[1',2':1,5]pyrrolo[2,3-d]pyridazine-3,5(2H,6H)-dione.

10. A compound according to claim 8, or a pharmaceutically acceptable salt thereof, selected from the group consisting of:

2-(4-fluorobenzyl)-10-hydroxy-4,6,8-trimethyl-7,8-dihydropyrazino[1',2':1,5]-pyrrolo[2,3-d]pyridazine-1,9(2H,6H)-dione;

6(S)-2-(4-fluorobenzyl)-10-hydroxy-8-isopropyl-4,6-dimethyl-7,8-dihydropyrazino[1',2':1,5]pyrrolo[2,3-d]pyridazine-1,9(2H,6H)-dione 8-ethyl-2-(4-fluorobenzyl)-10-hydroxy-4-methyl-6-(hydroxymethyl)-7,8-dihydropyrazino[1',2':1,5]pyrrolo[2,3-d]pyridazine-1,9(2H,6H)-dione;

6(S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide;

2-(3-chloro-4-fluorobenzyl)-N-ethyl-10-hydroxy-8-methyl-1,9-dioxo-1,2,6,7,8,9-hexahydropyrazino[1',2':1,5]pyrrolo[2,3-d]pyridazine-4-carboxamide;

6(S)-2-(3-chloro-4-fluorobenzyl)-10-hydroxy-8-isopropyl-N-ethyl-6-methyl-1,9-dioxo-1,2,6,7,8,9-hexahydropyrazino[1',2':1,5]pyrrolo[2,3-d]pyridazine-4-carboxamide;

6(S)-2-(4-fluorobenzyl)-10-hydroxy-8-isopropyl-N-ethyl-6-methyl-1,9-dioxo-1,2,6,7,8,9-hexahydropyrazino[1',2':1,5]pyrrolo[2,3-d]pyridazine-4-carboxamide;

6(S)-2-(3-chloro-4-fluorobenzyl)-10-hydroxy-8-isopropyl-N,N,6-trimethyl-1,9-dioxo-1,2,6,7,8,9-hexahydropyrazino[1',2':1,5]pyrrolo[2,3-d]pyridazine-4-carboxamide;

N-[(6S)-2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N-methylmethanesulfonamide;

N-[(6S)-2-(3-chloro-4-fluorobenzyl)-10-hydroxy-8-isopropyl-6-methyl-1,9-dioxo-1,2,6,7,8,9-hexahydropyrazino[1',2':1,5]pyrrolo[2,3-d]pyridazin-4-yl]-N-methylmethanesulfonamide;

2-(3-chloro-4-fluorobenzyl)-8-ethyl-10-hydroxy-4-(1,1-dioxidoisothiazolidin-2-yl)-6-methyl-7,8-dihydropyrazino[1',2':1,5]pyrrolo[2,3-d]pyridazine-1,9(2H,6H)-dione;

N-[(6S)-2-(4-fluorobenzyl)-10-hydroxy-8-isopropyl-6-methyl-1,9-dioxo-1,2,6,7,8,9-hexahydropyrazino[1',2':1,5]pyrrolo[2,3-d]pyridazin-4-yl]-N-methylmethanesulfonamide;

N-[2-(3-chloro-4-fluorobenzyl)-10-hydroxy-8-ethyl-6-methyl-1,9-dioxo-1,2,6,7,8,9-hexahydropyrazino[1',2':1,5]pyrrolo[2,3-d]pyridazin-4-yl]-N-ethylmethanesulfonamide;

6(S)-2-(3-chloro-4-fluorobenzyl)-8-ethyl-10-hydroxy-4-(ethylsulfonyl)-6-methyl-7,8-dihydropyrazino[1',2':1,5]pyrrolo[2,3-d]pyridazine-1,9(2H,6H)-dione;

6(S)-2-(3-chloro-4-fluorobenzyl)-10-hydroxy-8-ethyl-6-methyl-7,8-dihydropyrazino[1',2':1,5]pyrrolo[2,3-d]pyridazine-1,9(2H,6H)-dione;

6(S)-2-(4-fluorobenzyl)-10-hydroxy-8-isopropyl-6-methyl-7,8-dihydropyrazino[1',2':1,5]pyrrolo[2,3-d]pyridazine-1,9(2H,6H)-dione; and 2-(4-fluorobenzyl)-10-hydroxy-8-ethyl-6-hydroxymethyl-7,8-dihydropyrazino[1',2':1,5]pyrrolo[2,3-d]pyridazine-1,9(2H,6H)-dione.

11. A pharmaceutical composition comprising an effective amount of a compound according to claim 1, or a pharmaceutically acceptable salt thereof, and a pharmaceutically acceptable carrier.

12. A method for treating infection by HIV or for treating or delaying the onset of AIDS in a subject in need thereof which comprises administering to the subject an effective amount of the compound according claim 1, or a pharmaceutically acceptable salt thereof.

13. A pharmaceutical combination which is (i) a compound according to claim 1, or a pharmaceutically acceptable salt thereof, and (ii) an HIV infection/AIDS antiviral agent selected from the group consisting of HIV protease inhibitors, non-nucleoside HIV reverse transcriptase inhibitors and nucleoside HIV reverse transcriptase inhibitors; wherein the compound of (i) or its pharmaceutically acceptable salt and the HIV infection/AIDS antiviral agent of (ii) are each employed in an amount that renders the combination effective for inhibiting HIV integrase, for treating infection by HIV, or for treating or delaying the onset of AIDS.

* * * * *